United States Patent
Williams et al.

(10) Patent No.: US 11,161,010 B2
(45) Date of Patent: Nov. 2, 2021

(54) ACTIVITY AND WORKOUT UPDATES

(71) Applicant: Apple Inc., Cupertino, CA (US)

(72) Inventors: Aled Hywel Williams, San Francisco, CA (US); David Chance Graham, Campbell, CA (US); Christopher Wilson, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/378,136

(22) Filed: Apr. 8, 2019

(65) Prior Publication Data

US 2019/0232111 A1    Aug. 1, 2019

Related U.S. Application Data

(63) Continuation of application No. 15/616,480, filed on Jun. 7, 2017, now Pat. No. 10,272,294.
(Continued)

(51) Int. Cl.
    *G06F 3/048*        (2013.01)
    *A63B 24/00*      (2006.01)
(Continued)

(52) U.S. Cl.
CPC ............ *A63B 24/0062* (2013.01); *A61B 5/00* (2013.01); *A61B 5/11* (2013.01); *A61B 5/1118* (2013.01);
(Continued)

(58) Field of Classification Search
None
See application file for complete search history.

(56) References Cited

U.S. PATENT DOCUMENTS

| | | |
|---|---|---|
| 3,148,500 A | 9/1964 | Hayes |
| 4,205,628 A | 6/1980 | Null |
| | (Continued) | |

FOREIGN PATENT DOCUMENTS

| | | |
|---|---|---|
| AU | 2010249319 A1 | 6/2012 |
| AU | 2015101019 A4 | 9/2015 |
| | (Continued) | |

OTHER PUBLICATIONS

Corrected Notice of Allowance received for U.S. Appl. No. 15/355,956, dated Jan. 3, 2020, 2 pages.
(Continued)

*Primary Examiner* — Thanh T Vu
(74) *Attorney, Agent, or Firm* — Dentons US LLP

(57) ABSTRACT

The present disclosure generally relates to navigating, viewing, and sharing activity and workout data and interacting with workout and/or activity applications. In some examples, scrolling of activity data is based on the content being displayed. In some examples, friends' activity data may be viewed. In some examples, a notification and workout data for a friend's completed workout is received and displayed. In some example, the activity data received from friends is viewed and managed. In some examples, workout data for a multi-segment workout is displayed in a three-dimensional stack on a map. In some examples, a workout application operates in a limited mode until a touch input is received with a characteristic intensity that is greater than a threshold intensity.

30 Claims, 39 Drawing Sheets

Related U.S. Application Data

(60) Provisional application No. 62/348,908, filed on Jun. 11, 2016.

(51) Int. Cl.

| | | |
|---|---|---|
| *A61B 5/00* | (2006.01) | |
| *A61B 5/11* | (2006.01) | |
| *G06T 11/60* | (2006.01) | |
| *G06F 3/0481* | (2013.01) | |
| *G16H 40/67* | (2018.01) | |
| *G16H 20/30* | (2018.01) | |
| *A63B 71/06* | (2006.01) | |
| *G06F 3/0484* | (2013.01) | |
| *G06F 3/0485* | (2013.01) | |
| *G06F 3/0488* | (2013.01) | |
| *G06K 9/00* | (2006.01) | |
| *G16H 50/30* | (2018.01) | |

(52) U.S. Cl.
CPC ........ *A61B 5/6898* (2013.01); *A63B 24/0084* (2013.01); *A63B 71/0622* (2013.01); *G06F 3/0481* (2013.01); *G06F 3/0485* (2013.01); *G06F 3/04845* (2013.01); *G06F 3/04883* (2013.01); *G06K 9/00342* (2013.01); *G06T 11/60* (2013.01); *G16H 20/30* (2018.01); *G16H 40/67* (2018.01); *A61B 5/0022* (2013.01); *A63B 2024/0068* (2013.01); *A63B 2071/0655* (2013.01); *A63B 2071/0691* (2013.01); *A63B 2220/12* (2013.01); *A63B 2220/20* (2013.01); *A63B 2220/40* (2013.01); *A63B 2220/62* (2013.01); *A63B 2220/805* (2013.01); *A63B 2220/806* (2013.01); *A63B 2220/807* (2013.01); *A63B 2225/50* (2013.01); *A63B 2230/06* (2013.01); *A63B 2230/75* (2013.01); *G16H 50/30* (2018.01)

(56) References Cited

U.S. PATENT DOCUMENTS

| | | |
|---|---|---|
| 4,842,266 A | 6/1989 | Sweeney et al. |
| 5,072,412 A | 12/1991 | Henderson et al. |
| 5,208,790 A | 5/1993 | Sato |
| 5,220,541 A | 6/1993 | Vuilleumier |
| 5,233,687 A | 8/1993 | Henderson et al. |
| 5,276,785 A | 1/1994 | Mackinlay et al. |
| 5,394,521 A | 2/1995 | Henderson et al. |
| 5,423,863 A | 6/1995 | Felblinger et al. |
| 5,455,808 A | 10/1995 | Grupp et al. |
| 5,458,548 A | 10/1995 | Crossing et al. |
| 5,474,077 A | 12/1995 | Suga |
| 5,508,979 A | 4/1996 | Eisenegger |
| 5,564,002 A | 10/1996 | Brown |
| 5,659,693 A | 8/1997 | Hansen et al. |
| 5,678,015 A | 10/1997 | Goh |
| 5,788,655 A | 8/1998 | Yoshimura et al. |
| 5,815,657 A | 9/1998 | Williams et al. |
| 5,825,353 A | 10/1998 | Will |
| 5,841,435 A | 11/1998 | Dauerer et al. |
| 5,845,257 A | 12/1998 | Fu et al. |
| 5,864,337 A | 1/1999 | Marvin |
| 5,892,519 A | 4/1999 | Hirai |
| 5,986,655 A | 11/1999 | Chiu et al. |
| 5,999,195 A | 12/1999 | Santangeli |
| 6,013,008 A | 1/2000 | Fukushima |
| 6,043,818 A | 3/2000 | Nakano et al. |
| 6,095,949 A | 8/2000 | Arai |
| 6,095,984 A | 8/2000 | Amano et al. |
| 6,097,371 A | 8/2000 | Siddiqui et al. |
| 6,097,385 A | 8/2000 | Robinson |
| 6,230,169 B1 | 5/2001 | Nagae |
| 6,244,988 B1 | 6/2001 | Delman |
| 6,262,734 B1 | 7/2001 | Ishikawa |
| 6,359,839 B1 | 3/2002 | Schenk et al. |
| 6,377,698 B1 | 4/2002 | Cumoli et al. |
| 6,416,471 B1 | 7/2002 | Kumar et al. |
| 6,449,219 B1 | 9/2002 | Hepp et al. |
| 6,477,117 B1 | 11/2002 | Narayanaswami et al. |
| 6,496,780 B1 | 12/2002 | Harris et al. |
| 6,556,222 B1 | 4/2003 | Narayanaswami |
| 6,603,477 B1 | 8/2003 | Tittle |
| 6,628,309 B1 | 9/2003 | Dodson et al. |
| 6,639,584 B1 | 10/2003 | Li |
| 6,662,023 B1 | 12/2003 | Helle |
| 6,683,628 B1 | 1/2004 | Nakagawa et al. |
| 6,705,972 B1 | 3/2004 | Takano et al. |
| 6,710,788 B1 | 3/2004 | Freach et al. |
| 6,728,533 B2 | 4/2004 | Ishii |
| 6,809,724 B1 | 10/2004 | Shiraishi et al. |
| 6,837,827 B1 | 1/2005 | Lee et al. |
| 6,866,613 B1 | 3/2005 | Brown et al. |
| 6,871,076 B2 | 3/2005 | Samn |
| 6,912,694 B1 | 6/2005 | Harrison et al. |
| 7,003,495 B1 | 2/2006 | Burger et al. |
| 7,010,755 B2 | 3/2006 | Anderson et al. |
| 7,036,090 B1 | 4/2006 | Nguyen |
| 7,128,693 B2 | 10/2006 | Brown et al. |
| 7,203,380 B2 | 4/2007 | Chiu et al. |
| 7,251,454 B2 | 7/2007 | White |
| 7,257,254 B2 | 8/2007 | Tunney |
| 7,302,272 B2 | 11/2007 | Ackley |
| 7,302,650 B1 | 11/2007 | Allyn et al. |
| 7,305,350 B1 | 12/2007 | Bruecken |
| 7,330,875 B1 | 2/2008 | Parasnis et al. |
| 7,406,666 B2 | 7/2008 | Davis et al. |
| 7,515,509 B2 | 4/2009 | Klein |
| RE40,891 E | 9/2009 | Yasutake |
| 7,593,749 B2 | 9/2009 | Vallstrom et al. |
| 7,637,204 B2 | 12/2009 | Sumser et al. |
| 7,662,065 B1 | 2/2010 | Kahn et al. |
| 7,735,018 B2 | 6/2010 | Bakhash |
| 7,739,148 B2 | 6/2010 | Suzuki et al. |
| 7,751,285 B1 | 7/2010 | Cain |
| 7,773,460 B2 | 8/2010 | Holt |
| 7,843,769 B2 | 11/2010 | Ishida et al. |
| 7,873,356 B2 | 1/2011 | Flynt et al. |
| 7,898,542 B1 | 3/2011 | Yu et al. |
| 7,940,250 B2 | 5/2011 | Forstall |
| 7,970,827 B1 | 6/2011 | Cumberbatch et al. |
| 7,995,096 B1 | 8/2011 | Cressy et al. |
| 8,060,229 B2 | 11/2011 | Gupta et al. |
| 8,105,208 B2 | 1/2012 | Oleson et al. |
| 8,108,791 B2 | 1/2012 | Wang et al. |
| 8,121,945 B2 | 2/2012 | Rackle et al. |
| 8,266,550 B1 | 9/2012 | Cleron et al. |
| 8,312,371 B2 | 11/2012 | Ording |
| 8,321,006 B1 | 11/2012 | Snyder et al. |
| 8,341,557 B2 | 12/2012 | Pisula et al. |
| 8,364,855 B2 | 1/2013 | James et al. |
| 8,375,326 B2 | 2/2013 | Bucher et al. |
| 8,405,663 B2 | 3/2013 | Wikkerink et al. |
| 8,453,940 B2 | 6/2013 | Diamond |
| 8,462,997 B2 | 6/2013 | Pettit et al. |
| 8,467,770 B1 | 6/2013 | Ben Ayed |
| 8,475,339 B2 | 7/2013 | Hwang et al. |
| 8,477,139 B2 | 7/2013 | Robinet et al. |
| 8,496,563 B2 | 7/2013 | Komatsu et al. |
| 8,521,146 B2 | 8/2013 | Lee et al. |
| 8,543,081 B2 | 9/2013 | Scott et al. |
| 8,554,694 B1 | 10/2013 | Ward et al. |
| 8,566,403 B2 | 10/2013 | Pascal et al. |
| 8,584,031 B2 | 11/2013 | Moore et al. |
| 8,595,649 B2 | 11/2013 | Sherrard et al. |
| 8,595,798 B2 | 11/2013 | Anand et al. |
| 8,601,370 B2 | 12/2013 | Chiang et al. |
| 8,613,070 B1 | 12/2013 | Borzycki et al. |
| 8,624,836 B1 | 1/2014 | Miller et al. |
| 8,666,361 B2 | 3/2014 | Chu et al. |
| 8,676,170 B2 | 3/2014 | Porrati et al. |
| 8,677,284 B2 | 3/2014 | Aguilar |
| 8,681,105 B2 | 3/2014 | Huh et al. |

(56) References Cited

U.S. PATENT DOCUMENTS

| | | |
|---|---|---|
| 8,686,961 B2 | 4/2014 | Yamano |
| 8,700,158 B2 | 4/2014 | Mass et al. |
| 8,706,628 B2 | 4/2014 | Phillips |
| 8,732,609 B1 | 5/2014 | Bayersdorfer et al. |
| 8,784,115 B1 | 7/2014 | Chuang |
| 8,811,951 B1 | 8/2014 | Faaborg et al. |
| 8,825,445 B2 | 9/2014 | Hoffman et al. |
| 8,832,585 B2 | 9/2014 | Haggerty et al. |
| 8,850,351 B2 | 9/2014 | Beharie et al. |
| 8,866,761 B2 | 10/2014 | Enami |
| 8,868,338 B1 | 10/2014 | Chau et al. |
| 8,884,874 B1 | 11/2014 | Kim et al. |
| 8,903,671 B2 | 12/2014 | Park et al. |
| 8,931,703 B1 | 1/2015 | Mullen et al. |
| 8,934,963 B1 | 1/2015 | Farazi |
| 8,948,819 B2 | 2/2015 | Yun et al. |
| 8,963,894 B2 | 2/2015 | Klassen et al. |
| 8,990,006 B1 | 3/2015 | Wallace et al. |
| 8,996,639 B1 | 3/2015 | Faaborg et al. |
| 9,020,538 B1 | 4/2015 | White et al. |
| 9,070,092 B2 | 6/2015 | Chou et al. |
| 9,100,944 B2 | 8/2015 | Newham et al. |
| 9,141,270 B1 | 9/2015 | Stuart et al. |
| 9,173,052 B2 | 10/2015 | Hauser et al. |
| 9,191,988 B2 | 11/2015 | Newham |
| 9,224,291 B2 | 12/2015 | Moll-carrillo et al. |
| 9,230,076 B2 | 1/2016 | King et al. |
| 9,244,562 B1 | 1/2016 | Rosenberg et al. |
| 9,338,242 B1 | 5/2016 | Suchland et al. |
| 9,389,090 B1 | 7/2016 | Levine et al. |
| 9,400,489 B2 | 7/2016 | Kim et al. |
| 9,459,781 B2 | 10/2016 | Wilson et al. |
| 9,477,208 B2 | 10/2016 | Lee et al. |
| 9,489,074 B2 | 11/2016 | Oonishi |
| 9,547,425 B2 | 1/2017 | Wilson et al. |
| 9,557,881 B1 | 1/2017 | Jain et al. |
| 9,582,165 B2 | 2/2017 | Kocienda et al. |
| 9,589,445 B2 | 3/2017 | White et al. |
| 9,600,178 B2 | 3/2017 | Yun et al. |
| 9,712,629 B2 | 7/2017 | Molettiere et al. |
| 9,729,730 B2 | 8/2017 | Levesque et al. |
| 9,734,477 B2 | 8/2017 | Weast et al. |
| 9,813,642 B1 | 11/2017 | Chen et al. |
| 9,817,481 B2 | 11/2017 | Pantelopoulos et al. |
| 9,854,653 B1 | 12/2017 | Ackmann et al. |
| 9,880,805 B1 | 1/2018 | Guralnick |
| 9,904,906 B2 | 2/2018 | Kim et al. |
| 9,940,682 B2 | 4/2018 | Hoffman et al. |
| 10,019,136 B1 | 7/2018 | Ozog |
| 10,051,103 B1 | 8/2018 | Gordon et al. |
| 10,055,121 B2 | 8/2018 | Chaudhri et al. |
| 10,056,006 B1 | 8/2018 | Hsu-Hoffman et al. |
| 10,135,905 B2 | 11/2018 | Chaudhri et al. |
| 10,216,392 B2 | 2/2019 | Zhao |
| 10,220,258 B2 | 3/2019 | Gu et al. |
| 10,251,034 B2 | 4/2019 | Langlois et al. |
| 10,282,451 B1 | 5/2019 | Ho et al. |
| 10,300,334 B1 | 5/2019 | Chuang |
| 10,304,347 B2 | 5/2019 | Wilson et al. |
| 10,339,830 B2 | 7/2019 | Han et al. |
| 10,398,381 B1 | 9/2019 | Heneghan et al. |
| 10,425,284 B2 | 9/2019 | Dellinger et al. |
| 10,777,314 B1 | 9/2020 | Williams et al. |
| 2001/0031622 A1 | 10/2001 | Kivela et al. |
| 2001/0049470 A1 | 12/2001 | Mauit et al. |
| 2002/0029169 A1 | 3/2002 | Oki et al. |
| 2002/0045960 A1 | 4/2002 | Phillips et al. |
| 2002/0054066 A1 | 5/2002 | Kikinis et al. |
| 2002/0054541 A1 | 5/2002 | Hall |
| 2002/0068600 A1 | 6/2002 | Chihara et al. |
| 2002/0086774 A1 | 7/2002 | Warner |
| 2002/0087262 A1 | 7/2002 | Bullock et al. |
| 2002/0115478 A1 | 8/2002 | Fujisawa et al. |
| 2002/0118121 A1 | 8/2002 | Lehrman et al. |
| 2002/0131331 A1 | 9/2002 | Molander |
| 2002/0142734 A1 | 10/2002 | Wickstead |
| 2002/0180797 A1 | 12/2002 | Bachmann |
| 2003/0002391 A1 | 1/2003 | Biggs |
| 2003/0013483 A1 | 1/2003 | Ausems et al. |
| 2003/0023178 A1 | 1/2003 | Bischoff et al. |
| 2003/0027621 A1 | 2/2003 | Libby et al. |
| 2003/0044021 A1 | 3/2003 | Wilkinson et al. |
| 2003/0064860 A1 | 4/2003 | Yamashita et al. |
| 2003/0067497 A1 | 4/2003 | Pichon |
| 2003/0074647 A1 | 4/2003 | Andrew |
| 2003/0079057 A1 | 4/2003 | Ruskin et al. |
| 2003/0081506 A1 | 5/2003 | Karhu |
| 2003/0134714 A1 | 7/2003 | Oishi et al. |
| 2003/0164847 A1 | 9/2003 | Zaima et al. |
| 2003/0179229 A1 | 9/2003 | Van et al. |
| 2003/0179240 A1 | 9/2003 | Gest |
| 2003/0182628 A1 | 9/2003 | Lira |
| 2003/0210280 A1 | 11/2003 | Baker et al. |
| 2003/0214885 A1 | 11/2003 | Powell et al. |
| 2003/0216971 A1 | 11/2003 | Sick et al. |
| 2003/0226695 A1 | 12/2003 | Mault |
| 2004/0001105 A1 | 1/2004 | Chew et al. |
| 2004/0014567 A1 | 1/2004 | Mendel |
| 2004/0017733 A1 | 1/2004 | Sullivan |
| 2004/0021699 A1 | 2/2004 | Fildebrandt |
| 2004/0047244 A1 | 3/2004 | Iino et al. |
| 2004/0077462 A1 | 4/2004 | Brown et al. |
| 2004/0095379 A1 | 5/2004 | Chang et al. |
| 2004/0128286 A1 | 7/2004 | Yasushi et al. |
| 2004/0168107 A1 | 8/2004 | Sharp et al. |
| 2004/0181771 A1 | 9/2004 | Anonsen et al. |
| 2004/0192332 A1 | 9/2004 | Samn |
| 2004/0218472 A1 | 11/2004 | Narayanaswami et al. |
| 2004/0225966 A1 | 11/2004 | Besharat et al. |
| 2004/0246607 A1 | 12/2004 | Watson et al. |
| 2005/0041667 A1 | 2/2005 | Miller et al. |
| 2005/0075214 A1 | 4/2005 | Brown et al. |
| 2005/0079905 A1 | 4/2005 | Martens |
| 2005/0113650 A1 | 5/2005 | Pacione et al. |
| 2005/0124324 A1 | 6/2005 | Thomas et al. |
| 2005/0125744 A1 | 6/2005 | Hubbard et al. |
| 2005/0139852 A1 | 6/2005 | Chen et al. |
| 2005/0154798 A1 | 7/2005 | Nurmi |
| 2005/0156873 A1 | 7/2005 | Walter et al. |
| 2005/0172311 A1 | 8/2005 | Hjelt et al. |
| 2005/0188856 A1 | 9/2005 | Sumser et al. |
| 2005/0197063 A1 | 9/2005 | White |
| 2005/0200611 A1 | 9/2005 | Goto et al. |
| 2005/0202846 A1 | 9/2005 | Glass et al. |
| 2005/0216867 A1 | 9/2005 | Marvit et al. |
| 2005/0228735 A1 | 10/2005 | Duquette |
| 2005/0272564 A1 | 12/2005 | Pyles et al. |
| 2005/0278757 A1 | 12/2005 | Grossman et al. |
| 2006/0000900 A1 | 1/2006 | Fernandes et al. |
| 2006/0010098 A1 | 1/2006 | Goodnow et al. |
| 2006/0019649 A1 | 1/2006 | Feinleib et al. |
| 2006/0020174 A1 | 1/2006 | Matsumura et al. |
| 2006/0025923 A1 | 2/2006 | Dotan et al. |
| 2006/0026521 A1 | 2/2006 | Hotelling et al. |
| 2006/0035632 A1 | 2/2006 | Sorvari et al. |
| 2006/0052727 A1 | 3/2006 | Palestrant |
| 2006/0055662 A1 | 3/2006 | Rimas-Ribikauskas et al. |
| 2006/0055700 A1 | 3/2006 | Niles et al. |
| 2006/0069604 A1 | 3/2006 | Leukart et al. |
| 2006/0085763 A1 | 4/2006 | Leavitt et al. |
| 2006/0085765 A1 | 4/2006 | Peterson et al. |
| 2006/0092770 A1 | 5/2006 | Demas |
| 2006/0098109 A1 | 5/2006 | Ooki |
| 2006/0098634 A1 | 5/2006 | Umemoto et al. |
| 2006/0106741 A1 | 5/2006 | Janarthanan |
| 2006/0122748 A1 | 6/2006 | Nou |
| 2006/0125799 A1 | 6/2006 | Hillis et al. |
| 2006/0132456 A1 | 6/2006 | Anson |
| 2006/0155578 A1 | 7/2006 | Eisenberger et al. |
| 2006/0173749 A1 | 8/2006 | Ward et al. |
| 2006/0184800 A1 | 8/2006 | Rosenberg |
| 2006/0190833 A1 | 8/2006 | Sangiovanni et al. |
| 2006/0197753 A1 | 9/2006 | Hotelling |
| 2006/0214935 A1 | 9/2006 | Boyd et al. |

(56) References Cited

U.S. PATENT DOCUMENTS

| | | |
|---|---|---|
| 2006/0217104 A1 | 9/2006 | Cho |
| 2006/0250524 A1 | 11/2006 | Roche |
| 2006/0271605 A1 | 11/2006 | Petruzzo |
| 2007/0006096 A1 | 1/2007 | Kim et al. |
| 2007/0021269 A1 | 1/2007 | Shum |
| 2007/0030256 A1 | 2/2007 | Akaike et al. |
| 2007/0032733 A1 | 2/2007 | Burton |
| 2007/0033069 A1 | 2/2007 | Rao et al. |
| 2007/0033254 A1 | 2/2007 | Alhusseini et al. |
| 2007/0052712 A1 | 3/2007 | Saito et al. |
| 2007/0056727 A1 | 3/2007 | Newman |
| 2007/0067272 A1 | 3/2007 | Flynt et al. |
| 2007/0067733 A1 | 3/2007 | Moore et al. |
| 2007/0067738 A1 | 3/2007 | Flynt et al. |
| 2007/0071256 A1 | 3/2007 | Ito |
| 2007/0082707 A1 | 4/2007 | Flynt et al. |
| 2007/0094330 A1 | 4/2007 | Russell |
| 2007/0096765 A1 | 5/2007 | Kagan |
| 2007/0097113 A1 | 5/2007 | Lee et al. |
| 2007/0101279 A1 | 5/2007 | Chaudhri et al. |
| 2007/0113726 A1 | 5/2007 | Oliver et al. |
| 2007/0135043 A1 | 6/2007 | Hayes et al. |
| 2007/0136093 A1 | 6/2007 | Rankin et al. |
| 2007/0143433 A1 | 6/2007 | Daigle |
| 2007/0143495 A1 | 6/2007 | Porat |
| 2007/0150810 A1 | 6/2007 | Katz et al. |
| 2007/0150830 A1 | 6/2007 | Ording et al. |
| 2007/0150842 A1 | 6/2007 | Chaudhri et al. |
| 2007/0152980 A1 | 7/2007 | Kocienda et al. |
| 2007/0152984 A1 | 7/2007 | Ording et al. |
| 2007/0157089 A1 | 7/2007 | Van Os et al. |
| 2007/0162872 A1 | 7/2007 | Hong et al. |
| 2007/0169614 A1 | 7/2007 | Sasaki et al. |
| 2007/0177804 A1 | 8/2007 | Elias et al. |
| 2007/0188409 A1 | 8/2007 | Repetto et al. |
| 2007/0194110 A1 | 8/2007 | Esplin et al. |
| 2007/0194113 A1 | 8/2007 | Esplin et al. |
| 2007/0213955 A1 | 9/2007 | Ishida et al. |
| 2007/0239754 A1 | 10/2007 | Schnitman |
| 2007/0249949 A1 | 10/2007 | Hadley |
| 2007/0254712 A1 | 11/2007 | Chitti |
| 2007/0261537 A1 | 11/2007 | Eronen et al. |
| 2007/0271065 A1 | 11/2007 | Gupta et al. |
| 2007/0271340 A1 | 11/2007 | Goodman et al. |
| 2007/0279190 A1 | 12/2007 | Lugt et al. |
| 2007/0287477 A1 | 12/2007 | Tran |
| 2008/0016443 A1 | 1/2008 | Hiroshima et al. |
| 2008/0020803 A1 | 1/2008 | Rios et al. |
| 2008/0027673 A1 | 1/2008 | Trumm |
| 2008/0033779 A1 | 2/2008 | Coffman et al. |
| 2008/0040265 A1 | 2/2008 | Rackley, III et al. |
| 2008/0046839 A1 | 2/2008 | Mehra et al. |
| 2008/0051919 A1 | 2/2008 | Sakai et al. |
| 2008/0052643 A1 | 2/2008 | Ike et al. |
| 2008/0052945 A1 | 3/2008 | Matas et al. |
| 2008/0057926 A1 | 3/2008 | Forstall et al. |
| 2008/0058626 A1 | 3/2008 | Miyata et al. |
| 2008/0062141 A1 | 3/2008 | Chandhri |
| 2008/0076637 A1 | 3/2008 | Gilley et al. |
| 2008/0077936 A1 | 3/2008 | Goel et al. |
| 2008/0082145 A1 | 4/2008 | Skwarek et al. |
| 2008/0086318 A1 | 4/2008 | Gilley et al. |
| 2008/0096726 A1 | 4/2008 | Riley et al. |
| 2008/0100693 A1 | 5/2008 | Jobs et al. |
| 2008/0122796 A1 | 5/2008 | Jobs et al. |
| 2008/0127268 A1 | 5/2008 | Bergeron et al. |
| 2008/0141135 A1 | 6/2008 | Mason et al. |
| 2008/0150731 A1 | 6/2008 | Laukkanen et al. |
| 2008/0155428 A1 | 6/2008 | Lee |
| 2008/0161707 A1 | 7/2008 | Farringdon et al. |
| 2008/0168396 A1 | 7/2008 | Matas et al. |
| 2008/0180406 A1 | 7/2008 | Han et al. |
| 2008/0183909 A1 | 7/2008 | Lim et al. |
| 2008/0186808 A1 | 8/2008 | Lee |
| 2008/0192021 A1 | 8/2008 | Lim et al. |
| 2008/0194323 A1 | 8/2008 | Merkli et al. |
| 2008/0200312 A1 | 8/2008 | Tagliabue |
| 2008/0225013 A1 | 9/2008 | Muylkens et al. |
| 2008/0229226 A1 | 9/2008 | Rowbottom et al. |
| 2008/0246778 A1 | 10/2008 | Ham et al. |
| 2008/0247519 A1 | 10/2008 | Abella et al. |
| 2008/0254767 A1 | 10/2008 | Jin |
| 2008/0259829 A1 | 10/2008 | Rosenblatt |
| 2008/0300110 A1 | 12/2008 | Smith et al. |
| 2009/0005080 A1 | 1/2009 | Forstall et al. |
| 2009/0012988 A1 | 1/2009 | Brown |
| 2009/0027495 A1 | 1/2009 | Oskin et al. |
| 2009/0037326 A1 | 2/2009 | Chitti et al. |
| 2009/0051649 A1 | 2/2009 | Rondel |
| 2009/0057396 A1 | 3/2009 | Barbour et al. |
| 2009/0060170 A1 | 3/2009 | Coughlan et al. |
| 2009/0064055 A1 | 3/2009 | Chaudhri et al. |
| 2009/0070675 A1 | 3/2009 | Li |
| 2009/0073194 A1 | 3/2009 | Ording |
| 2009/0100342 A1 | 4/2009 | Jakobson |
| 2009/0102805 A1 | 4/2009 | Meijer et al. |
| 2009/0113315 A1 | 4/2009 | Fisher et al. |
| 2009/0118100 A1 | 5/2009 | Oliver et al. |
| 2009/0164567 A1 | 6/2009 | Hara |
| 2009/0164923 A1 | 6/2009 | Ovi |
| 2009/0170532 A1 | 7/2009 | Lee et al. |
| 2009/0172549 A1 | 7/2009 | Davidson |
| 2009/0177538 A1 | 7/2009 | Brewer et al. |
| 2009/0178007 A1 | 7/2009 | Matas et al. |
| 2009/0189915 A1 | 7/2009 | Mercer et al. |
| 2009/0192823 A1 | 7/2009 | Hawkins et al. |
| 2009/0195497 A1 | 8/2009 | Fitzgerald et al. |
| 2009/0199130 A1 | 8/2009 | Tsern et al. |
| 2009/0205041 A1 | 8/2009 | Michalske |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0231356 A1 | 9/2009 | Barnes et al. |
| 2009/0231960 A1 | 9/2009 | Hutcheson |
| 2009/0233771 A1 | 9/2009 | Quatrochi et al. |
| 2009/0239587 A1 | 9/2009 | Negron et al. |
| 2009/0244015 A1 | 10/2009 | Sengupta et al. |
| 2009/0249247 A1 | 10/2009 | Tseng et al. |
| 2009/0254624 A1 | 10/2009 | Baudin et al. |
| 2009/0256780 A1 | 10/2009 | Small et al. |
| 2009/0259958 A1 | 10/2009 | Ban |
| 2009/0262088 A1 | 10/2009 | Moll-Carrillo et al. |
| 2009/0276463 A1 | 11/2009 | Miller |
| 2009/0287103 A1 | 11/2009 | Pillai |
| 2009/0295753 A1 | 12/2009 | King et al. |
| 2009/0305732 A1 | 12/2009 | Marcellino et al. |
| 2009/0311993 A1 | 12/2009 | Horodezky |
| 2009/0313579 A1 | 12/2009 | Poulson |
| 2009/0319243 A1 | 12/2009 | Suarez-Rivera et al. |
| 2009/0319467 A1 | 12/2009 | Berg et al. |
| 2009/0327886 A1 | 12/2009 | Whytock et al. |
| 2010/0017748 A1 | 1/2010 | Taylor et al. |
| 2010/0019990 A1 | 1/2010 | Lee |
| 2010/0026640 A1 | 2/2010 | Kim et al. |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0054519 A1 | 3/2010 | Mulvey et al. |
| 2010/0060586 A1 | 3/2010 | Pisula et al. |
| 2010/0062818 A1 | 3/2010 | Haughay et al. |
| 2010/0062905 A1 | 3/2010 | Rottler et al. |
| 2010/0064255 A1 | 3/2010 | Rottler et al. |
| 2010/0075287 A1 | 3/2010 | Dohrmann |
| 2010/0076331 A1 | 3/2010 | Chan et al. |
| 2010/0079291 A1 | 4/2010 | Kroll et al. |
| 2010/0082481 A1 | 4/2010 | Lin et al. |
| 2010/0085203 A1 | 4/2010 | Kahn et al. |
| 2010/0095240 A1 | 4/2010 | Shiplacoff et al. |
| 2010/0110082 A1 | 5/2010 | Myrick et al. |
| 2010/0121700 A1 | 5/2010 | Wigder et al. |
| 2010/0123724 A1 | 5/2010 | Moore et al. |
| 2010/0131190 A1 | 5/2010 | Terauchi et al. |
| 2010/0138764 A1 | 6/2010 | Hatambeiki et al. |
| 2010/0141606 A1 | 6/2010 | Bae et al. |

(56) References Cited

U.S. PATENT DOCUMENTS

| | | |
|---|---|---|
| 2010/0145209 A1 | 6/2010 | Lee et al. |
| 2010/0151908 A1 | 6/2010 | Skarby et al. |
| 2010/0151918 A1 | 6/2010 | Annambhotla et al. |
| 2010/0156807 A1 | 6/2010 | Stallings et al. |
| 2010/0156833 A1 | 6/2010 | Kim et al. |
| 2010/0157742 A1 | 6/2010 | Relyea et al. |
| 2010/0178873 A1 | 7/2010 | Lee et al. |
| 2010/0179832 A1 | 7/2010 | Van et al. |
| 2010/0185446 A1 | 7/2010 | Homma et al. |
| 2010/0190468 A1 | 7/2010 | Scott et al. |
| 2010/0194692 A1 | 8/2010 | Orr et al. |
| 2010/0198453 A1 | 8/2010 | Dorogusker et al. |
| 2010/0202368 A1 | 8/2010 | Hans |
| 2010/0205563 A1 | 8/2010 | Haapsaari et al. |
| 2010/0211685 A1 | 8/2010 | Mcdowall et al. |
| 2010/0223145 A1 | 9/2010 | Dragt |
| 2010/0223563 A1 | 9/2010 | Green |
| 2010/0225962 A1 | 9/2010 | Okigami et al. |
| 2010/0226213 A1 | 9/2010 | Drugge |
| 2010/0235726 A1 | 9/2010 | Ording et al. |
| 2010/0243516 A1 | 9/2010 | Martin et al. |
| 2010/0251176 A1 | 9/2010 | Fong et al. |
| 2010/0271312 A1 | 10/2010 | Alameh et al. |
| 2010/0281374 A1 | 11/2010 | Schulz et al. |
| 2010/0292600 A1 | 11/2010 | Dibenedetto et al. |
| 2010/0295789 A1 | 11/2010 | Shin et al. |
| 2010/0295795 A1 | 11/2010 | Wilairat |
| 2010/0298899 A1 | 11/2010 | Donnelly et al. |
| 2010/0299436 A1 | 11/2010 | Khalid et al. |
| 2010/0299601 A1 | 11/2010 | Kaplan et al. |
| 2010/0305965 A1 | 12/2010 | Benjamin et al. |
| 2010/0331145 A1 | 12/2010 | Lakovic et al. |
| 2011/0003587 A1 | 1/2011 | Belz et al. |
| 2011/0003665 A1 | 1/2011 | Burton et al. |
| 2011/0004835 A1 | 1/2011 | Yanchar et al. |
| 2011/0010195 A1 | 1/2011 | Cohn |
| 2011/0016120 A1 | 1/2011 | Haughay et al. |
| 2011/0016425 A1 | 1/2011 | Homburg et al. |
| 2011/0018695 A1 | 1/2011 | Bells et al. |
| 2011/0029750 A1 | 2/2011 | Jang et al. |
| 2011/0029870 A1 | 2/2011 | May et al. |
| 2011/0032105 A1 | 2/2011 | Hoffman et al. |
| 2011/0040657 A1 | 2/2011 | Roswell |
| 2011/0047014 A1 | 2/2011 | De |
| 2011/0059769 A1 | 3/2011 | Brunolli |
| 2011/0061010 A1 | 3/2011 | Wasko |
| 2011/0066051 A1 | 3/2011 | Moon et al. |
| 2011/0071818 A1 | 3/2011 | Jiang |
| 2011/0071869 A1 | 3/2011 | Obrien et al. |
| 2011/0074699 A1 | 3/2011 | Marr et al. |
| 2011/0078025 A1 | 3/2011 | Shrivastav |
| 2011/0078622 A1 | 3/2011 | Missig et al. |
| 2011/0078624 A1 | 3/2011 | Missig et al. |
| 2011/0080411 A1 | 4/2011 | Wikkerink et al. |
| 2011/0081923 A1 | 4/2011 | Forutanpour et al. |
| 2011/0083111 A1 | 4/2011 | Forutanpour et al. |
| 2011/0088086 A1 | 4/2011 | Swink et al. |
| 2011/0098928 A1* | 4/2011 | Hoffman ............ A63B 71/0622 702/5 |
| 2011/0106553 A1 | 5/2011 | Tanaka et al. |
| 2011/0106954 A1 | 5/2011 | Chatterjee et al. |
| 2011/0112418 A1 | 5/2011 | Feild et al. |
| 2011/0125041 A1 | 5/2011 | Fischell et al. |
| 2011/0130168 A1 | 6/2011 | Vendrow et al. |
| 2011/0137678 A1 | 6/2011 | Williams |
| 2011/0137836 A1 | 6/2011 | Kuriyama et al. |
| 2011/0138329 A1 | 6/2011 | Wells et al. |
| 2011/0151415 A1 | 6/2011 | Darling |
| 2011/0157046 A1 | 6/2011 | Lee et al. |
| 2011/0159469 A1 | 6/2011 | Hwang et al. |
| 2011/0159959 A1 | 6/2011 | Mallinson et al. |
| 2011/0167369 A1 | 7/2011 | Van Os |
| 2011/0167382 A1 | 7/2011 | Van Os |
| 2011/0175832 A1 | 7/2011 | Miyazawa et al. |
| 2011/0177845 A1 | 7/2011 | Fasold |
| 2011/0181521 A1 | 7/2011 | Reid et al. |
| 2011/0183650 A1 | 7/2011 | Mckee |
| 2011/0193878 A1 | 8/2011 | Seo et al. |
| 2011/0197165 A1 | 8/2011 | Filippov et al. |
| 2011/0201911 A1 | 8/2011 | Johnson et al. |
| 2011/0202861 A1 | 8/2011 | Fritzley et al. |
| 2011/0202883 A1 | 8/2011 | Oh et al. |
| 2011/0205182 A1 | 8/2011 | Miyazawa et al. |
| 2011/0205851 A1 | 8/2011 | Harris |
| 2011/0213276 A1 | 9/2011 | Sarussi et al. |
| 2011/0218765 A1 | 9/2011 | Rogers |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0234152 A1 | 9/2011 | Frossen et al. |
| 2011/0234633 A1 | 9/2011 | Ogura et al. |
| 2011/0246509 A1 | 10/2011 | Migita et al. |
| 2011/0251892 A1 | 10/2011 | Laracey |
| 2011/0252146 A1 | 10/2011 | Santamaria et al. |
| 2011/0252349 A1 | 10/2011 | Chaudhri |
| 2011/0261079 A1 | 10/2011 | Ingrassia et al. |
| 2011/0265002 A1 | 10/2011 | Hong et al. |
| 2011/0271223 A1 | 11/2011 | Cruz moreno et al. |
| 2011/0275940 A1 | 11/2011 | Nims et al. |
| 2011/0279852 A1 | 11/2011 | Oda et al. |
| 2011/0296324 A1 | 12/2011 | Goossens et al. |
| 2011/0302518 A1 | 12/2011 | Zhang |
| 2011/0304685 A1 | 12/2011 | Khedouri et al. |
| 2011/0306389 A1 | 12/2011 | Nagayama |
| 2011/0306393 A1 | 12/2011 | Goldman et al. |
| 2011/0306421 A1 | 12/2011 | Nishimoto et al. |
| 2011/0307821 A1 | 12/2011 | Martens |
| 2011/0316858 A1 | 12/2011 | Shen et al. |
| 2012/0001922 A1 | 1/2012 | Escher et al. |
| 2012/0015778 A1 | 1/2012 | Lee et al. |
| 2012/0015779 A1 | 1/2012 | Powch et al. |
| 2012/0019400 A1 | 1/2012 | Patel et al. |
| 2012/0019513 A1 | 1/2012 | Fong et al. |
| 2012/0019610 A1 | 1/2012 | Hornyak et al. |
| 2012/0026110 A1 | 2/2012 | Yamano |
| 2012/0028707 A1 | 2/2012 | Raitt et al. |
| 2012/0030623 A1 | 2/2012 | Hoellwarth |
| 2012/0034897 A1 | 2/2012 | Kreitzer et al. |
| 2012/0035924 A1 | 2/2012 | Jitkoff et al. |
| 2012/0036029 A1 | 2/2012 | Esplin et al. |
| 2012/0036460 A1 | 2/2012 | Cieplinski et al. |
| 2012/0040719 A1 | 2/2012 | Lee et al. |
| 2012/0041767 A1 | 2/2012 | Hoffman et al. |
| 2012/0042039 A1 | 2/2012 | Mark |
| 2012/0044062 A1 | 2/2012 | Jersa et al. |
| 2012/0047447 A1 | 2/2012 | Haq |
| 2012/0059664 A1 | 3/2012 | Georgiev et al. |
| 2012/0059787 A1 | 3/2012 | Brown et al. |
| 2012/0060092 A1 | 3/2012 | Hill et al. |
| 2012/0066628 A1 | 3/2012 | Ens et al. |
| 2012/0066629 A1 | 3/2012 | Lee et al. |
| 2012/0071208 A1 | 3/2012 | Lee et al. |
| 2012/0071770 A1 | 3/2012 | Grey et al. |
| 2012/0079122 A1 | 3/2012 | Brown et al. |
| 2012/0083258 A1 | 4/2012 | Rabii |
| 2012/0084210 A1 | 4/2012 | Farahmand |
| 2012/0084729 A1 | 4/2012 | Lin |
| 2012/0092383 A1 | 4/2012 | Hysek et al. |
| 2012/0101887 A1 | 4/2012 | Harvey et al. |
| 2012/0102399 A1 | 4/2012 | Nicholson |
| 2012/0102434 A1 | 4/2012 | Zerhusen et al. |
| 2012/0105225 A1 | 5/2012 | Valtonen |
| 2012/0105358 A1 | 5/2012 | Momeyer et al. |
| 2012/0113008 A1 | 5/2012 | Makinen et al. |
| 2012/0116550 A1 | 5/2012 | Hoffman et al. |
| 2012/0116669 A1 | 5/2012 | Lee et al. |
| 2012/0117507 A1 | 5/2012 | Tseng et al. |
| 2012/0124499 A1 | 5/2012 | Tsai |
| 2012/0131441 A1 | 5/2012 | Jitkoff et al. |
| 2012/0136780 A1 | 5/2012 | El-awady et al. |
| 2012/0144306 A1 | 6/2012 | Moody et al. |
| 2012/0154293 A1 | 6/2012 | Hinckley et al. |
| 2012/0159380 A1 | 6/2012 | Kocienda et al. |
| 2012/0167008 A1 | 6/2012 | Zaman et al. |

(56) References Cited

U.S. PATENT DOCUMENTS

| | | |
|---|---|---|
| 2012/0179319 A1 | 7/2012 | Gilman et al. |
| 2012/0191603 A1 | 7/2012 | Nuzzi |
| 2012/0192113 A1 | 7/2012 | Higuchi |
| 2012/0197523 A1 | 8/2012 | Kirsch et al. |
| 2012/0204123 A1 | 8/2012 | Bauer et al. |
| 2012/0209829 A1 | 8/2012 | Thomas et al. |
| 2012/0214458 A1 | 8/2012 | Levien et al. |
| 2012/0218177 A1 | 8/2012 | Pang et al. |
| 2012/0218201 A1 | 8/2012 | Tamas et al. |
| 2012/0223935 A1 | 9/2012 | Renwick |
| 2012/0232414 A1 | 9/2012 | Mollicone et al. |
| 2012/0253485 A1 | 10/2012 | Weast et al. |
| 2012/0254804 A1 | 10/2012 | Sheha et al. |
| 2012/0258684 A1 | 10/2012 | Franz et al. |
| 2012/0271742 A1 | 10/2012 | Solomon |
| 2012/0274508 A1 | 11/2012 | Brown et al. |
| 2012/0283855 A1 | 11/2012 | Hoffman et al. |
| 2012/0290109 A1 | 11/2012 | Engelberg et al. |
| 2012/0302840 A1 | 11/2012 | Kubo |
| 2012/0303268 A1 | 11/2012 | Su et al. |
| 2012/0304084 A1 | 11/2012 | Kim et al. |
| 2012/0310674 A1 | 12/2012 | Faulkner et al. |
| 2012/0310760 A1 | 12/2012 | Phillips et al. |
| 2012/0317167 A1 | 12/2012 | Rahman et al. |
| 2012/0322508 A1 | 12/2012 | Forstall et al. |
| 2012/0324357 A1 | 12/2012 | Viegers et al. |
| 2012/0324390 A1 | 12/2012 | Tao |
| 2012/0326873 A1 | 12/2012 | Utter, II |
| 2013/0013327 A1 | 1/2013 | Horseman |
| 2013/0014019 A1 | 1/2013 | Kim et al. |
| 2013/0017846 A1 | 1/2013 | Schoppe |
| 2013/0019175 A1 | 1/2013 | Kotler et al. |
| 2013/0024781 A1 | 1/2013 | Douillet et al. |
| 2013/0024802 A1 | 1/2013 | Zeng |
| 2013/0026293 A1 | 1/2013 | Schneider et al. |
| 2013/0027341 A1 | 1/2013 | Mastandrea |
| 2013/0031490 A1 | 1/2013 | Joo et al. |
| 2013/0044072 A1 | 2/2013 | Kobayashi et al. |
| 2013/0046397 A1 | 2/2013 | Fadell et al. |
| 2013/0047034 A1 | 2/2013 | Salomon et al. |
| 2013/0050263 A1 | 2/2013 | Khoe et al. |
| 2013/0054150 A1 | 2/2013 | Sacks et al. |
| 2013/0054634 A1 | 2/2013 | Chakraborty et al. |
| 2013/0054720 A1 | 2/2013 | Kang et al. |
| 2013/0055147 A1 | 2/2013 | Vasudev et al. |
| 2013/0057566 A1 | 3/2013 | Kriese et al. |
| 2013/0063364 A1 | 3/2013 | Moore |
| 2013/0063383 A1 | 3/2013 | Anderssonreimer et al. |
| 2013/0067050 A1 | 3/2013 | Kotteri et al. |
| 2013/0067391 A1 | 3/2013 | Pittappilly et al. |
| 2013/0069893 A1 | 3/2013 | Brinda et al. |
| 2013/0076757 A1 | 3/2013 | Pritting |
| 2013/0081083 A1 | 3/2013 | Yu et al. |
| 2013/0082965 A1 | 4/2013 | Wada et al. |
| 2013/0093715 A1 | 4/2013 | Marsden et al. |
| 2013/0103814 A1 | 4/2013 | Carrasco et al. |
| 2013/0106603 A1 | 5/2013 | Weast et al. |
| 2013/0106684 A1 | 5/2013 | Weast et al. |
| 2013/0107674 A1 | 5/2013 | Gossweiler et al. |
| 2013/0110264 A1 | 5/2013 | Weast et al. |
| 2013/0111579 A1 | 5/2013 | Newman et al. |
| 2013/0115583 A1 | 5/2013 | Gordon et al. |
| 2013/0116967 A1 | 5/2013 | Akcasu et al. |
| 2013/0117383 A1 | 5/2013 | Hymel |
| 2013/0117696 A1 | 5/2013 | Robertson et al. |
| 2013/0117703 A1 | 5/2013 | Jang et al. |
| 2013/0120106 A1 | 5/2013 | Cauwels et al. |
| 2013/0132028 A1 | 5/2013 | Crankson et al. |
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0141365 A1 | 6/2013 | Lynn et al. |
| 2013/0141371 A1 | 6/2013 | Hallford et al. |
| 2013/0143512 A1 | 6/2013 | Hernandez et al. |
| 2013/0151285 A1 | 6/2013 | Mclaren et al. |
| 2013/0158367 A1 | 6/2013 | Pacione et al. |
| 2013/0169870 A1 | 7/2013 | Lee et al. |
| 2013/0173699 A1 | 7/2013 | Parks et al. |
| 2013/0174044 A1 | 7/2013 | Hill |
| 2013/0179784 A1 | 7/2013 | Bang |
| 2013/0184613 A1 | 7/2013 | Homsi et al. |
| 2013/0187923 A1 | 7/2013 | Yoshimoto et al. |
| 2013/0188322 A1 | 7/2013 | Lowe |
| 2013/0190083 A1 | 7/2013 | Toy et al. |
| 2013/0191785 A1 | 7/2013 | Rampson et al. |
| 2013/0197679 A1 | 8/2013 | Balakrishnan et al. |
| 2013/0198672 A1 | 8/2013 | Yoon et al. |
| 2013/0201098 A1 | 8/2013 | Schilit et al. |
| 2013/0203475 A1 | 8/2013 | Kil et al. |
| 2013/0205194 A1 | 8/2013 | Decker et al. |
| 2013/0205210 A1 | 8/2013 | Jeon et al. |
| 2013/0215044 A1 | 8/2013 | Ahn et al. |
| 2013/0215119 A1 | 8/2013 | Vanhoecke |
| 2013/0217979 A1 | 8/2013 | Blackadar et al. |
| 2013/0222270 A1 | 8/2013 | Winkler et al. |
| 2013/0225118 A1 | 8/2013 | Jang et al. |
| 2013/0227412 A1 | 8/2013 | Ornstein et al. |
| 2013/0231575 A1 | 9/2013 | Erkkila et al. |
| 2013/0231711 A1 | 9/2013 | Kaib |
| 2013/0233097 A1 | 9/2013 | Hayner et al. |
| 2013/0234924 A1 | 9/2013 | Janefalkar et al. |
| 2013/0234929 A1 | 9/2013 | Libin |
| 2013/0234969 A1 | 9/2013 | Yeh et al. |
| 2013/0243924 A1 | 9/2013 | Bhandari et al. |
| 2013/0246202 A1 | 9/2013 | Tobin |
| 2013/0253980 A1 | 9/2013 | Blom et al. |
| 2013/0254685 A1 | 9/2013 | Batraski et al. |
| 2013/0254705 A1 | 9/2013 | Mooring et al. |
| 2013/0260896 A1 | 10/2013 | Miura et al. |
| 2013/0262155 A1 | 10/2013 | Hinkamp |
| 2013/0262298 A1 | 10/2013 | Morley |
| 2013/0263043 A1 | 10/2013 | Sarbin |
| 2013/0263719 A1 | 10/2013 | Watterson et al. |
| 2013/0275875 A1 | 10/2013 | Gruber et al. |
| 2013/0290013 A1 | 10/2013 | Forrester |
| 2013/0295872 A1 | 11/2013 | Guday et al. |
| 2013/0295961 A1 | 11/2013 | Lehtiniemi et al. |
| 2013/0304276 A1 | 11/2013 | Flies |
| 2013/0318158 A1 | 11/2013 | Teng et al. |
| 2013/0320080 A1 | 12/2013 | Olson et al. |
| 2013/0322665 A1 | 12/2013 | Bennett et al. |
| 2013/0325358 A1 | 12/2013 | Oshima et al. |
| 2013/0325394 A1 | 12/2013 | Yuen et al. |
| 2013/0325396 A1 | 12/2013 | Yuen et al. |
| 2013/0326418 A1 | 12/2013 | Utsuki et al. |
| 2013/0330694 A1 | 12/2013 | Watterson |
| 2013/0331130 A1 | 12/2013 | Lee |
| 2013/0332113 A1 | 12/2013 | Piemonte et al. |
| 2013/0332286 A1 | 12/2013 | Medelius et al. |
| 2013/0332856 A1 | 12/2013 | Sanders et al. |
| 2013/0344905 A1 | 12/2013 | Kim et al. |
| 2013/0345971 A1 | 12/2013 | Stamm et al. |
| 2013/0345975 A1 | 12/2013 | Vulcano et al. |
| 2013/0345978 A1 | 12/2013 | Lush et al. |
| 2013/0346408 A1 | 12/2013 | Duarte et al. |
| 2014/0011481 A1 | 1/2014 | Kho |
| 2014/0013414 A1 | 1/2014 | Bruck |
| 2014/0015784 A1 | 1/2014 | Oonishi |
| 2014/0019522 A1 | 1/2014 | Weng et al. |
| 2014/0022183 A1 | 1/2014 | Ayoub et al. |
| 2014/0025737 A1 | 1/2014 | Kruglick |
| 2014/0032706 A1 | 1/2014 | Kuscher et al. |
| 2014/0036639 A1 | 2/2014 | Boni et al. |
| 2014/0037107 A1 | 2/2014 | Marino et al. |
| 2014/0038781 A1 | 2/2014 | Foley et al. |
| 2014/0040120 A1 | 2/2014 | Cho et al. |
| 2014/0040831 A1 | 2/2014 | Akasaka et al. |
| 2014/0043367 A1 | 2/2014 | Sakaino et al. |
| 2014/0047525 A1 | 2/2014 | Bonhoff |
| 2014/0055388 A1 | 2/2014 | Yook et al. |
| 2014/0058860 A1 | 2/2014 | Roh et al. |
| 2014/0058935 A1 | 2/2014 | Mijares |
| 2014/0059493 A1 | 2/2014 | Kim |
| 2014/0067096 A1 | 3/2014 | Aibara |

(56) References Cited

U.S. PATENT DOCUMENTS

| | | |
|---|---|---|
| 2014/0068520 A1 | 3/2014 | Missig et al. |
| 2014/0073256 A1 | 3/2014 | Newham et al. |
| 2014/0073298 A1 | 3/2014 | Rossmann |
| 2014/0074407 A1 | 3/2014 | Hernandez-silveira et al. |
| 2014/0074570 A1 | 3/2014 | Hope et al. |
| 2014/0074717 A1 | 3/2014 | Evans |
| 2014/0075003 A1 | 3/2014 | Tanaka et al. |
| 2014/0081666 A1 | 3/2014 | Teller et al. |
| 2014/0081854 A1 | 3/2014 | Sanchez et al. |
| 2014/0082533 A1 | 3/2014 | Kelley |
| 2014/0094124 A1 | 4/2014 | Dave et al. |
| 2014/0096083 A1 | 4/2014 | Kim et al. |
| 2014/0101169 A1 | 4/2014 | Kurata et al. |
| 2014/0108998 A1 | 4/2014 | Chaudhri et al. |
| 2014/0123005 A1 | 5/2014 | Forstall et al. |
| 2014/0123043 A1 | 5/2014 | Schmidt et al. |
| 2014/0126336 A1 | 5/2014 | Goeller et al. |
| 2014/0129959 A1 | 5/2014 | Battles et al. |
| 2014/0134947 A1 | 5/2014 | Stouder-studenmund |
| 2014/0136986 A1 | 5/2014 | Martin et al. |
| 2014/0139422 A1 | 5/2014 | Mistry et al. |
| 2014/0139637 A1 | 5/2014 | Mistry et al. |
| 2014/0143145 A1 | 5/2014 | Kortina et al. |
| 2014/0143678 A1 | 5/2014 | Mistry et al. |
| 2014/0143682 A1 | 5/2014 | Druck |
| 2014/0143737 A1 | 5/2014 | Mistry et al. |
| 2014/0149198 A1 | 5/2014 | Kim et al. |
| 2014/0149878 A1 | 5/2014 | Mischari et al. |
| 2014/0157167 A1 | 6/2014 | Zhu |
| 2014/0164241 A1 | 6/2014 | Neuwirth |
| 2014/0164955 A1 | 6/2014 | Thiruvidam et al. |
| 2014/0167986 A1 | 6/2014 | Parade et al. |
| 2014/0173439 A1 | 6/2014 | Gutierrez et al. |
| 2014/0176346 A1 | 6/2014 | Brumback et al. |
| 2014/0176475 A1 | 6/2014 | Myers et al. |
| 2014/0181183 A1 | 6/2014 | Houjou et al. |
| 2014/0181205 A1 | 6/2014 | Sherrets et al. |
| 2014/0181219 A1 | 6/2014 | Wang et al. |
| 2014/0187314 A1 | 7/2014 | Perry et al. |
| 2014/0187323 A1 | 7/2014 | Perry |
| 2014/0189577 A1 | 7/2014 | Shuttleworth et al. |
| 2014/0189584 A1 | 7/2014 | Weng et al. |
| 2014/0189589 A1 | 7/2014 | Kim et al. |
| 2014/0195972 A1 | 7/2014 | Lee et al. |
| 2014/0197946 A1 | 7/2014 | Park et al. |
| 2014/0197965 A1 | 7/2014 | Park et al. |
| 2014/0200691 A1 | 7/2014 | Lee et al. |
| 2014/0208250 A1 | 7/2014 | Ording et al. |
| 2014/0218369 A1 | 8/2014 | Yuen et al. |
| 2014/0223490 A1 | 8/2014 | Pan et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0244165 A1 | 8/2014 | Bells |
| 2014/0244494 A1 | 8/2014 | Davis et al. |
| 2014/0244495 A1 | 8/2014 | Davis et al. |
| 2014/0245161 A1 | 8/2014 | Yuen et al. |
| 2014/0245177 A1 | 8/2014 | Maklouf |
| 2014/0250391 A1 | 9/2014 | Jong et al. |
| 2014/0257537 A1 | 9/2014 | Stroupe et al. |
| 2014/0258935 A1 | 9/2014 | Nishida et al. |
| 2014/0267303 A1 | 9/2014 | Larkin et al. |
| 2014/0269614 A1 | 9/2014 | Maguire et al. |
| 2014/0275852 A1 | 9/2014 | Hong et al. |
| 2014/0275854 A1 | 9/2014 | Venkatraman et al. |
| 2014/0277628 A1 | 9/2014 | Nieminen et al. |
| 2014/0277843 A1 | 9/2014 | Langlois et al. |
| 2014/0278028 A1 | 9/2014 | Nye et al. |
| 2014/0278229 A1 | 9/2014 | Hong et al. |
| 2014/0280580 A1 | 9/2014 | Langlois et al. |
| 2014/0281957 A1 | 9/2014 | Weng et al. |
| 2014/0282103 A1 | 9/2014 | Crandall |
| 2014/0282153 A1 | 9/2014 | Christiansen et al. |
| 2014/0282254 A1 | 9/2014 | Feiereisen et al. |
| 2014/0287821 A1 | 9/2014 | Barclay et al. |
| 2014/0288680 A1 | 9/2014 | Hoffman et al. |
| 2014/0289660 A1 | 9/2014 | Min |
| 2014/0293755 A1 | 10/2014 | Geiser et al. |
| 2014/0298266 A1 | 10/2014 | Lapp |
| 2014/0304635 A1 | 10/2014 | Kristinsson et al. |
| 2014/0304664 A1 | 10/2014 | Lee et al. |
| 2014/0304738 A1 | 10/2014 | Nakaoka et al. |
| 2014/0306898 A1 | 10/2014 | Cueto |
| 2014/0310598 A1 | 10/2014 | Sprague et al. |
| 2014/0310618 A1 | 10/2014 | Venkatesh |
| 2014/0310643 A1 | 10/2014 | Karmanenko et al. |
| 2014/0317543 A1 | 10/2014 | Kim |
| 2014/0325384 A1 | 10/2014 | Kobayashi |
| 2014/0325408 A1 | 10/2014 | Leppanen et al. |
| 2014/0331314 A1 | 11/2014 | Fujioka |
| 2014/0336796 A1 | 11/2014 | Agnew |
| 2014/0336931 A1 | 11/2014 | Wilkins |
| 2014/0337207 A1 | 11/2014 | Zhang et al. |
| 2014/0337450 A1* | 11/2014 | Choudhary ............ G08B 5/36 709/206 |
| 2014/0337451 A1 | 11/2014 | Choudhary et al. |
| 2014/0337791 A1 | 11/2014 | Agnetta et al. |
| 2014/0344723 A1 | 11/2014 | Malik et al. |
| 2014/0344951 A1 | 11/2014 | Brewer |
| 2014/0347289 A1 | 11/2014 | Suh et al. |
| 2014/0359637 A1 | 12/2014 | Yan |
| 2014/0362056 A1 | 12/2014 | Zambetti et al. |
| 2014/0365126 A1 | 12/2014 | Vulcano et al. |
| 2014/0371887 A1 | 12/2014 | Hoffman et al. |
| 2014/0380229 A1 | 12/2014 | Volodin et al. |
| 2015/0004578 A1 | 1/2015 | Gilley et al. |
| 2015/0006376 A1 | 1/2015 | Nuthulapati et al. |
| 2015/0012425 A1 | 1/2015 | Mathew |
| 2015/0018632 A1 | 1/2015 | Khair |
| 2015/0019418 A1 | 1/2015 | Hotard et al. |
| 2015/0022438 A1 | 1/2015 | Hong |
| 2015/0026615 A1 | 1/2015 | Choi et al. |
| 2015/0033136 A1 | 1/2015 | Sasaki et al. |
| 2015/0039494 A1 | 2/2015 | Sinton et al. |
| 2015/0046814 A1 | 2/2015 | Haughay et al. |
| 2015/0052461 A1 | 2/2015 | Sullivan et al. |
| 2015/0055197 A1 | 2/2015 | Romanoff et al. |
| 2015/0057943 A1 | 2/2015 | Self et al. |
| 2015/0065302 A1 | 3/2015 | Ou et al. |
| 2015/0066758 A1 | 3/2015 | Denardis et al. |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0083970 A1 | 3/2015 | Koh et al. |
| 2015/0098309 A1 | 4/2015 | Adams et al. |
| 2015/0100245 A1 | 4/2015 | Huang et al. |
| 2015/0100537 A1 | 4/2015 | Grieves et al. |
| 2015/0100621 A1 | 4/2015 | Pan |
| 2015/0100982 A1 | 4/2015 | Sirpal et al. |
| 2015/0106025 A1 | 4/2015 | Keller et al. |
| 2015/0112700 A1 | 4/2015 | Sublett et al. |
| 2015/0113468 A1 | 4/2015 | Clark |
| 2015/0117162 A1 | 4/2015 | Tsai |
| 2015/0118657 A1 | 4/2015 | Shrake et al. |
| 2015/0121405 A1 | 4/2015 | Ekselius et al. |
| 2015/0130830 A1 | 5/2015 | Nagasaki et al. |
| 2015/0131121 A1 | 5/2015 | Kang |
| 2015/0142689 A1 | 5/2015 | Squires |
| 2015/0153943 A1 | 6/2015 | Wang |
| 2015/0153952 A1 | 6/2015 | Grossman et al. |
| 2015/0160806 A1 | 6/2015 | Fey et al. |
| 2015/0160856 A1 | 6/2015 | Jang et al. |
| 2015/0180746 A1 | 6/2015 | Day et al. |
| 2015/0180980 A1 | 6/2015 | Welinder et al. |
| 2015/0181314 A1 | 6/2015 | Swanson |
| 2015/0185703 A1 | 7/2015 | Tanaka |
| 2015/0185967 A1 | 7/2015 | Ly et al. |
| 2015/0185995 A1 | 7/2015 | Shoemaker et al. |
| 2015/0193805 A1 | 7/2015 | Filipiak |
| 2015/0194050 A1 | 7/2015 | Lee |
| 2015/0195179 A1 | 7/2015 | Skare et al. |

(56) References Cited

U.S. PATENT DOCUMENTS

| | | |
|---|---|---|
| 2015/0196804 A1 | 7/2015 | Koduri et al. |
| 2015/0199494 A1 | 7/2015 | Koduri et al. |
| 2015/0205492 A1 | 7/2015 | Nobil |
| 2015/0205509 A1 | 7/2015 | Scriven et al. |
| 2015/0205930 A1 | 7/2015 | Shaanan et al. |
| 2015/0217163 A1 | 8/2015 | Amis et al. |
| 2015/0220883 A1 | 8/2015 | B'far et al. |
| 2015/0248235 A1 | 9/2015 | Offenberg et al. |
| 2015/0254041 A1 | 9/2015 | Hoshihara et al. |
| 2015/0256491 A1 | 9/2015 | Eatough et al. |
| 2015/0269848 A1 | 9/2015 | Yuen et al. |
| 2015/0271120 A1 | 9/2015 | Langholz |
| 2015/0286372 A1 | 10/2015 | Swindell et al. |
| 2015/0286391 A1 | 10/2015 | Jacobs et al. |
| 2015/0293592 A1 | 10/2015 | Cheong et al. |
| 2015/0295901 A1 | 10/2015 | Woodward et al. |
| 2015/0297134 A1 | 10/2015 | Albert et al. |
| 2015/0301506 A1 | 10/2015 | Koumaiha |
| 2015/0301608 A1 | 10/2015 | Nagaraju et al. |
| 2015/0301691 A1 | 10/2015 | Qin |
| 2015/0312175 A1 | 10/2015 | Langholz |
| 2015/0324751 A1* | 11/2015 | Orenstein ............... G16H 40/67 702/3 |
| 2015/0331589 A1 | 11/2015 | Kawakita |
| 2015/0334546 A1 | 11/2015 | Diamond |
| 2015/0341695 A1 | 11/2015 | Pattan |
| 2015/0347711 A1 | 12/2015 | Soli et al. |
| 2015/0348009 A1 | 12/2015 | Brown et al. |
| 2015/0350141 A1 | 12/2015 | Yang et al. |
| 2015/0350861 A1 | 12/2015 | Soli et al. |
| 2015/0355804 A1 | 12/2015 | Nguyen et al. |
| 2015/0370469 A1 | 12/2015 | Leong et al. |
| 2015/0374310 A1 | 12/2015 | Lee |
| 2015/0379476 A1 | 12/2015 | Chaudhri et al. |
| 2016/0004393 A1 | 1/2016 | Faaborg et al. |
| 2016/0014266 A1 | 1/2016 | Bhatt |
| 2016/0015275 A1 | 1/2016 | Samadani et al. |
| 2016/0019360 A1 | 1/2016 | Pahwa et al. |
| 2016/0021168 A1 | 1/2016 | Chaudhri et al. |
| 2016/0022202 A1 | 1/2016 | Peterson et al. |
| 2016/0027282 A1 | 1/2016 | Lee |
| 2016/0027420 A1 | 1/2016 | Eronen |
| 2016/0028869 A1 | 1/2016 | Bhatt |
| 2016/0034133 A1 | 2/2016 | Wilson et al. |
| 2016/0034148 A1 | 2/2016 | Christopher et al. |
| 2016/0034152 A1 | 2/2016 | Wilson et al. |
| 2016/0034166 A1 | 2/2016 | Christopher et al. |
| 2016/0034167 A1 | 2/2016 | Wilson et al. |
| 2016/0036996 A1 | 2/2016 | Midholt et al. |
| 2016/0044269 A1 | 2/2016 | Kang |
| 2016/0048298 A1 | 2/2016 | Choi et al. |
| 2016/0054710 A1 | 2/2016 | Jo et al. |
| 2016/0058336 A1 | 3/2016 | Blahnik et al. |
| 2016/0058337 A1 | 3/2016 | Blahnik et al. |
| 2016/0061613 A1 | 3/2016 | Jung et al. |
| 2016/0061623 A1 | 3/2016 | Pahwa et al. |
| 2016/0062582 A1 | 3/2016 | Wilson et al. |
| 2016/0062589 A1 | 3/2016 | Wan et al. |
| 2016/0062605 A1 | 3/2016 | Iskander |
| 2016/0065707 A1 | 3/2016 | Yang et al. |
| 2016/0065708 A1 | 3/2016 | Yang et al. |
| 2016/0066005 A1 | 3/2016 | Davis et al. |
| 2016/0066277 A1 | 3/2016 | Yang et al. |
| 2016/0070275 A1 | 3/2016 | Anderson et al. |
| 2016/0072896 A1 | 3/2016 | Petersen et al. |
| 2016/0073034 A1 | 3/2016 | Mukherjee et al. |
| 2016/0085937 A1 | 3/2016 | Dettinger et al. |
| 2016/0089569 A1 | 3/2016 | Blahnik |
| 2016/0098137 A1 | 4/2016 | Kim et al. |
| 2016/0107031 A1 | 4/2016 | Palatsi et al. |
| 2016/0117147 A1 | 4/2016 | Zambetti et al. |
| 2016/0135731 A1 | 5/2016 | Drennan |
| 2016/0140828 A1 | 5/2016 | Deforest |
| 2016/0150063 A1 | 5/2016 | Choi et al. |
| 2016/0156584 A1 | 6/2016 | Hum et al. |
| 2016/0180568 A1 | 6/2016 | Bullivant et al. |
| 2016/0188181 A1 | 6/2016 | Smith |
| 2016/0189444 A1 | 6/2016 | Madhok et al. |
| 2016/0193502 A1 | 7/2016 | Kim et al. |
| 2016/0196635 A1 | 7/2016 | Cho et al. |
| 2016/0202889 A1 | 7/2016 | Shin et al. |
| 2016/0210099 A1 | 7/2016 | Hampapuram et al. |
| 2016/0212374 A1 | 7/2016 | Usbergo et al. |
| 2016/0217601 A1 | 7/2016 | Tsuda et al. |
| 2016/0220225 A1 | 8/2016 | Wang et al. |
| 2016/0226713 A1 | 8/2016 | Dellinger et al. |
| 2016/0235374 A1 | 8/2016 | Miller et al. |
| 2016/0239724 A1 | 8/2016 | Arfvidsson et al. |
| 2016/0250517 A1 | 9/2016 | Tilvis et al. |
| 2016/0253864 A1 | 9/2016 | Weber et al. |
| 2016/0256082 A1 | 9/2016 | Ely et al. |
| 2016/0256741 A1 | 9/2016 | Holma et al. |
| 2016/0259542 A1 | 9/2016 | Chaudhri et al. |
| 2016/0261675 A1 | 9/2016 | Block et al. |
| 2016/0263435 A1 | 9/2016 | Venkatraman et al. |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0301794 A1 | 10/2016 | Schlakman et al. |
| 2016/0324457 A1 | 11/2016 | Dagum |
| 2016/0327911 A1 | 11/2016 | Eim et al. |
| 2016/0328736 A1 | 11/2016 | Wang et al. |
| 2016/0332025 A1 | 11/2016 | Repka |
| 2016/0342141 A1 | 11/2016 | Koumaiha |
| 2016/0346607 A1 | 12/2016 | Rapfogel |
| 2016/0357363 A1 | 12/2016 | Decker et al. |
| 2016/0358133 A1 | 12/2016 | Van Os et al. |
| 2016/0358134 A1 | 12/2016 | Van Os et al. |
| 2016/0358180 A1 | 12/2016 | Van Os et al. |
| 2016/0370879 A1 | 12/2016 | Sharma |
| 2016/0371464 A1 | 12/2016 | Bricker |
| 2016/0375306 A1 | 12/2016 | Gu et al. |
| 2016/0379511 A1 | 12/2016 | Dawson et al. |
| 2017/0001073 A1 | 1/2017 | Krueger et al. |
| 2017/0004507 A1 | 1/2017 | Henderson et al. |
| 2017/0010677 A1 | 1/2017 | Roh et al. |
| 2017/0011210 A1 | 1/2017 | Cheong et al. |
| 2017/0013408 A1 | 1/2017 | Grzywaczewski et al. |
| 2017/0014037 A1 | 1/2017 | Coppola et al. |
| 2017/0019517 A1 | 1/2017 | Wilder et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0026430 A1 | 1/2017 | Beckhardt et al. |
| 2017/0032168 A1 | 2/2017 | Kim |
| 2017/0041549 A1 | 2/2017 | Kim et al. |
| 2017/0053542 A1 | 2/2017 | Wilson et al. |
| 2017/0063753 A1 | 3/2017 | Probasco et al. |
| 2017/0065224 A1 | 3/2017 | Rahko et al. |
| 2017/0068407 A1 | 3/2017 | Wilson et al. |
| 2017/0068439 A1 | 3/2017 | Mohseni |
| 2017/0093769 A1 | 3/2017 | Lind et al. |
| 2017/0093780 A1 | 3/2017 | Lieb et al. |
| 2017/0095695 A1 | 4/2017 | Mangusson et al. |
| 2017/0123571 A1 | 5/2017 | Huang et al. |
| 2017/0123640 A1 | 5/2017 | Wilson et al. |
| 2017/0134321 A1 | 5/2017 | Ushio et al. |
| 2017/0153606 A1 | 6/2017 | Pitis et al. |
| 2017/0153804 A1 | 6/2017 | Kim et al. |
| 2017/0161014 A1 | 6/2017 | Kikugawa et al. |
| 2017/0169185 A1 | 6/2017 | Weng |
| 2017/0192730 A1 | 7/2017 | Yang et al. |
| 2017/0209766 A1 | 7/2017 | Riley et al. |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0266494 A1 | 9/2017 | Crankson et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |

(56) References Cited

U.S. PATENT DOCUMENTS

| | | |
|---|---|---|
| 2017/0319941 A1 | 11/2017 | Smith et al. |
| 2017/0330297 A1 | 11/2017 | Cronin et al. |
| 2017/0333752 A1 | 11/2017 | Korkala et al. |
| 2017/0344257 A1 | 11/2017 | Gnedin et al. |
| 2017/0348562 A1 | 12/2017 | Jung et al. |
| 2017/0353815 A1 | 12/2017 | Jagannathan et al. |
| 2017/0354845 A1 | 12/2017 | Williams et al. |
| 2017/0357439 A1 | 12/2017 | Lemay et al. |
| 2017/0357520 A1 | 12/2017 | De vries et al. |
| 2017/0359623 A1 | 12/2017 | Folse et al. |
| 2018/0000426 A1 | 1/2018 | Li |
| 2018/0001184 A1 | 1/2018 | Tran et al. |
| 2018/0034765 A1 | 2/2018 | Keszler et al. |
| 2018/0039406 A1 | 2/2018 | Kong et al. |
| 2018/0053200 A1 | 2/2018 | Cronin et al. |
| 2018/0056132 A1 | 3/2018 | Foley et al. |
| 2018/0065025 A1 | 3/2018 | Toda et al. |
| 2018/0067633 A1 | 3/2018 | Wilson et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0081515 A1 | 3/2018 | Block et al. |
| 2018/0108243 A1 | 4/2018 | Scherer |
| 2018/0126248 A1 | 5/2018 | Dion et al. |
| 2018/0137937 A1 | 5/2018 | Gass et al. |
| 2018/0140903 A1 | 5/2018 | Poure et al. |
| 2018/0143761 A1 | 5/2018 | Choi et al. |
| 2018/0150709 A1 | 5/2018 | Ha |
| 2018/0164974 A1 | 6/2018 | Park |
| 2018/0189077 A1 | 7/2018 | Gupta et al. |
| 2018/0206766 A1 | 7/2018 | Blahnik et al. |
| 2018/0225297 A1 | 8/2018 | Andrew et al. |
| 2018/0272190 A1 | 9/2018 | Miura et al. |
| 2018/0294053 A1 | 10/2018 | Runyon et al. |
| 2018/0318647 A1 | 11/2018 | Foley et al. |
| 2018/0329584 A1 | 11/2018 | Williams et al. |
| 2018/0339195 A1 | 11/2018 | Bernotas |
| 2018/0345078 A1 | 12/2018 | Blahnik et al. |
| 2018/0349022 A1 | 12/2018 | Chaudhri et al. |
| 2018/0350144 A1 | 12/2018 | Rathod |
| 2018/0356243 A1 | 12/2018 | Mehta et al. |
| 2019/0003849 A1 | 1/2019 | Pahwa et al. |
| 2019/0008467 A1 | 1/2019 | Averina et al. |
| 2019/0025995 A1 | 1/2019 | Williams |
| 2019/0034049 A1 | 1/2019 | Williams et al. |
| 2019/0034050 A1 | 1/2019 | Williams et al. |
| 2019/0037004 A1 | 1/2019 | Chaudhri et al. |
| 2019/0057593 A1 | 2/2019 | Park et al. |
| 2019/0104951 A1 | 4/2019 | Valys et al. |
| 2019/0158645 A1 | 5/2019 | Yang et al. |
| 2019/0172016 A1 | 6/2019 | Chaudhri et al. |
| 2019/0184234 A1 | 6/2019 | Packles et al. |
| 2019/0209777 A1 | 7/2019 | O'connell et al. |
| 2019/0220243 A1 | 7/2019 | Decker et al. |
| 2019/0232110 A1 | 8/2019 | Williams et al. |
| 2019/0250813 A1 | 8/2019 | Block et al. |
| 2019/0274565 A1 | 9/2019 | Soli et al. |
| 2019/0279520 A1 | 9/2019 | Wilson et al. |
| 2019/0297478 A1 | 9/2019 | Langlois et al. |
| 2019/0334782 A1 | 10/2019 | Dellinger et al. |
| 2019/0334907 A1 | 10/2019 | Rodden et al. |
| 2019/0336044 A1 | 11/2019 | Williams et al. |
| 2019/0336045 A1 | 11/2019 | Williams et al. |
| 2019/0336827 A1 | 11/2019 | Intonato et al. |
| 2019/0339822 A1 | 11/2019 | Devine et al. |
| 2019/0339849 A1 | 11/2019 | Williams et al. |
| 2019/0342616 A1 | 11/2019 | Domm et al. |
| 2019/0349463 A1 | 11/2019 | Soli et al. |
| 2019/0387982 A1 | 12/2019 | Buller |
| 2020/0014967 A1 | 1/2020 | Putnam |
| 2020/0101365 A1 | 4/2020 | Wilson et al. |
| 2020/0120170 A1 | 4/2020 | Amitay et al. |
| 2020/0125037 A1 | 4/2020 | Jo et al. |
| 2020/0133206 A1 | 4/2020 | Jo et al. |
| 2020/0159894 A1 | 5/2020 | Keen et al. |
| 2020/0201540 A1 | 6/2020 | Zambetti et al. |
| 2020/0213437 A1 | 7/2020 | Bhatt |
| 2020/0297249 A1 | 9/2020 | Williams et al. |
| 2020/0348827 A1 | 11/2020 | Wilson et al. |
| 2020/0356242 A1 | 11/2020 | Wilson et al. |
| 2020/0357522 A1 | 11/2020 | Pahwa et al. |
| 2020/0358897 A1 | 11/2020 | Dellinger et al. |
| 2020/0381100 A1 | 12/2020 | Williams et al. |
| 2020/0382613 A1 | 12/2020 | Sundstrom et al. |
| 2021/0007632 A1 | 1/2021 | Blahnik et al. |
| 2021/0007633 A1 | 1/2021 | Blahnik et al. |
| 2021/0042028 A1 | 2/2021 | Block et al. |
| 2021/0073741 A1 | 3/2021 | Chaudhri et al. |
| 2021/0092488 A1 | 3/2021 | Folse et al. |
| 2021/0095987 A1 | 4/2021 | Pahwa et al. |
| 2021/0110908 A1 | 4/2021 | Blahnik et al. |
| 2021/0113116 A1 | 4/2021 | Chen et al. |
| 2021/0145321 A1 | 5/2021 | Chen et al. |
| 2021/0173431 A1 | 6/2021 | Yang et al. |
| 2021/0191584 A1 | 6/2021 | Williams et al. |
| 2021/0193293 A1 | 6/2021 | Blahnik et al. |
| 2021/0203765 A1 | 7/2021 | Yang et al. |
| 2021/0252337 A1 | 8/2021 | Devine et al. |
| 2021/0252341 A1 | 8/2021 | Devine et al. |
| 2021/0252369 A1 | 8/2021 | Devine et al. |
| 2021/0255747 A1 | 8/2021 | Devine et al. |
| 2021/0255758 A1 | 8/2021 | Devine et al. |
| 2021/0255826 A1 | 8/2021 | Devine et al. |
| 2021/0263700 A1 | 8/2021 | Decker et al. |

FOREIGN PATENT DOCUMENTS

| | | |
|---|---|---|
| AU | 2016100796 A4 | 6/2016 |
| CA | 2781636 A1 | 7/2010 |
| CA | 2792987 A1 | 10/2011 |
| CA | 2815518 A1 | 5/2012 |
| CA | 2897539 A1 | 10/2014 |
| CH | 707412 A2 | 6/2014 |
| CN | 1337638 A | 2/2002 |
| CN | 1397904 A | 2/2003 |
| CN | 1443427 A | 9/2003 |
| CN | 1536511 A | 10/2004 |
| CN | 1585943 A | 2/2005 |
| CN | 1782685 A | 6/2006 |
| CN | 1818843 A | 8/2006 |
| CN | 1997050 A | 7/2007 |
| CN | 1997957 A | 7/2007 |
| CN | 101061484 A | 10/2007 |
| CN | 101098535 A | 1/2008 |
| CN | 101118469 A | 2/2008 |
| CN | 101150810 A | 3/2008 |
| CN | 101203821 A | 6/2008 |
| CN | 101382438 A | 3/2009 |
| CN | 101505320 A | 8/2009 |
| CN | 101541387 A | 9/2009 |
| CN | 101627349 A | 1/2010 |
| CN | 101651870 A | 2/2010 |
| CN | 101702112 A | 5/2010 |
| CN | 101819486 A | 9/2010 |
| CN | 101822020 A | 9/2010 |
| CN | 101827363 A | 9/2010 |
| CN | 101828411 A | 9/2010 |
| CN | 101836894 A | 9/2010 |
| CN | 101873386 A | 10/2010 |
| CN | 101939740 A | 1/2011 |
| CN | 101978374 A | 2/2011 |
| CN | 101981987 A | 2/2011 |
| CN | 201928419 U | 8/2011 |
| CN | 102301415 A | 12/2011 |
| CN | 102339201 A | 2/2012 |
| CN | 102426490 A | 4/2012 |
| CN | 102438092 A | 5/2012 |
| CN | 102448555 A | 5/2012 |
| CN | 102646081 A | 8/2012 |
| CN | 102687176 A | 9/2012 |
| CN | 102695302 A | 9/2012 |
| CN | 102754071 A | 10/2012 |
| CN | 102763066 A | 10/2012 |
| CN | 102772211 A | 11/2012 |

(56) References Cited

FOREIGN PATENT DOCUMENTS

| | | |
|---|---|---|
| CN | 102790826 A | 11/2012 |
| CN | 102804238 A | 11/2012 |
| CN | 102989159 A | 3/2013 |
| CN | 103154954 A | 6/2013 |
| CN | 103212197 A | 7/2013 |
| CN | 103297610 A | 9/2013 |
| CN | 103370924 A | 10/2013 |
| CN | 103399480 A | 11/2013 |
| CN | 103403627 A | 11/2013 |
| CN | 103558916 A | 2/2014 |
| CN | 103562832 A | 2/2014 |
| CN | 103576902 A | 2/2014 |
| CN | 103577108 A | 2/2014 |
| CN | 103577982 A | 2/2014 |
| CN | 103581456 A | 2/2014 |
| CN | 103607660 A | 2/2014 |
| CN | 103713843 A | 4/2014 |
| CN | 103744671 A | 4/2014 |
| CN | 103793075 A | 5/2014 |
| CN | 103902165 A | 7/2014 |
| CN | 103902808 A | 7/2014 |
| CN | 103914238 A | 7/2014 |
| CN | 103973899 A | 8/2014 |
| CN | 104102388 A | 10/2014 |
| CN | 104160362 A | 11/2014 |
| CN | 104205785 A | 12/2014 |
| CN | 104281257 A | 1/2015 |
| CN | 104288983 A | 1/2015 |
| CN | 104360735 A | 2/2015 |
| CN | 104434314 A | 3/2015 |
| CN | 104501043 A | 4/2015 |
| CN | 104508426 A | 4/2015 |
| CN | 105190659 A | 12/2015 |
| CN | 105531730 A | 4/2016 |
| CN | 105874447 A | 8/2016 |
| CN | 205608658 U | 9/2016 |
| CN | 106537397 A | 3/2017 |
| CN | 106709235 A | 5/2017 |
| CN | 106878550 A | 6/2017 |
| CN | 107710197 A | 2/2018 |
| EP | 831629 A2 | 3/1998 |
| EP | 977132 A2 | 2/2000 |
| EP | 1079371 A1 | 2/2001 |
| EP | 1659504 A2 | 5/2006 |
| EP | 1674977 A2 | 6/2006 |
| EP | 1679879 A2 | 7/2006 |
| EP | 1705883 A1 | 9/2006 |
| EP | 1744242 A2 | 1/2007 |
| EP | 1777611 A1 | 4/2007 |
| EP | 1832969 A2 | 9/2007 |
| EP | 1885109 A2 | 2/2008 |
| EP | 1935339 A1 | 6/2008 |
| EP | 2025368 A2 | 2/2009 |
| EP | 2040146 A2 | 3/2009 |
| EP | 1964022 B1 | 3/2010 |
| EP | 2194508 A1 | 6/2010 |
| EP | 2284646 A1 | 2/2011 |
| EP | 2302493 A2 | 3/2011 |
| EP | 2312512 A1 | 4/2011 |
| EP | 2341315 A1 | 7/2011 |
| EP | 2360902 A2 | 8/2011 |
| EP | 2367098 A2 | 9/2011 |
| EP | 2413577 A2 | 2/2012 |
| EP | 2423810 A1 | 2/2012 |
| EP | 2426902 A1 | 3/2012 |
| EP | 2437148 A2 | 4/2012 |
| EP | 2547117 A1 | 1/2013 |
| EP | 2602759 A2 | 6/2013 |
| EP | 2615607 A2 | 7/2013 |
| EP | 2632139 A2 | 8/2013 |
| EP | 2653961 A1 | 10/2013 |
| EP | 2672377 A2 | 12/2013 |
| EP | 2677775 A1 | 12/2013 |
| EP | 2693382 A2 | 2/2014 |
| EP | 2720126 A1 | 4/2014 |
| EP | 2733598 A2 | 5/2014 |
| EP | 2738640 A2 | 6/2014 |
| EP | 2821912 A1 | 1/2015 |
| GB | 2370208 A | 6/2002 |
| GB | 2475669 A | 6/2011 |
| GB | 2550639 A | 11/2017 |
| JP | 6187118 A | 7/1994 |
| JP | 8110955 A | 4/1996 |
| JP | 9-251084 A | 9/1997 |
| JP | 11-160470 A | 6/1999 |
| JP | 11-232013 A | 8/1999 |
| JP | 2000-122957 A | 4/2000 |
| JP | 2001-076078 A | 3/2001 |
| JP | 2001-318852 A | 11/2001 |
| JP | 2002-73486 A | 3/2002 |
| JP | 2002-507718 A | 3/2002 |
| JP | 2002-190007 A | 7/2002 |
| JP | 2002-271451 A | 9/2002 |
| JP | 2002-342356 A | 11/2002 |
| JP | 2002-351768 A | 12/2002 |
| JP | 2003-30245 A | 1/2003 |
| JP | 2003-296246 A | 10/2003 |
| JP | 2003-337863 A | 11/2003 |
| JP | 2004-102609 A | 4/2004 |
| JP | 2004-113466 A | 4/2004 |
| JP | 2004-519033 A | 6/2004 |
| JP | 2004-258738 A | 9/2004 |
| JP | 2005-79814 A | 3/2005 |
| JP | 2005-532607 A | 10/2005 |
| JP | 2005-339017 A | 12/2005 |
| JP | 2006-230679 A | 9/2006 |
| JP | 2007-260288 A | 10/2007 |
| JP | 2007-330513 A | 12/2007 |
| JP | 2008-097202 A | 4/2008 |
| JP | 2008-104758 A | 5/2008 |
| JP | 2008-183339 A | 8/2008 |
| JP | 2008-272301 A | 11/2008 |
| JP | 2009-78134 A | 4/2009 |
| JP | 2009-147889 A | 7/2009 |
| JP | 2009-239867 A | 10/2009 |
| JP | 2010-12335 A | 1/2010 |
| JP | 2010-517725 A | 5/2010 |
| JP | 2010-122901 A | 6/2010 |
| JP | 2010-124181 A | 6/2010 |
| JP | 2010-162297 A | 7/2010 |
| JP | 2010-181280 A | 8/2010 |
| JP | 2010-245940 A | 10/2010 |
| JP | 2010-257051 A | 11/2010 |
| JP | 2011-125633 A | 6/2011 |
| JP | 3168099 U | 6/2011 |
| JP | 2011-183101 A | 9/2011 |
| JP | 2011-192126 A | 9/2011 |
| JP | 2011-198184 A | 10/2011 |
| JP | 2011-206323 A | 10/2011 |
| JP | 2011-209786 A | 10/2011 |
| JP | 2011-259253 A | 12/2011 |
| JP | 2011-530101 A | 12/2011 |
| JP | 2012-35071 A | 2/2012 |
| JP | 2012-53642 A | 3/2012 |
| JP | 2012-59264 A | 3/2012 |
| JP | 2012-505478 A | 3/2012 |
| JP | 2012-123475 A | 6/2012 |
| JP | 2012-147432 A | 8/2012 |
| JP | 2012-517630 A | 8/2012 |
| JP | 2012-203832 A | 10/2012 |
| JP | 2012-524640 A | 10/2012 |
| JP | 2012-230503 A | 11/2012 |
| JP | 2012-531607 A | 12/2012 |
| JP | 2012-533117 A | 12/2012 |
| JP | 2013-29925 A | 2/2013 |
| JP | 2013-506225 A | 2/2013 |
| JP | 2013-54468 A | 3/2013 |
| JP | 2013-103020 A | 5/2013 |
| JP | 2013-117690 A | 6/2013 |
| JP | 2013-530458 A | 7/2013 |
| JP | 2013-175188 A | 9/2013 |
| JP | 2013-544140 A | 12/2013 |
| JP | 2014-503861 A | 2/2014 |
| JP | 2014-44719 A | 3/2014 |

(56) References Cited

FOREIGN PATENT DOCUMENTS

| | | |
|---|---|---|
| JP | 2014-44724 A | 3/2014 |
| JP | 2014-123197 A | 7/2014 |
| JP | 2014-216868 A | 11/2014 |
| JP | 2015-210587 A | 11/2015 |
| JP | 2015-531916 A | 11/2015 |
| JP | 2016-502875 A | 2/2016 |
| JP | 2016-528016 A | 9/2016 |
| JP | 2016-177151 A | 10/2016 |
| JP | 2016-202751 A | 12/2016 |
| JP | 2017-134689 A | 8/2017 |
| JP | 2017-211994 A | 11/2017 |
| JP | 2017-532069 A | 11/2017 |
| KR | 10-2004-0067514 A | 7/2004 |
| KR | 20-0425314 Y1 | 9/2006 |
| KR | 10-2011-0017076 A | 2/2011 |
| KR | 10-2012-0023657 A | 3/2012 |
| KR | 10-2013-0111569 A | 10/2013 |
| KR | 10-2013-0111570 A | 10/2013 |
| KR | 20130109466 A | 10/2013 |
| KR | 10-2013-0135282 A | 12/2013 |
| KR | 10-2014-0018044 A | 2/2014 |
| KR | 10-2014-0064687 A | 5/2014 |
| KR | 10-2014-0070877 A | 6/2014 |
| KR | 10-2014-0105309 A | 9/2014 |
| KR | 10-2015-0001287 A | 1/2015 |
| KR | 10-2017-0003608 A | 1/2017 |
| TW | 498240 B | 8/2002 |
| TW | 200512616 A | 4/2005 |
| TW | 201210368 A | 3/2012 |
| TW | M435665 U | 8/2012 |
| TW | 201240499 A | 10/2012 |
| TW | 201419115 A | 5/2014 |
| WO | 1999/28815 A1 | 6/1999 |
| WO | 1999/41682 A2 | 8/1999 |
| WO | 1999/66394 A1 | 12/1999 |
| WO | 1999/66395 A2 | 12/1999 |
| WO | 2001/171433 A1 | 9/2001 |
| WO | 2002/08881 A2 | 1/2002 |
| WO | 2002/27530 A2 | 4/2002 |
| WO | 2002/054157 A1 | 7/2002 |
| WO | 2003/093765 A2 | 11/2003 |
| WO | 2004/056107 A1 | 7/2004 |
| WO | 2004/063862 A2 | 7/2004 |
| WO | 2004/095414 A1 | 11/2004 |
| WO | 2005/070289 A1 | 8/2005 |
| WO | 2005/109829 A1 | 11/2005 |
| WO | 2006012343 A2 | 2/2006 |
| WO | 2006/036069 A1 | 4/2006 |
| WO | 2006/037545 A2 | 4/2006 |
| WO | 2006/094308 A2 | 9/2006 |
| WO | 2006/112641 A1 | 10/2006 |
| WO | 2006/094308 A3 | 12/2006 |
| WO | 2007/000012 A1 | 1/2007 |
| WO | 2007/018881 A2 | 2/2007 |
| WO | 2007/102110 A2 | 9/2007 |
| WO | 2007/142703 A1 | 12/2007 |
| WO | 2007/149731 A1 | 12/2007 |
| WO | 2009/085378 A1 | 7/2009 |
| WO | 2009/129402 A1 | 10/2009 |
| WO | 2010/017627 A1 | 2/2010 |
| WO | 2010/126825 A1 | 11/2010 |
| WO | 2011/000893 A1 | 1/2011 |
| WO | 2011/041427 A2 | 4/2011 |
| WO | 2011/062871 A2 | 5/2011 |
| WO | 2011/084857 A1 | 7/2011 |
| WO | 2011/084859 A1 | 7/2011 |
| WO | 2011/130849 A8 | 10/2011 |
| WO | 2011/149231 A2 | 12/2011 |
| WO | 2012/021507 A2 | 2/2012 |
| WO | 2012/061438 A2 | 5/2012 |
| WO | 2012/061440 A2 | 5/2012 |
| WO | 2012/078079 A2 | 6/2012 |
| WO | 2012/128361 A1 | 9/2012 |
| WO | 2012/161434 A2 | 11/2012 |
| WO | 2013/051048 A1 | 4/2013 |
| WO | 2013/052789 A1 | 4/2013 |
| WO | 2013/097895 A1 | 7/2013 |
| WO | 2013/109762 A1 | 7/2013 |
| WO | 2013/109777 A1 | 7/2013 |
| WO | 2013/109916 A1 | 7/2013 |
| WO | 2013/111239 A1 | 8/2013 |
| WO | 2013/135270 A1 | 9/2013 |
| WO | 2013/169842 A2 | 11/2013 |
| WO | 2013/169849 A2 | 11/2013 |
| WO | 2013/169851 A2 | 11/2013 |
| WO | 2013/169854 A2 | 11/2013 |
| WO | 2013/169870 A1 | 11/2013 |
| WO | 2013/169875 A2 | 11/2013 |
| WO | 2013/169877 A2 | 11/2013 |
| WO | 2013/169882 A2 | 11/2013 |
| WO | 2013/173838 A2 | 11/2013 |
| WO | 2014/002711 A1 | 1/2014 |
| WO | 2014/022711 A1 | 2/2014 |
| WO | 2014/024000 A1 | 2/2014 |
| WO | 2014/074407 A1 | 5/2014 |
| WO | 2014/078114 A1 | 5/2014 |
| WO | 2014/081181 A1 | 5/2014 |
| WO | 2014/105276 A1 | 7/2014 |
| WO | 2014/105278 A1 | 7/2014 |
| WO | 2014/105279 A1 | 7/2014 |
| WO | 2014/207294 A1 | 12/2014 |
| WO | 2015/027133 A1 | 2/2015 |
| WO | 2015/179592 A1 | 11/2015 |
| WO | 2015/198488 A1 | 12/2015 |
| WO | 2016/022203 A1 | 2/2016 |
| WO | 2016/036522 A2 | 3/2016 |
| WO | 2016/036582 A2 | 3/2016 |
| WO | 2016/126733 A1 | 8/2016 |
| WO | 2017/037242 A1 | 3/2017 |
| WO | 2018/222313 A1 | 12/2018 |
| WO | 2019/017508 A1 | 1/2019 |
| WO | 2019/024603 A1 | 2/2019 |
| WO | 2019/231982 A1 | 12/2019 |

OTHER PUBLICATIONS

Examiner's Answer to Appeal Brief received for U.S. Appl. No. 15/128,952, dated Jan. 8, 2020, 9 pages.
Non-Final Office Action received for U.S. Appl. No. 16/147,523, dated Dec. 27, 2019, 11 pages.
Office Action received for Chinese Patent Application No. 201810105846.X, dated Nov. 28, 2019, 9 pages (5 pages of English Translation and 4 pages of Official Copy).
Office Action received for Danish Patent Application No. PA201870378, dated Jan. 6, 2020, 3 pages.
Office Action received for European Patent Application No. 16837432.0, dated Jan. 10, 2020, 7 pages.
Office Action received for European Patent Application No. 19721883.7, dated Jan. 10, 2020, 4 pages.
"3c Blogger Kisplay Share", Samsung GALAXY Tab S Hands-on SideSync 3.0 Is Amazing Jul. 4, 2014, 4 pages.
Accepted Outlook Meetings Move to Deleted Folder, Available online at:—https://social.technet.microsoft.com/Forums/office/en-US/f3301c9a-a93f-49f7-be13-c642e285f150/accepted-outlook-meetings-move-to-deleted-folder?forum=outlook, Jan. 13, 2011, 4 pages.
Advisory Action received for U.S. Appl. No. 14/732,773, dated Nov. 9, 2018, 6 pages.
Advisory Action received for U.S. Appl. No. 14/752,776, dated Aug. 31, 2018, 3 pages.
Advisory Action received for U.S. Appl. No. 14/815,898, dated Aug. 30, 2016, 3 pages.
Advisory Action received for U.S. Appl. No. 14/822,769, dated Apr. 30, 2018, 4 pages.
Advisory Action received for U.S. Appl. No. 14/833,014, dated Jan. 27, 2017, 3 pages.
Advisory Action received for U.S. Appl. No. 14/839,922, dated Mar. 24, 2017, 4 pages.
Advisory Action received for U.S. Appl. No. 14/869,877, dated Jan. 5, 2017, 3 pages.

(56) References Cited

OTHER PUBLICATIONS

Advisory Action received for U.S. Appl. No. 14/870,793, dated Apr. 13, 2017, 3 pages.
Airshow, "Airshow App for Mobile Devices", 2012, 4 pages.
Apk Root, "Butterfly 3d Live Wallpaper 1.0 Apk", Available at <http://net-suckga-ilauncher2.apk-dl.com/butterfly-3d-live-wallpaper>, Feb. 26, 2013, 7 pages.
Apple, "Iphone User Guide", iPhone first generation, Available at: <http://pocketpccentral.net/iphone/products/1 g_iphone.htm>, Jun. 29, 2007, 124 pages.
Apple, "Iphone User's Guide", Available at <http://mesnotices.20minutes.fr/manuel-notice-mode-emploi/APPLE/IPHONE%2D%5FE#>, Retrieved on Mar. 27, 2008, Jun. 2007, 137 pages.
Avdonin, Nikita, "Astroviewer 3d", Available at<:https:jjwww.youtube.comjwatch?v=zY0tslx3JHY/>, Nov. 5, 2013, 2 pages.
Axiang's Network Notebook, Deep Analysis on Samsung's 2013 New Flagship: Tell You What Kind of Mobile Phone Galaxy S4 Is!, Apr. 22, 2013, 4 pages.
Block Eliza et al., "U.S. Appl. No. 15/554,204 Entitled "sharing User-configurable Graphical Constructs", Filed on Aug. 28, 2017", 247 pages.
Bogdanov, Alexei, "Skmei 1016", XP054977588, Available online at <URL:https://www.youtube.com/watch?v=E4g4Fug05Fw>, Jun. 21, 2014, 2 pages (Official copy only).
Castellini, Rick, "Google Earth", Retrieved from <https://www.youtube.com/watch?v=bgjMSBXsFZQ>, Feb. 12, 2013, 3 pages.
Cazlar, "[ios] Mapsgps (formerly Pebbgps) is Now Available—Now with Colour Turn-by-turn Directions!", Online Available at <https://forums.pebble.com/t/ios-mapsgps-formerly-pebbgps-is-now-available-now-with-colour-turn-by-turn-directions/5584>, 2013, 31 pages.
Certification of Examination received for Australian Patent Application No. 2018100158, dated Oct. 23, 2018, 2 pages.
Chan, Christine, "Handoff Your Browser to Your Iphone or Ipad! Plus a Chance to Win a Copy!", Apr. 12, 2011, 2 pages.
Cho, H. S., "Satisfactory Innovative Smart-watch (fitbit Force) . . . Review after Seven Days of Use, Such as the Amount of Sleep and Movement (improving Sleep is the Object of X-blue", Online Available at: <https://x-blueuv.blogspot.com/2013/12/fitbit-force.html>, Dec. 3, 2013, 6 pages (Official copy only).
CNET, "Google Fit's Automatic Activity Tracking is Getting Smarter on Android Wear", Available online at: https://www.youtube.com/watch?v=lttzlCid_d8, May 18, 2016, 1 page.
Codrington, Simon, "Intuitive Scrolling Interfaces with Css Scroll Snap Points", Online Available at: https://www.sitepoint.com/intuitive-scrolling-interfaces-with-css-scroll-snap-points/, Dec. 8, 2015, 14 pages.
Corrected Notice of Allowance received for U.S. Appl. No. 14/815,879, dated Jul. 13, 2017, 3 pages.
Corrected Notice of Allowance received for U.S. Appl. No. 14/815,879, dated Jul. 28, 2017, 3 pages.
Corrected Notice of Allowance received for U.S. Appl. No. 14/815,879, dated Sep. 21, 2017, 2 pages.
Corrected Notice of Allowance received for U.S. Appl. No. 14/836,754, dated May 23, 2018, 2 pages.
Corrected Notice of Allowance received for U.S. Appl. No. 14/841,402, dated May 4, 2018, 2 pages.
Decision on Opposition received for Australian Patent Application No. 2015298710, dated Aug. 20, 2018, 20 pages.
Decision to Grant received for Danish Patent Application No. PA201570665, dated Apr. 26, 2017, 2 pages.
Decision to Grant received for Danish Patent Application No. PA201670320, dated Oct. 18, 2018, 2 pages.
Decision to Grant received for European Patent Application No. 16706081.3, dated Nov. 29, 2018, 2 pages.
Decision to Refuse received for European Application No. 13811085.3, dated Sep. 11, 2018, 21 pages.
Decision to Refuse received for European Patent Application No. 15771747.1, dated Aug. 10, 2018, 22 pages.
"Deluxe Moon-guide", available online at:—https://web.archive.org/web/20130520161057/http://www.lifewaresolutions.com/deluxe_moon_guide_ip.html, May 20, 2013, 5 pages.
"Dwprogressbar V2: Stepping and Events", davidwalsh.name/dwprogressbar-2-stepping-events-mootools-progress-bar, retrieved from the Wayback Machine Aug. 31, 2008, 4 pages.
Easyvideoguides, "Mapquest", available on : https://www.youtube.com/watch?v=7sDIDNM2bCI, Dec. 26, 2007, 4 pages.
Ehowtech, "How to Get Written Directions on a Garmin : Using a Garmin", available online at: https://www.youtube.com/watch?v=s_EKT6qH4LI, Dec. 2, 2012, 1 page.
Ellis, Benus, "Use a Phone Number in the Google Calendar Where Line for One Click Calling", Available online at: https://ellisbenus.com/ellis-benus/use-a-phone-number-in-the-google-calender-where-line-for-one-click-calling, Ellis Benus-Small Business Web Guru, Oct. 3, 2012, 2 pages.
Evgenyevich, Sergey, "Earth & Moon in Hd Gyro 3d", Available at <https://www.youtube.com/watch?v=IRwNcaSYrls/>, Dec. 1, 2013, 2 pages.
Examiner's Answer for Appeal Brief received for U.S. Appl. No. 11/850,005, dated Apr. 10, 2018, 34 pages.
Examiner's Answer to Appeal Brief received for U.S. Appl. No. 14/870,793, dated Apr. 16, 2018, 15 pages.
Examiner's Answer to Appeal Brief received for U.S. Appl. No. 14/833,014, dated Nov. 2, 2017, 48 pages.
Extended European Search Report (includes Partial European Search Report and European Search Opinion) received for European Patent Application No. 13174706.5, dated Jan. 8, 2015, 8 pages.
Extended European Search Report (includes Partial European Search Report and European Search Opinion) received for European Patent Application No. 16190252.3, dated Mar. 1, 2017, 10 pages.
Extended European Search Report received for European Patent Application No. 16762356.0, dated Nov. 9, 2018, 10 pages.
Extended European Search Report received for European Patent Application No. 16804040.0, dated Feb. 26, 2018, 9 pages.
Extended European Search Report received for European Patent Application No. 18154145.9, dated Mar. 2, 2018, 8 pages.
Farber, Dan, "Jobs: Today Apple is Going to Reinvent the Phone", ZDNet, available at <http://www.zdnet.com/blog/btl/jobs-today-apple-is-going-to-reinvent-the-phone/4249>, Jan. 9, 2007, 3 pages.
Feldman, Ari, "Excerpts From: Designing Arcade Computer Game Graphics", Available online at: http://www.phatcode.net/res/269/files/dacgg.pdf, Jan. 1, 2001, 35 pages.
Final Office Action received for U.S. Appl. No. 14/822,769, dated Nov. 9, 2016, 18 pages.
Final Office Action received for U.S. Appl. No. 11/850,005, dated Jul. 8, 2011, 9 pages.
Final Office Action received for U.S. Appl. No. 11/850,005, dated May 22, 2014, 13 pages.
Final Office Action received for U.S. Appl. No. 11/850,005, dated Nov. 16, 2015, 13 pages.
Final Office Action received for U.S. Appl. No. 11/850,005, dated Sep. 14, 2012, 9 pages.
Final Office Action received for U.S. Appl. No. 12/205,847, dated Apr. 25, 2012, 42 pages.
Final Office Action received for U.S. Appl. No. 12/240,975, dated Aug. 29, 2012, 47 pages.
Final Office Action received for U.S. Appl. No. 14/599,424, dated Jun. 28, 2018, 12 pages.
Final Office Action received for U.S. Appl. No. 14/599,425, dated Jun. 12, 2018, 45 pages.
Final Office Action received for U.S. Appl. No. 14/599,425, dated May 19, 2017, 24 pages.
Final Office Action received for U.S. Appl. No. 14/599,425, dated Oct. 8, 2015, 20 pages.
Final Office Action received for U.S. Appl. No. 14/732,773, dated Jul. 13, 2018, 48 pages.
Final Office Action received for U.S. Appl. No. 14/752,776, dated May 29, 2018, 36 pages.
Final Office Action received for U.S. Appl. No. 14/815,890, dated Feb. 26, 2018, 20 pages.
Final Office Action received for U.S. Appl. No. 14/815,890, dated Nov. 21, 2016, 18 pages.

(56) References Cited

OTHER PUBLICATIONS

Final Office Action received for U.S. Appl. No. 14/815,898, dated Jun. 9, 2016, 19 pages.
Final Office Action received for U.S. Appl. No. 14/822,769, dated Jan. 4, 2018, 25 pages.
Final Office Action received for U.S. Appl. No. 14/833,014, dated Oct. 26, 2016, 32 pages.
Final Office Action received for U.S. Appl. No. 14/836,754, dated Jun. 14, 2017, 23 pages.
Final Office Action received for U.S. Appl. No. 14/839,922, dated Dec. 14, 2016, 22 pages.
Final Office Action received for U.S. Appl. No. 14/841,402, dated Aug. 25, 2017, 17 pages.
Final Office Action received for U.S. Appl. No. 14/841,606, dated Sep. 7, 2018, 34 pages.
Final Office Action received for U.S. Appl. No. 14/841,614, dated May 10, 2018, 13 pages.
Final Office Action received for U.S. Appl. No. 14/841,623, dated Sep. 5, 2017, 16 pages.
Final Office Action received for U.S. Appl. No. 14/863,069, dated Jul. 5, 2018, 19 pages.
Final Office Action received for U.S. Appl. No. 14/864,759, dated Sep. 4, 2018, 24 pages.
Final Office Action received for U.S. Appl. No. 14/869,877, dated Apr. 26, 2018, 18 pages.
Final Office Action received for U.S. Appl. No. 14/869,877, dated Aug. 3, 2016, 13 pages.
Final Office Action received for U.S. Appl. No. 14/870,726, dated Apr. 19, 2017, 17 pages.
Final Office Action received for U.S. Appl. No. 14/870,793, dated Jan. 19, 2017, 16 pages.
Final Office Action received for U.S. Appl. No. 15/128,952, dated Jul. 18, 2018, 19 pages.
Final Office Action received for U.S. Appl. No. 14/815,879, dated Mar. 24, 2016, 46 pages.
Final Office Action received for U.S. Appl. No. 14/836,754, dated Mar. 22, 2016, 17 pages.
Final Office Action received for U.S. Appl. No. 14/836,754, dated Mar. 31, 2017, 24 pages.
First Action Interview received for U.S. Appl. No. 14/815,890, dated Aug. 12, 2016, 3 pages.
Frakes, Dan, "How to Get Started with Airplay", availble at: https://www.macworld.com/article/2039770/how-to-get-started-with-airplay.html, Macworld, May 27, 2013, 8 pages.
Fuchphone Extras, "Lg G Watch—Designs | Watch Faces", Available online at: https://www.youtube.com/watch?v=ygxzgdi_MSE, Jul. 27, 2014, 1 page.
Fuchphone Extras, "Samsung Gear Live—Designs | Watch Faces", Available online at: https://www.youtube.com/watch?v=fFjtVAxyimE, Jul. 26, 2014, 1 page.
Garmin, "Fenix 5x Owner's Manual", Online Available at :—https://web.archive.org/web/20180127170640/https://static.garmin.com/pumac/fenix5x_OM_EN.pdf, Jan. 27, 2018, 42 pages.
"Google Earth 7.0.1.8244", retrieved from the Internet: http://dl.google.com/dl/earth/client/ge7/release_7_0_1/googleearth-win-bundle-7.0.1.8244.exe, Oct. 29, 2012, 1 page.
"Google Earth on Android—Androidcentral.com", Available online at:—https://www.youtube.com/watch?v=1WxN1RunrE4, Feb. 22, 2010, 1 page.
Gottabemobile, "How to Change Watch Faces on Android Wear", available online at URL:https://www.youtube.com/watch?v=B8iRGkGg6a8, Jul. 9, 2014, 4 pages.
Graphs and Charts, "Online available at: <https://www.teachervision.com/lesson-planning/graph-chart-teacher-resources" retrieved on Dec. 12, 2018, 4 pages.
GSM, Arena, "Neonode N2 User Interface", 3:06 minutes video, available at <https://www.youtube.com/watch?v=MfDMHmlZRLc>, uploaded on Feb. 13, 2007, 2 pages.
"Gt-i9500(galaxy S4) User Manual, Samsung", Rev.1.1, May 2013, 14 pages.

Hancock et al., "Shallow-depth 3d Interaction: Design and Evaluation of One-two- and Three-touch Techniques", Proceedings of SIGCHI, Apr. 28-May 3, 2007, pp. 1147-1156.
Haris, "Google Maps Navigation on Android 2.0", Sizzled Core, Online available at <http://www.sizzledcore.com/2009/10/29/google-maps-navigation-on-android-20/>, Oct. 29, 2009, 6 pages.
Horowitz, Paul, "Always Show Scroll Bars in Mac Os X", Os X Daily, available online at: URL:http:jjosxdaily.com/2011/08/03/show-scroll-bars-mac-os-x-lion/, Aug. 3, 2011, 7 pages.
Intention to Grant received for Danish Patent Application No. PA201570496, dated Feb. 17, 2016, 6 pages.
Intention to Grant received for Danish Patent Application No. PA201570563, dated Mar. 17, 2016, 7 pages.
Intention to Grant received for Danish Patent Application No. PA201570665, dated Feb. 28, 2017, 2 pages.
Intention to Grant received for Danish Patent Application No. PA201570668, dated Mar. 27, 2017, 2 pages.
Intention to Grant received for Danish Patent Application No. PA201670320, dated May 17, 2018, 2 pages.
Intention to Grant received for European Patent Application No. 13174706.5, dated Nov. 22, 2018, 12 pages.
Intention to Grant received for European Patent Application No. 16706081.3, dated Jul. 18, 2018, 8 pages.
Intention to Grant received for European Patent Application No. 16706081.3, dated Jun. 11, 2018, 7 pages.
International Preliminary Report on Patentability received for PCT Application No. PCT/US2016/037686, dated Mar. 1, 2018, 12 pages.
International Preliminary Report on Patentability received for PCT Patent Application No. PCT/US2008/074341, dated Mar. 9, 2010, 8 pages.
International Preliminary Report on Patentability received for PCT Patent Application No. PCT/US2009/039621, dated Dec. 23, 2010, 7 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2015/019317, dated Dec. 15, 2016, 18 pages.
International Preliminary Report on Patentability received for PCT Patent Application No. PCT/US2015/032474, dated Dec. 15, 2016, 7 pages.
International Preliminary Report on Patentability received for PCT Patent Application No. PCT/US2015/034604, dated Feb. 16, 2017, 21 pages.
International Preliminary Report on Patentability received for PCT Patent Application No. PCT/US2015/034606, dated Feb. 16, 2017, 11 pages.
International Preliminary Report on Patentability received for PCT Patent Application No. PCT/US2015/034607, dated Feb. 16, 2017, 18 pages.
International Preliminary Report on Patentability received for PCT Patent Application No. PCT/US2015/038173, dated Jan. 5, 2017, 10 pages.
International Preliminary Report on Patentability received for PCT Patent Application No. PCT/US2015/038174, dated Jan. 5, 2017, 27 pages.
International Preliminary Report on Patentability received for PCT Patent Application No. PCT/US2015/041424, dated Feb. 2, 2017, 13 pages.
International Preliminary Report on Patentability received for PCT Patent Application No. PCT/US2015/044517, dated Mar. 16, 2017, 10 pages.
International Preliminary Report on Patentability received for PCT Patent Application No. PCT/US2015/046262, dated Mar. 16, 2017, 26 pages.
International Preliminary Report on Patentability received for PCT Patent Application No. PCT/US2015/046892, dated Mar. 16, 2017, 14 pages.
International Preliminary Report on Patentability received for PCT Patent Application No. PCT/US2015/047282, dated Mar. 16, 2017, 26 pages.

(56) References Cited

OTHER PUBLICATIONS

International Preliminary Report on Patentability received for PCT Patent Application No. PCT/US2015/053353, dated Sep. 21, 2017, 15 pages.
International Preliminary Report on Patentability received for PCT Patent Application No. PCT/US2016/014997, dated Dec. 21, 2017, 16 pages.
International Preliminary Report on Patentability received for PCT Patent Application No. PCT/US2016/016216, dated May 4, 2017, 14 pages.
International Preliminary Report on Patentability received for PCT Patent Application No. PCT/US2016/017271, dated Sep. 21, 2017, 13 pages.
International Preliminary Report on Patentability received for PCT Patent Application No. PCT/US2016/021403, dated Sep. 21, 2017, 21 pages.
International Preliminary Report on Patentability received for PCT Patent Application No. PCT/US2016/034175, dated Dec. 14, 2017, 14 pages.
International Preliminary Report on Patentability received for PCT Patent Application No. PCT/US2017/035554, dated Dec. 20, 2018, 39 pages.
International Preliminary Report on Patentability received for PCT Patent Application No. PCT/US2017/036608, dated Dec. 27, 2018, 12 pages.
International Preliminary Report on Patentability received for PCT Patent Application No. PCT/US2015/046787, dated Mar. 16, 2017, 19 pages.
International Search Report & Written Opinion received for PCT Patent Application No. PCT/US2016/014997, dated Aug. 31, 2016, 21 pages.
International Search Report and Written Opinion received for PCT Application No. PCT/US2015/034604, dated Nov. 9, 2015, 30 pages.
International Search Report and Written Opinion received for PCT Application No. PCT/US2015/046892, dated Jan. 27, 2016, 20 pages.
International Search Report and Written Opinion received for PCT Patent Application No. PCT/US2008/074341, dated Nov. 27, 2009, 12 pages.
International Search Report and Written Opinion received for PCT Patent Application No. PCT/US2009/039621, dated May 29, 2009, 8 pages.
International Search Report and Written Opinion received for PCT Patent Application No. PCT/US2015/019317, dated Aug. 25, 2015, 24 pages.
International Search Report and Written Opinion received for PCT Patent Application No. PCT/US2015/032474, dated Aug. 19, 2015, 8 pages.
International Search Report and Written Opinion received for PCT Patent Application No. PCT/US2015/034606, dated Dec. 2, 2015, 17 pages.
International Search Report and Written Opinion received for PCT Patent Application No. PCT/US2015/038173 dated Sep. 25, 2015, 13 pages.
International Search Report and Written Opinion received for PCT Patent Application No. PCT/US2015/038174, dated Jan. 18, 2016, 38 pages.
International Search Report and Written Opinion received for PCT Patent Application No. PCT/US2015/041424, dated Mar. 31, 2016, 18 pages.
International Search Report and Written Opinion received for PCT Patent Application No. PCT/US2015/044517, dated Oct. 28, 2015, 13 pages.
International Search Report and Written Opinion received for PCT Patent Application No. PCT/US2015/046262, dated Mar. 15, 2016, 34 pages.
International Search Report and Written Opinion received for PCT Patent Application No. PCT/US2015/046787, dated Apr. 1, 2016, 26 pages.
International Search Report and Written Opinion received for PCT Patent Application No. PCT/US2015/047282, dated May 9, 2016, 33 pages.
International Search Report and Written Opinion received for PCT Patent Application No. PCT/US2015/053353, dated May 9, 2016, 21 pages.
International Search Report and Written Opinion received for PCT Patent Application No. PCT/US2016/016216, dated Jun. 27, 2016, 18 pages.
International Search Report and Written Opinion received for PCT Patent Application No. PCT/US2016/017271, dated Sep. 1, 2016, 18 pages.
International Search Report and Written Opinion received for PCT Patent Application No. PCT/US2016/021403, dated May 12, 2016, 23 pages.
International Search Report and Written Opinion received for PCT Patent Application No. PCT/US2016/034175, dated Oct. 7, 2016, 17 pages.
International Search Report and Written Opinion received for PCT Patent Application No. PCT/US2016/037686, dated Sep. 9, 2016, 19 pages.
International Search Report and Written Opinion received for PCT Patent Application No. PCT/US2017/035554, dated Sep. 22, 2017, 42 pages.
International Search Report and Written Opinion received for PCT Patent Application No. PCT/US2017/036608, dated Oct. 20, 2017, 15 pages.
International Search Report and Written Opinion received for PCT Patent Application No. PCT/US2018/031662, dated Sep. 27, 2018, 17 pages.
International Search Report and Written Opinion received for PCT Patent Application No. PCT/US2015/034607, dated Dec. 1, 2015, 23 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Invitation to Additional Fees and Partial International Search Report received for PCT Patent Application No. PCT/US2015/034604 dated Sep. 4, 2015, 6 pages.
Invitation to Additional Fees and Partial International Search Report received for PCT Patent Application No. PCT/US2015/034606 dated Sep. 9, 2015, 6 pages.
Invitation to Pay Addition Fees and Partial International Search Report received for PCT Patent Application No. PCT/US2016/014997, dated May 2, 2016, 5 pages.
Invitation to Pay Addition Fees and Partial International Search Report received for PCT Patent Application No. PCT/US2016/016216, dated Apr. 20, 2016, 6 pages.
Invitation to Pay Addition Fees and Partial International Search Report received for PCT Patent Application No. PCT/US2018/031662, dated Jul. 16, 2018, 13 pages.
Invitation to Pay Addition Fees received for PCT Patent Application No. PCT/US2017/036608, dated Aug. 14, 2017, 2 pages.
Invitation to Pay Additional Fee received for European Patent Application No. 15747595.5, dated Feb. 9, 2018, 6 pages.
Invitation to Pay Additional Fees and Partial Search Report received for PCT Patent Application No. PCT/US2015/046892, dated Nov. 4, 2015, 5 pages.
Invitation to Pay Additional Fees received for PCT Patent Application No. PCT/US2015/019317, dated May 22, 2015, 7 pages.
Invitation to Pay Additional Fees received for PCT Patent Application No. PCT/US2015/034607, dated Sep. 30, 2015, 4 pages.
Invitation to Pay Additional Fees received for PCT Patent Application No. PCT/US2015/038174, dated Oct. 5, 2015, 5 pages.
Invitation to Pay Additional Fees received for PCT Patent Application No. PCT/US2015/041424, dated Nov. 12, 2015, 6 pages.
Invitation to Pay Additional Fees received for PCT Patent Application No. PCT/US2015/046262, dated Nov. 23, 2015, 7 pages.
Invitation to Pay Additional Fees received for PCT Patent Application No. PCT/US2015/046787, dated Dec. 15, 2015, 8 pages.
Invitation to Pay Additional Fees received for PCT Patent Application No. PCT/US2015/047282, dated Dec. 22, 2015, 7 pages.

(56) References Cited

OTHER PUBLICATIONS

Invitation to Pay Additional Fees received for PCT Patent Application No. PCT/US2015/053353, dated Jan. 21, 2016, 7 pages.
Invitation to Pay Additional Fees received for PCT Patent Application No. PCT/US2016/017271, dated May 25, 2016, 7 pages.
Invitation to Pay Additional Fees received for PCT Patent Application No. PCT/US2016/034175, dated Aug. 11, 2016, 3 pages.
Invitation to Pay Additional Fees received for PCT Patent Application No. PCT/US2017/035554, dated Jul. 20, 2017, 2 pages.
Invitation to Restrict or Pay Additional Fees received for PCT Patent Application No. PCT/US2016/016216, dated Dec. 19, 2016, 9 pages.
"IOS Security", White Paper, Available online at https://web.archive.org/web/20150526223200/http://www.apple.com/business/docs/iOS_Security_Guide.pdf, Apr. 2015, 55 pages.
"IPHONE User Guide for iOS 7.1 Software", available online at https://manuals.info.apple.com/MANUALS/1000/MA1681/en_US/iphone_ios7_user_guide.pdf, Mar. 10, 2014, pp. 1-162.
"IPHONE, User Guide for iOS 7.1 Software", 162 pages.
"IOS 9241-10:1996 Ergonomic Requirements for Office Work with Visual Display Terminals (vdts)—Part 10", Dialogue Principles, International Standard—ISO, Zuerich, CH, vol. 9241-10, May 1, 1996, 17 pages.
"IOS 9241-11:1998 Ergonomic Requirements for Office Work with Visual Display Terminals (vdts)—Part 11", Guidance on usability, International Standard—ISO, Zuerich, CH, vol. 9241-11, Mar. 15, 1998, 27 pages.
"IOS 9241-12:1998 Ergonomic Requirements for Office Work with Visual Display Terminals (vdts)—Part 12", Presentation of Information, International Standard—ISO, Zuerich, CH, vol. 9241-12, Dec. 1, 1998, 52 pages.
IOS 9241-13:1998, "Ergonomic Requirements for Office Work with Visual Display Terminals (vdts)", Part 13: User guidance, International Standard ISO, Zuerich, CH, vol. 9241-13, Jul. 15, 1998, 40 pages.
Jenbsjourney, "Wondering About a Fitbit?", Available at: https://jenbsjourney.blogspot.kr/2013/08/wondering-about-fitbit.html, Aug. 6, 2013, 12 pages.
Joire, Myriam, "Neonode N1m Review", available at <http://www.youtube.com/watch?v=Tj-KS2kflr0>, Jun. 29, 2007, 3 pages.
"Kidizoom Smartwatch", Available online at <URL:https://www.vtechnl.com/media/downloads/Kidizoom-Smart-Watch.pdf>, Jun. 24, 2014, 23 pages.
"Kinect Gesture Commands—Kinect Voice Commands", Xbox Wire, Available Online At: <https://hwcdn.libsyn.com/p/4/4/c/44c89c7f273167b4/Xbox_One_Kinect_Voice_Gesture.pdf?c_id=6458139&cs_id=6458139&expiration=1555411736&hwt=fe78eb09654ea677c9fbf836ad2ed82b > 2013, 2 pages.
"Living Earth", available at: http;//www.livingcarthapp.com/, 2014, 6 pages.
"Microsoft Outlook 2010(tm) a Beginners Guide", Available online at:—http://www.reading.ac.uk/web/files/its/outlook2010.pdf, Apr. 1, 2012, 24 pages.
Microsoft, "Working Screenshot of Microsoft Office 2003", Aug. 19, 2003, 14 pages.
Minutes of Oral Proceedings received for European Patent Application No. 13811085.3, mailed on Sep. 11, 2018, 3 pages.
Minutes of Oral Proceedings received for European Patent Application No. 15771747.1, mailed on Aug. 10, 2018, 11 pages.
Minutes of the Oral Proceedings received for European Application No. 08798713.7, mailed on Aug. 6, 2018, 4 pages.
"Mugs", Online Available at: https://web.archive.org/web/20151029034349/http://le-mugs.com/, Oct. 29, 2015.
"My Calstep", http://www.surprisesoftware.com/mycalstep/, retrieved from the Wayback Machine, May 9, 2007, 2 pages.
Nerdtalk, "The Best Android Clock Widgets", available at: https://www.youtube.com/watch?v=E1bAprWByfU, Apr. 25, 2011, 1 page.
"New, but Unsigned—Easy Stopwatch for Symbian", XP55393563, Available online at http://www.allaboutsymbian.com/flow/item/19490_New_but_unsigned-Easy_StopWatc.php, Mar. 15, 2014, 15 pages.
Non-Final Office Action received for U.S. Appl. No. 14/836,754, dated Nov. 17, 2015, 15 pages.
Non-Final Office Action received for U.S. Appl. No. 15/608,848, dated Nov. 2, 2018, 21 pages.
Non-Final Office Action received for U.S. Appl. No. 11/850,005, dated Apr. 12, 2017, 11 pages.
Non-Final Office Action received for U.S. Appl. No. 11/850,005, dated Mar. 18, 2011, 10 pages.
Non-Final Office Action received for U.S. Appl. No. 11/850,005, dated May 29, 2015, 12 pages.
Non-Final Office Action received for U.S. Appl. No. 11/850,005, dated Nov. 10, 2011, 11 pages.
Non-Final Office Action received for U.S. Appl. No. 11/850,005, dated Oct. 24, 2013, 11 pages.
Non-Final Office Action received for U.S. Appl. No. 12/205,847, dated Oct. 3, 2011, 59 pages.
Non-Final Office Action received for U.S. Appl. No. 12/240,975, dated Mar. 5, 2012, 39 pages.
Non-Final Office Action received for U.S. Appl. No. 14/503,372, dated Dec. 5, 2014, 11 pages.
Non-Final Office Action received for U.S. Appl. No. 14/599,424, dated Jan. 17, 2018, 13 pages.
Non-Final Office Action received for U.S. Appl. No. 14/599,425, dated Jan. 11, 2018, 42 pages.
Non-Final Office Action received for U.S. Appl. No. 14/599,425, dated Mar. 17, 2015, 16 pages.
Non-Final Office Action received for U.S. Appl. No. 14/599,425, dated Oct. 26, 2016, 22 pages.
Non-Final Office Action received for U.S. Appl. No. 14/732,773, dated Jan. 19, 2018, 45 pages.
Non-Final Office Action received for U.S. Appl. No. 14/752,776, dated Jan. 2, 2018, 30 pages.
Non-Final Office Action received for U.S. Appl. No. 14/752,776, dated Nov. 5, 2018, 48 pages.
Non-Final Office Action received for U.S. Appl. No. 14/805,403, dated Nov. 16, 2017, 21 pages.
Non-Final Office Action received for U.S. Appl. No. 14/815,879, dated Dec. 15, 2016, 33 pages.
Non-Final Office Action received for U.S. Appl. No. 14/815,890, dated Dec. 18, 2018, 21 pages.
Non-Final Office Action received for U.S. Appl. No. 14/815,890, dated Jun. 6, 2017, 19 pages.
Non-Final Office Action received for U.S. Appl. No. 14/815,890, dated Oct. 19, 2015, 5 pages.
Non-Final Office Action received for U.S. Appl. No. 14/822,769, dated Feb. 5, 2016, 14 pages.
Non-Final Office Action received for U.S. Appl. No. 14/822,769, dated Jun. 29, 2016, 14 pages.
Non-Final Office Action received for U.S. Appl. No. 14/822,769, dated May 4, 2017, 21 pages.
Non-Final Office Action received for U.S. Appl. No. 14/822,769, dated May 24, 2018, 30 pages.
Non-Final Office Action received for U.S. Appl. No. 14/833,014, dated Mar. 21, 2016, 26 pages.
Non-Final Office Action received for U.S. Appl. No. 14/836,754, dated Aug. 16, 2017, 25 pages.
Non-Final Office Action received for U.S. Appl. No. 14/836,754, dated Oct. 21, 2016, 18 pages.
Non-Final Office Action received for U.S. Appl. No. 14/839,916, dated Feb. 4, 2016, 19 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 14/839,922, dated Feb. 25, 2016, 20 pages.
Non-Final Office Action received for U.S. Appl. No. 14/841,402, dated Jan. 25, 2017, 18 pages.

(56) References Cited

OTHER PUBLICATIONS

Non-Final Office Action received for U.S. Appl. No. 14/841,606, dated Dec. 7, 2017, 30 pages.
Non-Final Office Action received for U.S. Appl. No. 14/841,608, dated Apr. 12, 2017, 9 pages.
Non-Final Office Action received for U.S. Appl. No. 14/841,614, dated Jul. 27, 2017, 13 pages.
Non-Final Office Action received for U.S. Appl. No. 14/841,623, dated Feb. 2, 2017, 17 pages.
Non-Final Office Action received for U.S. Appl. No. 14/863,069, dated Oct. 5, 2017, 19 pages.
Non-Final Office Action received for U.S. Appl. No. 14/864,759, dated Mar. 20, 2018, 20 pages.
Non-Final Office Action received for U.S. Appl. No. 14/869,877, dated Jan. 29, 2016, 18 pages.
Non-Final Office Action received for U.S. Appl. No. 14/869,877, dated Jun. 16, 2017, 17 pages.
Non-Final Office Action received for U.S. Appl. No. 14/869,877, dated Oct. 5, 2018, 19 pages.
Non-Final Office Action received for U.S. Appl. No. 14/870,726, dated Sep. 16, 2016, 12 pages.
Non-Final Office Action received for U.S. Appl. No. 14/870,793, dated Apr. 19, 2016, 17 pages.
Non-Final Office Action received for U.S. Appl. No. 15/128,952, dated Dec. 29, 2017, 13 pages.
Non-Final Office Action received for U.S. Appl. No. 15/183,663, dated Jul. 9, 2018, 13 pages.
Non-Final Office Action received for U.S. Appl. No. 15/352,215, dated Sep. 20, 2018, 31 pages.
Non-Final Office Action received for U.S. Appl. No. 15/614,121, dated Nov. 30, 2018, 28 pages.
Non-Final Office Action received for U.S. Appl. No. 16/103,699, dated Nov. 30, 2018, 14 pages.
Non-Final Office Action received for U.S. Appl. No. 14/815,879, dated Nov. 6, 2015, 35 pages.
Non-Final Office Action received for U.S. Appl. No. 14/815,898, dated Dec. 1, 2015, 22 pages.
Non-Final Office Action received for U.S. Appl. No. 14/815,907, dated Jan. 12, 2016, 22 pages.
Non-Final Office Action received for U.S. Appl. No. 14/815,909, dated Nov. 27, 2015, 12 pages.
Notice of Acceptance received for Australian Patent Application No. 2015267240, dated Apr. 10, 2018, 3 pages.
Notice of Acceptance received for Australian Patent Application No. 2015267671, dated Apr. 4, 2018, 3 pages.
Notice of Acceptance received for Australian Patent Application No. 2015279544, dated Mar. 1, 2018, 3 pages.
Notice of Acceptance received for Australian Patent Application No. 2015312215, dated Oct. 9, 2017, 3 pages.
Notice of Acceptance received for Australian Patent Application No. 2016229847, dated Sep. 12, 2018, 3 pages.
Notice of Acceptance received for Australian Patent Application No. 2016231598, dated Mar. 1, 2018, 3 pages.
Notice of Acceptance received for Australian Patent Application No. 2015279545, dated Feb. 9, 2018, 3 pages.
Notice of Allowance received for Chinese Patent Application No. 201210399033.9, dated Jun. 20, 2016, 3 pages (2 pages of English Translation and 1 page of Official copy).
Notice of Allowance received for Chinese Patent Application No. 201520358505.5, dated Jan. 13, 2016, 3 pages (2 pages of English Translation and 1 page of Official copy).
Notice of Allowance received for Chinese Patent Application No. 201520594249.x, dated Jul. 12, 2016, 4 pages (2 pages of English Translation and 2 pages of Official copy).
Notice of Allowance received for Danish Patent Application No. PA201570495, dated Feb. 22, 2017, 1 page.
Notice of Allowance received for Danish Patent Application No. PA201570496, dated Apr. 18, 2016, 2 pages.
Notice of Allowance received for Danish Patent Application No. PA201570563, dated May 24, 2016, 2 pages.
Notice of Allowance received for Danish Patent Application No. PA201570666, dated Sep. 15, 2016, 1 page.
Notice of Allowance received for Danish Patent Application No. PA201570667, dated Nov. 11, 2016, 2 pages.
Notice of Allowance received for Danish Patent Application No. PA201570668, dated Oct. 30, 2017, 2 pages.
Notice of Allowance received for Japanese Patent Application No. 2016-535045, dated Mar. 2, 2018, 4 pages (1 page of English Translation and 3 pages of Official copy).
Notice of Allowance received for Japanese Patent Application No. 2016-569669, dated Mar. 19, 2018, 4 pages (1 page of English Translation and 3 pages of Official copy).
Notice of Allowance received for Japanese Patent Application No. 2017-505450, dated Mar. 9, 2018, 10 pages (7 pages of English Translation and 3 pages of Official copy).
Notice of Allowance received for Korean Patent Application No. 10-2016-7032902, dated Sep. 7, 2018, 3 pages (1 page of English Translation and 2 pages of Official copy).
Notice of Allowance received for Korean Patent Application No. 10-2016-7033638, dated May 31, 2017, 5 pages (2 pages of English Translation and 3 pages of Official copy).
Notice of Allowance received for Korean Patent Application No. 10-2017-7005939, dated Mar. 30, 2018, 5 pages (2 pages of English Translation and 3 pages of Official copy).
Notice of Allowance received for Netherland Patent Application No. 2019753, dated Jul. 6, 2018, 6 pages (2 pages of English Translation and 4 pages of Official copy).
Notice of Allowance received for Taiwanese Patent Application No. 104108223, dated Jan. 10, 2017, 3 pages (Official copy only).
Notice of Allowance received for Taiwanese Patent Application No. 104117509, dated Mar. 31, 2017, 3 pages (Official copy only).
Notice of Allowance received for Taiwanese Patent Application No. 104123593, dated Oct. 1, 2018, 6 pages (3 pages of English Translation and 3 pages Official copy).
Notice of Allowance received for Taiwanese Patent Application No. 104124962, dated Jul. 27, 2017, 3 pages (Official copy only).
Notice of Allowance received for Taiwanese Patent Application No. 104124963, dated Sep. 28, 2017, 5 pages (1 page of English Translation of Search report and 4 pages of Official copy).
Notice of Allowance received for Taiwanese Patent Application No. 104124995, dated Jul. 27, 2017, 3 pages (Official copy only).
Notice of Allowance received for Taiwanese Patent Application No. 104124997, dated Jun. 16, 2017, 5 pages (1 page of English Translation of Search report and 4 pages of Official copy).
Notice of Allowance received for Taiwanese Patent Application No. 104124998, dated Mar. 31, 2017, 3 pages (Official copy only).
Notice of Allowance received for Taiwanese Patent Application No. 104128519, dated Nov. 20, 2017, 5 pages (2 page of English Translation and 3 pages of Official copy).
Notice of Allowance received for Taiwanese Patent Application No. 104128684, dated Feb. 23, 2017, 3 pages (Official copy only).
Notice of Allowance received for Taiwanese Patent Application No. 104128685, dated May 3, 2017, 3 pages (Official copy only).
Notice of Allowance received for Taiwanese Patent Application No. 104128689, dated Aug. 28, 2018, 5 pages (2 pages of English Translation and 3 pages of Official copy).
Notice of Allowance received for U.S. Appl. No. 12/205,847, dated Aug. 20, 2012, 13 pages.
Notice of Allowance received for U.S. Appl. No. 12/240,975, dated Feb. 28, 2013, 6 pages.
Notice of Allowance received for U.S. Appl. No. 14/599,424, dated Dec. 13, 2018, 6 pages.
Notice of Allowance received for U.S. Appl. No. 14/599,425, dated Dec. 19, 2018, 9 pages.
Notice of Allowance received for U.S. Appl. No. 14/805,403, dated Jul. 11, 2018, 15 pages.
Notice of Allowance received for U.S. Appl. No. 14/815,879, dated Jun. 26, 2017, 8 pages.
Notice of Allowance received for U.S. Appl. No. 14/815,898, dated Dec. 5, 2016, 3 pages.
Notice of Allowance received for U.S. Appl. No. 14/815,898, dated Oct. 24, 2016, 14 pages.

(56) References Cited

OTHER PUBLICATIONS

Notice of Allowance received for U.S. Appl. No. 14/815,907, dated Jul. 28, 2016, 9 pages.
Notice of Allowance received for U.S. Appl. No. 14/815,907, dated Nov. 30, 2016, 2 pages.
Notice of Allowance received for U.S. Appl. No. 14/815,909, dated Jun. 9, 2016, 3 pages.
Notice of Allowance received for U.S. Appl. No. 14/815,909, dated May 3, 2016, 12 pages.
Notice of Allowance received for U.S. Appl. No. 14/815,909, dated May 20, 2016, 2 pages.
Notice of Allowance received for U.S. Appl. No. 14/815,909, dated Sep. 6, 2016, 2 pages.
Notice of Allowance received for U.S. Appl. No. 14/822,769, dated Nov. 29, 2018, 12 pages.
Notice of Allowance received for U.S. Appl. No. 14/836,754, dated May 10, 2018, 27 pages.
Notice of Allowance received for U.S. Appl. No. 14/839,916, dated Aug. 31, 2016, 11 pages.
Notice of Allowance received for U.S. Appl. No. 14/839,916, dated Jan. 10, 2018, 19 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Notice of Allowance received for U.S. Appl. No. 14/841,402, dated Apr. 26, 2018, 16 pages.
Notice of Allowance received for U.S. Appl. No. 14/841,608, dated Nov. 14, 2017, 5 pages.
Notice of Allowance received for U.S. Appl. No. 14/841,614, dated Oct. 24, 2018, 10 pages.
Notice of Allowance received for U.S. Appl. No. 14/841,623, dated Feb. 23, 2018, 8 pages.
Notice of Allowance received for U.S. Appl. No. 14/864,759, dated Dec. 14, 2018, 10 pages.
Notice of Allowance received for U.S. Appl. No. 14/870,726, dated Sep. 11, 2018, 9 pages.
Notice of Allowance received for U.S. Appl. No. 15/616,480, dated Jan. 3, 2019, 8 pages.
Nova, "Tour of the Solar System", Retrieved from <http://www.pbs.org/wgbh/nova/space/tour-solar-system.html>, May 24, 2013, 14 pages.
Npasqua, "Maps: Ability to Swipe Step by Step in Turn-by-turn Mode, 2012, Apple Support Communities", https://discussions.apple.com/thread/4424256?start=O&tstart=0, Oct. 12, 2012, 4 pages.
Oates, Nathan, "Pebbgps", Available online at:—https://pebble.devpost.com/submissions/21694-pebbgps, Mar. 16, 2014, 2 pages.
Office Action received for Australian Patent Application No. 2015101019, dated Oct. 14, 2015, 3 pages.
Office Action received for Australian Patent Application No. 2015100734, dated Jul. 29, 2015, 5 pages.
Office Action received for Australian Patent Application No. 2015101019, dated Apr. 7, 2016, 4 pages.
Office Action received for Australian Patent Application No. 2015101020, dated Oct. 26, 2015, 8 pages.
Office Action received for Australian Patent Application No. 2015101021, dated Apr. 26, 2016, 4 pages.
Office Action received for Australian Patent Application No. 2015101021, dated Oct. 28, 2015, 10 pages.
Office Action received for Australian Patent Application No. 2015267240, dated Apr. 10, 2017, 5 pages.
Office Action received for Australian Patent Application No. 2015267240, dated Mar. 21, 2018, 5 pages.
Office Action received for Australian Patent Application No. 2015267671, dated Apr. 5, 2017, 2 pages.
Office Action received for Australian Patent Application No. 2015279544, dated Apr. 18, 2017, 4 pages.
Office Action received for Australian Patent Application No. 2015279544, dated Feb. 13, 2018, 5 pages.
Office Action received for Australian Patent Application No. 2015298710, dated Apr. 13, 2017, 3 pages.
Office Action received for Australian Patent Application No. 2015298710, dated Feb. 15, 2017, 2 pages.
Office Action received for Australian Patent Application No. 2015298710, dated Nov. 6, 2018, 4 pages.
Office Action received for Australian Patent Application No. 2015298710, dated Sep. 24, 2018, 4 pages.
Office Action received for Australian Patent Application No. 2015312215, dated Oct. 13, 2016, 3 pages.
Office Action received for Australian Patent Application No. 2016100411, dated Jun. 10, 2016, 3 pages.
Office Action received for Australian Patent Application No. 2016100476, dated Jun. 9, 2016, 4 pages.
Office Action received for Australian Patent Application No. 2016100765, dated Aug. 5, 2016, 2 pages.
Office Action received for Australian Patent Application No. 2016100765, dated Dec. 16, 2016, 3 pages.
Office Action received for Australian Patent Application No. 2016100796, dated Aug. 26, 2016, 6 pages.
Office Action received for Australian Patent Application No. 2016100796, dated Feb. 13, 2017, 4 pages.
Office Action received for Australian Patent Application No. 2016215440, dated Mar. 13, 2018, 3 pages.
Office Action received for Australian Patent Application No. 2016229847, dated Jul. 3, 2018, 4 pages.
Office Action received for Australian Patent Application No. 2016231598, dated Apr. 7, 2017, 5 pages.
Office Action received for Australian Patent Application No. 2016270323, dated Nov. 26, 2018, 4 pages.
Office Action received for Australian Patent Application No. 2017100231, dated Apr. 13, 2017, 3 pages.
Office Action received for Australian Patent Application No. 2017100667, dated Aug. 3, 2017, 9 pages.
Office Action received for Australian Patent Application No. 2017101375, dated Dec. 1, 2017, 3 pages.
Office Action received for Australian Patent Application No. 2017101375, dated Feb. 19, 2018, 4 pages.
Office Action received for Australian Patent Application No. 2018100158, dated Apr. 23, 2018, 5 pages.
Office Action received for Australian Patent Application No. 2018200428, dated Mar. 7, 2018, 4 pages.
Office Action received for Australian Patent Application No. 2018200428, dated Nov. 15, 2018, 4 pages.
Office Action received for Australian Patent Application No. 2015101019, dated Feb. 12, 2016, 4 pages.
Office Action received for Australian Patent Application No. 2015279545, dated Apr. 13, 2017, 3 pages.
Office Action received for Chinese Patent Application No. 201520595384.6, dated Mar. 25, 2016, 3 pages (1 page of English Translation and 2 pages of Official copy).
Office Action received for Chinese Patent Application No. 201210399033.9, dated Nov. 27, 2014, 7 pages (Official copy only).
Office Action received for Chinese Patent Application No. 201210399033.9, dated Oct. 8, 2015, 8 pages (3 pages of English Translation and 5 pages of Official copy).
Office Action received for Chinese Patent Application No. 201510284850.3, dated Jul. 9, 2018, 11 pages (2 pages of English Translation and 9 pages of Official copy).
Office Action received for Chinese Patent Application No. 201510284850.3, dated Nov. 28, 2017, 15 pages (5 pages of English Translation and 10 pages of Official copy).
Office Action received for Chinese Patent Application No. 201510479088.4, dated Mar. 12, 2018, 20 pages (6 pages of English Translation and 14 pages of Official copy).
Office Action received for Chinese Patent Application No. 201510481525.6, dated Aug. 29, 2018, 10 pages (5 pages of English Translation and 5 pages of Official copy).
Office Action received for Chinese Patent Application No. 201510481525.6, dated Nov. 29, 2017, 9 pages (3 pages of English Translation and 6 pages of Official copy).

(56) References Cited

OTHER PUBLICATIONS

Office Action received for Chinese Patent Application No. 201510483268.x, dated Dec. 1, 2017, 11 pages (5 pages of English Translation and 6 pages of Official copy).
Office Action received for Chinese Patent Application No. 201510483268.x, dated Oct. 19, 2018, 10 pages (5 pages of English Translation and 5 pages of Official copy).
Office Action received for Chinese Patent Application No. 201510483305.7, dated Aug. 31, 2018, 10 pages (5 pages of English Translation and 5 pages of Official copy).
Office Action received for Chinese Patent Application No. 201510483305.7, dated Dec. 1, 2017, 13 pages (5 pages of English Translation and 8 pages of Official copy).
Office Action received for Chinese Patent Application No. 201510484514.3, dated Apr. 4, 2018, 12 pages (5 pages of English Translation and 7 pages of Official copy).
Office Action received for Chinese Patent Application No. 201510557356.x, dated Dec. 29, 2017, 11 pages (5 pages of English Translation and 6 pages of Official copy).
Office Action received for Chinese Patent Application No. 201520594249.x, dated Mar. 25, 2016, 3 pages (1 page of English Translation and 2 pages of Official copy).
Office Action received for Chinese Patent Application No. 201520595384.6, dated Dec. 30, 2016, 2 pages (Official copy only).
Office Action received for Chinese Patent Application No. 201520595384.6, dated Jul. 22, 2016, 3 pages (1 page of English Translation and 2 pages of Official copy).
Office Action received for Chinese Patent Application No. 201520595385.0, dated Dec. 30, 2016, 2 pages (Official copy only).
Office Action received for Chinese Patent Application No. 201520595385.0, dated Jul. 22, 2016, 3 pages (1 page of English Translation and 2 pages of Official copy).
Office Action received for Chinese Patent Application No. 201520595385.0, dated Mar. 25, 2016, 3 pages (1 page of English Translation and 2 pages of Official copy).
Office Action received for Chinese Patent Application No. 201520595408.8, dated Dec. 9, 2015, 4 pages. (2 pages of English Translation and 2 pages of Official copy).
Office Action received for Chinese Patent Application No. 201520595408.8, dated Dec. 30, 2016, 2 pages (Official copy only).
Office Action received for Chinese Patent Application No. 201520595408.8, dated Jul. 25, 2016, 3 pages (1 page of English Translation and 2 pages of Official copy).
Office Action received for Chinese Patent Application No. 201520595408.8, dated Mar. 25, 2016, 3 pages (1 page of English Translation and 2 pages of Official copy).
Office Action received for Chinese Patent Application No. 201520595538.1, dated Dec. 30, 2016, 2 pages (Official copy only).
Office Action received for Chinese Patent Application No. 201520595538.1, dated Jul. 22, 2016, 3 pages (1 page of English Translation and 2 pages of Official copy).
Office Action received for Chinese Patent Application No. 201520595538.1, dated Mar. 25, 2016, 3 pages (1 page of English Translation and 2 pages of Official copy).
Office Action received for Chinese Patent Application No. 201520679198.0, dated Jun. 24, 2016, 5 pages (3 pages of English Translation and 2 pages of Official copy).
Office Action received for Chinese Patent Application No. 201520679198.0, dated Mar. 7, 2016, 6 pages (4 pages of English Translation and 2 pages of Official copy).
Office Action received for Chinese Patent Application No. 201520679198.0, dated Nov. 18, 2015, 4 pages (2 pages English Translation and 2 pages Official copy).
Office Action received for Chinese Patent Application No. 201580028677.9, dated May 25, 2018, 14 pages (4 pages of English Translation and 10 pages of Official copy).
Office Action received for Chinese Patent Application No. 201580037927.5, dated Jul. 20, 2018, 21 pages (6 pages of English Translation and 15 pages of Official copy).
Office Action received for Chinese Patent Application No. 201620509515.9, dated Nov. 9, 2016, 2 pages (1 page of English Translation and 1 page of Official copy).
Office Action received for Chinese Patent Application No. 201621208900.6, dated Apr. 26, 2017, 2 pages (Official copy only).
Office Action received for Chinese Patent Application No. 201520594249.x, dated Dec. 9, 2015, 4 pages (2 pages of English Translation and 2 pages of Official copy).
Office Action received for Chinese Patent Application No. 201520595384.6, dated Dec. 9, 2015, 4 pages. (2 pages of English Translation and 2 pages of Official copy).
Office Action received for Chinese Patent Application No. 201520595385.0, dated Dec. 9, 2015, 4 pages (2 pages of English Translation and 2 pages of Official copy).
Office Action received for Chinese Patent Application No. 201520595538.1, dated Dec. 9, 2015, 4 pages (2 pages of English Translation and 2 pages of Official copy).
Office Action received for Danish Patent Application No. PA201570495, dated Dec. 9, 2016, 2 pages.
Office Action received for Danish Patent Application No. PA201570495, dated May 4, 2016, 8 pages.
Office Action received for Danish Patent Application No. PA201570495, dated Oct. 29, 2015, 7 pages.
Office Action received for Danish Patent Application No. PA201570497, dated Feb. 21, 2017, 3 pages.
Office Action received for Danish Patent Application No. PA201570497, dated May 17, 2016, 6 pages.
Office Action received for Danish Patent Application No. PA201570497, dated Nov. 15, 2016, 2 pages.
Office Action received for Danish Patent Application No. PA201570497, dated Oct. 24, 2017, 2 pages.
Office Action received for Danish Patent Application No. PA201570498, dated Feb. 6, 2017, 2 pages.
Office Action received for Danish Patent Application No. PA201570498, dated Jun. 2, 2016, 8 pages.
Office Action received for Danish Patent Application No. PA201570498, dated Oct. 26, 2017, 5 pages.
Office Action received for Danish Patent Application No. PA201570498, dated Oct. 30, 2015, 7 pages.
Office Action received for Danish Patent Application No. PA201570499, dated Feb. 14, 2017, 2 pages.
Office Action received for Danish Patent Application No. PA201570499, dated Jun. 16, 2016, 8 pages.
Office Action received for Danish Patent Application No. PA201570499, dated Jun. 19, 2018, 4 pages.
Office Action received for Danish Patent Application No. PA201570499, dated Nov. 1, 2017, 6 pages.
Office Action received for Danish Patent Application No. PA201570499, dated Nov. 3, 2015, 7 pages.
Office Action received for Danish Patent Application No. PA201570665, dated Mar. 31, 2016, 9 pages.
Office Action received for Danish Patent Application No. PA201570665, dated Sep. 5, 2016, 3 pages.
Office Action received for Danish Patent Application No. PA201570666, dated Feb. 2, 2016, 9 pages.
Office Action received for Danish Patent Application No. PA201570666, dated Jun. 27, 2016, 4 pages.
Office Action received for Danish Patent Application No. PA201570667, dated Apr. 1, 2016, 7 pages.
Office Action received for Danish Patent Application No. PA201570667, dated Sep. 2, 2016, 2 pages.
Office Action received for Danish Patent Application No. PA201570668, dated Apr. 8, 2016, 8 pages.
Office Action received for Danish Patent Application No. PA201570668, dated Sep. 9, 2016, 3 pages.
Office Action received for Danish Patent Application No. PA201670319, dated Aug. 2, 2016, 6 pages.
Office Action received for Danish Patent Application No. PA201670319, dated Jun. 21, 2017, 6 pages.
Office Action received for Danish Patent Application No. PA201670319, dated Nov. 24, 2016, 7 pages.
Office Action received for Danish Patent Application No. PA201670320, dated Aug. 4, 2016, 9 pages.

(56) References Cited

OTHER PUBLICATIONS

Office Action received for Danish Patent Application No. PA201670320, dated Dec. 5, 2016, 4 pages.
Office Action received for Danish Patent Application No. PA201670320, dated Jan. 18, 2018, 2 pages.
Office Action received for Danish Patent Application No. PA201670320, dated Jul. 3, 2017, 4 pages.
Office Action received for Danish Patent Application No. PA201670362, dated Jan. 29, 2018, 3 pages.
Office Action received for Danish Patent Application No. PA201670362, dated Jun. 1, 2017, 6 pages.
Office Action received for Danish Patent Application No. PA201670362, dated Nov. 21, 2016, 11 pages.
Office Action received for Danish Patent Application No. PA201670656, dated Jun. 14, 2017, 3 pages.
Office Action received for Danish Patent Application No. PA201670656, dated May 30, 2018, 5 pages.
Office Action received for Danish Patent Application No. PA201670656, dated Nov. 3, 2016, 8 pages.
Office Action received for Danish Patent Application No. PA201670749, dated Jan. 30, 2017, 11 pages.
Office Action received for Danish Patent Application No. PA201670749, dated Oct. 3, 2017, 3 pages.
Office Action received for Danish Patent Application No. PA201670751, dated Jan. 13, 2017, 9 pages.
Office Action received for Danish Patent Application No. PA201670751, dated Nov. 13, 2017, 2 pages.
Office Action received for Danish Patent Application No. PA201770191, dated Jan. 25, 2018, 3 pages.
Office Action received for Danish Patent Application No. PA201770191, dated Nov. 21, 2018, 4 pages.
Office Action received for Danish Patent Application No. PA201770423, dated Jun. 12, 2018, 7 pages.
Office Action received for Danish Patent Application No. PA201570496, dated Oct. 29, 2015, 6 pages.
Office Action received for Danish Patent Application No. PA201570497, dated Oct. 30, 2015, 6 pages.
Office Action received for European Patent Application No. 08798713.7, dated Feb. 9, 2012, 7 pages.
Office Action received for European Patent Application No. 08798713.7, dated Jul. 29, 2014, 18 pages.
Office Action received for European Patent Application No. 08798713.7, dated Jun. 22, 2011, 10 pages.
Office Action received for European Patent Application No. 13174706.5, dated Oct. 16, 2017, 8 pages.
Office Action received for European Patent Application No. 13811085.3, dated Apr. 20, 2018, 15 pages.
Office Action received for European Patent Application No. 15711969.4, dated Nov. 17, 2017, 9 pages.
Office Action received for European Patent Application No. 15730890.9, dated Aug. 3, 2017, 4 pages.
Office Action received for European Patent Application No. 15730924.6, dated Dec. 12, 2017, 8 pages.
Office Action received for European Patent Application No. 15730925.3, dated Apr. 12, 2018, 8 pages.
Office Action received for European Patent Application No. 15739109.5, dated Jan. 31, 2018, 7 pages.
Office Action received for European Patent Application No. 15739110.3, dated Jan. 31, 2018, 8 pages.
Office Action received for European Patent Application No. 15747595.5, dated Jun. 27, 2018, 8 pages.
Office Action received for European Patent Application No. 15759998.6, dated Dec. 19, 2018, 6 pages.
Office Action received for European Patent Application No. 15759998.6, dated Jul. 16, 2018, 6 pages.
Office Action received for European Patent Application No. 16190252.3, dated Feb. 19, 2018, 7 pages.
Office Action received for European Patent Application No. 18154145.9, dated Apr. 3, 2018, 6 pages.
Office Action received for European Patent Application No. 15771747.1, dated Oct. 31, 2017, 7 pages.
Office Action received for German Patent Application No. 112015003083.2, dated Mar. 9, 2018, 12 pages (5 pages of English Translation and 7 pages of Official copy).
Office Action received for Japanese Patent Application No. 2016-535045, dated May 12, 2017, 10 pages (5 pages of English Translation and 5 pages of Official copy).
Office Action received for Japanese Patent Application No. 2016-557650, dated Apr. 13, 2018, 9 pages (5 pages of English Translation and 4 pages of Official copy).
Office Action received for Japanese Patent Application No. 2016-557650, dated Aug. 10, 2017, 10 pages (5 pages of English Translation and 5 pages of Official copy).
Office Action received for Japanese Patent Application No. 2016-557650, dated Nov. 9, 2018, 6 pages (3 pages of English Translation and 3 pages of Official copy).
Office Action received for Japanese Patent Application No. 2016-569945, dated Nov. 10, 2017, 8 pages (4 pages of English Translation and 4 pages of Official copy).
Office Action received for Japanese Patent Application No. 2016-569945, dated Sep. 10, 2018, 11 pages (6 pages of English Translation and 5 pages of Official copy).
Office Action received for Japanese Patent Application No. 2017-505450, dated Jun. 20, 2017, 8 pages (4 pages of English Translation and 4 pages of Official copy).
Office Action received for Japanese Patent Application No. 2017-510631, dated Mar. 2, 2018, 12 pages (7 pages of English Translation and 5 pages of Official copy).
Office Action received for Japanese Patent Application No. 2017-545918, dated Sep. 14, 2018, 12 pages (7 pages of English Translation and 5 pages of Official copy).
Office Action received for Japanese Patent Application No. 2018-014096, dated Jun. 29, 2018, 20 pages (11 pages of English Translation and 9 pages of Official copy).
Office Action received for Japanese Patent Application No. 2018-014096, dated Nov. 6, 2018, 15 pages (7 pages of English Translation and 8 pages of Official copy).
Office Action received for Japanese Patent Application No. 2018-107114, dated Oct. 9, 2018, 4 pages (2 pages of English Translation and 2 pages of Official copy).
Office Action received for Korean Patent Application No. 10-2016-7014577, dated Dec. 26, 2017, 14 pages (6 pages of English Translation and 8 pages of Official copy).
Office Action received for Korean Patent Application No. 10-2016-7014577, dated Oct. 31, 2018, 11 pages (5 pages of English Translation and 6 pages of Official copy).
Office Action received for Korean Patent Application No. 10-2016-7033638, dated Jan. 31, 2017, 6 pages (2 pages of English Translation and 4 pages of Official copy).
Office Action received for Korean Patent Application No. 10-2017-7005939, dated Jun. 30, 2017, 6 pages (2 pages of English Translation and 4 pages of Official copy).
Office Action received for Korean Patent Application No. 10-2017-7024570, dated Sep. 28, 2018, 14 pages (6 pages of English Translation and 8 pages of Official copy).
Office Action received for Netherland Patent Application No. 2015245, dated Jan. 24, 2017, 11 pages (1 page of English Translation and 10 pages of Official copy).
Office Action received for Netherland Patent Application No. 2019753, dated Apr. 12, 2018, 8 pages (3 page of English Translation and 5 pages of Official copy).
Office Action received for Netherlands Patent Application No. 2015239, dated Oct. 28, 2016, 13 pages (5 pages of English Translation and 8 pages of Official copy).
Office Action received for Taiwanese Patent Application No. 104108223, dated Apr. 25, 2016, 10 pages (5 pages of English Translation and 5 pages of Official copy).
Office Action received for Taiwanese Patent Application No. 104117509, dated Aug. 22, 2016, 6 pages (3 pages of English Translation and 3 pages of Official copy).

(56) References Cited

OTHER PUBLICATIONS

Office Action received for Taiwanese Patent Application No. 104123593, dated May 24, 2016, 57 pages (26 pages of English Translation and 31 pages of Official copy).
Office Action received for Taiwanese Patent Application No. 104123593, dated Sep. 13, 2016, 8 pages (3 pages of English Translation and 5 pages of Official copy).
Office Action received for Taiwanese Patent Application No. 104124962, dated Nov. 29, 2016, 6 pages (3 pages of English Translation and 3 pages of Official copy).
Office Action received for Taiwanese Patent Application No. 104124963, dated Jan. 5, 2017, 11 pages (5 pages of English Translation and 6 pages of Official copy).
Office Action received for Taiwanese Patent Application No. 104124995, dated Dec. 1, 2016, 6 pages (3 pages of English Translation and 3 pages of Official copy).
Office Action received for Taiwanese Patent Application No. 104124997, dated Dec. 8, 2016, 12 pages (5 pages of English Translation and 7 pages of Official copy).
Office Action received for Taiwanese Patent Application No. 104124998, dated Nov. 29, 2016, 6 pages (3 pages of English Translation and 3 pages of Official copy).
Office Action received for Taiwanese Patent Application No. 104128519, dated Mar. 29, 2017, 16 pages (7 pages of English Translation and 9 pages of Official copy).
Office Action received for Taiwanese Patent Application No. 104128684, dated Nov. 8, 2016, 24 pages (9 pages of English Translation and 15 pages of Official copy).
Office Action received for Taiwanese Patent Application No. 104128685, dated Jan. 4, 2017, 40 pages (15 pages of English Translation and 25 pages of Official copy).
Office Action received for Taiwanese Patent Application No. 104128689, dated Aug. 21, 2017, 8 pages (3 pages of English Translation and 5 pages of Official copy).
Office Action received for Taiwanese Patent Application No. 104128689, dated Nov. 14, 2016, 12 pages (5 pages of English Translation and 7 pages of Official copy).
Office Action received for Taiwanese Patent Application No. 104128705, dated Aug. 29, 2016, 18 pages (7 pages of English Translation and 11 pages of Official copy).
Office Action received for Taiwanese Patent Application No. 104128705, dated Mar. 16, 2017, 3 pages (Official copy only).
Office Action received for Taiwanese Patent Application No. 104132636, dated Mar. 23, 2017, 25 pages (10 pages of English Translation and 15 pages of Official copy).
Office Action received for Taiwanese Patent Application No. 104132636, dated Oct. 31, 2017, 10 pages (4 pages of English Translation and 6 pages of Official copy).
Office Action received for Taiwanese Patent Application No. 104120843, dated Jan. 30, 2016, 5 pages (1 page of English Translation of Search Report and 4 pages of Official copy).
Office Action Received for Australian Patent Application no. 2015101183, dated Nov. 6, 2015, 4 pages.
PA201570497, "Link to Wayback Machine with Link to Google Play Showing Different Layouts of Complications Associated with a Clock Face", available online at <https://play.google.com/store/apps/details?id=com.levelup.beautifulwidgets.free&hl=da >, Sep. 9, 2013, 6 pages.
Park, Will, "Neonode N2 Unboxing Pics!", available at <http://www.intomobile.com/2007/07/18/neonode-n2-unboxing-pics/>, Jul. 18, 2007, 7 pages.
"Pentax K20d Operating Manual", http://www.ricoh-imaging.eu/en/operating-manuals-download.html, 2008, pp. 173-174.
Pre-interview First Office Action received for U.S. Appl. No. 14/815,890, dated May 26, 2016, 4 pages.
Rainmaker, "Garmin Fenix3 New Auto Climb Functionality", Available online at: https://www.youtube.com/watch?v=iuavOSNpVRc, Feb. 19, 2015, 1 page.

Razykdreviews, "In Depth Review of Apple Watch Activity and Workout App", available at <URL: https://www.youtube.com/watch?v=GkKI3qlK0ow>, May 11, 2015, 1 page.
Rehman, A, "Install Android 4.2 Gesture-based Keyboard & Clock App on Jelly Bean 4.1 or Higher", Excerpts From, Available online at <http://www.addictivetips.com/android/install-android-4-2-keyboard-clock-app-apk-on-jelly-bean-4-1-x/>, Nov. 3, 2012, 4 pages.
"Responding to a Meeting Invitation", Available online at:—https://web.archive.org/web/20121128174157/https://www.zimbra.com/desktop7/help/en_US/Calendar/Responding_to_an_invitation.htm, Nov. 28, 2012, 1 page.
Restriction Requirement received for U.S. Appl. No. 14/815,890, dated Feb. 22, 2016, 5 Pages, 5 pages.
"Reuse Animations—Synfig Animation Studio", Available online at: https://wiki.synfig.org/index.php?title=Doc:Reuse_Animations&oldid=18173, May 20, 2013, 5 pages.
Rizknows, "Garmin Connect Mobile App—Review #2", https://www.youtube.com/watch?v=7my3wMpeRbE, Oct. 22, 2015, 1 page.
Rizknows, "Tom Tom Multisport Cardio Review", Online available at:—https://www.youtube.com/watch?v=WoVCzLrSN9A, Sep. 4, 2015, 1 page.
Samsung, "Sm-g900f User Manual", English (EU). Rev.1.0, Mar. 2014, 249 pages.
Search Report and Opinion received for Danish Patent Application No. PA201770191, dated Jun. 30, 2017, 9 pages.
Search Report and Opinion received for Danish Patent Application No. PA201770423, dated Oct. 4, 2017, 10 pages.
Search Report and Opinion received for Netherland Patent Application No. 2015232, dated Jan. 25, 2017, 9 pages (1 page of English Translation and 8 pages of Official copy).
Search Report and Opinion received for Netherlands Patent Application No. 2015242, dated Jul. 4, 2017, 20 pages (10 pages of English Translation of Search Opinion and 10 pages of Official copy).
Search Report and Opinion received for Netherlands Patent Application No. 2015364, dated Jul. 4, 2017, 12 pages (5 pages of English Translation of Search Opinion and 7 pages of Official copy).
Search Report and Opinion received for Netherlands Patent Application No. 2018531, dated Jul. 27, 2017, 14 pages (6 pages of English Translation and 8 pages of Official copy).
Shankland, Stephen, "Chrome OS Gets 'ok Google' Voice Search Control", available online at <http://www.cnet.com/news/chrome-os-gets-ok-google-voice-search-control/>, May 21, 2014, 4 pages.
Shen et al., "Informing the Design of Direct-touch Tabletops", IEEE Sep./Oct. 2006, Sep./Oct. 2006, pp. 36-46.
Smartwatch, "App Earth Space HD Live Wallpaper Apk for Smart Watch", Version 1.7, Android version 2.2, Aug. 27, 2013, 1 page.
Smith, "Garmin Fenix 5 Activity/smart Watch Review", Online Available at:—https://www.youtube.com/watch?v=6PkQxXQxpoU, Sep. 2, 2017, 1 page.
"Solar Walk Free", Vito Technology, Jun. 19, 2014, 9 pages.
Sony, "Live View™ Micro Display", Extended User Guide, Aug. 2010, 27 pages.
Sony, "Sony Smartwatch", User Guide, Dec. 2011, 18 pages.
Sportstechguides, "Garmin Fenix 5: How to Add Power Data Fields", Online Available at:—https://www.youtube.com/watch?v=ZkPptnnXEiQ, Apr. 29, 2017, 2 pages.
Sportstechguides, "Garmin Fenix 5: How to Set Up Run Alerts", Online Available at:—https://www.youtube.com/watch?v=gSMwv8vlhB4, May 13, 2017, 2 pages.
Studio 39, "Clock & Calendar for Smartwatch 2", https://www.youtube.com/watch?v=Uj-K2vMnrj8, Nov. 20, 2013, 2 pages.
Summons to Attend Oral Proceedings received for European Patent Application No. 08798713.7, mailed on Mar. 26, 2018, 11 pages.
Summons to Attend Oral Proceedings received for European Patent Application No. 13811085.3, mailed on Jan. 26, 2018, 14 pages.
Summons to Attend Oral Proceedings received for European Patent Application No. 15711969.4, mailed on Oct. 22, 2018, 12 pages.
Summons to Attend Oral Proceedings received for European Patent Application No. 15730890.9, mailed on Sep. 10, 2018, 11 pages.
Summons to Attend Oral Proceedings received for European Patent Application No. 15730924.6, mailed on Jun. 13, 2018, 10 pages.

(56) References Cited

OTHER PUBLICATIONS

Summons to Attend Oral Proceedings received for European Patent Application No. 15739109.5, mailed on Aug. 23, 2018, 9 pages.
Summons to Attend Oral Proceedings received for European Patent Application No. 15739109.5, mailed on Oct. 4, 2018, 3 pages.
Summons to Attend Oral Proceedings received for European Patent Application No. 15739110.3, mailed on Aug. 23, 2018, 10 pages.
Summons to Attend Oral Proceedings received for European Patent Application No. 15739110.3, mailed on Oct. 2, 2018, 3 pages.
Summons to Attend Oral Proceedings received for European Patent Application No. 16190252.3, mailed on Oct. 30, 2018, 13 pages.
Summons to Attend Oral Proceedings received for European Patent Application no. 15771747.1, mailed on May 25, 2018, 17 pages.
Sun Set, "Sun Set Solar Image Clock", Available at <https://web.archive.orgjweb/20140719005410/http://www.sunsetclock.com/>, 2013, 5 pages.
Supplemental Notice of Allowance received for U.S. Appl. No. 14/805,403, dated Oct. 4, 2018, 3 pages.
Supplemental Notice of Allowance received for U.S. Appl. No. 14/841,608, dated Jan. 25, 2018, 2 pages.
Supplemental Notice of Allowance received for U.S. Appl. No. 15/616,480, dated Mar. 28, 2019, 2 pages.
"Suunto Spartan Trainer Wrist Hr 1.12", Online Available at:—https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones", Online Available at: https://www.youtube.com/watch?v=aixfoCnS0OU, Mar. 19, 2018, 2 page.
Tablet Talk, "Tablet Talk App: Frequently Asked Questions—tablet Talk.", available at https://web.archive.org/web/20140625102903/http://1www.tablettalapp.com/faq, Jun. 25, 2014, pp. 1-6.
Talkandroid, "Android Wear Walkthrough", Available online at: https://www.youtube.com/watch?v=4xntpZac4sw, Jun. 30, 2014, 1 page.
The Gadget Pill, "Sygic for Android Navigation with Hud", Available online at:—https://www.youtube.com/watch?v=fGqrycRevGU, Mar. 23, 2014, 1 page.
Tomtom, "Tomtom Runner & Multi-sport Reference Guide", Online available at:—https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
"Tropical Fish 14", Available online at: https://www.turbosquid.com/3d-models/tropical-fish-3d-models/388510, Feb. 4, 2008, 2 pages.
Tweedie, Steven, "Create and Customize Your Own Emojis with 'makemoji' for iphone", Available online at: http://www.businessinsider.com/create-custom-emojis-with-makemoji-app-2014-8, Aug. 19, 2014, 6 pages.
"Uikit User Interface Catalog: Page Controls", Available online at https://web.archive.org/web/20140703123442/https://developer.apple.com/library/ios/documentation/userexperience/conceptual/UIKitUICatalog/UIPageControl.html, Dec. 16, 2013, 4 pages.
"Utilization of Galaxy S4-S Health, Chaton and Samsung Hub", Available at: http://seeit.kr/1263, Jun. 12, 2013, 25 pages (Official copy only).
Viticci, Frederico, "Checking Time Zones with Living Earth—Macstories", Available at <https://www.macstories.net/reviews/checking-time-zones-with-living-earth/>, Dec. 11, 2013, pp. 1-5.
Whitwam, Ryan, "Facer is Fast Becoming the De Facto Custom Watch Face Maker for Android Wear", Available online at: http://www.androidpolice.com/2014/09/19/facer-is-fast-becoming-the-de-facto-custom-watch-face-maker-for-android-wear, Sep. 19, 2014, 11 pages.
Written Opinion issued from International Preliminary Examining Authority for PCT Application No. PCT/US2016/016216, dated Feb. 20, 2017, 12 pages.
Zlelik, "Garmin Fenix 5 Open Water Swimming Activity Demo", Online Available at:—https://www.youtube.com/watch?v=iSVhdvw2dcs, Jun. 9, 2017, 1 page.
Zukerman, Erez, "6 Beautiful, Interesting & Versatile Timer Apps [android]", available at:http://www.makeuseof.com/tag/beautiful-interesting-versatile-timer-apps-android/, May 18, 2012, 5 pages.
Final Office Action received for U.S. Appl. No. 14/732,773, dated Jun. 21, 2019, 32 pages.
Final Office Action received for U.S. Appl. No. 15/608,848, dated Jun. 26, 2019, 27 pages.
Non-Final Office Action received for U.S. Appl. No. 15/627,069, dated Jun. 21, 2019, 22 pages.
Notice of Allowance received for Korean Patent Application No. 10-2016-7014577, dated May 30, 2019, 5 pages (2 pages of English Translation and 3 pages of Official Copy).
Notice of Allowance received for U.S. Appl. No. 14/863,069, dated Jun. 18, 2019, 6 pages.
Office Action received for Korean Patent Application No. 10-2017-7034558, dated Jun. 4, 2019, 7 pages (3 pages of English Translation and 4 pages of Official Copy).
Decision to Grant received for European Patent Application No. 15739110.3, dated Sep. 19, 2019, 2 pages.
"Fitbit App", Available online at: http://web.archive.org/web/20180114083150/https://www.fitbit.com/au/app, Jan. 14, 2018, 8 pages.
Intention to Grant received for European Patent Application No. 15739110.3, dated Sep. 11, 2019, 6 pages.
International Search Report and Written Opinion received for PCT Patent Application No. PCT/US2019/024790, dated Sep. 11, 2019, 18 pages.
Non-Final Office Action received for U.S. Appl. No. 16/144,849, dated Sep. 17, 2019, 9 pages.
Notice of Acceptance received for Australian Patent Application No. 2018202751, dated Sep. 4, 2019, 3 pages.
Office Action received for Australian Patent Application No. 2018204286, dated Sep. 5, 2019, 5 pages.
Office Action received for Australian Patent Application No. 2019100495, dated Sep. 17, 2019, 7 pages.
Office Action received for Japanese Patent Application No. 2018-080122, dated Aug. 9, 2019, 5 pages (2 pages of English Translation and 3 pages of Official Copy).
Advisory Action received for U.S. Appl. No. 15/554,204, dated Mar. 12, 2020, 3 pages.
Applicant Initiated Interview Summary received for U.S. Appl. No. 16/265,938, dated Mar. 11, 2020, 5 pages.
Corrected Notice of Allowance received for U.S. Appl. No. 15/600,243, dated Mar. 13, 2020, 3 pages.
Decision to Refuse received for European Patent Application No. 19190231.1, dated Jan. 14, 2020, 2 pages.
Final Office Action received for U.S. Appl. No. 15/627,069, dated Mar. 2, 2020, 22 pages.
Non-Final Office Action received for U.S. Appl. No. 16/138,809, dated Feb. 28, 2020, 22 pages.
Non-Final Office Action received for U.S. Appl. No. 16/144,753, dated Mar. 5, 2020, 9 pages.
Non-Final Office Action received for U.S. Appl. No. 16/145,033, dated Mar. 4, 2020, 50 pages.
Notice of Acceptance received for Australian Patent Application No. 2018204286, dated Feb. 27, 2020, 3 pages.
Notice of Allowance received for Chinese Patent Application No. 201510557356.X, dated Mar. 5, 2020, 2 pages (1 page of English Translation and 1 pages of Official Copy).
Notice of Allowance received for Chinese Patent Application No. 201810105846.X, dated Feb. 18, 2020, 2 pages (1 page of English Translation and 1 page of Official Copy).
Notice of Allowance received for U.S. Appl. No. 15/614,121, dated Mar. 6, 2020, 8 pages.
Notice of Allowance received for U.S. Appl. No. 16/144,849, dated Mar. 6, 2020, 9 pages.
Office Action received for Australian Patent Application No. 2019100495, dated Mar. 6, 2020, 3 pages.
Office Action received for Danish Patent Application No. PA201870380, dated Mar. 5, 2020, 2 pages.
Office Action received for Japanese Patent Application No. 2019-162293, dated Jan. 31, 2020, 8 pages (4 pages of English Translation and 4 pages of Official Copy).

(56) References Cited

OTHER PUBLICATIONS

Office Action received for Korean Patent Application No. 10-2019-7025538, dated Feb. 17, 2020, 12 pages (6 pages of English Translation and 6 pages of Official Copy).
Supplemental Notice of Allowance received for U.S. Appl. No. 14/833,014, dated Mar. 12, 2020, 2 pages.
Wesley, "Apple Watch Series 1", Online available at: http://toolbox.info/blog/archives/1737-unknown.html, May 28, 2015, 5 pages (Official copy only) (See Communication under 37 CFR § 1.98(a) (3)).
Youtube, "Apple Watch Series 3", Online available at: https://www.youtube.com/watch?v=iBPr9gEfkK8, Nov. 21, 2017, 15 pages (Official copy only) (See Communication under 37 CFR § 1.98(a) (3)).
Decision to Grant received for Danish Patent Application No. PA201870385, dated Mar. 26, 2020, 2 pages.
Examiner's Pre-Review Report received for Japanese Patent Application No. 2018-080122, dated Feb. 25, 2020, 6 pages (3 pages of English Translation and 3 pages of Official Copy).
Extended European Search Report received for European Patent Application No. 19203942.8, dated Apr. 1, 2020, 10 pages.
Final Office Action received for U.S. Appl. No. 16/265,938, dated Apr. 7, 2020, 45 pages.
Non-Final Office Action received for U.S. Appl. No. 16/389,722, dated Apr. 3, 2020, 15 pages.
Non-Final Office Action received for U.S. Appl. No. 16/407,590, dated Apr. 10, 2020, 12 pages.
Notice of Acceptance received for Australian Patent Application No. 2018206772, dated Mar. 17, 2020, 3 pages.
Supplemental Notice of Allowance received for U.S. Appl. No. 16/588,950, dated Apr. 1, 2020, 2 pages.
Vanhemert, Kyle, "Why Siri Could Be the Killer App for Smartwatches", XP002798416, Retrieved from the Internet: URL: https://www.wired.com/2013/12/what-can-a-smartwatch-really-do/, Dec. 19, 2013, 14 pages.
Advisory Action received for U.S. Appl. No. 14/863,099, dated Sep. 8, 2016, 3 pages.
Advisory Action received for U.S. Appl. No. 16/144,849, dated Aug. 12, 2019, 5 pages.
Decision on Acceptance received for Australian Patent Application No. 2015298710, dated Jul. 19, 2019, 18 pages.
Examiner's Answer to Appeal Brief received for U.S. Appl. No. 14/774,664, dated May 31, 2018, 28 pages.
Examiner's Answer to Appeal Brief received for U.S. Appl. No. 14/863,099, dated Jul. 28, 2017, 31 pages.
Final Office Action received for U.S. Appl. No. 14/774,664, dated Aug. 25, 2017, 23 pages.
Final Office Action received for U.S. Appl. No. 14/863,099, dated Apr. 21, 2016, 20 pages.
Final Office Action received for U.S. Appl. No. 15/925,652, dated Aug. 1, 2019, 30 pages.
International Preliminary Report on Patentability received for PCT Patent Application No. PCT/US2014/027882, dated Sep. 24, 2015, 8 pages.
International Search Report and Written Opinion received for PCT Patent Application No. PCT/US2013/032498, dated Feb. 10, 2014, 18 pages.
International Search Report and Written Opinion received for PCT Patent Application No. PCT/US2014/027882, date Oct. 10, 2014, 11 pages.
Invitation to Pay Addition Fees received for PCT Patent Application No. PCT/US2014/027882, dated Aug. 5, 2014, 2 pages.
Non-Final Office Action received for U.S. Appl. No. 14/774,664, dated Mar. 7, 2017, 23 pages.
Non-Final Office Action received for U.S. Appl. No. 14/863,099, dated Dec. 2, 2015, 12 pages.
Notice of Acceptance received for Australian Patent Application No. 2019201583, dated Jul. 15, 2019, 3 pages.
Notice of Allowance received for Chinese Patent Application No. 201580029054.3, dated Jul. 19, 2019, 2 pages (1 page of English Translation and 1 page of Official Copy).

Notice of Allowance received for Japanese Patent Application No. 2017-545918, dated Jul. 22, 2019, 4 pages (1 page of English Translation and 3 pages of Official Copy).
Office Action received for Australian Patent Application No. 2019100490, dated Jul. 26, 2019, 4 pages.
Office Action received for Chinese Patent Application No. 201610371774.4, dated Jul. 8, 2019, 6 pages (3 pages of English Translation and 3 pages of Official copy).
Supplementary European Search Report received for European Patent Application No. 17810749.6, dated Aug. 6, 2019, 6 pages.
Dharmasena, Anusha, "iMessage-send as text message Option", YouTube, Available online at: <https://www.youtube.com/watch?v=hXG-MdlW6FA>, Feb. 18, 2013, 1 page.
Applicant Initiated Interview Summary received for U.S. Appl. No. 16/144,864, dated Apr. 29, 2020, 4 pages.
Applicant-Initiated Interview Summary received for U.S. Appl. No. 16/147,523, dated Apr. 27, 2020, 3 pages.
Intention to Grant received for European Patent Application No. 15759998.6, dated Apr. 17, 2020, 10 pages.
Non-Final Office Action received for U.S. Appl. No. 16/363,945, dated Apr. 24, 2020, 13 pages.
Non-Final Office Action received for U.S. Appl. No. 16/418,786, dated Apr. 24, 2020, 16 pages.
Notice of Allowance received for U.S. Appl. No. 16/144,849, dated Apr. 17, 2020, 2 pages.
Office Action received for Chinese Patent Application No. 201680012936.3, dated Mar. 20, 2020, 23 pages (11 pages of English Translation and 12 pages of Official Copy).
Office Action received for Chinese Patent Application No. 201710439448.7, dated Mar. 27, 2020, 13 pages (7 pages of English Translation and 6 pages of Official Copy).
Office Action received for Korean Patent Application No. 10-2018-7035747, dated Apr. 9, 2020, 11 pages (5 pages of English Translation and 6 pages of Official Copy).
Corrected Notice of Allowance received for U.S. Appl. No. 15/798,257, dated Jul. 9, 2019, 2 pages.
Extended European Search Report received for European Patent Application No. 19163212.4, dated Jun. 25, 2019, 11 pages.
Non-Final Office Action received for U.S. Appl. No. 15/600,243, dated Jun. 27, 2019, 17 pages.
Notice of Allowance received for Chinese Patent Application No. 201510484514.3, dated Jun. 6, 2019, 2 pages (1 page of English Translation and 1 page of Official Copy).
Office Action received for Australian Patent Application No. 2018279037, dated Jun. 18, 2019, 5 pages.
Office Action received for Japanese Patent Application No. 2018-014096, dated May 8, 2019, 14 pages (7 pages of English Translation and 7 pages of Official Copy).
Wikipedia, "Enhanced Multi-Level Precedence and Pre-emption Service", Available online at: https://de.wikipedia.org/w/index.php?%20title=Enhanced%20Multi%E3%83%BCLevel_Precedence_And_Pre-emption_Service&oldid=123047429, Oct. 2013, 2 pages. (Official copy only) (See Communication under 37 CFR § 1.98(a) (3)).
Decision on Appeal received for U.S. Appl. No. 14/774,664, dated Sep. 12, 2019, 8 pages.
International Search Report and Written Opinion received for PCT Patent Application No. PCT/US2019/024570, dated Aug. 8, 2019, 18 pages.
Office Action received for Chinese Patent Application No. 201510557356.X, dated Aug. 15, 2019, 12 pages (7 pages of English Translation and 5 pages of Official Copy).
Office Action received for Danish Patent Application No. PA201870385, dated Aug. 23, 2019, 3 pages.
Office Action received for Japanese Patent Application No. 2016-569945, dated Jul. 29, 2019, 6 pages (3 pages of English Translation and 3 pages of Official Copy).
Office Action received for Korean Patent Application No. 10-2018-7018904, dated Aug. 20, 2019, 8 pages (3 pages of English Translation and 5 pages of Official Copy).
Applicant Initiated Interview Summary received for U.S. Appl. No. 15/554,204, dated Oct. 11, 2019, 5 pages.
Decision to Grant received for European Patent Application No. 15711969.4, dated Sep. 26, 2019, 2 pages.

(56) References Cited

OTHER PUBLICATIONS

Notice of Allowance received for Chinese Patent Application No. 201580028505.1, dated Sep. 19, 2019, 2 pages (1 page of English Translation and 1 page of Official Copy).
Notice of Allowance received for Japanese Patent Application No. 2017-562330, dated Sep. 20, 2019, 4 pages (1 page of English Translation and 3 pages of Official Copy).
Office Action received for Australian Patent Application No. 2019222943, dated Oct. 3, 2019, 3 pages.
Office Action received for Chinese Patent Application No. 201680008151.9, dated Aug. 27, 2019, 24 pages (11 pages of English Translation and 13 pages of Official Copy).
Office Action received for Chinese Patent Application No. 201810105846.X, dated Aug. 27, 2019, 12 pages (5 pages of English Translation and 7 pages of Official Copy).
Office Action received for Japanese Patent Application No. 2017-505842, dated Sep. 9, 2019, 7 pages (3 pages of English Translation and 4 pages of Official Copy).
Office Action received for Korean Patent Application No. 10-2017-7034558, dated Sep. 25, 2019, 9 pages (4 pages of English Translation and 5 pages of Official Copy).
Summons to Attend Oral Proceedings received for European Patent Application No. 15730925.3, dated Oct. 2, 2019, 8 pages.
Applicant-Initiated Interview Summary received for U.S. Appl. No. 16/259,954, dated Mar. 23, 2020, 3 pages.
Corrected Notice of Allowance received for U.S. Appl. No. 14/732,773, dated Mar. 24, 2020, 3 pages.
Corrected Notice of Allowance received for U.S. Appl. No. 15/600,243, dated Mar. 31, 2020, 5 pages.
Examiner's Answer to Appeal Brief received for U.S. Appl. No. 14/815,890, dated Mar. 20, 2020, 16 pages.
Invitation to Pay Search Fees received for European Patent Application No. 15753796.0, dated Mar. 24, 2020, 3 pages.
Notice of Allowance received for Japanese Patent Application No. 2017-505842, dated Mar. 16, 2020, 4 pages (1 page of English Translation and 3 pages of Official Copy).
Office Action received for Australian Patent Application No. 2019100495, dated Mar. 16, 2020, 3 pages.
Office Action received for Chinese Patent Application No. 201580046788.2, dated Feb. 25, 2020, 14 pages (7 pages of English Translation and 7 pages of Official Copy).
Office Action received for Korean Patent Application No. 10-2019-7038235, dated Mar. 9, 2020, 15 pages (7 pages of English Translation and 8 pages of Official Copy).
Supplemental Notice of Allowance received for U.S. Appl. No. 16/144,849, dated Mar. 31, 2020, 2 pages.
Advisory Action received for U.S. Appl. No. 14/732,773, dated Aug. 23, 2019, 6 pages.
Certificate of Examination received for Australian Patent Application No. 2018101855, dated Aug. 6, 2019, 2 pages.
Corrected Notice of Allowance received for U.S. Appl. No. 15/798,257, dated Aug. 26, 2019, 2 pages.
Decision on Appeal received for U.S. Appl. No. 14/863,099, dated Aug. 22, 2019, 9 pages.
Decision on Opposition received for Australian Patent Application No. 2015298710, dated Aug. 9, 2019, 4 pages.
Invitation to Pay Addition Fee received for PCT Patent Application No. PCT/US2019/024790, dated Jul. 18, 2019, 10 pages.
Office Action received for Chinese Patent Application No. 201380081349.6, dated Jul. 15, 2019, 10 pages (5 pages of English Translation and 5 pages of Official copy).
Office Action received for European Patent Application No. 17810749.6, dated Aug. 20, 2019, 9 pages.
Supplemental Notice of Allowance received for U.S. Appl. No. 14/863,069, dated Aug. 15, 2019, 3 pages.
Applicant-Initiated Interview Summary received for U.S. Appl. No. 15/614,121, dated Feb. 13, 2020, 4 pages.
Applicant-Initiated Interview Summary received for U.S. Appl. No. 15/705,849, dated Feb. 14, 2020, 3 pages.
Brief Communication regarding Oral Proceedings received for European Patent Application No. 15730925.3, mailed on Feb. 18, 2020, 7 pages.
Corrected Notice of Allowance received for U.S. Appl. No. 14/732,773, dated Feb. 10, 2020, 3 pages.
Corrected Notice of Allowance received for U.S. Appl. No. 15/600,243, dated Feb. 5, 2020, 3 pages.
Intention to Grant received for European Patent Application No. 15747595.5, dated Feb. 17, 2020, 8 pages.
Non-Final Office Action received for U.S. Appl. No. 15/608,848, dated Feb. 6, 2020, 12 pages.
Non-Final Office Action received for U.S. Appl. No. 16/144,735, dated Feb. 19, 2020, 10 pages.
Non-Final Office Action received for U.S. Appl. No. 16/259,954, dated Feb. 5, 2020, 10 pages.
Notice of Allowance received for U.S. Appl. No. 16/144,671, dated Feb. 10, 2020, 17 pages.
Office Action received for Australian Patent Application No. 2018206772, dated Feb. 6, 2020, 4 pages.
Office Action received for Chinese Patent Application No. 201380081349.6, dated Jan. 16, 2020, 11 pages (6 pages of English Translation and 5 pages of Official Copy).
Office Action received for Japanese Patent Application No. 2018-014096, dated Jan. 6, 2020, 17 pages (8 pages of English Translation and 9 pages of Official Copy).
Extended European Search Report received for European Patent Application No. 17813824.4, dated Dec. 5, 2019, 7 pages.
How to Send and Receive files over Bluetooth on an Android Phone, Online Available at: https://web.archive.org/web/20160529062240/http://www.androidtipsandhacks.com/android/send-receive-files-bluetooth-android-phone/, May 29, 2016, 7 pages.
KAMCORD—Wikipedia, Online Available at: https://en.wikipedia.org/w/index.php?title=Kamcord&oldid=712263010, Mar. 28, 2016, 2 pages.
Kamcord Developers, Online Available at: https://web.archive.org/web/20140827043641 /http://www.kamcord.com/developers/, Aug. 27, 2014, 7 pages.
Kamcord Developers—Quick Start Guide, Online Available at: https://web.archive.org/web/20140801055705/https://www.kamcord.com/developers/docs/ios/features-and-settings/, Aug. 1, 2014, 10 pages.
Notice of Allowance received for Japanese Patent Application No. 2018-068846, dated Dec. 9, 2019, 4 pages (1 page of English Translation and 3 pages of Official Copy).
Notice of Allowance received for U.S. Appl. No. 14/732,773, dated Dec. 18, 2019, 21 pages.
Notice of Allowance received for U.S. Appl. No. 15/600,243, dated Dec. 12, 2019, 7 pages.
Office Action received for Chinese Patent Application No. 201610371774.4, dated Dec. 2, 2019, 6 pages (3 pages of English Translation and 3 pages of Official Copy).
Office Action received for Chinese Patent Application No. 201680047983.1, dated Nov. 28, 2019, 9 pages (4 pages of English Translation and 5 pages of Official Copy).
Office Action received for Chinese Patent Application No. 201811330077.X, dated Nov. 13, 2019, 14 pages (6 pages of English Translation and 8 pages of Official Copy).
Office Action received for Korean Patent Application No. 10-2019-7025781, dated Nov. 26, 2019, 10 pages (4 pages of English Translation and 6 pages of Official Copy).
Applicant Initiated Interview Summary received for U.S. Appl. No. 16/144,849, dated Jan. 21, 2020, 6 pages.
Applicant-Initiated Interview Summary received for U.S. Appl. No. 15/554,204, dated Jan. 31, 2020, 3 pages.
Final Office Action received for U.S. Appl. No. 15/405,122, dated Jan. 21, 2020, 36 pages.
Intention to Grant received for Danish Patent Application No. PA201870385, dated Jan. 24, 2020, 2 pages.
Non-Final Office Action received for U.S. Appl. No. 16/144,864, dated Jan. 31, 2020, 29 pages.
Notice of Allowance received for Japanese Patent Application No. 2016-569945, dated Jan. 7, 2020, 4 pages (1 page of English Translation and 3 pages of Official Copy).

(56) References Cited

OTHER PUBLICATIONS

Office Action received for Australian Patent Application No. 2018279037, dated Jan. 17, 2020, 4 pages.
Summons to Attend Oral Proceedings received for European Patent Application No. 16804040.0, dated Jan. 24, 2020, 11 pages.
Wikipedia, "Emoji", Available online at: https://en.wikipedia.org/w/index.php?title=Emoji&oldid=648831795, Feb. 25, 2015, 12 pages.
Wikipedia, "Emoticon", Available online at: https://en.wikipedia.org/w/index.php?title=Emoticon&oldid=648776142, Feb. 25, 2015, 9 pages.
Advisory Action received for U.S. Appl. No. 16/144,864, dated Jul. 29, 2019, 6 pages.
Decision to Grant received for Danish Patent Application No. PA201870379, dated Jul. 5, 2019, 2 pages.
Decision to Grant received for European Patent Application No. 13174706.5, dated Jul. 11, 2019, 2 pages.
Office Action received for Chinese Patent Application No. 201510284850.3, dated Jun. 21, 2019, 10 pages (4 pages of English Translation and 6 pages of Official Copy).
Office Action received for Chinese Patent Application No. 201580028505.1, dated Jun. 20, 2019, 7 pages (3 pages of English Translation and 4 pages of Official Copy).
Office Action received for European Patent Application No. 15760008.1, dated Jul. 16, 2019, 9 pages.
Office Action received for Korean Patent Application No. 10-2017-7024570, dated Jul. 10, 2019, 6 pages (3 pages of English Translation and 3 pages of Official Copy).
Advisory Action received for U.S. Appl. No. 14/841,606, dated Feb. 28, 2019, 3 pages.
Android Central, "Beweather Weather App for Android", Available online at: <https://www.youtube.com/watch?v=G2EY2K-XkSI>, Sep. 1, 2011, 1 page.
Clark, Josh, "Designing Great iphone Apps", O'Reilly Japan Co., O'Reilly Tim, vol. 1, May 24, 2012, 5 pages (Official copy only) (See Communication under 37 CFR § 1.98(a) (3)).
Corrected Notice of Allowance received for U.S. Appl. No. 14/822,769, dated Jan. 17, 2019, 8 pages.
Corrected Notice of Allowance received for U.S. Appl. No. 14/841,614, dated Jan. 8, 2019, 3 pages.
Corrected Notice of Allowance received for U.S. Appl. No. 15/183,663, dated Feb. 25, 2019, 3 pages.
Corrected Notice of Allowance received for U.S. Appl. No. 15/183,663, dated Mar. 27, 2019, 2 pages.
Decision to Refuse received for European Patent Application No. 15730924.6, dated Mar. 15, 2019, 12 pages.
Evergreen et al., "Bar Chart", Better Evaluation, Available Online at: https://www.betterevaluation.org/en/evaluation-options/BarChart, Oct. 31, 2014, 8 pages.
Extended European Search Report received for European Patent Application No. 16837432.0, dated Mar. 11, 2019, 10 pages.
Extended European Search Report received for European Patent Application No. 18213157.3, dated Apr. 12, 2019, 8 pages.
Final Office Action received for U.S. Appl. No. 14/815,890, dated May 14, 2019, 22 pages.
Final Office Action received for U.S. Appl. No. 15/352,215, dated Mar. 7, 2019, 22 pages.
Final Office Action received for U.S. Appl. No. 15/614,121, dated Apr. 8, 2019, 32 pages.
Final Office Action received for U.S. Appl. No. 16/144,864, dated May 17, 2019, 24 pages.
Fukuda, Kazuhiro, "Xperia Z1 Perfect Manual", Sotec Co., Ltd., No. 1, Nov. 15, 2013, pp. 217-218.
Gazer, "iphone 4s Super Manual", Shuwa System Co., Saito Kazukuni, vol. 1, Jun. 6, 2013, 7 pages (Official copy only) (See Communication under 37 CFR § 1.98(a) (3)).
Geary, David, "Programming Html5 Canvas", O'Reilly Japan, Inc., No. 1, Jul. 23, 2014, pp. 327-330.
Intention to Grant received for Danish Patent Application No. PA201870379, dated May 2, 2019, 2 pages.
Intention to Grant received for European Patent Application No. 13174706.5, dated Apr. 30, 2019, 7 pages.
Intention to Grant received for European Patent Application No. 15739110.3, dated Mar. 7, 2019, 8 pages.
Kenney, Briley, "How to Customize a Smartwatch and Other Personalization Questions", Available online at: <https://smartwatches.org/learn/customize-smartwatch/>, Jan. 23, 2014, 3 pages.
Minutes of Oral Proceedings received for European Patent Application No. 15730924.6, mailed on Mar. 13, 2019, 4 pages.
Minutes of the Oral Proceedings received for European Application No. 15711969.4, mailed on May 16, 2019, 7 pages.
Multi-set Bar Chart, The Data Visualization Catalogue, Available Online at: https://datavizcatalogue.com/methods/multiset_barchart.htmlFeb. 8, 2014, 3 pages.
Non-Final Office Action received for U.S. Appl. No. 15/554,204, dated Apr. 17, 2019, 19 pages.
Non-Final Office Action received for U.S. Appl. No. 11/850,005, dated Dec. 31, 2018, 14 pages.
Non-Final Office Action received for U.S. Appl. No. 14/841,606, dated May 8, 2019, 28 pages.
Non-Final Office Action received for U.S. Appl. No. 15/128,952, dated Apr. 1, 2019, 20 pages.
Non-Final Office Action received for U.S. Appl. No. 15/925,652, dated Apr. 5, 2019, 28 pages.
Non-Final Office Action received for U.S. Appl. No. 16/144,849, dated Dec. 31, 2018, 28 pages.
Non-Final Office Action received for U.S. Appl. No. 16/144,864, dated Dec. 18, 2018, 19 pages.
Non-Final Office Action received for U.S. Appl. No. 14/732,773, dated Feb. 8, 2019, 32 pages.
Notice of Acceptance received for Australian Patent Application No. 2016215440, dated Feb. 28, 2019, 3 pages.
Notice of Allowance received for Chinese Patent Application No. 201510483305.7, dated Jan. 8, 2019, 3 pages (1 page of English Translation and 2 pages of Official copy).
Notice of Allowance received for Chinese Patent Application No. 201580028677.9, dated Apr. 2, 2019, 2 pages (1 pages of English Translation and 1 pages of Official copy).
Notice of Allowance received for Japanese Patent Application No. 2016-557650, dated Apr. 9, 2019, 4 pages (1 page of English Translation and 3 pages of Official copy).
Notice of Allowance received for Japanese Patent Application No. 2018-074971, dated Apr. 23, 2019, 4 pages (1 page of English Translation and 3 pages of Official copy).
Notice of Allowance received for Japanese Patent Application No. 2018-107114, dated Mar. 22, 2019, 4 pages (1 page of English Translation and 3 pages of Official copy.
Notice of Allowance received for U.S. Appl. No. 14/863,069, dated Feb. 6, 2019, 6 pages.
Notice of Allowance received for U.S. Appl. No. 15/183,663, dated Jan. 17, 2019, 6 pages.
Notice of Allowance received for U.S. Appl. No. 16/103,699, dated Apr. 11, 2019, 8 pages.
Obara, Yuuta, "Iphone Application Selection for Univesity Students", Shuwa System Co., Saito Kazukuni, vol. 1, May 16, 2013, 4 pages (Official copy only) (See Communication under 37 CFR § 1.98(a) (3)).
Octoba, "Just Install It—Utilizing Method for Android Application Business", ASCII Media Works Co. Takano Kiyoshi, vol. 1, Apr. 25, 2013, 6 pages (Official copy only) (See Communication under 37 CFR § 1.98(a) (3)).
Office Action received for Australian Patent Application No. 2016215440, dated Jan. 22, 2019, 2 pages.
Office Action received for Australian Patent Application No. 2017286296, dated May 8, 2019, 4 pages.
Office Action received for Australian Patent Application No. 2018101855, dated Feb. 22, 2019, 4 pages.
Office Action received for Australian Patent Application No. 2018202751, dated Apr. 2, 2019, 4 pages.
Office Action received for Australian Patent Application No. 2018204286, dated Apr. 17, 2019, 5 pages.
Office Action received for Australian Patent Application No. 2018206772, dated Apr. 1, 2019, 4 pages.

(56) References Cited

OTHER PUBLICATIONS

Office Action received for Chinese Patent Application No. 201510483268.x, dated Apr. 16, 2019, 6 pages (3 pages of English Translation and 3 pages of Official copy).
Office Action received for Chinese Patent Application No. 201510484514.3, dated Dec. 24, 2018, 10 pages (5 pages of English Translation and 5 pages of Official copy).
Office Action received for Chinese Patent Application No. 201510557356.x, dated Nov. 23, 2018, 12 pages (5 pages of English Translation and 7 pages of Official copy).
Office Action received for Chinese Patent Application No. 201580028505.1, dated Jan. 16, 2019, 15 pages (5 pages of English Translation and 10 pages of Official copy).
Office Action received for Chinese Patent Application No. 201580029054.3, dated Dec. 5, 2018, 12 pages (6 pages of English Translation and 6 pages of Official copy).
Office Action received for Chinese Patent Application No. 201580046788.2, dated Apr. 15, 2019, 13 pages (6 pages of English Translation and 7 pages of Official copy).
Office Action received for Chinese Patent Application No. 201610371774.4, dated Dec. 19, 2018, 13 pages (5 pages of English Translation and 8 pages of Official copy).
Office Action received for Chinese Patent Application No. 201680047983.1, dated Mar. 18, 2019, 18 pages (6 pages of English Translation and 12 pages of Official copy).
Office Action received for Chinese Patent Application No. 201810105846.x, dated Feb. 25, 2019, 10 pages (5 pages of English Translation and 5 pages of Official copy).
Office Action received for Chinese Patent Application No. 201380081349.6, dated Feb. 26, 2019, 12 pages (6 pages of English Translation and 6 pages of Official Copy).
Office Action received for Japanese Patent Application No. 2018-068846, dated Jan. 8, 2019, 6 pages (3 pages of English Translation and 3 pages of Official copy).
Office Action received for Danish Patent Application No. PA201670656, dated May 2, 2019, 4 pages.
Office Action received for Danish Patent Application No. PA201770423, dated Mar. 29, 2019, 6 pages.
Office Action received for Danish Patent Application No. PA201870378, dated Feb. 25, 2019, 3 pages.
Office Action received for Danish Patent Application No. PA201870379, dated Feb. 28, 2019, 3 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for European Patent Application No. 15747595.5, dated Apr. 15, 2019, 4 pages.
Office Action received for European Patent Application No. 16708014.2, dated Apr. 3, 2019, 7 pages.
Office Action received for European Patent Application No. 16804040.0, dated May 13, 2019, 12 pages.
Office Action received for European Patent Application No. 15730925.3, dated Feb. 27, 2019, 5 pages.
Office Action received for German Patent Application No. 112015002326.7, dated Feb. 20, 2019, 7 pages (2 pages of English Translation and 5 pages of Official copy).
Office Action received for Japanese Patent Application No. 2017-505842, dated Feb. 22, 2019, 11 pages (6 pages of English Translation and 5 pages of Official copy).
Office Action received for Japanese Patent Application No. 2017-505847, dated Feb. 12, 2019, 13 pages (6 pages of English Translation and 7 pages of Official copy).
Office Action received for Japanese Patent Application No. 2017-562330, dated Jan. 18, 2019, 11 pages (6 pages of English Translation and 5 pages of Official copy).
Office Action received for Japanese Patent Application No. 2018-074971, dated Jan. 28, 2019, 6 pages (3 pages of English Translation and 3 pages of Official copy).
Office Action received for Japanese Patent Application No. 2018-080122, dated Jan. 28, 2019, 11 pages (6 pages of English Translation and 5 pages of Official copy).
Office Action received for Korean Patent Application No. 10-2017-7034558, dated Dec. 15, 2018, 15 pages (7 pages of English Translation and 8 pages of Official copy).
Office Action received for Taiwanese Patent Application No. 104132636, dated Dec. 13, 2018, 26 pages (9 pages of English Translation and 17 pages of Official copy).
Partial Supplementary European Search Report received for European Patent Application No. 17810749.6, dated Apr. 25, 2019, 8 pages.
Preliminary Opinion received for European Patent Application No. 15730890.9, dated Mar. 7, 2019, 4 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Search Report and Opinion received for Danish Patent Application No. PA201870385, dated Nov. 16, 2018, 10 pages.
Shiota, Shinji, "Windows 7 Dojo", Weekly ASCII, ASCII Mediaworks Inc., vol. 798, Aug. 31 , 2010, 3 pages.
Summons to Attend Oral Proceedings received for European Patent Application No. 16190252.3, dated Jan. 8, 2019, 3 pages.
Supplemental Notice of Allowance received for U.S. Appl. No. 14/863,069, dated Mar. 29, 2019, 3 pages.
Supplemental Notice of Allowance received for U.S. Appl. No. 14/863,069, dated Mar. 1, 2019, 3 pages.
Supplemental Notice of Allowance received for U.S. Appl. No. 14/870,726, dated Mar. 6, 2019, 6 pages.
Teunmo, "Data Field: Visual Pace Alarm", Garmin Forum; Available online at: https://forums.garmin.com/forum/developers/connect-ig/connect-ig-showcase/115996-data-field-visual-pace-alarm, Nov. 17, 2015, 10 pages.
Visual Pace Alarm App, Available Online at: https://apps.garmin.com/en-US/apps/3940f3a2-4847-4078-a911-d77422966c82, Oct. 19, 2016, 1 page.
Xperia ZL2 SOL25, "Instruction Manual", Detailed version, KDDI Corporation, No. 1, vol. 1, Jun. 2014, 4 pages.
"Android 2.3.4 User's Guide", Online available at: https://static.googleusercontent.com/media/www.google.com/en//help/hc/pdfs/mobile/AndroidUsersGuide-2.3.4.pdf, May 20, 2011, 384 pages.
Extended European Search Report for European Application No, 19185318.3, dated Nov. 20, 2019, 8 pages.
Intention to Grant received for European Patent Application No. 15759998.6, dated Nov. 21, 2019, 12 pages.
International Preliminary Report on Patentability received for PCT Patent Application No. PCT/US2018/031662, dated Nov. 28, 2019, 12 pages.
Internet Blog Post, "[PC] Pre-Customization of Black Desert's Characters", Online Available at: https://blog.naver.com/hsh6051/220209813968, Dec. 14, 2014, 41 pages (21 pages of English translation and 20 pages of Official Copy).
Non-Final Office Action received for U.S. Appl. No. 15/705,849, dated Nov. 12, 2019, 15 pages.
Notice of Allowance received for Chinese Patent Application No. 201510483268.X, dated Nov. 6, 2019, 2 pages (1 page of English translation and 1 page of Official Copy).
Notice of Allowance received for U.S. Appl. No. 14/833,014, dated Nov. 20, 2019, 5 pages.
Notice of Allowance received for U.S. Appl. No. 15/352,215, dated Nov. 27, 2019, 20 pages.
Notice of Allowance received for U.S. Appl. No. 15/355,956, dated Nov. 22, 2019, 29 pages.
Office Action received for Australian Patent Application No. 2018204286, dated Nov. 12, 2019, 5 pages.
Office Action received for Australian Patent Application No. 2018206772, dated Nov. 6, 2019, 4 pages.
Office Action received for Korean Patent Application No. 10-2019-7029673, dated Nov. 5, 2019, 10 pages (4 pages of English Translation and 6 pages of Official Copy).
Applicant-Initiated Interview Summary received for U.S. Appl. No. 15/627,069, dated Nov. 4, 2019, 6 pages.

(56) References Cited

OTHER PUBLICATIONS

Applicant-Initiated Interview Summary received for U.S. Appl. No. 15/600,243, dated Nov. 1, 2019, 6 pages.
Applicant-Initiated Interview Summary received for U.S. Appl. No. 15/608,848, dated Nov. 1, 2019, 3 pages.
Certificate of Examination received for Australian Patent Application No. 2019100490, dated Oct. 16, 2019, 2 pages.
Decision on Appeal received for U.S. Appl. No. 14/833,014, dated Oct. 30, 2019, 10 pages.
Final Office Action received for U.S. Appl. No. 15/554,204, dated Oct. 31, 2019, 22 pages.
Jepson, Tom, "How to auto-forward specific emails in gmail?", Available online at: http://www.tomjepson.co.uk/how-to-auto-forward-specific-emails-in-gmail/, May 19, 2013, 7 pages.
Netsapiens, "Click to Call in MS Outlook", Available online at: https://netsapiens.com/click-to-call-in-ms-outlook-windows-apps/, May 4, 2012, 8 pages.
Non-Final Office Action received for U.S. Appl. No. 15/614,121, dated Nov. 4, 2019, 44 pages.
Non-Final Office Action received for U.S. Appl. No. 16/265,938, dated Nov. 4, 2019, 28 pages.
Notice of Acceptance received for Australian Patent Application No. 2015298710, dated Oct. 8, 2019, 3 pages.
Notice of Allowance received for Chinese Patent Application No. 201580037927.5, dated Oct. 17, 2019, 3 pages (1 page of English Translation and 2 pages of Official Copy).
Office Action received for Australian Patent Application No. 2018201089, dated Oct. 11, 2019, 4 pages.
Office Action received for Danish Patent Application No. PA201770191, dated Oct. 25, 2019, 4 pages.
Remote Phone Call, Available online at https://web.archive.org/web/20140625104844/https://www.justremotephone.com/, Jun. 25, 2014, 22 pages.
Corrected Notice of Allowance received for U.S. Appl. No. 15/798,257, dated Jun. 12, 2019, 4 pages.
Corrected Notice of Allowance received for U.S. Appl. No. 16/103,699, dated May 29, 2019, 2 pages.
Final Office Action received for U.S. Appl. No. 11/850,005, dated Jun. 6, 2019, 14 pages.
Final Office Action received for U.S. Appl. No. 14/869,877, dated Jun. 11, 2019, 35 pages.
Final Office Action received for U.S. Appl. No. 16/144,849, dated Jun. 7, 2019, 29 pages.
Intention to Grant received for European Patent Application No. 15711969.4, dated May 29, 2019, 11 pages.
Non-Final Office Action received for U.S. Appl. No. 15/355,956, dated May 31, 2019, 32 pages.
Non-Final Office Action received for U.S. Appl. No. 15/405,122, dated May 31, 2019, 43 pages.
Notice of Allowance received for Chinese Patent Application No. 201510481525.6, dated May 27, 2019, 2 pages (1 page of English Translation and 1 page of Official Copy).
Notice of Allowance received for Japanese Patent Application No. 2017-505847, dated May 20, 2019, 4 pages (1 page of English Translation and 3 pages of Official Copy).
Notice of Allowance received for U.S. Appl. No. 15/798,257, dated May 22, 2019, 14 pages.
Office Action received for Australian Patent Application No. 2016270323, dated May 29, 2019, 4 pages.
Office Action received for Chinese Patent Application No. 201510479088.4, dated May 7, 2019, 6 pages (3 pages of English Translation and 3 pages of Official Copy).
Office Action received for Chinese Patent Application No. 201580037927.5, dated Apr. 22, 2019, 9 pages (4 pages of English Translation and 5 pages of Official Copy).
Office Action received for European Patent Application No. 15759998.6, dated May 29, 2019, 6 pages.
Android Central, "Changing the watchface on your Android Wear device", Retrieved From: https://www.youtube.com/watch?v=YYwFe2K_qil, Jul. 2, 2014, 4 pages.

Omar Romero, "Sony Smartwatch 2 Custom Watchfaces Tutorial", Retrieved From: https://www.youtube.com/watch?v=8odbxqwSQR8, May 1, 2014, 2 pages.
Ebpman Tech Reviews, "LG G3 Tips: How to customize the clock face", Available online at: https://www.youtube.com/watch?v=evraMWFb1fY, Jul. 25, 2014, 3 pages.
Stateoftech, "Samsung Galaxy Gear Tips—Change the Clock Face", Retrieved from: https://www.youtube.com/watch?v=GOom7AZUAjY, Dec. 11, 2013, 2 pages.
Watchophilia, "Mickey Mouse Watches", Online Available at: https://web.archive.org/web/20130929065422/https://www.watchophilia.com/photogallery/nnickey-mouse/, Sep. 29, 2013, 16 pages.
Watchuseek, "The watch every father needs: M-I-C-K-E-Y, M-O-U-S-E. Mickey Mouse", Online Available at: https://forums.watchuseek.com/f2/watch-every-father-needs-m-i-c-k-e-y-m-o-u-s-e-mickey-mouse-855069.html, 2013, 3 pages.
Applicant-Initiated Interview Summary received for U.S. Appl. No. 15/405,122, dated Dec. 22, 2020, 5 pages.
Applicant-Initiated Interview Summary received for U.S. Appl. No. 16/533,540, dated Dec. 21, 2020, 4 pages.
Decision on Appeal received for U.S. Appl. No. 15/128,952, dated Dec. 28, 2020, 23 pages.
Non-Final Office Action received for U.S. Appl. No. 17/031,874, dated Dec. 28, 2020, 14 pages.
Notice of Allowance received for Korean Patent Application No. 10-2018-7035747, dated Dec. 9, 2020, 5 pages (2 pages of English Translation and 3 pages of Official Copy).
Notice of Allowance received for U.S. Appl. No. 16/102,146, dated Dec. 17, 2020, 5 pages.
Office Action received for Chinese Patent Application No. 201680012936.3, dated Dec. 1, 2020, 21 pages (8 pages of English Translation and 13 pages of Official Copy).
Office Action received for Japanese Patent Application No. 2018-080122, dated Nov. 27, 2020, 16 pages (8 pages of English Translation and 8 pages of Official Copy).
Office Action received for Korean Patent Application No. 10-2020-7026036, dated Dec. 7, 2020, 8 pages (3 pages of English Translation and 5 pages of Official Copy).
Result of Consultation received for European Patent Application No. 17810749.6, mailed on Dec. 15, 2020, 3 pages.
Advisory Action received for U.S. Patent Application No. 16/144,864, dated Jul. 6, 2020, 6 pages.
Applicant Initiated Interview Summary received for U.S. Appl. No. 16/389,722, dated Jul. 7, 2020, 5 pages.
Applicant-Initiated Interview Summary received for U.S. Appl. No. 15/705,849, dated Jun. 29, 2020, 3 pages.
Applicant-Initiated Interview Summary received for U.S. Appl. No. 16/145,033, dated Jun. 29, 2020, 5 pages.
Examiner's Answer to Appeal Brief received for U.S. Appl. No. 14/869,877, dated Jun. 26, 2020, 14 pages.
Notice of Allowance received for Japanese Patent Application No. 2019-096219, dated Jun. 26, 2020, 4 pages (1 page of English Translation and 3 pages of Official Copy).
Office Action received for Chinese Patent Application No. 201811330077.X, dated May. 18, 2020, 9 pages (3 pages of English Translation and 6 pages of Official Copy).
Office Action Received for Danish Patent Application No. PA201670656, dated Jul. 1, 2020, 4 pages.
Office Action received for Japanese Patent Application No. 2019-044107, dated May. 29, 2020, 6 pages (3 pages of English Translation and 3 pages of Official Copy).
Non-Final Office Action received for U.S. Appl. No. 15/405,122, dated Sep. 24, 2020, 30 pages.
Notice of Allowance received for U.S. Appl. No. 16/102,146, dated Oct. 5, 2020, 5 pages.
Notice of Allowance received for U.S. Appl. No. 16/144,864, dated Sep. 29, 2020, 2 pages.
Final Office Action received for U.S. Appl. No. 16/144,753, dated Sep. 22, 2020, 9 pages.
Final Office Action received for U.S. Appl. No. 16/145,033, dated Sep. 22, 2020, 49 pages.
Notice of Allowance received for U.S. Appl. No. 16/363,945, dated Sep. 23, 2020, 10 pages.

(56) References Cited

OTHER PUBLICATIONS

Summons to Attend Oral Proceedings received for European Patent Application No. 18154145.9, mailed on Sep. 17, 2020, 11 pages.
Applicant Initiated Interview Summary received for U.S. Appl. No. 16/144,735, dated Jun. 18, 2020, 3 pages.
Applicant Initiated Interview Summary received for U.S. Appl. No. 16/144,753, dated Jun. 18, 2020, 3 pages.
Applicant-Initiated Interview Summary received for U.S. Appl. No. 16/144,864, dated Jun. 22, 2020, 3 pages.
Decision to Grant received for European Patent Application No. 15759998.6, dated Jun. 18, 2020, 2 pages.
Notice of Allowance received for Chinese Patent Application No. 201610371774.4, dated Jun. 4, 2020, 2 pages (1 page of English Translation and 1 page of Official Copy).
Notice of Allowance received for Chinese Patent Application No. 201680008151.9, dated Jun. 16, 2020, 2 pages (1 page of English Translation and 1 page of Official Copy).
Office Action received for Australian Patent Application No. 2017277971, dated Jun. 3, 2020, 3 pages.
Applicant-Initiated Interview Summary received for U.S. Appl. No. 16/138,809, dated Dec. 16, 2020, 7 pages.
Board Decision received for Chinese Patent Application No. 201380081349.6, mailed on Nov. 23, 2020, 2 pages (1 page of English Translation and 1 page of Official Copy).
Final Office Action received for U.S. Appl. No. 16/389,722, dated Dec. 8, 2020, 18 pages.
Non-Final Office Action received for U.S. Appl. No. 16/820,383, dated Dec. 14, 2020, 11 pages.
Non-Final Office Action received for U.S. Appl. No. 17/031,859, dated Dec. 15, 2020, 13 pages.
Notice of Allowance received for U.S. Appl. No. 16/144,753, dated Dec. 4, 2020, 22 pages.
Notice of Allowance received for U.S. Appl. No. 16/407,590, dated Dec. 16, 2020, 6 pages.
Office Action received for Australian Patent Application No. 2020204259, dated Nov. 30, 2020, 8 pages.
Office Action received for Australian Patent Application No. 2020204506, dated Dec. 7, 2020, 6 pages.
Office Action received for European Patent Application No. 16762356.0, dated Dec. 11, 2020, 7 pages.
Applicant Initiated Interview Summary received for U.S. Appl. No. 16/363,945, dated Aug. 13, 2020, 5 pages.
Invitation to Pay Additional Fees received for PCT Patent Application No. PCT/US2020/031528, dated Jul. 30, 2020, 11 pages.
Non-Final Office Action received for U.S. Appl. No. 15/925,652, dated Aug. 7, 2020, 39 pages.
Office Action received for Australian Patent Application No. 2019250251, dated Aug. 6, 2020, 3 pages.
Office Action received for European Patent Application No. 15753796.0, dated Aug. 4, 2020, 9 pages.
Summons to Attend Oral Proceedings received for European Patent Application No. 17810749.6, mailed on Aug. 12, 2020, 11 pages.
Extended European Search Report received for European Patent Application No. 20176616.9, dated Sep. 8, 2020, 7 Pages.
International Search Report and Written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Chinese Patent Application No. 201910858933.7, dated Aug. 18, 2020, 14 pages (7 pages of English Translation and 7 pages of Official Copy).
Office Action received for Danish Patent Application No. PA201970532, dated May 29, 2020, 3 pages.
Office Action received for Japanese Patent Application No. 2018-014096, dated Aug. 28, 2020, 4 pages (2 pages of English Translation and 2 pages of Official Copy).
Office Action received for Japanese Patent Application No. 2019-162293, dated Jul. 27, 2020, 9 pages (5 pages of English Translation and 4 pages of Official Copy).
Office Action received for Korean Patent Application No. 10-2019-7029673, dated Sep. 3, 2020, 9 pages (4 pages of English Translation and 5 pages of Official Copy).
Result of Consultation received for European Patent Application No. 18154145.9, dated Sep. 4, 2020, 3 pages.
Search Report and Opinion received for Danish Patent Application No. PA201970532, dated Nov. 8, 2019, 9 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Applicant-Initiated Interview Summary received for U.S. Appl. No. 15/405,122, dated May 21, 2020, 5 pages.
Non-Final Office Action received for U.S. Appl. No. 15/627,069, dated May 26, 2020, 25 pages.
Non-Final Office Action received for U.S. Appl. No. 16/377,892, dated May 21, 2020, 9 pages.
Notice of Acceptance received for Australian Patent Application No. 2017286296, dated May 1, 2020, 3 pages.
Notice of Acceptance received for Australian Patent Application No. 2018279037, dated May 13, 2020, 3 pages.
Notice of Acceptance received for Australian Patent Application No. 2019222943, dated May 5, 2020, 3 pages.
Office Action received for Chinese Patent Application No. 201510479088.4, dated Apr. 22, 2020, 7 pages (3 pages of English Translation and 4 pages of Official Copy).
Office Action received for European Patent Application No. 18213157.3, dated May 15, 2020, 7 pages.
Applicant Initiated Interview Summary received for U.S. Appl. No. 15/608,848, dated Oct. 26, 2020, 3 pages.
Applicant-Initiated Interview Summary received for U.S. Appl. No. 15/925,652, dated Nov. 3, 2020, 4 pages.
Applicant-Initiated Interview Summary received for U.S. Appl. No. 16/144,753, dated Nov. 4, 2020, 3 pages.
Applicant-Initiated Interview Summary received for U.S. Appl. No. 16/147,523, dated Oct. 26, 2020, 3 pages.
European Search Report received for European Patent Application No. 20182116.2, dated Oct. 21, 2020, 4 pages.
Extended European Search Report received for European Patent Application No. 20185974.1, dated Oct. 28, 2020, 7 pages.
Notice of Allowance received for U.S. Appl. No. 16/144,735, dated Oct. 28, 2020, 13 pages.
Office Action received for Australian Patent Application No. 2020203919, dated Oct. 19, 2020, 5 pages.
Office Action received for Chinese Patent Application No. 201680013193.1, dated Sep. 7, 2020, 6 pages (3 pages of English Translation and 3 pages of Official Copy).
Office Action received for Japanese Patent Application No. 2020-104679, dated Sep. 18, 2020, 13 pages (7 pages of English Translation and 6 pages of Official Copy).
Office Action received for Korean Patent Application No. 10-2018-7035747, dated Oct. 14, 2020, 6 pages (3 pages of English Translation and 3 pages of Official Copy).
Applicant Initiated Interview Summary received for U.S. Appl. No. 15/608,848, dated May 12, 2020, 5 pages.
Final Office Action received for U.S. Appl. No. 15/705,849, dated May 1, 2020, 17 pages.
Final Office Action received for U.S. Appl. No. 16/144,735, dated May 4, 2020, 12 pages.
Notice of Allowance received for U.S. Appl. No. 16/259,954, dated May 7, 2020, 9 pages.

(56) References Cited

OTHER PUBLICATIONS

Office Action received for Chinese Patent Application No. 201680008151.9, dated Apr. 20, 2020, 6 pages (3 pages of English Translation and 3 pages of Official Copy).
Office Action received for Chinese Patent Application No. 201680013193.1, dated Mar. 25, 2020, 21 pages (8 pages of English Translation and 13 pages of Official Copy).
Applicant-Initiated Interview Summary received for U.S. Appl. No. 16/102,146, dated Aug. 31, 2020, 4 pages.
Corrected Notice of Allowance received for U.S. Appl. No. 15/554,204, dated Aug. 19, 2020, 3 pages.
Final Office Action received for U.S. Appl. No. 15/608,848, dated Aug. 21, 2020, 15 pages.
Final Office Action received for U.S. Appl. No. 16/138,809, dated Aug. 27, 2020, 24 pages.
Final Office Action received for U.S. Appl. No. 16/407,590, dated Aug. 25, 2020, 14 pages.
Notice of Allowance received for U.S. Appl. No. 15/614,121, dated Aug. 27, 2020, 8 pages.
Office Action received for Australian Patent Application No. 2017277971, dated Aug. 12, 2020, 3 pages.
Office Action received for Chinese Patent Application No. 201380081349.6, dated Jul. 15, 2020, 9 pages (4 pages of English Translation and 5 pages of Official Copy).
Office Action received for Chinese Patent Application No. 201680012936.3, dated Aug. 18, 2020, 15 pages (5 pages of English Translation and 10 pages of Official Copy).
Office Action received for Korean Patent Application No. 10-2019-7025538, dated Aug. 15, 2020, 8 pages (4 pages of English Translation and 4 pages of Official Copy).
Applicant-Initiated Interview Summary received for U.S. Appl. No. 16/145,033, dated Nov. 24, 2020, 4 pages.
Decision on Appeal received for U.S. Appl. No. 14/815,890, mailed on Nov. 24, 2020, 13 pages.
International Preliminary Report on Patentability received for PCT Patent Application No. PCT/US2019/024570, dated Nov. 19, 2020, 10 pages.
International Preliminary Report on Patentability received for PCT Patent Application No. PCT/US2019/024790, dated Nov. 19, 2020, 11 pages.
International Search Report and Written Opinion received for PCT Patent Application No. PCT/US2020/035199, dated Oct. 30, 2020, 20 pages.
Invitation to Pay Additional Fees received for PCT Patent Application No. PCT/US2020/035199, dated Sep. 8, 2020, 12 pages.
Notice of Allowance received for U.S. Appl. No. 15/925,652, dated Nov. 20, 2020, 9 pages.
Office Action received for Chinese Patent Application No. 201710439448.7, dated Oct. 10, 2020, 19 pages (8 pages of English Translation and 11 pages of Official Copy).
Office Action received for Chinese Patent Application No. 201811136445.7, dated Oct. 28, 2020, 17 pages (10 pages of English Translation and 7 pages of Official Copy).
Record of Oral Hearing received for U.S. Appl. No. 14/815,890, dated Nov. 20, 2020, 18 pages.
Result of Consultation received for European Patent Application No. 18154145.9, dated Nov. 30, 2020, 17 pages.
Result of Consultation received for European Patent Application No. 15730925.3, dated Nov. 24, 2020, 4 pages.
Applicant-Initiated Interview Summary received for U.S. Appl. No. 16/377,892, dated Oct. 13, 2020, 5 pages.
Final Office Action received for U.S. Appl. No. 15/627,069, dated Oct. 20, 2020, 25 pages.
Non-Final Office Action received for U.S. Appl. No. 16/894,309, dated Oct. 15, 2020, 24 pages.
Notice of Allowance received for U.S. Appl. No. 15/705,849, dated Oct. 16, 2020, 14 pages.
Notice of Allowance received for U.S. Appl. No. 16/265,938, dated Oct. 15, 2020, 8 pages.
Notice of Allowance received for U.S. Appl. No. 16/556,023, dated Oct. 15, 2020, 8 pages.
Office Action received for European Patent Application No. 19163212.4, dated Oct. 12, 2020, 4 pages.
Result of Consultation received for European Patent Application No. 19721883.7, dated Oct. 7, 2020, 3 pages.
Applicant-Initiated Interview Summary received for U.S. Appl. No. 16/407,590, dated Nov. 17, 2020, 6 pages.
Bagala et al., "Evaluation of Accelerometer-Based Fall Detection Algorithms on Real-World Falls", PloS ONE, vol. 7, No. 5, May 16, 2012, 9 pages.
Decision to Refuse received for European Patent Application No. 16804040.0, dated Nov. 4, 2020, 18 pages.
International Search Report and Written Opinion received for PCT Patent Application No. PCT/US2020/031528, dated Sep. 23, 2020, 18 pages.
Minutes of the Oral Proceedings received for European Patent Application No. 16804040.0, mailed on Nov. 2, 2020, 6 pages.
Non-Final Office Action received for U.S. Appl. No. 16/533,540, dated Oct. 23, 2020, 34 pages.
Non-Final Office Action received for U.S. Appl. No. 16/806,981, dated Nov. 13, 2020, 22 pages.
Office Action received for Chinese Patent Application No. 201580046788.2, dated Sep. 22, 2020, 10 pages (5 pages of English Translation and 5 pages of Official Copy).
Office Action received for European Patent Application No. 20182116.2, dated Nov. 6, 2020, 9 pages.
Office Action received for Japanese Patent Application No. 2019-151358, dated Oct. 2, 2020, 5 pages (2 pages of English Translation and 3 pages of Official Copy).
Office Action received for Korean Patent Application No. 10-2019-7025781, dated Oct. 30, 2020, 10 pages (4 pages of English Translation and 6 pages of Official Copy).
Final Office Action received for U.S. Appl. No. 16/418,786, dated Jan. 13, 2021, 14 pages.
Notice of Acceptance received for Australian Patent Application No. 2018268972, dated Dec. 18, 2020, 3 pages.
Notice of Allowance received for Japanese Patent Application No. 2018-014096, dated Jan. 5, 2021, 3 pages (1 page of English Translation and 2 pages of Official Copy).
Notice of Allowance received for Japanese Patent Application No. 2020-104679, dated Jan. 4, 2021, 4 pages (1 page of English Translation and 3 pages of Official Copy).
Notice of Allowance received for U.S. Appl. No. 16/556,023, dated Jan. 13, 2021, 8 pages.
Office Action received for Australian Patent Application No. 2020203919, dated Dec. 23, 2020, 5 pages.
Office Action received for Japanese Patent Application No. 2019-191137, dated Nov. 20, 2020, 9 pages (5 pages of English Translation and 4 pages of Official Copy).
Summons to Attend Oral Proceedings received for European Patent Application No. 19724963.4, dated Dec. 23, 2020, 8 pages.
Supplemental Notice of Allowance received for U.S. Appl. No. 15/925,652, dated Jan. 6, 2021, 2 pages.
Final Office Action received for U.S. Appl. No. 16/147,523, dated Aug. 4, 2020, 15 pages.
Google, "How to create a "My Map" in Google Maps", Available Online at: https://www.youtube.com/watch?v=TftFnot5uXw, Dec. 8, 2008, 2 pages.
Non-Final Office Action received for U.S. Appl. No. 16/102,146, dated Jul. 27, 2020, 16 pages.
Notice of Acceptance received for Australian Patent Application No. 2020204153, dated Jul. 6, 2020, 3 pages.
Notice of Allowance received for U.S. Appl. No. 15/705,849, dated Jul. 28, 2020, 10 pages.
Notice of Allowance received for U.S. Appl. No. 16/144,864, dated Jul. 28, 2020, 27 pages.
Office Action received for Australian Patent Application No. 2018201089, dated Jul. 23, 2020, 4 pages.
Office Action received for Chinese Patent Application No. 201680047983.1, dated Jul. 1, 2020, 6 pages (3 pages of English Translation and 3 pages of Official Copy).

(56) References Cited

OTHER PUBLICATIONS

Office Action received for European Patent Application No. 19724963.4, dated Jul. 28, 2020, 6 pages.
Applicant-Initiated Interview Summary received for U.S. Appl. No. 16/138,809, dated Jun. 9, 2020, 4 pages.
Applicant-Initiated Interview Summary received for U.S. Appl. No. 16/265,938, dated May 28, 2020, 5 pages.
Applicant-Initiated Interview Summary received for U.S. Appl. No. 16/407,590, dated Jun. 5, 2020, 3 pages.
Brief Communication Regarding Oral Proceedings received for European Patent Application No. 16804040.0, mailed on May 28, 2020, 15 pages.
Examiner's Answer to Appeaf Brief received for U.S. Appl. No. 11/850,005, dated Jun. 5, 2020, 19 pages.
Final Office Action received for U.S. Appl. No. 16/144,864, dated May 28, 2020, 29 pages.
Intention to Grant received for European Patent Application No. 15730925.3, dated May 28, 2020, 10 pages.
Minutes of the Oral Proceedings received for European Patent Application No. 15730925.3, dated May 26, 2020, 11 pages.
Office Action received for European Patent Application No. 19721883.7, dated May 28, 2020, 11 pages.
Decision to Refuse received for European Patent Application No. 17810749.6, dated Jan. 29, 2021, 24 pages.
Minutes of the Oral Proceedings received for European Patent Application No. 17810749.6, mailed on Jan. 26, 2021, 8 pages.
Notice of Allowance received for Chinese Patent Application No. 201710439448.7, dated Jan. 26, 2021, 2 pages (1 page of English Translation and 1 page of Official Copy).
Result of Consultation received for European Patent Application No. 17810749.6, mailed on Jan. 18, 2021, 3 pages.
Result of Consultation received for European Patent Application No. 17810749.6, mailed on Jan. 21, 2021, 18 pages.
Notice of Acceptance received for Australian Patent Application No. 2017277971, dated Feb. 17, 2021, 3 pages.
2RaZ Tech&Moto, "Sony Smartwatch 2 update—new feartures and watchface creator!!! New!!!", Online available on:—https://www.youtube.com/watch?v=k3jjBv7QZSk, May 8, 2014, 3 pages.
Decision on Acceptance received for Australian Patent Application No. 2018201089, mailed on Apr. 20, 2021, 28 pages.
Office Action received for Chinese Patent Application No. 201811136445.7, dated Apr. 14, 2021, 7 pages (4 pages of English Translation and 3 pages of Official Copy).
Office Action received for Danish Patent Application No. PA202170113, dated Apr. 15, 2021, 2 pages.
Rowinski Dan, "Why the All-In-One Smartwatch Isn't Happening Any Time Soon", Online available at:—https://web.archive.org/web/20140123074218if_/https://readwrite.com/2014/01/20/smartwatch-wearable-fitness-remote-control/, Jan. 20, 2014, 6 pages.
Stateoftech,"Samsung Galaxy Gear Tips—Installing and Customizing Clock Faces", Online available at:—https://www.youtube.com/watch?v=p2GzpL3xlUo, Dec. 12, 2013, 3 pages.
Techcloud,"How to Create Custom Watch Face for Samsung Galaxy Gear Smartwatch just in Few Seconds", Online available at:—https://www.youtube.com/watch?v=6rO-_SREDjQ, Oct. 9, 2013, 3 pages.
Theunlockr,"How to Change the Watch Face on the Galaxy Gear", Online available at:—https://www.youtube.com/watch?v=Z7EBG5aBiZg, Jan. 3, 2014, 3 pages.
Advisory Action received for U.S. Appl. No. 16/377,892, dated Apr. 9, 2021, 4 pages.
Advisory Action received for U.S. Appl. No. 16/389,722, dated Mar. 9, 2021, 5 pages.
Adeniyi Samuel, "How to connect a second PS4 controller to a PlayStation 4 console", Online available on:—https://www.youtube.com/watch?v=mOZX_SrNISE, May 28, 2017, 2 pages.
Allison Conor, "Working out with Fiit's wearable-powered boutique fitness classes", Online available at:—https://www.wareable.com/wearable-tech/fiit-fitness-classes-review-3849, May 14, 2018, 8 pages.

Applicant Initiated Interview Summary received for U.S. Appl. No. 16/894,309, dated Jan. 26, 2021, 3 pages.
Applicant-Initiated Interview Summary received for U.S. Appl. No. 15/627,069, dated Jan. 22, 2021, 4 pages.
Applicant-Initiated Interview Summary received for U.S. Appl. No. 16/377,892, dated Mar. 26, 2021, 2 pages.
Applicant-Initiated Interview Summary received for U.S. Appl. No. 16/389,722, dated Feb. 11, 2021, 4 pages.
Applicant-Initiated Interview Summary received for U.S. Appl. No. 16/418,786, dated Mar. 30, 2021, 4 pages.
Applicant-Initiated Interview Summary received for U.S. Appl. No. 16/820,383, dated Mar. 11, 2021, 2 pages.
Applicant-Initiated Interview Summary received for U.S. Appl. No. 17/031,859, dated Feb. 26, 2021, 4 pages.
Applicant-Initiated Interview Summary received for U.S. Appl. No. 17/031,874, dated Feb. 26, 2021, 4 pages.
CBS This Morning, "This smart mirror puts a personal trainer in your reflection", Available on: https://www.youtube.com/watch?v=nSmTTZcpVGg, Oct. 13, 2018, 4 pages.
Decision on Appeal received for Korean Patent Application No. 10-2019-7025538, mailed on Feb. 24, 2021, 20 pages (4 pages of English Translation and 16 pages of Official Copy).
Decision on Appeal received for U.S. Appl. No. 11/850,005, mailed on Mar. 1, 2021, 6 pages.
Decision to Refuse received for European Patent Application No. 18154145.9, dated Feb. 17, 2021, 20 pages.
Examiner Interview Summary received for U.S. Appl. No. 16/806,981, dated Mar. 26, 2021, 2 pages.
Extended European Search Report received for European Patent Application No. 20203526.7, dated Jan. 29, 2021, 13 pages.
Final Office Action received for U.S. Appl. No. 16/377,892, dated Jan. 28, 2021, 11 pages.
Final Office Action received for U.S. Appl. No. 16/894,309, dated Feb. 24, 2021, 30 pages.
Hamilton Jim, "Peloton Tips", Online available on:—https://www.youtube.com/watch?app=desktop&v=OneXtB0kaD4, Oct. 23, 2015, 3 pages.
Intention to Grant received for Danish Patent Application No. PA201670656, dated Jan. 18, 2021, 2 pages.
Minutes of the Oral Proceedings received for European Patent Application No. 18154145.9, mailed on Feb. 12, 2021, 8 pages.
Non-Final Office Action received for U.S. Appl. No. 15/405,122, dated Apr. 2, 2021, 35 pages.
Non-Final Office Action received for U.S. Appl. No. 15/608,848, dated Feb. 12, 2021, 14 pages.
Non-Final Office Action received for U.S. Appl. No. 16/145,033, dated Feb. 9, 2021, 55 pages.
Non-Final Office Action received for U.S. Appl. No. 16/888,629, dated Mar. 31, 2021, 14 pages.
Notice of Acceptance received for Australian Patent Application No. 2019250251, dated Feb. 18, 2021, 3 pages.
Notice of Allowance received for Chinese Patent Application No. 201510479088.4, dated Jan. 21, 2021, 2 pages (1 page of English Translation and 1 page of Official Copy).
Notice of Allowance received for Japanese Patent Application No. 2019-151358, dated Jan. 22, 2021, 4 pages (1 page of English Translation and 3 pages of Official Copy).
Notice of Allowance received for Japanese Patent Application No. 2019-191137, dated Mar. 8, 2021, 4 pages (1 page of English Translation and 3 pages of Official Copy).
Notice of Allowance received for Korean Patent Application No. 10-2019-7025538, dated Mar. 10, 2021, 5 pages (2 pages of English Translation and 3 pages of Official Copy).
Notice of Allowance received for Korean Patent Application No. 10-2019-7038235, dated Feb. 9, 2021, 4 pages (1 page of English Translation and 3 pages of Official Copy).
Notice of Allowance received for U.S. Appl. No. 14/815,890, dated Feb. 12, 2021, 8 pages.
Notice of Allowance received for U.S. Appl. No. 15/925,652, dated Mar. 9, 2021, 9 pages.
Notice of Allowance received for U.S. Appl. No. 16/144,753, dated Feb. 10, 2021, 8 pages.

(56) References Cited

OTHER PUBLICATIONS

Notice of Allowance received for U.S. Appl. No. 16/144,864, dated Feb. 9, 2021, 13 pages.
Notice of Allowance received for U.S. Appl. No. 16/144,864, dated Mar. 12, 2021, 2 pages.
Notice of Allowance received for U.S. Appl. No. 16/144,864, dated Mar. 30, 2021, 2 pages.
Notice of Allowance received for U.S. Appl. No. 16/407,590, dated Apr. 9, 2021, 3 pages.
Notice of Allowance received for U.S. Appl. No. 16/407,590, dated Mar. 22, 2021, 6 pages.
Notice of Allowance received for U.S. Appl. No. 16/820,383, dated Mar. 31, 2021, 11 pages.
Office Action received for Chinese Patent Application No. 201380081349.6, dated Jan. 5, 2021, 16 pages (7 pages of English Translation and 9 pages of Official Copy).
Office Action received for Chinese Patent Application No. 201680013193.1, dated Feb. 1, 2021, 8 pages (3 pages of English Translation and 5 pages of Official Copy).
Office Action received for Chinese Patent Application No. 201680047983.1, dated Feb. 1, 2021, 6 pages (3 pages of English Translation and 3 pages of Official Copy).
Office Action received for Chinese Patent Application No. 202010606407.4, dated Jan. 27, 2021, 16 pages (7 pages of English Translation and 9 pages of Official Copy).
Office Action received for European Patent Application No. 16708014.2, dated Mar. 4, 2021, 7 pages.
Office Action received for European Patent Application No. 16837432.0, dated Jan. 27, 2021, 7 pages.
Office Action received for European Patent Application No. 18727543.3, dated Mar. 26, 2021, 7 pages.
Office Action received for Japanese Patent Application No. 2019-563407, dated Feb. 5, 2021, 5 pages (2 pages of English Translation and 3 pages of Official Copy).
Office Action received for Japanese Patent Application No. 2020-000492, dated Dec. 11, 2020, 6 pages (3 pages English Translation and 3 pages of Official Copy).
Office Action received for Japanese Patent Application No. 2020-010239, dated Jan. 4, 2021, 6 pages (3 pages of English Translation and 3 pages of Official Copy).
Office Action received for Korean Patent Application No. 10-2019-7033834, dated Jan. 22, 2021, 13 pages (6 pages of English Translation and 7 pages of Official Copy).
Office Action received for Korean Patent Application No. 10-2020-7026035, dated Feb. 19, 2021, 13 pages (6 pages of English Translation and 7 pages of Official Copy).
Search Report and Opinion received for Danish Patent Application No. PA202070614, dated Jan. 14, 2021, 9 pages.
Search Report and Opinion received for Danish Patent Application No. PA202070815, dated Mar. 16, 2021, 8 pages.
Summons to Attend Oral Proceedings received for European Patent Application No. 15760008.1, dated Feb. 5, 2021, 11 pages.
Supplemental Notice of Allowance received for U.S. Appl. No. 14/815,890, dated Mar. 10, 2021, 2 pages.
Supplemental Notice of Allowance received for U.S. Appl. No. 15/925,652, dated Feb. 17, 2021, 3 pages.
Supplemental Notice of Allowance received for U.S. Appl. No. 15/925,652, dated Jan. 26, 2021, 3 pages.
Supplemental Notice of Allowance received for U.S. Appl. No. 16/556,023, dated Feb. 3, 2021, 2 pages.
Vicky's Blog, "How to Log in to PS4 Automatically with Particular User?", Online available on:—https://www.youtube.com/watch?v=kqdlzXAvOkY, May 30, 2018, 3 pages.
Yoyodavid, "How to Use Multiple Accounts on the Playstation 4", Online available at:—https://www.youtube.com/watch?v=5V21obRMeKE, Jan. 9, 2014, 3 pages.
Applicant Initiated Interview Summary received for U.S. Appl. No. 15/608,848, dated Apr. 13, 2021, 4 pages.
Final Office Action received for U.S. Appl. No. 16/533,540, dated Apr. 19, 2021, 38 pages.
Final Office Action received for U.S. Appl. No. 16/806,981, dated Apr. 14, 2021, 24 pages.
Final Office Action received for U.S. Appl. No. 17/031,859, dated Apr. 16, 2021, 14 pages.
Final Office Action received for U.S. Appl. No. 17/031,874, dated Apr. 16, 2021, 17 pages.
Notice of Acceptance received for Australian Patent Application No. 2020204506, dated Apr. 8, 2021, 3 pages.
Notice of Acceptance received for Australian Patent Application No. 2021200787, dated Mar. 19, 2021, 3 pages.
Notice of Allowance received for Japanese Patent Application No. 2019-162293, dated Apr. 9, 2021, 4 pages (1 page of English Translation and 3 pages of Official Copy).
Notice of Allowance received for U.S. Appl. No. 16/138,809, dated Apr. 16, 2021, 11 pages.
Office Action received for Australian Patent Application No. 2020203919, dated Mar. 30, 2021, 5 pages.
Office Action received for Chinese Patent Application No. 201680012936.3, dated Mar. 3, 2021, 12 pages (5 pages of English Translation and 7 pages of Official Copy).
Office Action received for Chinese Patent Application No. 201810411708.4, dated Feb. 26, 2021, 16 pages (8 pages of English Translation and 8 pages of Official Copy).
Office Action received for Japanese Patent Application No. 2018-184532, dated Mar. 1, 2021, 11 pages (6 pages of English Translation and 5 pages of Official Copy).
Office Action received for Korean Patent Application No. 10-2019-7029673, dated Apr. 8, 2021, 7 pages (3 pages of English Translation and 4 pages of Official Copy).
Applicant-Initiated Interview Summary received for U.S. Appl. No. 15/627,069, dated Jul. 20, 2020, 5 pages.
Decision to Grant received for European Patent Application No. 15747595.5, dated Jul. 16, 2020, 2 pages.
Notice of Allowance received for Korean Patent Application No. 10-2018-7018904, dated Jun. 26, 2020, 4 pages (1 page of English Translation and 3 pages of Official copy).
Notice of Allowance received for U.S. Appl. No. 15/554,204, dated Jul. 13, 2020, 10 pages.
Notice of Allowance received for U.S. Appl. No. 16/144,735, dated Jul. 21, 2020, 13 pages.
Office Action received for Australian Patent Application No. 2018268972, dated Jul. 9, 2020, 4 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Applicant-Initiated Interview Summary received for U.S. Appl. No. 16/145,033, dated Apr. 30, 2021, 4 pages.
Non-Final Office Action received for U.S. Appl. No. 17/192,161, dated May 13, 2021, 28 pages.
Notice of Allowance received for Chinese Patent Application No. 201680013193.1, dated May 7, 2021, 5 pages (1 page of English Translation and 4 pages of Official Copy).
Notice of Allowance received for Chinese Patent Application No. 201680047983.1, dated Apr. 28, 2021, 3 pages (1 page of English Translation and 2 pages of Official Copy).
Notice of Allowance received for Japanese Patent Application No. 2018-080122, dated May 7, 2021, 28 pages (1 page of English Translation and 27 pages of Official Copy).
Notice of Allowance received for U.S. Appl. No. 11/850,005, dated May 14, 2021, 10 pages.
Office Action received for European Patent Application No. 21150414.7, dated May 3, 2021, 8 pages.
Summons to Attend Oral Proceedings received for European Patent Application No. 16762356.0, dated May 10, 2021, 10 pages.
Summons to Oral Proceedings received for European Patent Application No. 15771747.1, dated Apr. 29, 2021, 8 pages.
European Search Report received for European Patent Application No. 21165295.3, dated Jun. 18, 2021, 4 pages.
Office Action received for European Patent Application No. 21165295.3, dated Jul. 1, 2021, 10 pages.
Advisory Action received for U.S. Appl. No. 16/806,981, dated Jun. 14, 2021, 6 pages.

(56) References Cited

OTHER PUBLICATIONS

Applicant Initiated Interview Summary received for U.S. Appl. No. 17/030,318, dated Jul. 30, 2021, 4 pages.
Applicant Initiated Interview Summary received for U.S. Appl. No. 17/030,321, dated Jul. 30, 2021, 2 pages.
Applicant-Initiated Interview Summary received for U.S. Appl. No. 15/405,122, dated Jul. 7, 2021, 4 pages.
Applicant-Initiated Interview Summary received for U.S. Appl. No. 16/533,540, dated Aug. 16, 2021, 6 pages.
Applicant-Initiated Interview Summary received for U.S. Appl. No. 16/888,629, dated Aug. 4, 2021, 5 pages.
Applicant-Initiated Interview Summary received for U.S. Appl. No. 16/894,309, dated Jun. 25, 2021, 4 pages.
Applicant-Initiated Interview Summary received for U.S. Appl. No. 17/031,859, dated Jun. 30, 2021, 4 pages.
Applicant-Initiated Interview Summary received for U.S. Appl. No. 17/031,874, dated Jun. 30, 2021, 4 pages.
Applicant-Initiated Interview Summary received for U.S. Appl. No. 17/192,161, dated Jun. 29, 2021, 4 pages.
Board Decision received for Chinese Patent Application No. 201680012936.3, dated Jun. 16, 2021, 2 pages (1 page of English Translation and 1 page of Official Copy).
Board Opinion received for Chinese Patent Application No. 201510284850.3, dated Jul. 2, 2021, 13 pages (3 pages of English Translation and 10 pages of Official Copy).
Brief Communication Regarding Oral Proceedings received for European Patent Application No. 19724963.4, dated Jun. 22, 2021, 2 pages.
Communication of the Board of Appeal received for European Patent Application No. 15771747.1, dated Aug. 25, 2021, 9 pages.
Corrected Notice of Allowance received for U.S. Appl. No. 16/377,892, dated Aug. 11, 2021, 3 pages.
Corrected Notice of Allowance received for U.S. Appl. No. 16/820,383, dated Aug. 13, 2021, 2 pages.
Corrected Notice of Allowance received for U.S. Appl. No. 16/820,383, dated Aug. 19, 2021, 2 pages.
Decision to Grant received for Danish Patent Application No. PA201670656, dated Jun. 21, 2021, 2 pages.
Decision to Grant received for German Patent Application No. 112015002326.7, dated Jun. 15, 2021, 10 pages (1 page of English Translation and 9 pages of Official Copy).
European Search Report received for European Patent Application No. 21168916.1, dated Jul. 14, 2021, 5 pages.
Examiner-Initiated Interview Summary received for U.S. Appl. No. 16/806,981, dated May 24, 2021, 4 pages.
Final Office Action received for U.S. Appl. No. 16/145,033, dated Jul. 6, 2021, 113 pages.
Final Office Action received for U.S. Appl. No. 17/030,321, dated Apr. 2, 2021, 28 pages.
Final Office Action received for U.S. Appl. No. 17/192,161, dated Aug. 16, 2021, 22 pages.
Gym Book—Strength Training Planner, Logger and Analyzer, GymBookApp, Available Online at:—https://web.archive.org/web/20160401104508/https://gymbookapp.com/, Apr. 1, 2016, 10 pages.
Intention to Grant received for European Patent Application No. 15730925.3, dated Aug. 16, 2021, 10 pages.
Intention to Grant received for European Patent Application No. 18213157.3, dated May 19, 2021, 8 pages.
Invitation to Pay Additional Fees received for PCT Patent Application No. PCT/US2021/017736, dated Jun. 15, 2021, 14 pages.
Non-Final Office Action received for U.S. Appl. No. 17/013,778, dated Aug. 20, 2021, 9 pages.
Non-Final Office Action received for U.S. Appl. No. 16/994,352, dated Jul. 30, 2021, 11 pages.
Non-Final Office Action received for U.S. Appl. No. 16/147,523, dated Jul. 21, 2021, 20 pages.
Non-Final Office Action received for U.S. Appl. No. 16/389,722, dated Jun. 3, 2021, 17 pages.
Non-Final Office Action received for U.S. Appl. No. 16/806,981, dated Sep. 1, 2021, 27 pages.
Non-Final Office Action received for U.S. Appl. No. 16/935,002, dated Jun. 25, 2021, 20 pages.
Non-Final Office Action received for U.S. Appl. No. 16/943,737, dated Jun. 25, 2021, 18 pages.
Non-Final Office Action received for U.S. Appl. No. 17/030,318, dated Apr. 2, 2021, 28 pages.
Non-Final Office Action received for U.S. Appl. No. 17/030,318, dated Dec. 3, 2020, 22 pages.
Non-Final Office Action received for U.S. Appl. No. 17/030,321, dated Dec. 15, 2020, 25 pages.
Non-Final Office Action received for U.S. Appl. No. 17/068,386, dated Jul. 15, 2021, 16 pages.
Non-Final Office Action received for U.S. Appl. No. 17/103,436, dated Aug. 18, 2021, 16 pages.
Non-Final Office Action received for U.S. Appl. No. 17/116,775, dated Aug. 24, 2021, 20 Pages.
Notice of Acceptance received for Australian Patent Application No. 2018201089, dated May 28, 2021, 3 pages.
Notice of Acceptance received for Australian Patent Application No. 2020204259, dated Jun. 11, 2021, 3 pages.
Notice of Acceptance received for Australian Patent Application No. 2020256383, dated Aug. 3, 2021, 3 pages.
Notice of Allowance received for Chinese Patent Application No. 201680012936.3, dated Jul. 13, 2021, 4 pages (1 page of English Translation and 3 pages of Official Copy).
Notice of Allowance received for Chinese Patent Application No. 201811136445.7, dated Aug. 11, 2021, 2 pages (1 page of English Translation and 1 page of Official Copy).
Notice of Allowance received for Japanese Patent Application No. 2019-563407, dated Aug. 20, 2021, 4 pages (1 page of English Translation and 3 pages of Official Copy).
Notice of Allowance received for Japanese Patent Application No. 2020-000492, dated Jul. 16, 2021, 4 pages (1 page of English Translation and 3 pages of Official Copy).
Notice of Allowance received for Korean Patent Application No. 10-2019-7025781, dated Jun. 29, 2021, 5 pages (2 pages of English Translation and 3 pages of Official Copy).
Notice of Allowance received for Korean Patent Application No. 10-2019-7029673, dated Aug. 3, 2021, 3 pages (1 page of English Translation and 2 pages of Official Copy).
Notice of Allowance received for Korean Patent Application No. 10-2019-7033834, dated Jul. 3, 2021, 4 pages (2 page of English Translation and 2 pages of Official Copy).
Notice of Allowance received for Korean Patent Application No. 10-2020-7026036, dated Jul. 26, 2021, 4 pages (1 page of English Translation and 3 pages of Official Copy).
Notice of Allowance received for U.S. Appl. No. 15/608,848, dated Aug. 25, 2021, 9 pages.
Notice of Allowance received for U.S. Appl. No. 15/627,069, dated Jun. 17, 2021, 14 pages.
Notice of Allowance received for U.S. Appl. No. 16/138,809, dated Jul. 20, 2021, 6 pages.
Notice of Allowance received for U.S. Appl. No. 16/377,892, dated May 24, 2021, 9 pages.
Notice of Allowance received for U.S. Appl. No. 16/820,383, dated Jul. 21, 2021, 11 pages.
Office Action received for Australian Patent Application No. 2019266054, dated Aug. 23, 2021, 4 pages.
Office Action received for Australian Patent Application No. 2019266054, dated Jun. 29, 2021, 3 pages.
Office Action received for Australian Patent Application No. 2020203919, dated Jul. 19, 2021, 7 pages.
Office Action received for Australian Patent Application No. 2020210234, dated Jul. 30, 2021, 7 pages.
Office Action received for Australian Patent Application No. 2020239743, dated Mar. 25, 2021, 8 pages.
Office Action received for Australian Patent Application No. 2020239748, dated Apr. 21, 2021, 6 pages.
Office Action received for Australian Patent Application No. 2020239752, dated Jun. 4, 2021, 8 pages.
Office Action received for Australian Patent Application No. 2020256383, dated Jun. 4, 2021, 3 pages.

(56) References Cited

OTHER PUBLICATIONS

Office Action received for Chinese Patent Application No. 201380081349.6, dated Jun. 2, 2021, 17 pages (8 pages of English Translation and 9 pages of Official Copy).
Office Action received for Chinese Patent Application No. 201580046788.2, dated Mar. 25, 2021, 9 pages (4 pages of English Translation and 5 pages of Official Copy).
Office Action received for Chinese Patent Application No. 201780034193.4, dated Jun. 8, 2021, 16 pages (7 pages of English Translation and 9 pages of Official Copy).
Office Action received for Chinese Patent Application No. 201780034203.4, dated Jul. 14, 2021, 12 pages (5 pages of English Translation and 7 pages of Official Copy).
Office Action received for Chinese Patent Application No. 201910858933.7, dated Jun. 29, 2021, 8 pages (3 pages of English Translation and 5 pages of Official Copy).
Office Action received for Chinese Patent Application No. 202010606407.4, dated Jun. 2, 2021, 12 pages (5 pages of English Translation and 7 pages of Official Copy).
Office Action received for European Patent Application No. 19721883.7, dated Jun. 15, 2021, 9 pages.
Office Action received for European Patent Application No. 20176616.9, dated Jun. 10, 2021, 4 pages.
Office Action received for European Patent Application No. 20182116.2, dated May 25, 2021, 9 pages.
Office Action received for European Patent Application No. 21168916.1, dated Aug. 23, 2021, 8 pages.
Office Action received for Japanese Patent Application No. 2020-115940, dated May 7, 2021, 3 pages (1 page of English Translation and 2 pages of Official Copy).
Result of Consultation received for European Patent Application No. 19724963.4, dated Jul. 8, 2021, 3 pages.
Result of Consultation received for European Patent Application No. 19724963.4, dated May 31, 2021, 3 pages.
Search Report and Opinion received for Danish Patent Application No. PA202070612, dated Jun. 7, 2021, 9 pages.
Search Report and Opinion received for Danish Patent Application No. PA202070613, dated Jan. 22, 2021, 9 pages.
Search Report and Opinion received for Danish Patent Application No. PA202070615, dated Jan. 22, 2021, 9 pages.
Search Report and Opinion received for Danish Patent Application No. PA202070616, dated Feb. 3, 2021, 8 pages.
Search Report received for Netherlands Patent Application No. 2015236, dated Apr. 21, 2021, 19 pages (13 pages of English Translation and 6 pages of Official Copy).
Supplemental Notice of Allowance received for U.S. Appl. No. 15/627,069, dated Jul. 12, 2021, 2 pages.
Phonebuff, "Hybrid Stopwatch & Timer Android App Review", Available Online at https://www.youtube.com/watch?v=B43oCFPiWvY, Apr. 4, 2012, 7 pages.
Lyons et al., "Facet: A Multi-Segment Wrist Worn System", Online available at: <http://fetlab.io/publications/2012Faceta%20multisegment%20wrist%20worn%20system.pdf>, Oct. 7-10, 2012, pp. 123-129.
Phandroid, "How to record & stream using YouTube Gaming", Available online at https://www.youtube.com/watch?v=8H5Q1L9M_ql, Jun. 1, 2016, 3 pages.
Sansford Steve, "Streaming Android Games with OBS On Linux", Available online at: https://www.youtube.com/watch?v=twyh32Ud8vQ, May 20, 2016, 3 pages.
Sony, "Sony Smartwatch 3 SWR50", User Guide, Jul. 2014, 31 pages.
Xzulas, "PS4 to Twitch—How to Broadcast Gameplay—Camera and Audio Settings", Available online at: https://www.youtube.com/watch?v=TyTR64RF0wl, Nov. 3, 2014, 4 pages.
Non-Final Office Action received for U.S. Appl. No. 16/679,967, dated Sep. 2, 2021, 12 pages.

* cited by examiner

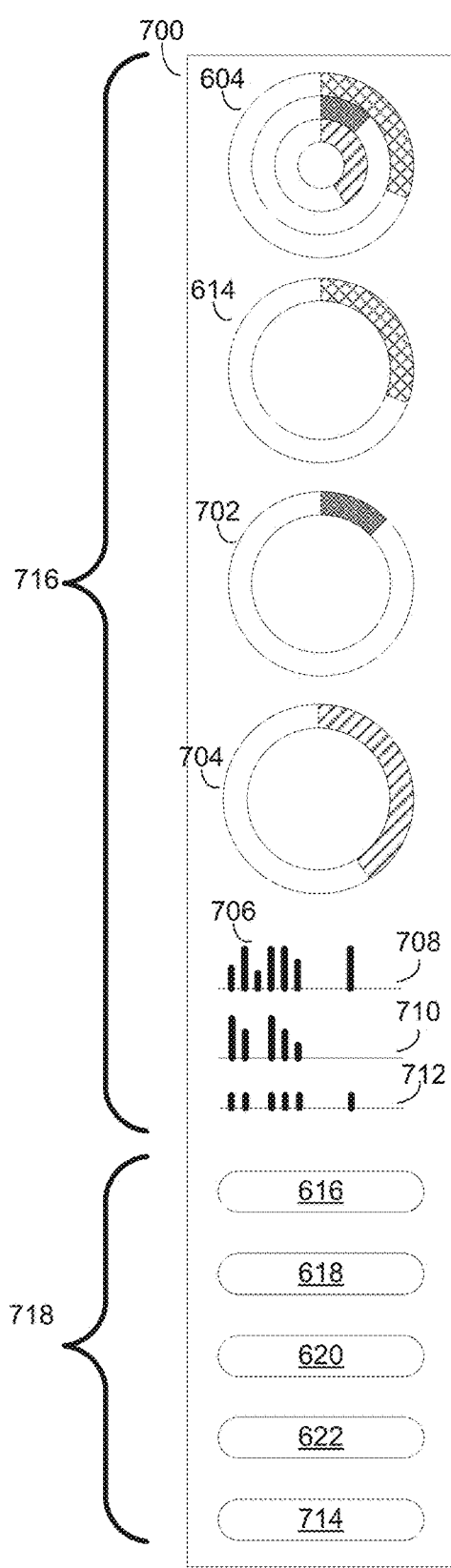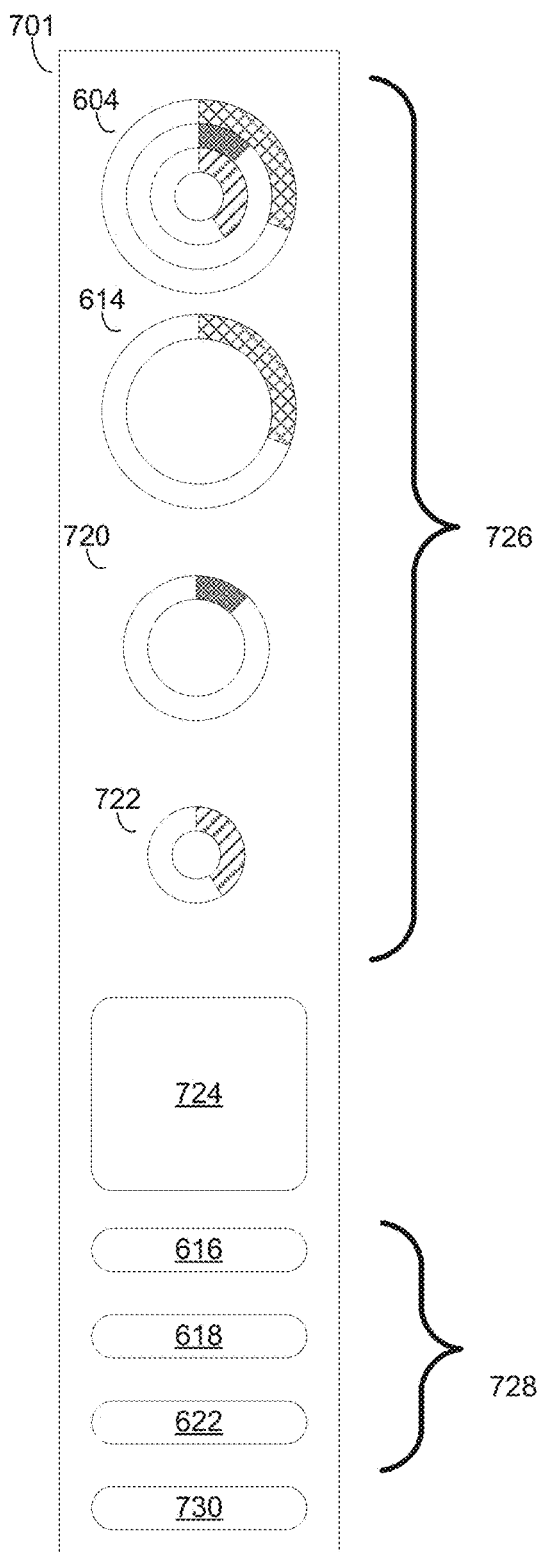
FIG. 7A
FIG. 7B

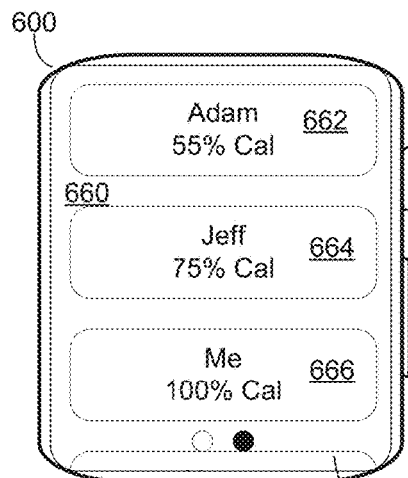
FIG. 10A
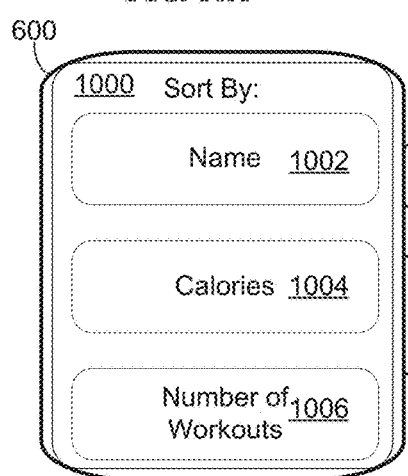
FIG. 10B
FIG. 10C
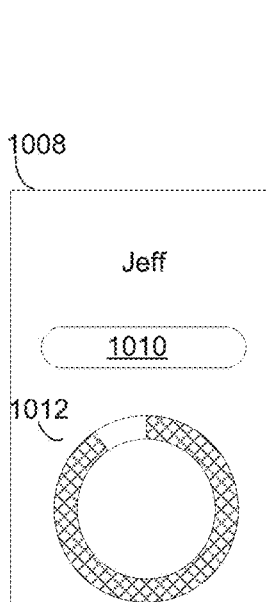
FIG. 10D
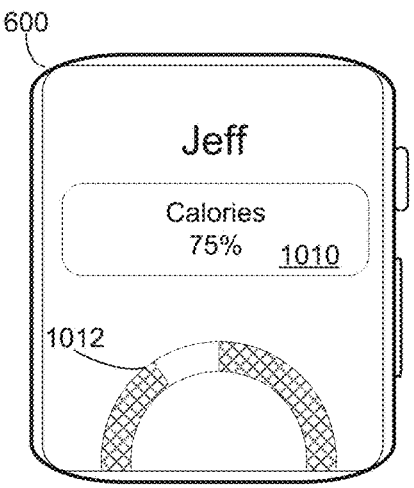
FIG. 10E
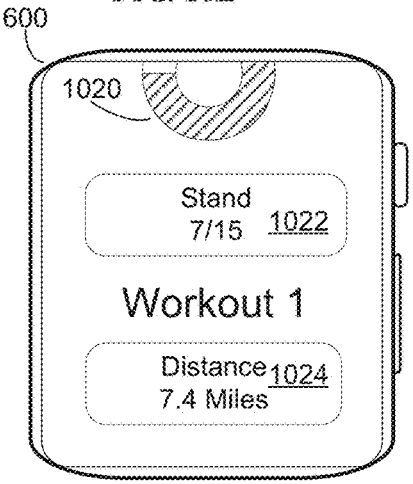
FIG. 10F
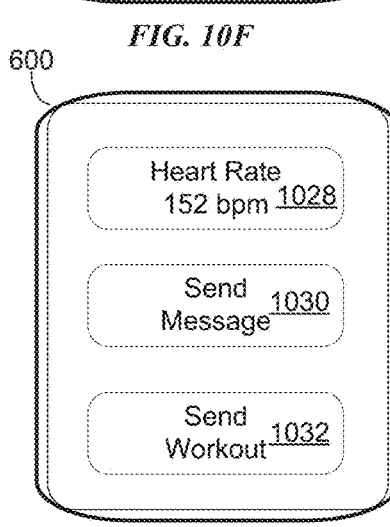
FIG. 10G

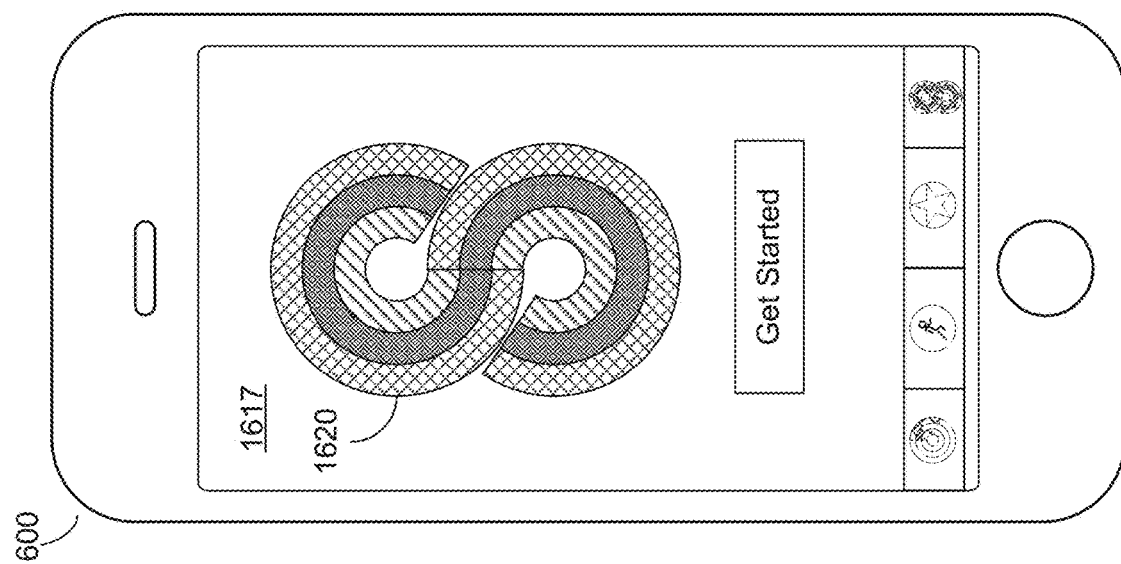
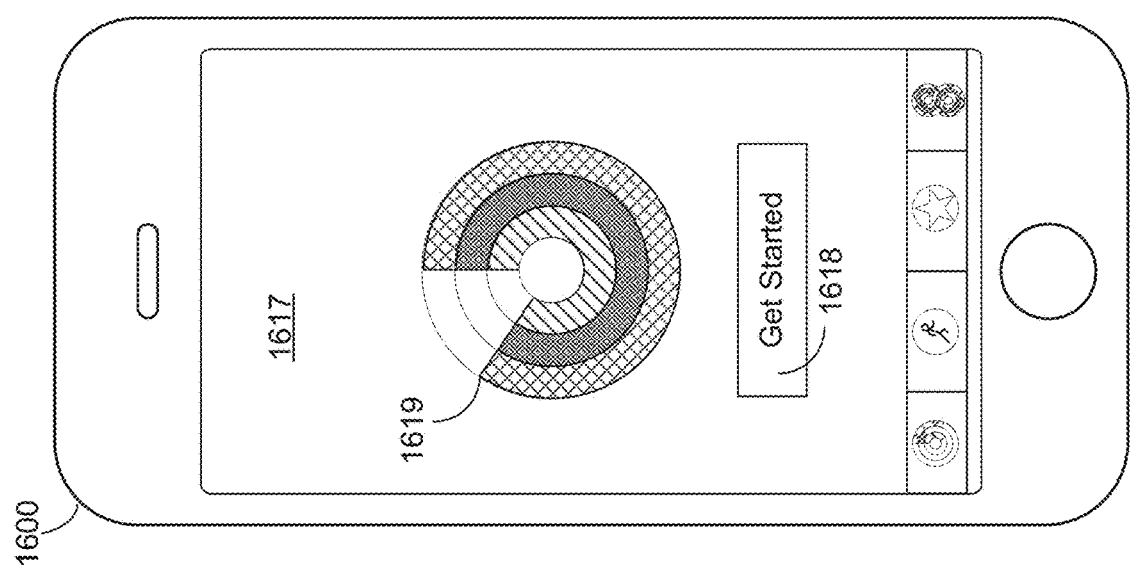
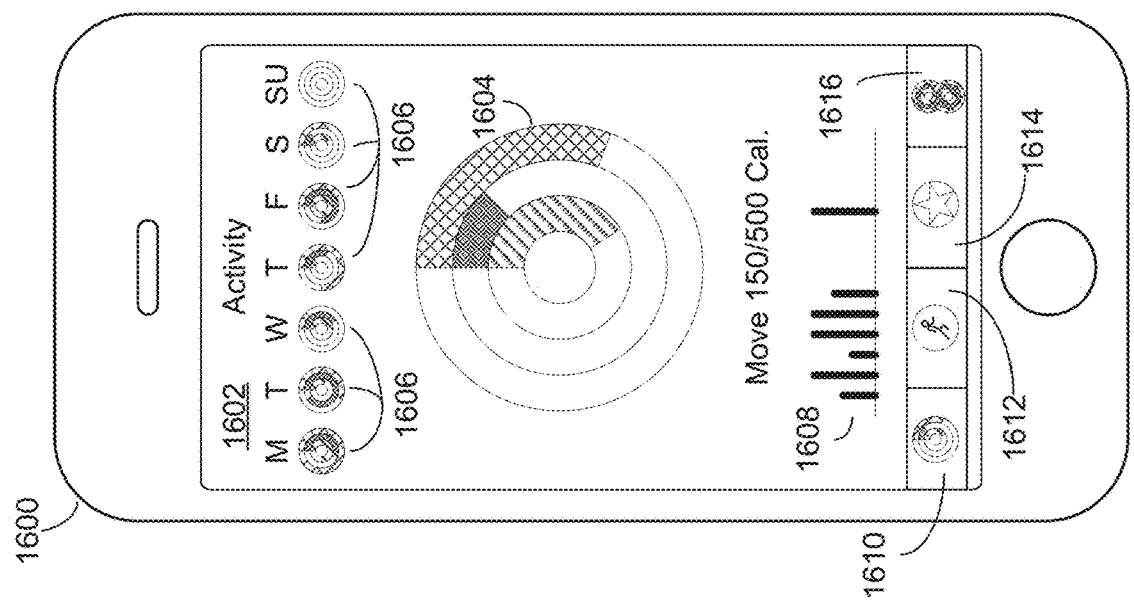

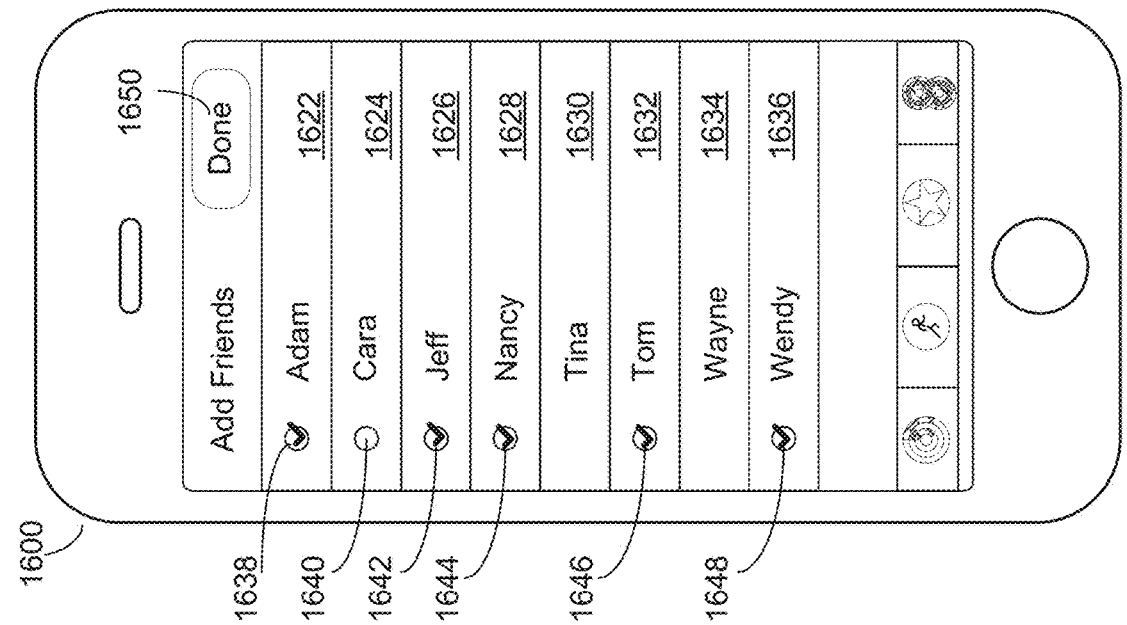

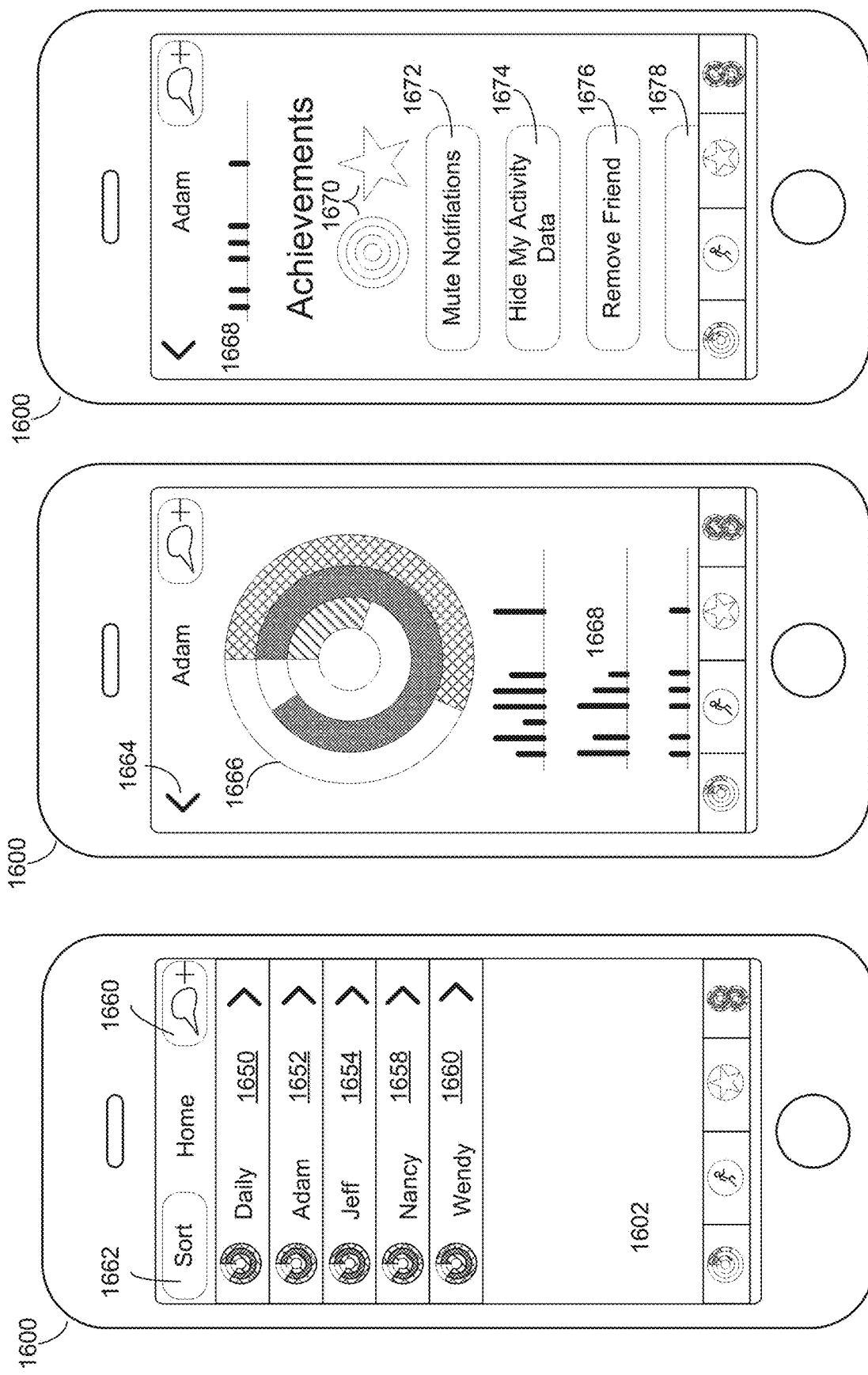

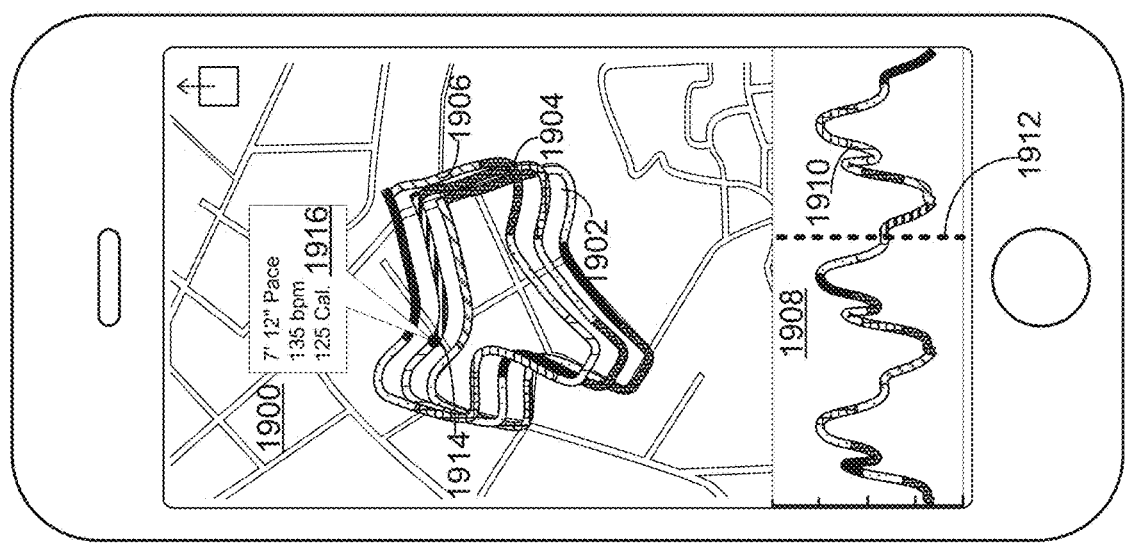

ACTIVITY AND WORKOUT UPDATES

CROSS-REFERENCE TO RELATED APPLICATIONS

This application is a continuation of U.S. patent application Ser. No. 15/616,480, entitled "ACTIVITY AND WORKOUT UPDATES", filed on Jun. 7, 2017, which claims priority to U.S. provisional patent application 62/348,908, entitled "ACTIVITY AND WORKOUT UPDATES", filed on Jun. 11, 2016, the contents of which are hereby incorporated by reference in their entirety.

FIELD

The present disclosure relates generally to computer user interfaces, and more specifically to techniques for interacting with workout or activity applications.

BACKGROUND

Approximately 133 million Americans currently suffer from at least one chronic health condition. This number is expected to rise to approximately 165 million by the year 2020. This deterioration in health can be attributed largely to a sedentary lifestyle with little to no physical activity. For example, lack of sufficient physical activity can increase the risk of developing diabetes, hypertension, colon cancer, depression and anxiety, obesity, and weak muscles and bones. In addition, recent studies have found that extended periods of inactivity (e.g., sitting at a desk), can lead to serious health risks, such as an increased risk of a heart attack.

BRIEF SUMMARY

Some techniques for viewing and sharing activity data using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for viewing and sharing activity data. Such methods and interfaces optionally complement or replace other methods for viewing and sharing activity data. Such methods and interfaces reduce the cognitive burden on a user and produce a more efficient human-machine interface. For battery-operated computing devices, such methods and interfaces conserve power and increase the time between battery charges.

In an embodiment, at a portable electronic device having a display, a graphical representation of activity data is generated for output on the display. The graphical representation includes a goal portion and a workout portion. The goal portion and the workout portion each extend beyond a displayable area of the display. The goal portion includes a first goal graphical element for a first goal metric. The workout portion includes a first workout graphical element for a first workout metric. A first portion of the graphical representation is displayed on the display. The displayed first portion includes a first graphical element. In response to receiving a first scroll input and while the displayed first portion is of the goal portion, the display of the first graphical element is replaced with a display of the first goal graphical element. In response to receiving a first scroll input and while the displayed first portion is not of the goal portion, the first graphical element is translated by an amount based on a magnitude of the first scroll input and displaying at least portion of the first workout graphical element.

In an embodiment, at a portable electronic device having a display, contact information for a plurality of contacts, including a first contact, is displayed. Activity summary data for the first contact is received from one or more external electronic devices. The activity summary data for the first contact includes a first goal metric. First user input selecting the first contact is received. In response to receiving the first user input selecting the first contact, a portion of a graphical representation of the activity summary is displayed on the display. The graphical representation includes a first goal graphical element for the first goal metric.

In an embodiment, at a portable electronic device having a display, a notification and workout summary data are receiving from an external electronic device. The workout summary data is for a completed workout of a remote user associated with the external electronic device. A first graphical element representing the notification is displayed on the display. A first user input is received selecting the first graphical element while displaying the first graphical element. In response to the first user input, a portion of a graphical representation of the workout summary data is displayed In an embodiment, at a portable electronic device having a display and a touch-sensitive scree, contact information is displayed, including first contact information for a first plurality of contacts, including a first contact. The first contact information corresponds to the first contact. First user input is received indicating a selection of the first contact. In response to receiving the first user input, a determination is made whether the portable electronic device has access to activity data associated with the first contact. In accordance with a determination that the portable electronic device has access to activity data associated with the first contact, a portion of a graphical representation of the activity data is displayed. In accordance with a determination that the electronic device does not have access to activity data associated with the first contact, a graphical element is displayed indicating that activity data is not available for the first contact.

In an embodiment, at a portable electronic device having a display, first workout data for a first segment of a multi-segment workout route is received. The first workout data includes a plurality of locations for the multi-segment workout route and a plurality of workout metrics associated with the plurality of locations. Second workout data for a second segment of the multi-segment workout route is received. The second workout data includes a plurality of locations for the multi-segment workout route and a plurality of workout metrics associated with the plurality of locations. A first graphical representation of the first workout data and a second graphical representation of the second workout data are displayed over a map. The first and second graphical representations are displayed in a three-dimensional stack. The appearance of the first graphical representation is based on the plurality of workout metrics of the first workout data and the second graphical representation is based on the plurality of workout metrics of the second workout data.

In an embodiment, on a portable electronic device with a display and a pressure sensitive touch screen, an indication to start a workout is received. In response to receiving the indication start a workout, a plurality of workout metrics for the workout are recorded with a workout application of the electronic device. A first user input is received on the pressure sensitive touch screen while recording the plurality of workout metrics. The first user input has a characteristic intensity. In response to receiving the first user input, a determination is made whether the workout application is in a locked state and whether the characteristic intensity exceeds a threshold intensity. In accordance with a determination that the workout application is in a locked state and the first user input does not exceed the threshold intensity, the workout application of the electronic device continues to record the plurality of workout metrics for the workout. In accordance with a determination that the workout application is in a locked state and the first user input exceeds the threshold intensity, recording with the workout application is stopped. In accordance with a determination that the workout application is in an unlocked state, the first user input according is processed according to the workout application.

An embodiment of a transitory computer-readable storage medium stores one or more programs configured to be executed by one or more processors of an electronic device with a display. The one or more programs includes instructions for: generating, for output on the display, a graphical representation of activity data, wherein the graphical representation includes a goal portion and a workout portion, wherein the goal portion and the workout portion each extend beyond a displayable area of the display, wherein the goal portion includes a first goal graphical element for a first goal metric, and wherein the workout portion includes a first workout graphical element for a first workout metric; displaying a first portion of the graphical representation on the display, wherein the displayed first portion includes a first graphical element; in response to receiving a first scroll input: while the displayed first portion is of the goal portion, replacing the display of the first graphical element with a display of the first goal graphical element; and while the displayed first portion is not of the goal portion, translating the first graphical element by an amount based on a magnitude of the first scroll input and displaying at least portion of the first workout graphical element.

An embodiment of a transitory computer-readable storage medium stores one or more programs configured to be executed by one or more processors of an electronic device with a display. The one or more programs includes instructions for: displaying contact information for a plurality of contacts, including a first contact; receiving, from one or more external electronic devices, activity summary data for the first contact, wherein the activity summary data for the first contact includes a first goal metric; receiving first user input selecting the first contact; in response to receiving the first user input selecting the first contact, displaying a portion of a graphical representation of the activity summary on the display, wherein the graphical representation includes a first goal graphical element for the first goal metric.

An embodiment of a transitory computer-readable storage medium stores one or more programs configured to be executed by one or more processors of an electronic device with a display. The one or more programs includes instructions for: receiving, from an external electronic device, a notification and workout summary data for a completed workout of a remote user associated with the external electronic device; displaying, on the display, a first graphical element representing the notification; receiving a first user input selecting the first graphical element while displaying the first graphical element; in response to the first user input, displaying a portion of a graphical representation of the workout summary data.

An embodiment of a transitory computer-readable storage medium stores one or more programs configured to be executed by one or more processors of an electronic device with a display. The one or more programs includes instructions for: displaying contact information, including first contact information, for a first plurality of contacts, including a first contact, wherein the first contact information corresponds to the first contact; receiving first user input indicating a selection of the first contact; in response to receiving the first user input, determining whether the portable electronic device has access to activity data associated with the first contact; in accordance with a determination that the portable electronic device has access to activity data associated with the first contact, displaying a portion of a graphical representation of the activity data; and in accordance with a determination that the electronic device does not have access to activity data associated with the first contact, displaying a graphical element indicating that activity data is not available for the first contact.

An embodiment of a transitory computer-readable storage medium stores one or more programs configured to be executed by one or more processors of an electronic device with a display. The one or more programs includes instructions for: receiving first workout data for a first segment of a multi-segment workout route, wherein the first workout data includes a plurality of locations for the multi-segment workout route and a plurality of workout metrics associated with the plurality of locations; receiving second workout data for a second segment of the multi-segment workout route, wherein the second workout data includes a plurality of locations for the multi-segment workout route and a plurality of workout metrics associated with the plurality of locations; and displaying a first graphical representation of the first workout data and a second graphical representation of the second workout data over a map, wherein the first and second graphical representations are displayed in a three-dimensional stack, wherein the appearance of the first graphical representation is based on the plurality of workout metrics of the first workout data and the second graphical representation is based on the plurality of workout metrics of the second workout data.

An embodiment of a transitory computer-readable storage medium stores one or more programs configured to be executed by one or more processors of an electronic device with a display. The one or more programs includes instructions for: receiving an indication to start a workout; in response to receiving the indication start a workout, recording with a workout application of the electronic device a plurality of workout metrics for the workout; receiving a first user input on the pressure sensitive touch screen while recording the plurality of workout metrics, wherein the first user input has a characteristic intensity; in response to receiving the first user input, determining: whether the workout application is in a locked state, and whether the characteristic intensity exceeds a threshold intensity; in accordance with a determination that the workout application is in a locked state and the first user input does not exceed the threshold intensity, continuing to record with the workout application of the electronic device the plurality of workout metrics for the workout; in accordance with a determination that the workout application is in a locked state and the first user input exceeds the threshold intensity, stopping the recording with the workout application; in accordance with a determination that the workout application is in an unlocked state, processing the first user input according to the workout application.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for viewing and sharing activity data, thereby increasing the effectiveness, efficiency, and user satisfaction with such devices. Such methods and interfaces may complement or replace other methods for viewing and sharing activity data.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIGS. 7A-7K illustrate user interfaces of a portable electronic device navigating and viewing activity data in accordance with some embodiments.

FIGS. 10A-10G illustrate user interfaces of a portable electronic device navigating and viewing contact's activity data in accordance with some embodiments.

FIGS. 16A-16J illustrate exemplary user interfaces navigating and sharing activity data in accordance with some embodiments.

FIGS. 19A-19D illustrate exemplary user interfaces for viewing and navigating workout data in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for viewing, navigating, and sharing activity or workout data and interacting with workout applications. For example, there is a need for display of workout and other activity data in a manner that allows for efficient navigation, even during a workout, easy viewing, and convenient sharing with friends. As another example, there is also a need for interfaces with workout applications that allow for easy interaction with the workout application during the work while at the same time preventing inadvertent functions form being activated during the workout. Such techniques can reduce the cognitive burden on a user who use activity and workout applications, thereby enhancing productivity. Further, such techniques can reduce processor and battery power otherwise wasted on redundant user inputs.

Below, FIGS. 1A-1B, 2, 3, 4A-4B, and 5A-5H provide a description of exemplary devices for performing the techniques for managing event notifications. FIGS. 6A-6E illustrate exemplary user interfaces for a workout or activity application.

FIGS. 7A-7K illustrate user interfaces of a portable electronic device navigating and viewing activity data in accordance with some embodiments. FIG. 8 is a flow diagram illustrating a method for navigating and viewing activity data using a portable electronic device in accordance with some embodiments. The user interfaces in FIGS. 7A-7K are used to illustrate the processes described below, including the processes in FIG. 8.

Figure 11:
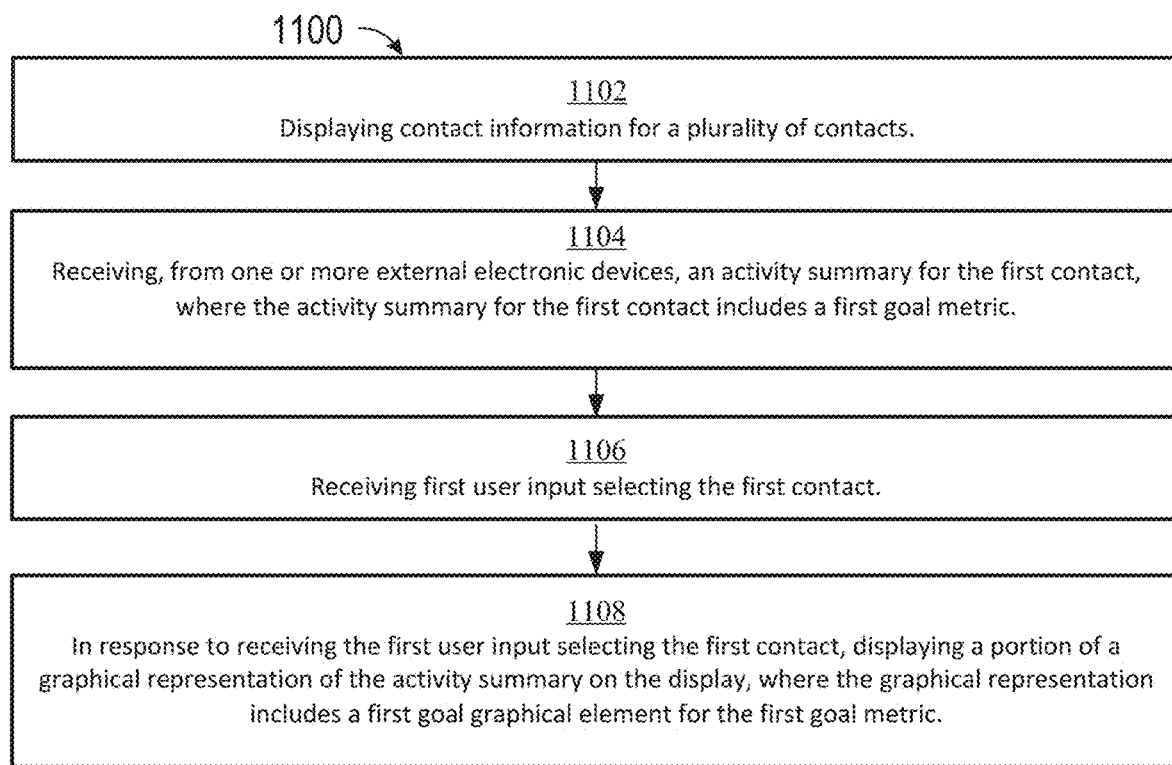
FIG. 11 is a flow diagram illustrating a method for navigating and viewing contact's activity data using a portable electronic device in accordance with some embodiments.

FIGS. 10A-10G illustrate user interfaces of a portable electronic device navigating and viewing contact's activity data in accordance with some embodiments. FIG. 11 is a flow diagram illustrating a method for navigating and viewing contact's activity data using a portable electronic device in accordance with some embodiments. The user interfaces in FIGS. 10A-10G are used to illustrate the processes described below, including the processes in FIG. 11.

FIGS. 13A-13F illustrate exemplary user interfaces for activity and workout monitoring and sharing, in accordance with some embodiments. FIG. 14 is a flow diagram illustrating a method for activity and workout monitoring and sharing using a portable electronic device in accordance with some embodiments. The user interfaces in FIGS. 13A-13F are used to illustrate the processes described below, including the processes in FIG. 14.

Figure 16J:
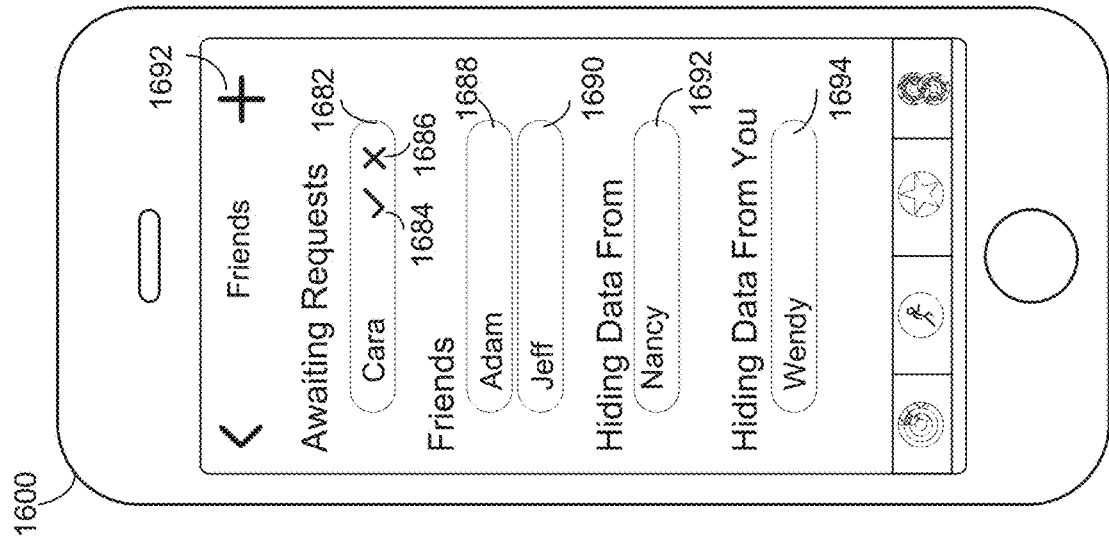

FIGS. 16A-16J illustrate exemplary user interfaces navigating and sharing activity data in accordance with some embodiments. FIG. 17 is a flow diagram illustrating a method for navigating and sharing activity data using a portable electronic device in accordance with some embodiments. The user interfaces in FIGS. 16A-16J are used to illustrate the processes described below, including the processes in FIG. 17.

Figure 19C:
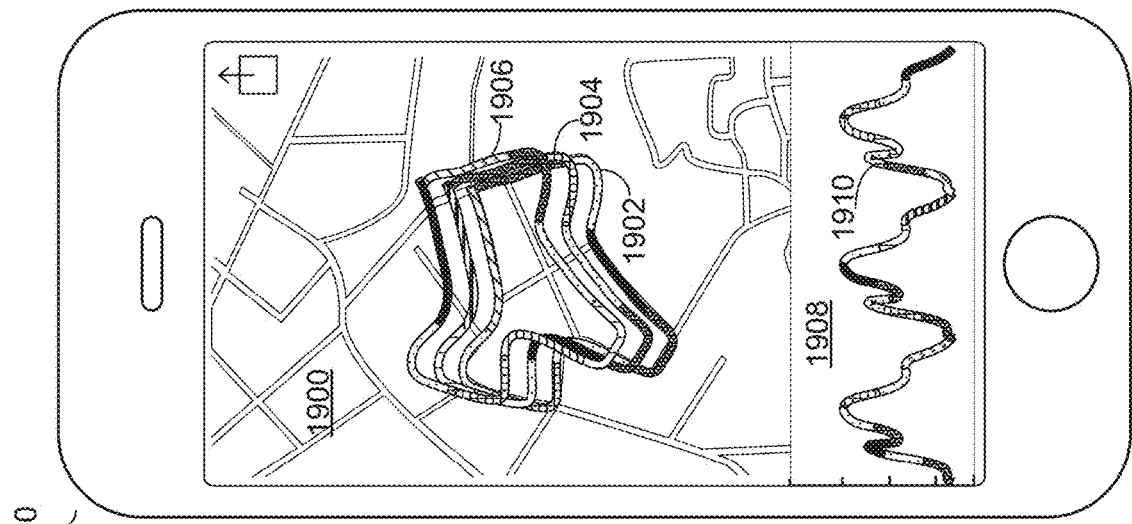
Figure 19B:
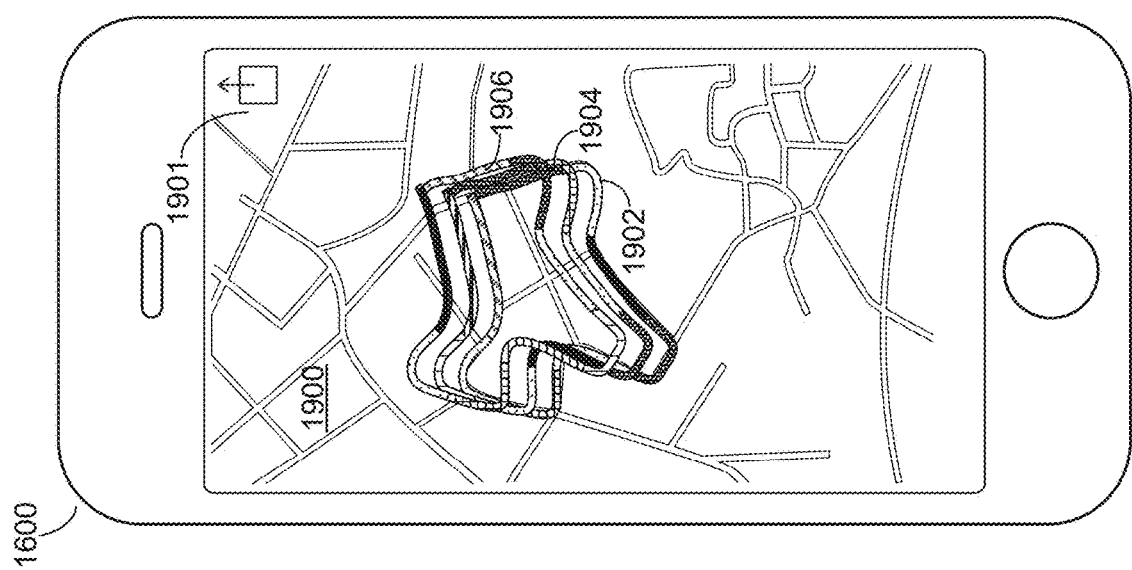

FIGS. 19A-19D illustrate exemplary user interfaces for viewing and navigating workout data in accordance with some embodiments. FIG. 20 is a flow diagram illustrating a method 2000 for viewing and navigating workout data using a portable electronic device in accordance with some embodiments. The user interfaces in FIGS. 19A-19D are used to illustrate the processes described below, including the processes in FIG. 20.

FIGS. 22A-22F illustrate exemplary user interfaces for pausing a workout and preventing inadvertent activation of other functions on the portable electronic device in accordance with some embodiments. FIG. 23 is a flow diagram illustrating a method 2300 for pausing a workout and preventing inadvertent activation of the other functions on a portable electronic device during a workout in accordance with some embodiments. The user interfaces in FIGS. 22A-22F are used to illustrate the processes described below, including the processes in FIG. 23.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
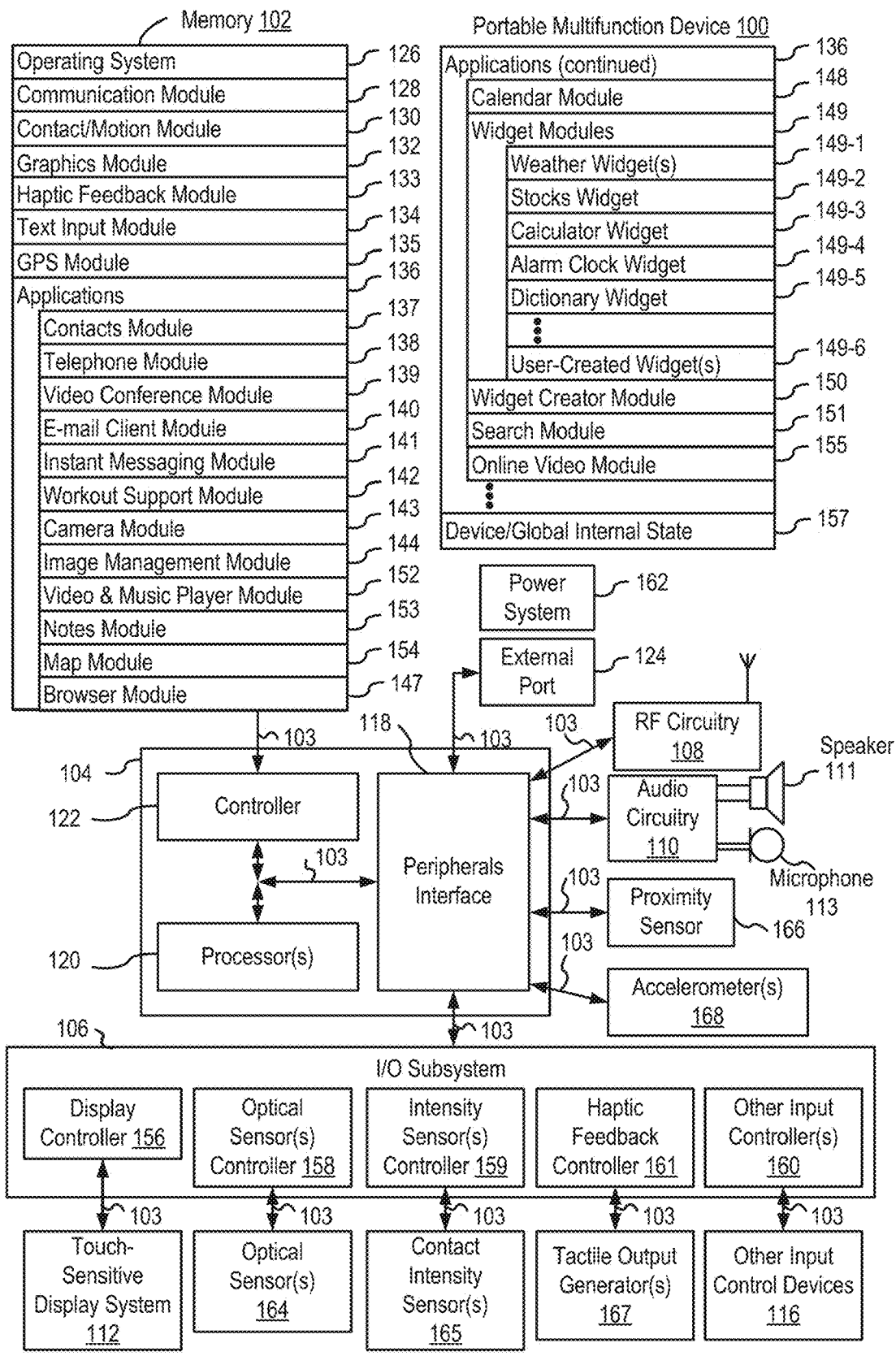
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons is, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228, 700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad (not shown) for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
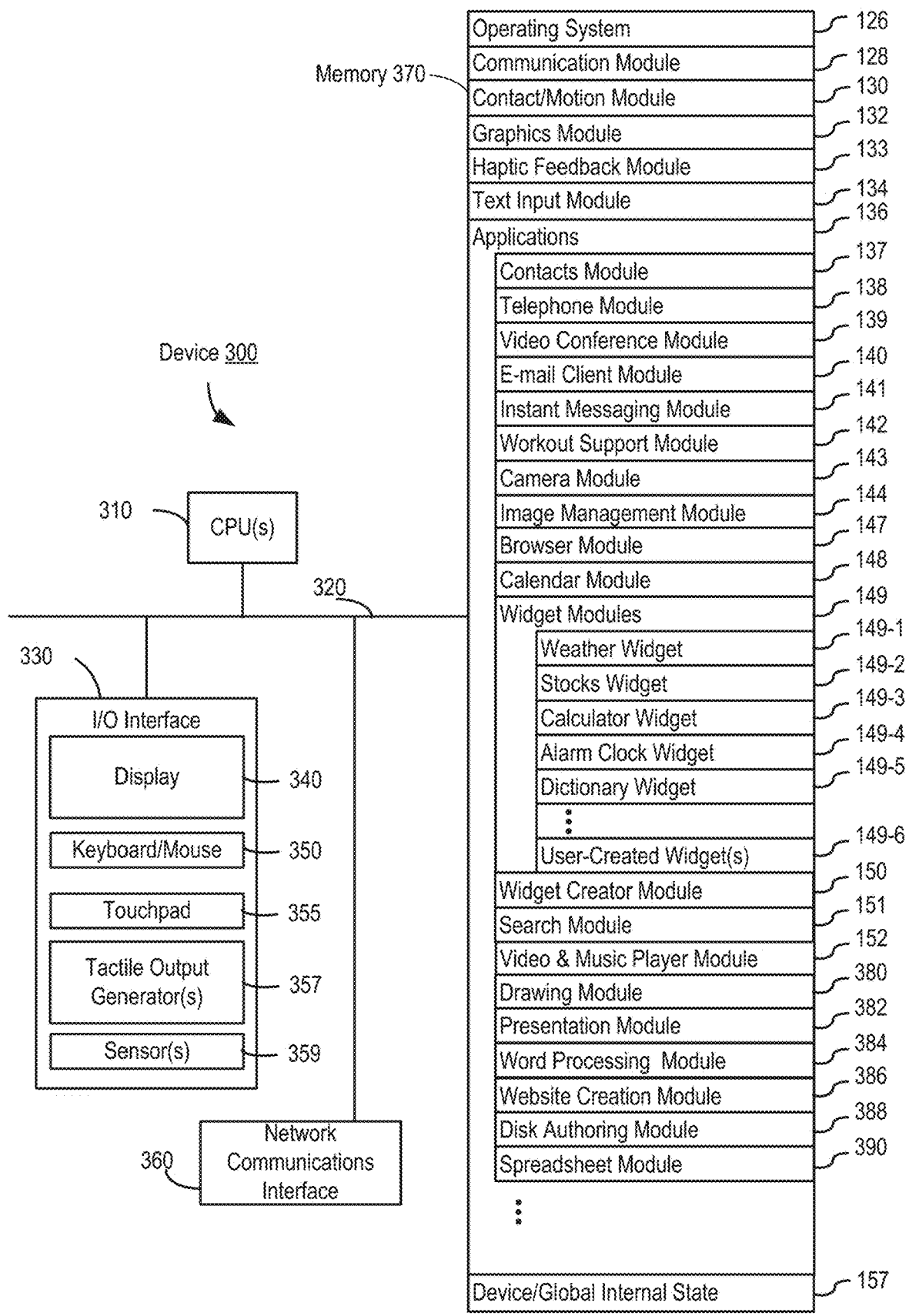
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
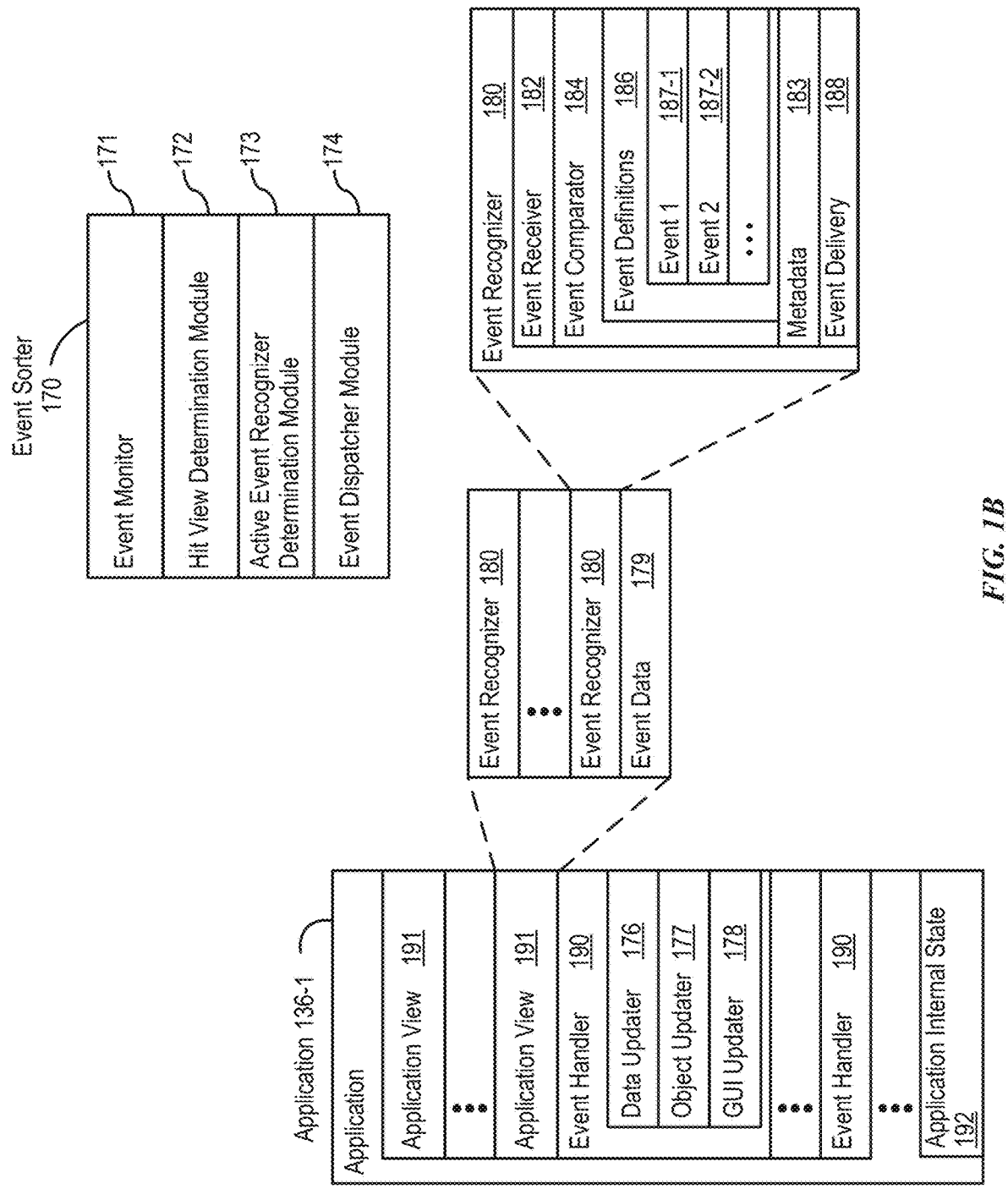
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
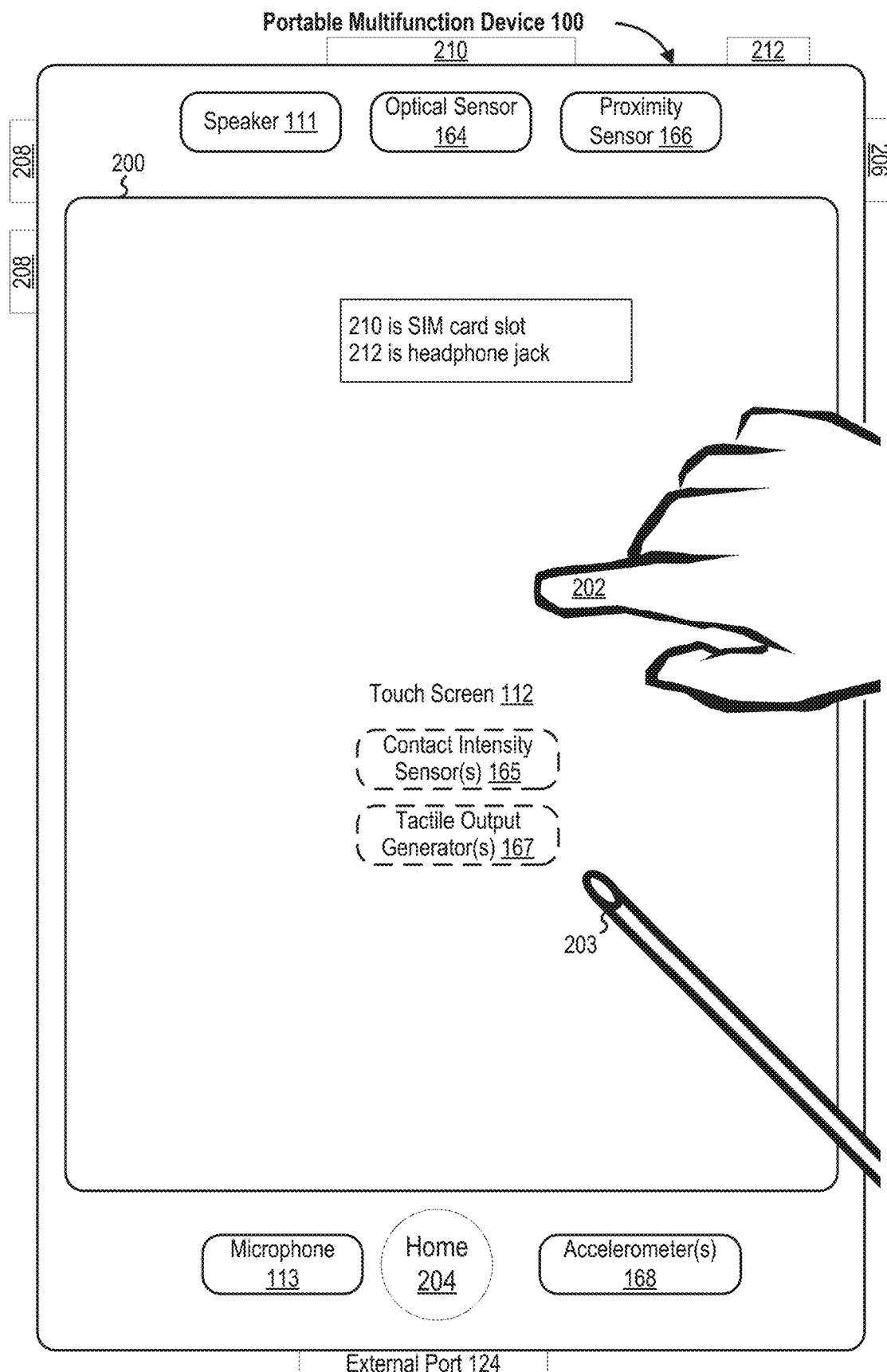
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
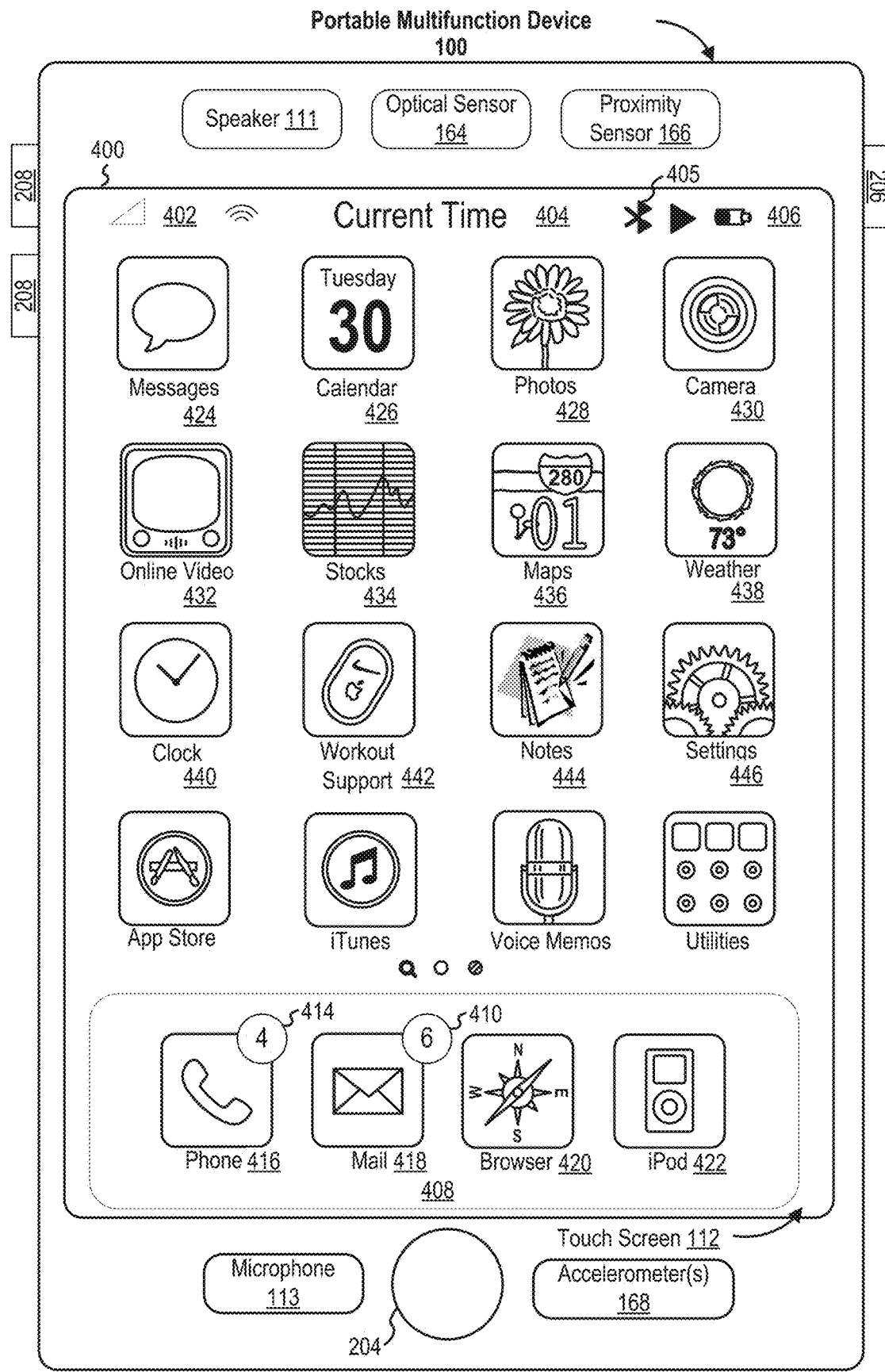
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

- Signal strength indicator(s) 402 for wireless communication(s), such as cellular and Wi-Fi signals;
- Time 404;
- Bluetooth indicator 405;
- Battery status indicator 406;
- Tray 408 with icons for frequently used applications, such as:
    - Icon 416 for telephone module 138, labeled "Phone," which optionally includes an indicator 414 of the number of missed calls or voicemail messages;
    - Icon 418 for e-mail client module 140, labeled "Mail," which optionally includes an indicator 410 of the number of unread e-mails;
    - Icon 420 for browser module 147, labeled "Browser;" and
    - Icon 422 for video and music player module 152, also referred to as iPod (trademark of Apple Inc.) module 152, labeled "iPod;" and
- Icons for other applications, such as:
    - Icon 424 for IM module 141, labeled "Messages;"
    - Icon 426 for calendar module 148, labeled "Calendar;"
    - Icon 428 for image management module 144, labeled "Photos;"
    - Icon 430 for camera module 143, labeled "Camera;"
    - Icon 432 for online video module 155, labeled "Online Video;"
    - Icon 434 for stocks widget 149-2, labeled "Stocks;"

Icon 436 for map module 154, labeled "Maps;"
Icon 438 for weather widget 149-1, labeled "Weather;"
Icon 440 for alarm clock widget 149-4, labeled "Clock;"
Icon 442 for workout support module 142, labeled "Workout Support;"
Icon 444 for notes module 153, labeled "Notes;" and
Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
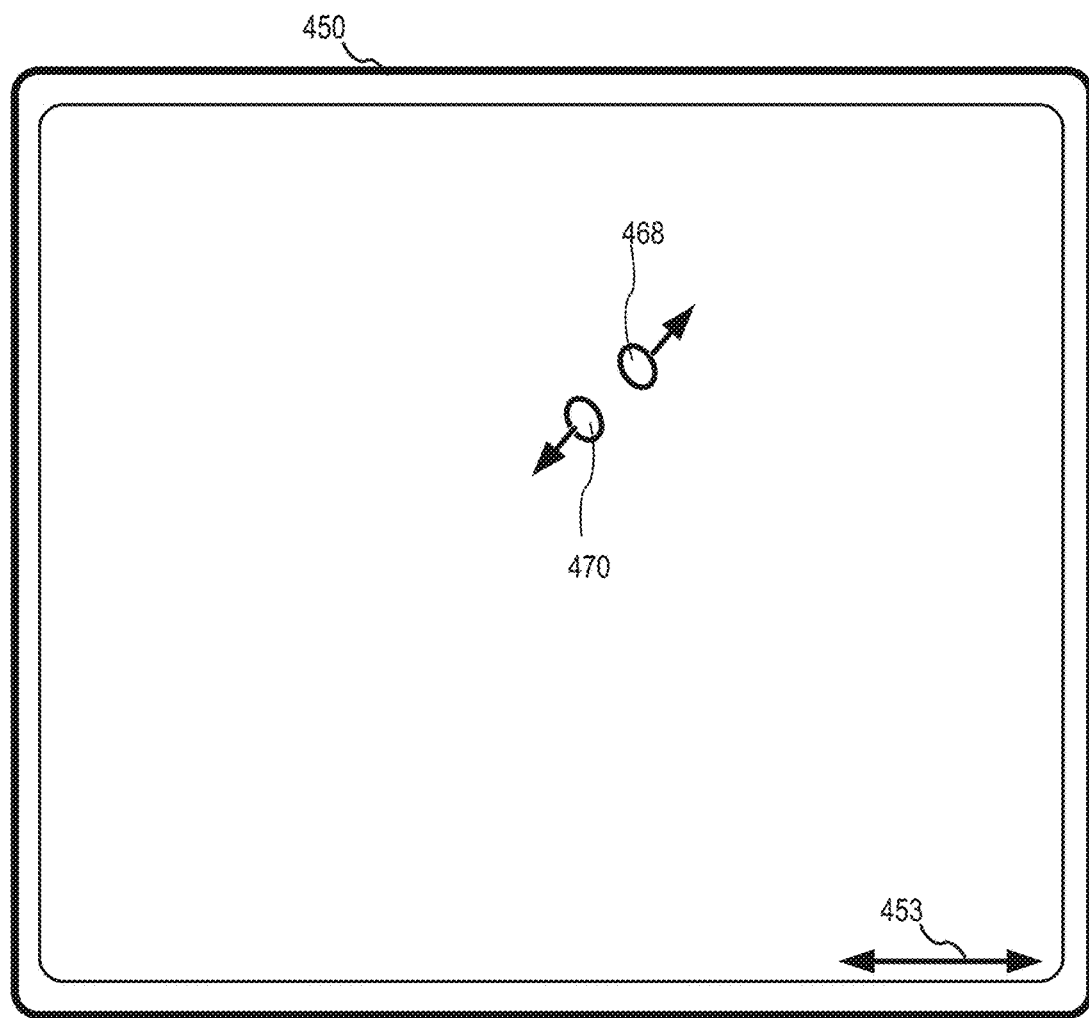
FIG. 4B illustrates an exemplary user interface for a multifunction device with a touch-sensitive surface that is separate from the display in accordance with some embodiments.
Figure 4B:
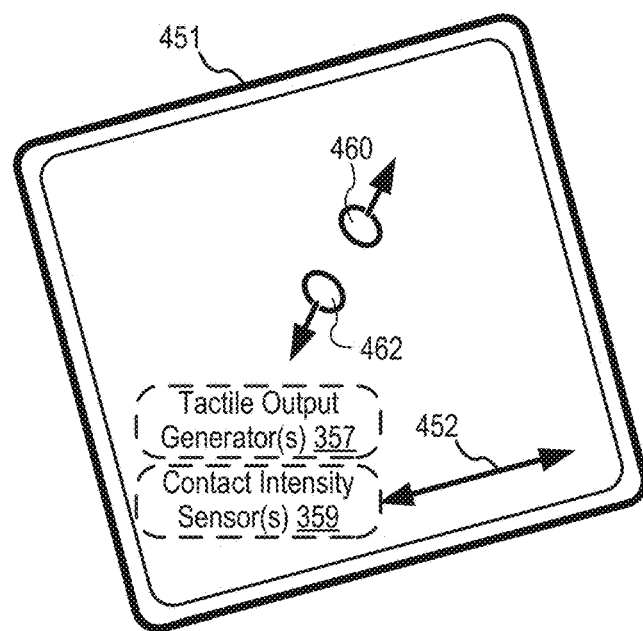

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
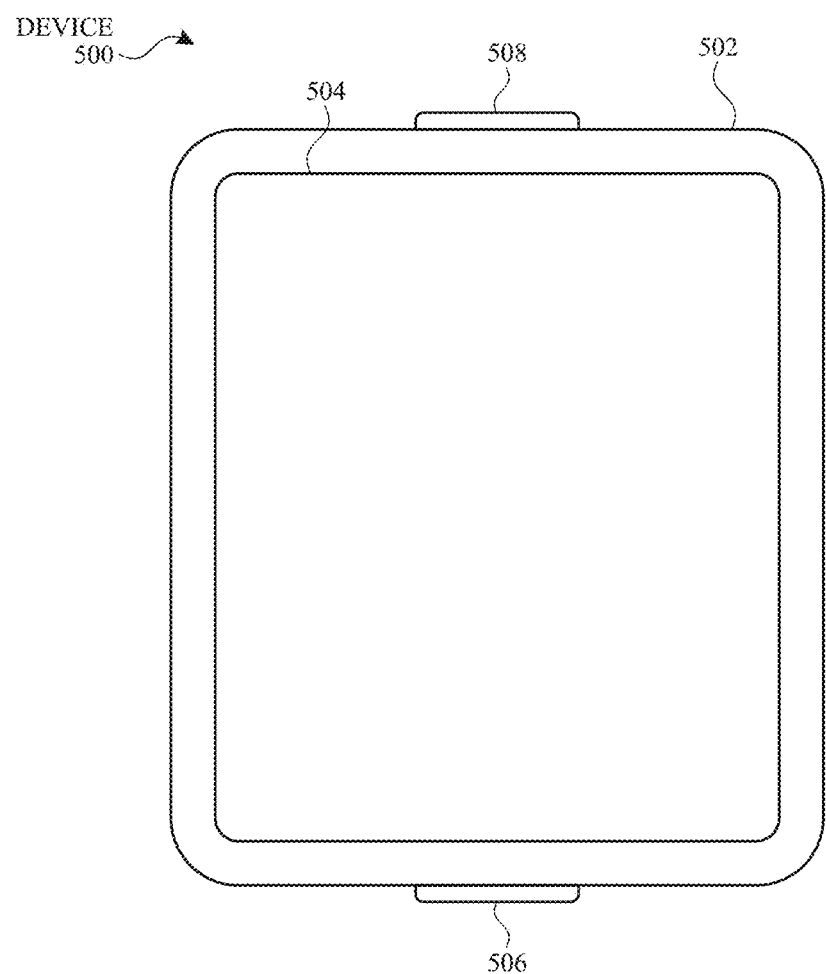
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
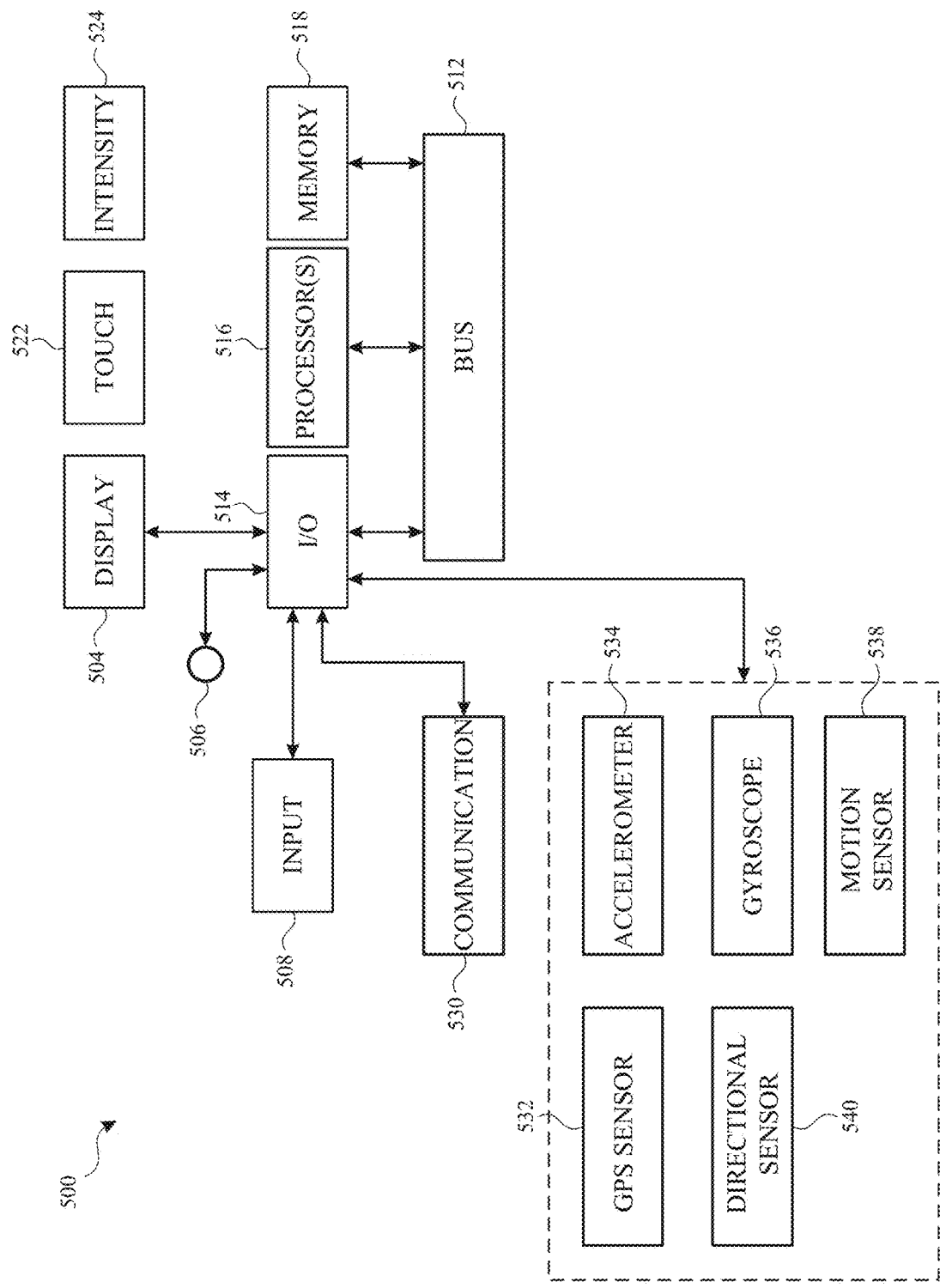
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including method 800 (FIG. 8), method 11 (FIG. 11), method 1400 (FIG. 14), method 1700 (FIG. 17), method 2000 (FIG. 20), and method 2300 (FIG. 23). Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1, 3, and 5). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Figure 5C:
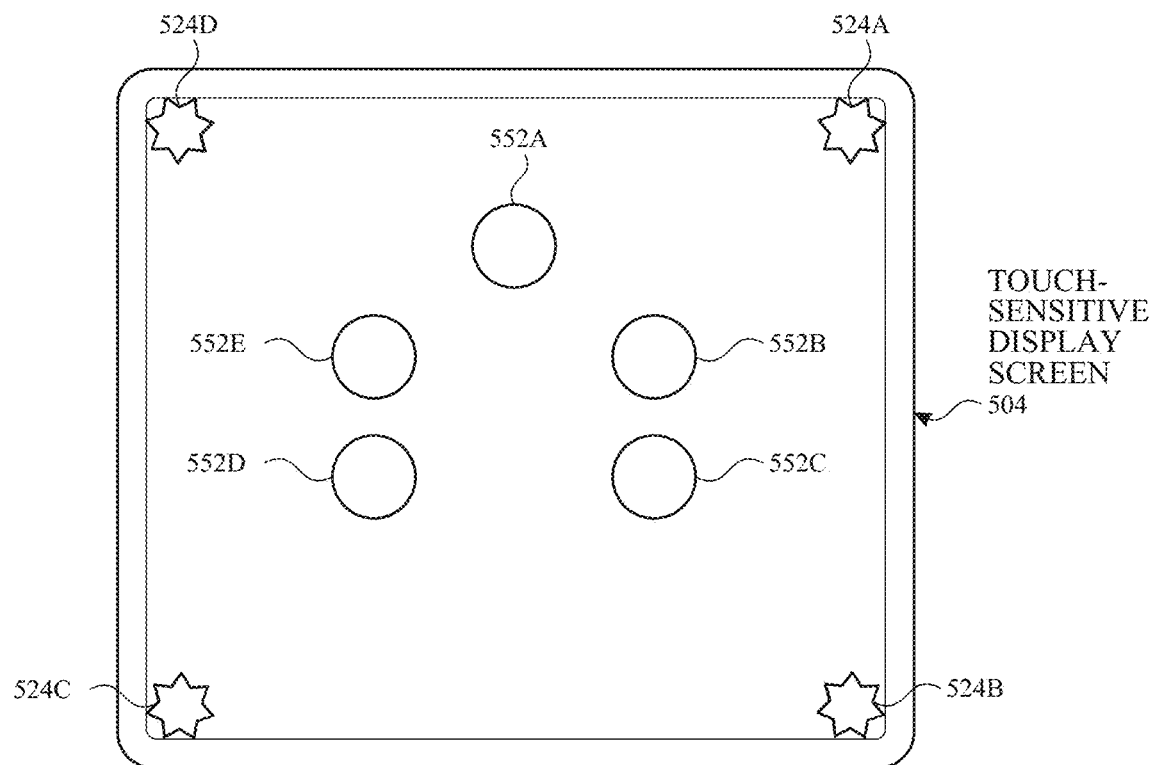
FIGS. 5C-5D illustrate exemplary components of a personal electronic device having a touch-sensitive display and intensity sensors in accordance with some embodiments.
Figure 5C:
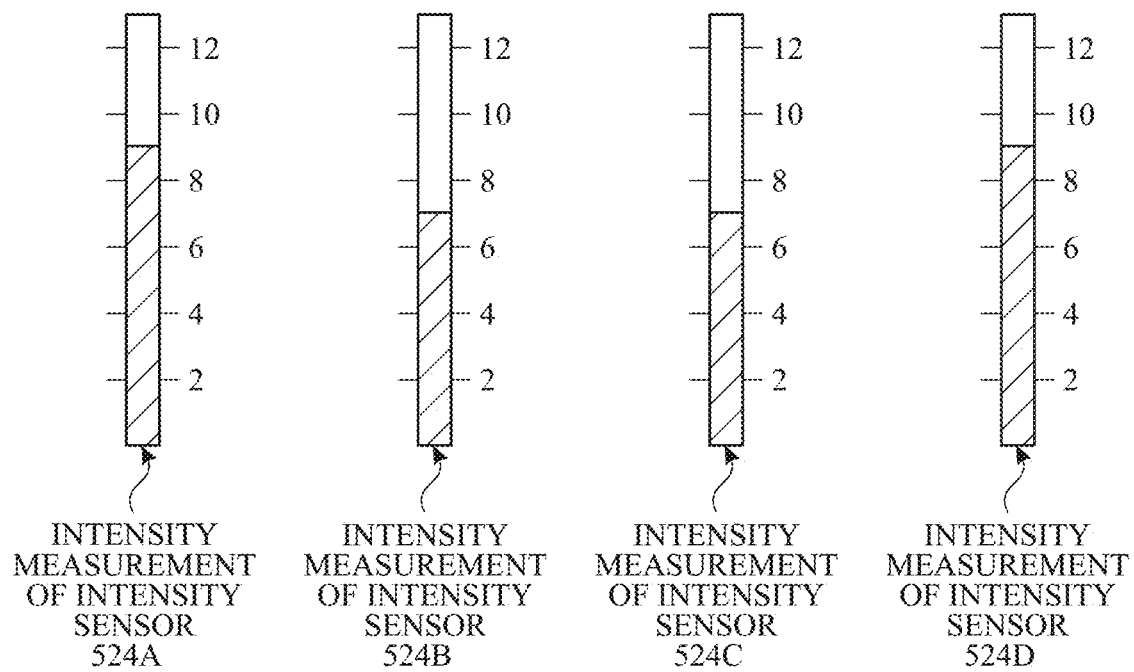
Figure 5D:
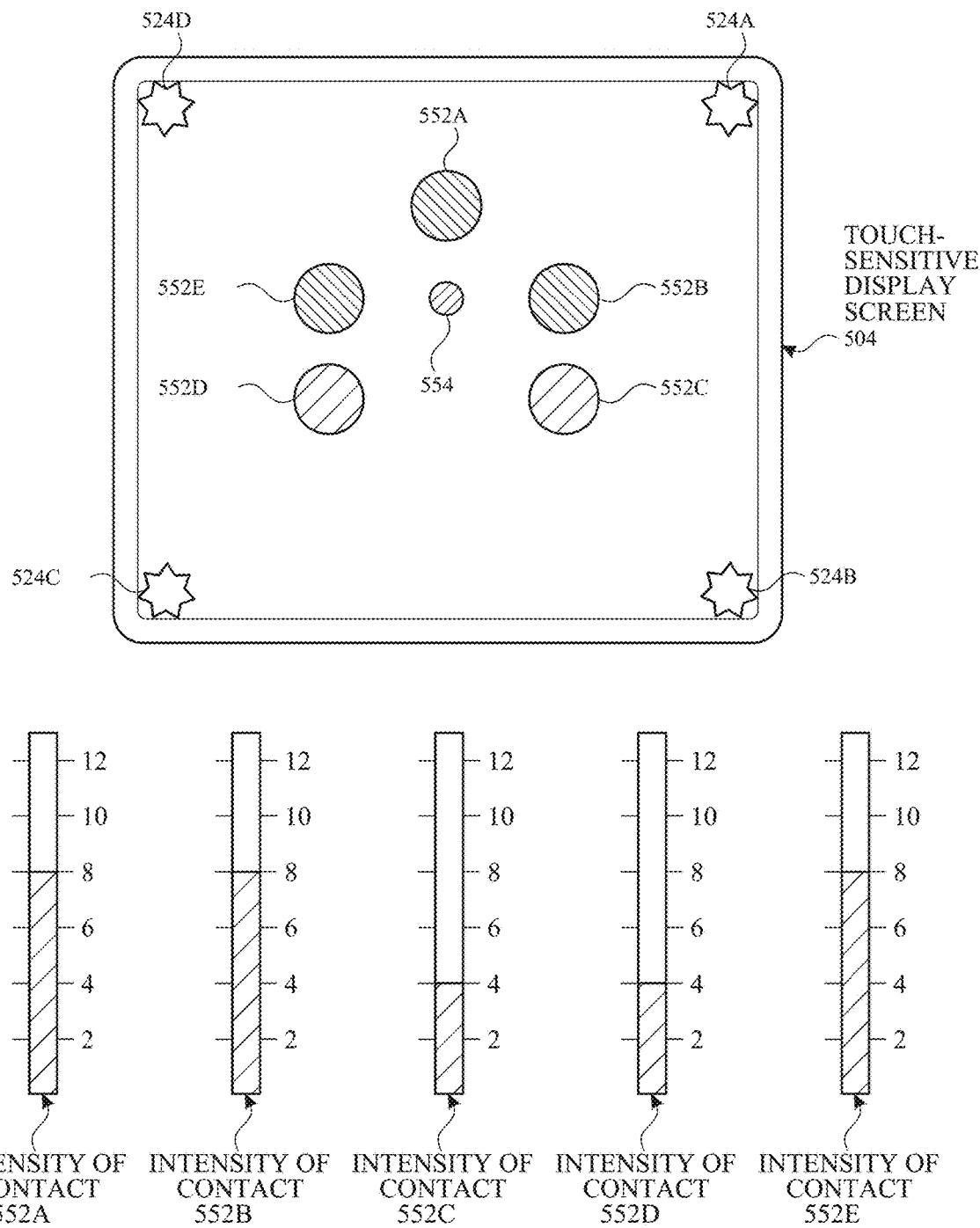

FIG. 5C illustrates detecting a plurality of contacts 552A-552E on touch-sensitive display screen 504 with a plurality of intensity sensors 524A-524D. FIG. 5C additionally includes intensity diagrams that show the current intensity measurements of the intensity sensors 524A-524D relative to units of intensity. In this example, the intensity measurements of intensity sensors 524A and 524D are each 9 units of intensity, and the intensity measurements of intensity sensors 524B and 524C are each 7 units of intensity. In some implementations, an aggregate intensity is the sum of the intensity measurements of the plurality of intensity sensors 524A-524D, which in this example is 32 intensity units. In some embodiments, each contact is assigned a respective intensity that is a portion of the aggregate intensity. FIG. 5D illustrates assigning the aggregate intensity to contacts 552A-552E based on their distance from the center of force 554. In this example, each of contacts 552A, 552B, and 552E are assigned an intensity of contact of 8 intensity units of the aggregate intensity, and each of contacts 552C and 552D are assigned an intensity of contact of 4 intensity units of the aggregate intensity. More generally, in some implementations, each contact j is assigned a respective intensity $I_j$ that is a portion of the aggregate intensity, A, in accordance with a predefined mathematical function, $I_j = A \cdot (D_j / \Sigma D_i)$, where $D_j$ is the distance of the respective contact j to the center of force, and $\Sigma D_i$ is the sum of the distances of all the respective contacts (e.g., i=1 to last) to the center of force. The operations described with reference to FIGS. 5C-5D can be performed using an electronic device similar or identical to device 100, 300, or 500. In some embodiments, a characteristic intensity of a contact is based on one or more intensities of the contact. In some embodiments, the intensity sensors are used to determine a single characteristic intensity (e.g., a single characteristic intensity of a single contact). It should be noted that the intensity diagrams are not part of a displayed user interface, but are included in FIGS. 5C-5D to aid the reader.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

Figure 5E:
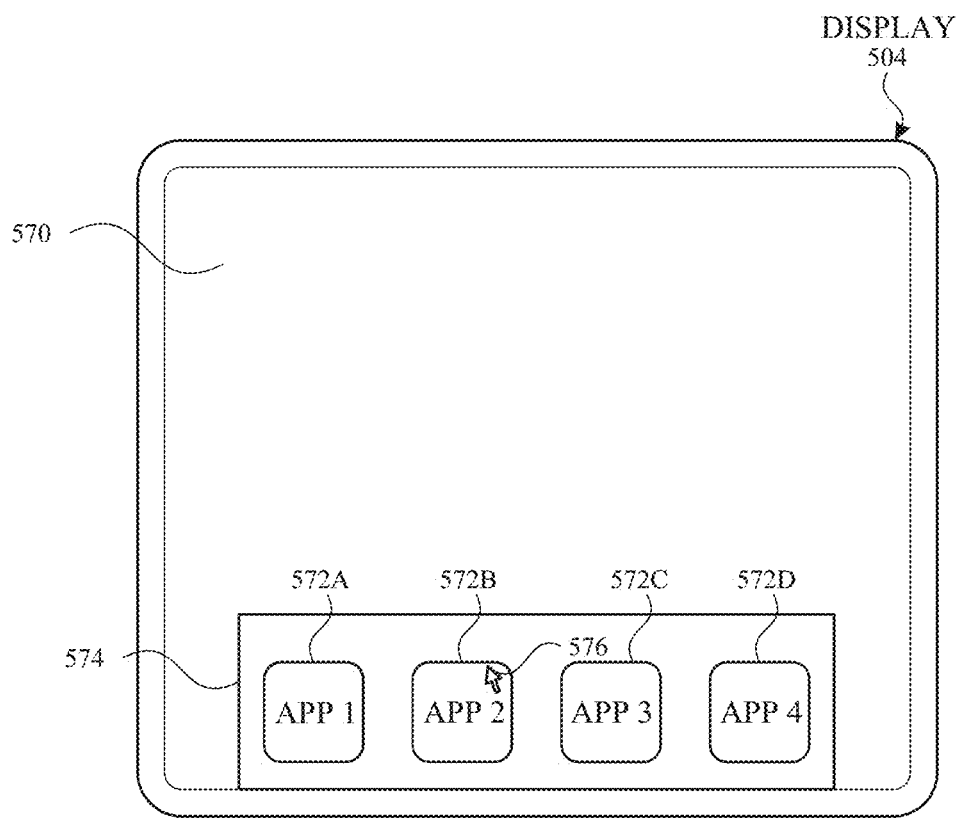
FIGS. 5E-5H illustrate exemplary components and user interfaces of a personal electronic device in accordance with some embodiments.
Figure 5E:
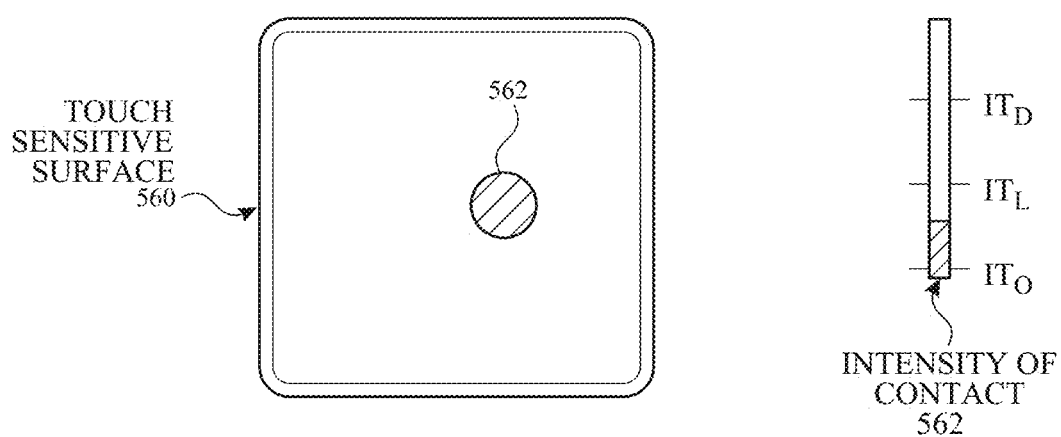
Figure 5F:
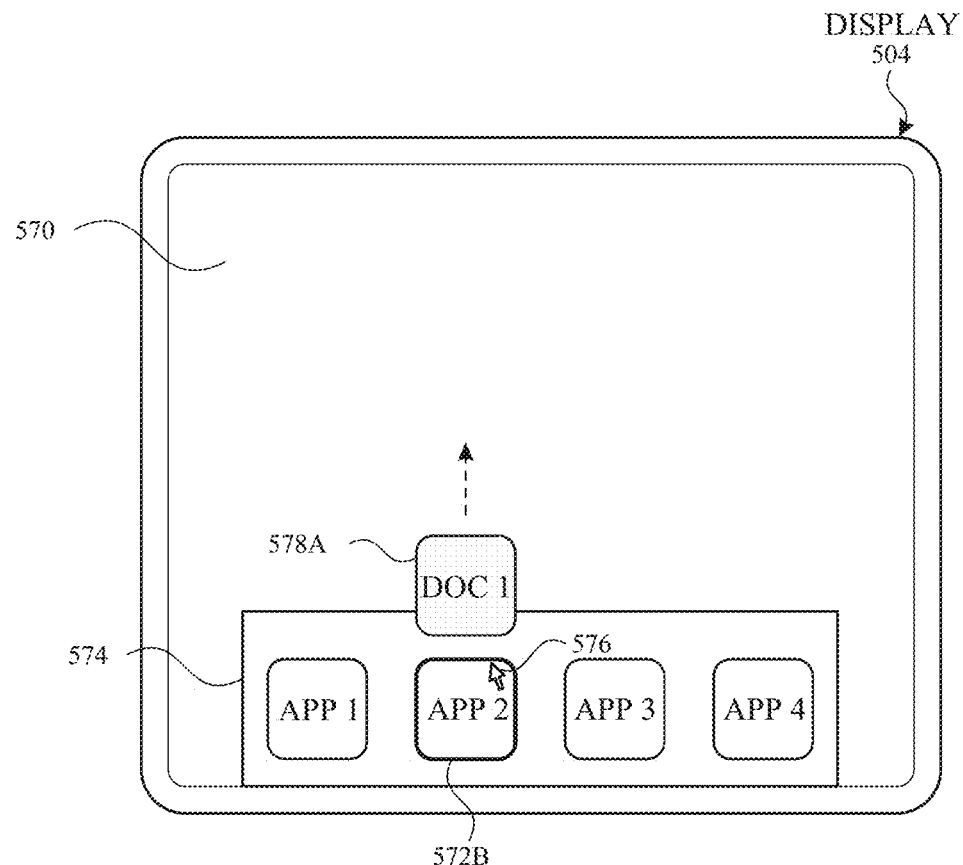
Figure 5F:
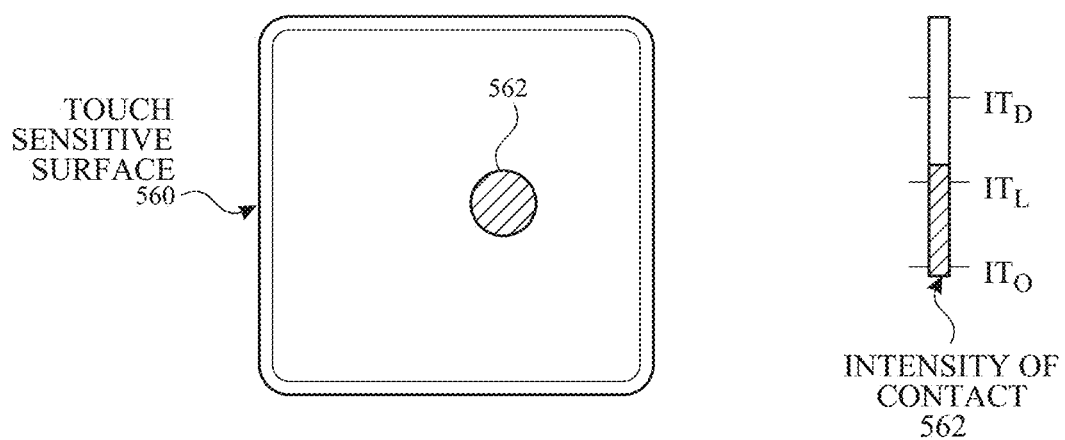
Figure 5G:
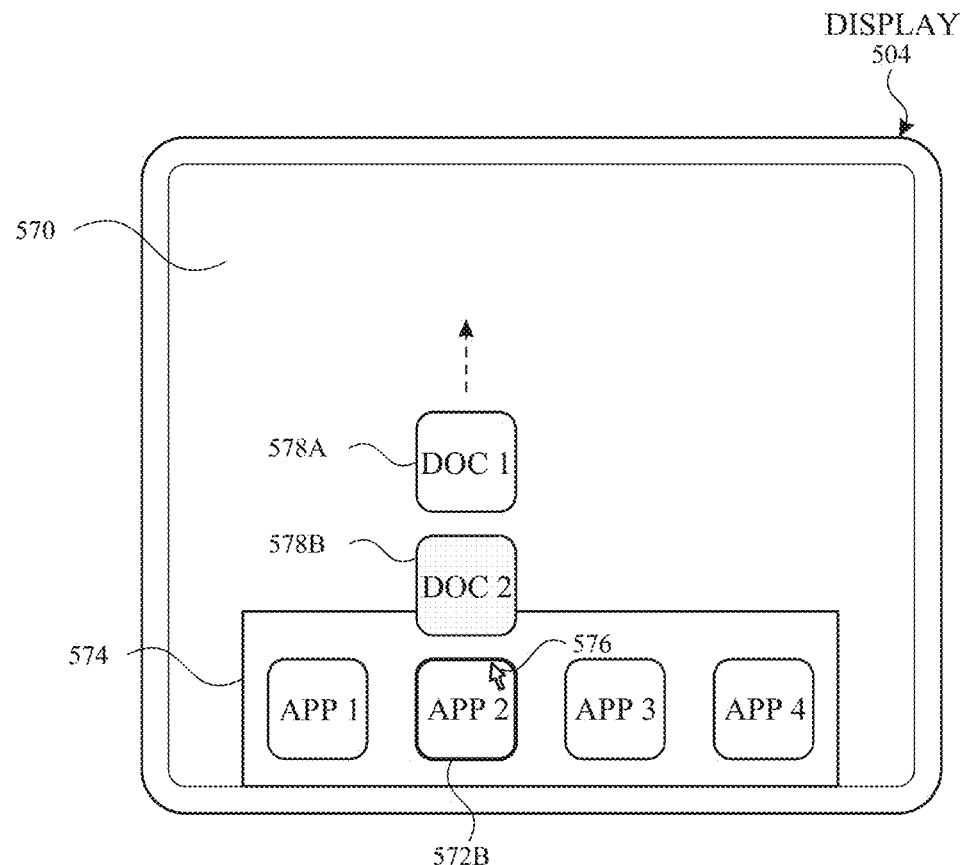
Figure 5G:
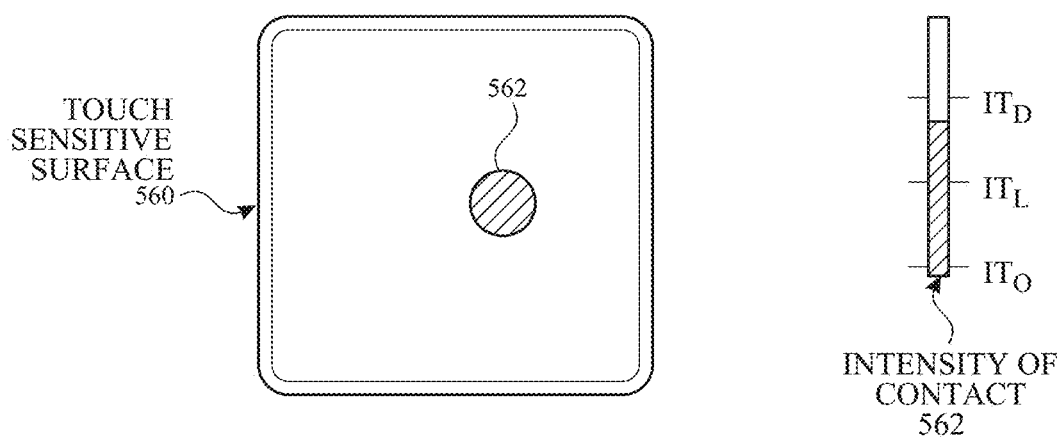
Figure 5H:
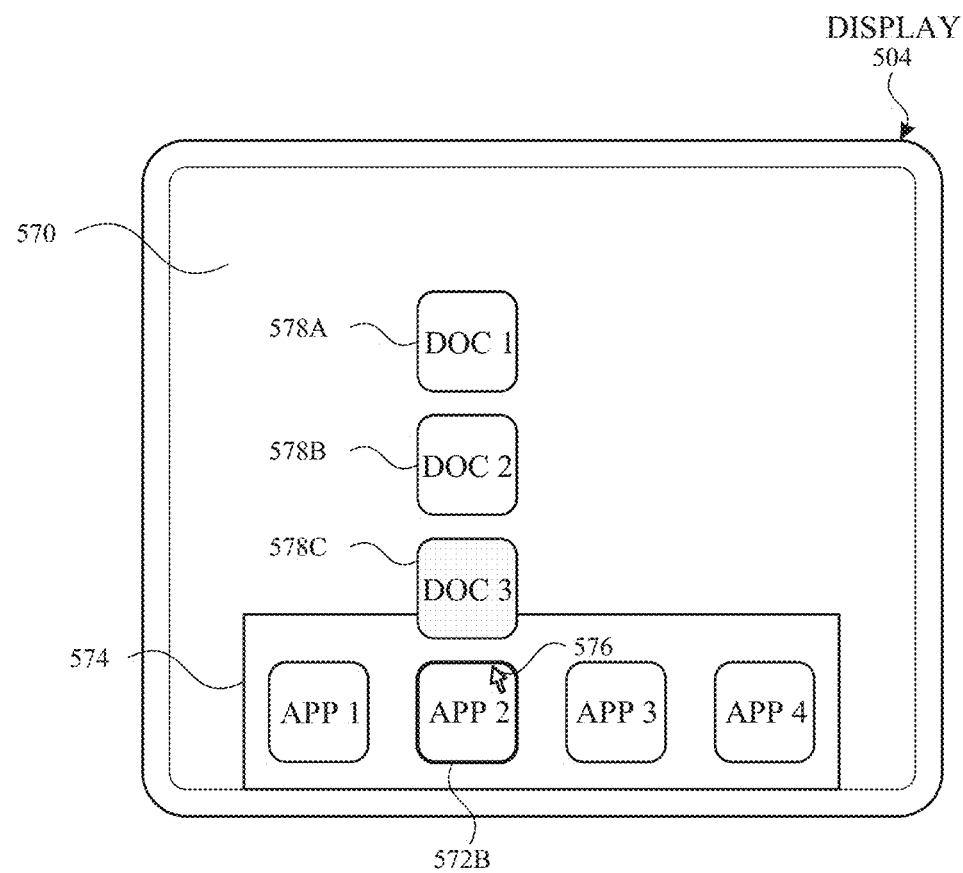
Figure 5H:
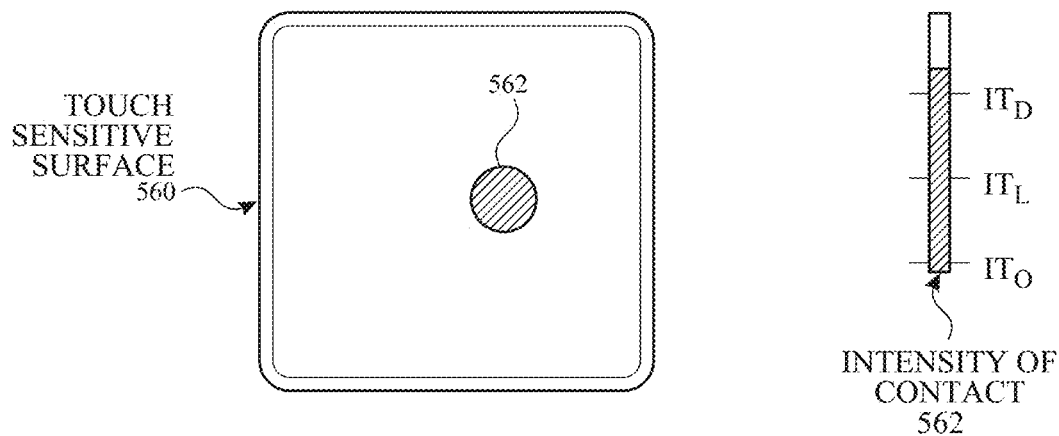

FIGS. 5E-5H illustrate detection of a gesture that includes a press input that corresponds to an increase in intensity of a contact 562 from an intensity below a light press intensity threshold (e.g., "$IT_L$") in FIG. 5E, to an intensity above a deep press intensity threshold (e.g., "$IT_D$") in FIG. 5H. The gesture performed with contact 562 is detected on touch-sensitive surface 560 while cursor 576 is displayed over application icon 572B corresponding to App 2, on a displayed user interface 570 that includes application icons 572A-572D displayed in predefined region 574. In some embodiments, the gesture is detected on touch-sensitive display 504. The intensity sensors detect the intensity of contacts on touch-sensitive surface 560. The device determines that the intensity of contact 562 peaked above the deep press intensity threshold (e.g., "$IT_D$"). Contact 562 is maintained on touch-sensitive surface 560. In response to the detection of the gesture, and in accordance with contact 562 having an intensity that goes above the deep press intensity threshold (e.g., "$IT_D$") during the gesture, reduced-scale representations 578A-578C (e.g., thumbnails) of recently opened documents for App 2 are displayed, as shown in FIGS. 5F-5H. In some embodiments, the intensity, which is compared to the one or more intensity thresholds, is the characteristic intensity of a contact. It should be noted that the intensity diagram for contact 562 is not part of a displayed user interface, but is included in FIGS. 5E-5H to aid the reader.

In some embodiments, the display of representations 578A-578C includes an animation. For example, representation 578A is initially displayed in proximity of application icon 572B, as shown in FIG. 5F. As the animation proceeds, representation 578A moves upward and representation 578B is displayed in proximity of application icon 572B, as shown in FIG. 5G. Then, representations 578A moves upward, 578B moves upward toward representation 578A, and representation 578C is displayed in proximity of application icon 572B, as shown in FIG. 5H. Representations 578A-578C form an array above icon 572B. In some embodiments, the animation progresses in accordance with an intensity of contact 562, as shown in FIGS. 5F-5G, where the representations 578A-578C appear and move upwards as the intensity of contact 562 increases toward the deep press intensity threshold (e.g., "$IT_D$"). In some embodiments, the intensity, on which the progress of the animation is based, is the characteristic intensity of the contact. The operations described with reference to FIGS. 5E-5H can be performed using an electronic device similar or identical to device 100, 300, or 500.

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

Attention is now directed towards embodiments of user interfaces ("UI") and associated processes that are implemented on an electronic device, such as portable multifunction device 100, device 300, or device 500.

FIGS. 6A-6E and 7A-7K illustrate exemplary user interfaces for activity and workout monitoring, in accordance with some embodiments. The user interfaces in these figures are used to illustrate the processes described below, including the processes in FIG. 8.

Figure 6A:
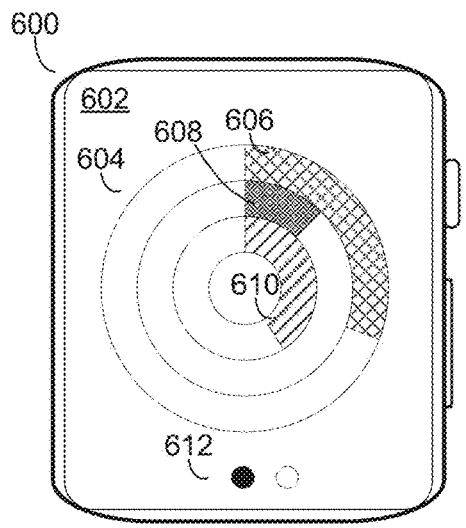
FIGS. 6A-6E illustrate user interfaces of a portable electronic device executing a workout or activity application in accordance with some embodiments.

FIG. 6A illustrates portable electronic device 600. In some embodiments, device 600 includes some or all of the features of device 100, device 300, or device 500, described above with respect to FIGS. 1A-1B, 2-3, 4A-4B, and 5A-5H. Portable electronic device 600 is displaying user interface 602 for a workout or activity application, which may help track data relating to the physical activity, health, and/or biological state of a user of portable electronic device 600. Portable electronic device 600 may be carried with or worn on the user. For example, portable electronic device 600 may be a watch worn on a wrist of the user. Portable electronic device may also be other types of devices.

User interface 602 includes goal summary graphical element 604 representing the progress towards a set of goals. The progress towards each of the goals in the set of goals is represented by goal graphical elements 606, 608, and 610. For example, goal graphical element 606 may represent the progress towards a goal for the total calories burned in the day, goal graphical element 608 may represent a goal for the total time the user has spent being active that day, and goal graphical element 610 may be related to a goal for the number of hours today that user has stood up at least once. Goal summary graphical element 604 may be updated as sensors on portable electronic device 600 measure additional activity data.

User interface 602 also includes page indicator 612 that indicates other pages are available for viewing. For example, indicator 612 shows there is another page accessible from the current page. The solid dot in indicator 612 indicates that user interface 602, which is currently being viewed, is the first of two pages. The non-filled indicator on the right side of the solid-filled indicator shows that there is one other page that is not being displayed but can be accessed from user interface 602. This page may be accessed, for example, by a swipe gesture on the touch screen of portable electronic device 600. When the page is changed, indicator 612 is updated to reflect the page that is being displayed.

Figure 6B:
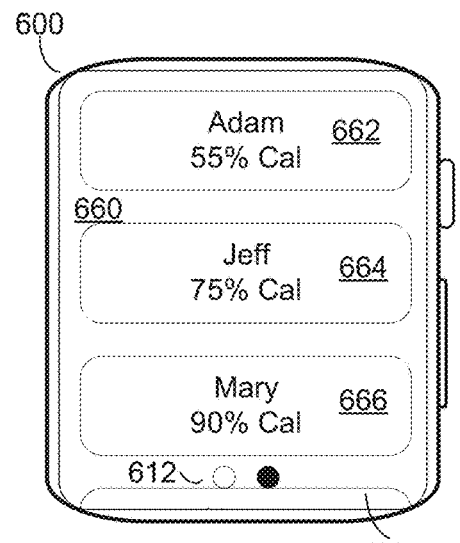

For example, a swipe gesture to the left may display the last page and an updated indicator will be displayed showing the first dot open and the last dot filled. The result of this example is depicted in FIG. 6B, which includes user interface 660 showing contact information 662, 664, 666, and 668 (although contact information 668 is only partially displayed) for a plurality of contacts (Adam, Jeff, Mary, and Nancy). Contact information 662, 664, 666, and 668 include the first names of the contacts. The contact information could include other fields in addition to or instead of first names, such as, last names, initials, pictures, group names, or usernames. Displayed with contact information 662, 664, 666, and 668 is a goal metric for each contact. In FIG. 6B, the goal metric is the progress towards each contact's goal for total calories burned for the day. The progress is indicated as a percentage of the goal.

Figure 6C:
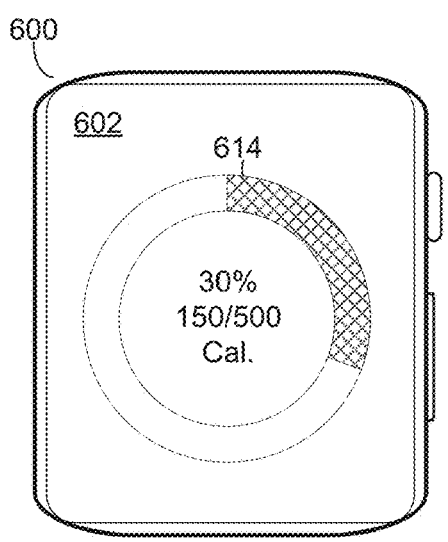

Referring back to FIG. 6A, in addition to viewing additional pages from user interface 602, other user input, such as a vertical scroll gesture, can be used to access additional information of user interface 602. For example, a scroll gesture may scroll user interface 602 so that a new portion of user interface 602 is displayed. This result is depicted in FIG. 6C, which shows that goal summary graphical element 604 has been replaced with goal graphical element 614, which includes similar data for a goal metric as goal graphical element 606 of FIG. 6A. Goal graphical element 614 also includes text specifying the current progress towards the goal. Indicator 612 is not included in FIG. 6C for ease of presentation. Indicator 612, however, could be present in any of FIGS. 6C-6E or may not be present in FIGS. 6A-6B.

Figure 6E:
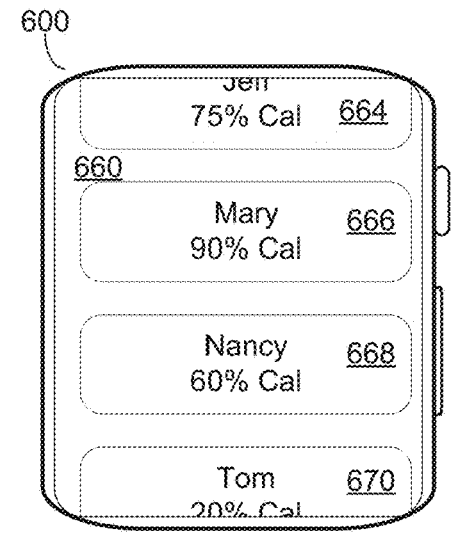
Figure 6D:
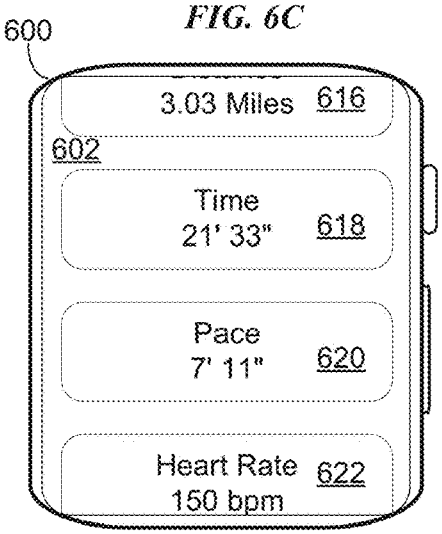

If one or more additional scroll gestures are received while portable electronic device 600 is in the state depicted in FIG. 6D, additional portions of user interface 602 may be displayed, such as the portion depicted in FIG. 6D. This portion includes workout graphical elements 616, 618, 620, and 622 for respective workout metrics. In this case, the graphical elements are text. In other cases, the graphical elements can include other elements, for example text, images, video, and animations.

Scrolling may be possible for user interface 660 of FIG. 6B. For example, if a scroll input (e.g., a swipe gesture on the touch screen or rotation of a rotatable input) is received for user interface 660 as depicted in FIG. 6B, then user interface 660 may be scrolled to display contact information for additional contacts as depicted in FIG. 6E (e.g., contact information 670 for the contact named Tom).

FIG. 7A depicts graphical representation 700 of activity data. The activity data is, for example, for a user of portable electronic device 600 (FIGS. 6A-6E). Portions of graphical representation 702 may be displayed on portable electronic device 600 as part of a user interface (e.g., user interface 602). Graphical representation 702 includes goal graphical elements 604, 614, 702, 704, and 706. Goal graphical elements 604 and 614 are described with respect to FIGS. 6A and 6D, respectively. Goal graphical elements 702 and 704 may be similar to goal graphical element 614 except they present different goal metrics (e.g., activity time and number hours where a user has stood).

Goal summary graphical element 706 displays a chronological representation of the goal metrics associated with goal graphical elements 614, 702, and 704. Specifically, graph 708 corresponds to the goal metric associated with goal graphical element 614 and depicts the magnitude of calories burned as a function of the time of day with the morning being on the left side of the graph and night being on the right side of the graph. Graph 710 similarly corresponds to the goal metric associated with goal graphical element 702. Graph 712 similarly corresponds to the goal metric associated with goal graphical element 704, except graph 712 depicts binary data (e.g., whether for each hour in the day the user stood up). Graphs 708, 710, and 712 may be color-coded to their respective goal graphical elements.

Workout graphical elements 616, 618, 620, and 622 correspond to different workout metrics for a workout of the user. For example, these graphical elements may correspond to the time of a workout, the distance of a workout, the pace of a workout, and an average or a maximum heart rate for a workout. These graphical elements may represent the most recent workout a user completed. In other cases, these or additional graphical elements may represent multiple workouts or today's workout(s).

Graphical representation 700 may also include additional graphical elements, such as graphical element 714. Graphical element 714 could represent other data and information that may be interesting or useful to the user.

The goal related graphical elements (e.g., goal summary graphical elements 604, goal graphical elements 614, 702, and 704, and goal graphical element 706) are included in goal portion 716 of graphical representation 700. The elements in this portion are more suited for being displayed one at a time when displayed on a smaller screen. For example, it may not be desirable to display half of goal graphical element 614 and half of graphical element 702. Instead, it may be more desirable to only display one of these elements at a time and to make it easy for a user to switch between the elements. In some embodiments, doing so may assist the user with consumption of related information, thereby reducing cognitive burden while interacting with the electronic device and improving the human-device interface.

The workout related graphical elements (e.g., workout graphical elements 616, 618, 620, and 622) are included in workout portion 718. In contrast to the elements of the goal portion, the elements of the workout portion may be suitable for viewing even when multiple elements are being displayed at once. Accordingly, it may be desirable for a user to have more control on what workout graphical elements are currently displayed. Embodiments described below allow for the same user input to be treated differently depending on what is being displayed. This is enable a user to user a single type of user input to scroll through the data in a manner that maintains the most useful scroll style for each portion of the graphical presentation.

FIG. 7B depicts graphical representation 701 of activity data. Graphical representation 701 is similar to graphical representation 700 with a few exceptions. First, instead of goal graphical indicators 702 and 704 of graphical representation 700, goal graphical elements 720 and 722, which correspond to the goal metrics for goal graphical indicators 702 and 704, are included and sized the same as goal graphical element 614. Second, there are no elements in graphical representation 701 for chronological goal data, as depicted in goal graphical elements 706. Third, graphical representation 701 includes graphical elements 724 and 730 that are not included in either goal portion 726 or workout portion 728. Graphical elements 724 and 730 may be other types of graphical elements, such as a summary of activity data for friends or a description of other data. Fourth, workout portion 728 excludes workout graphical elements 616 and 714.

Graphical representations 700 and 701 extend beyond the displayable area when displayed on of the display of portable electronic device 600. In some cases, graphical representation 700 and 701 may have widths that correspond with the width of the displayable area of the display of portable electronic device 600 and have heights that are multiples of the height of the displayable area of the display of portable electronic device 600. The reverse could also be true (i.e., height corresponds but width is many multiples). Additionally, as explained above, the different portions of the graphical representations may have suitable scrolling styles that are different. Specifically, as explained in more detail in the following paragraphs with respect to FIGS. 7C-7K, the goal portion of a graphical representation of activity data may be more suited to scrolling an entire graphical element at a time while the workout portion may be suited to a more continuous scrolling style.

Figure 7C:
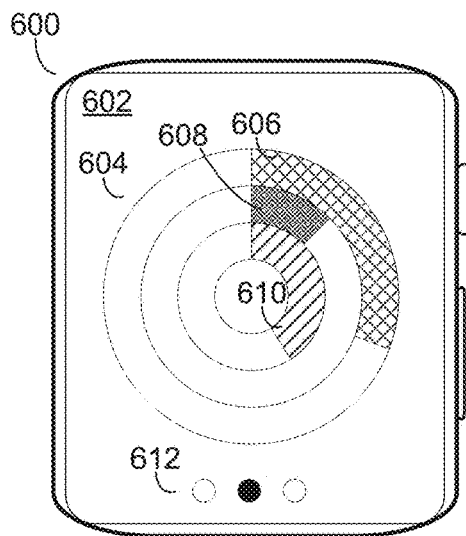

FIG. 7C, which is the same as FIG. 6A, depicts user interface 602 that is displaying a portion of graphical representation 700. The displayed portion of graphical representation 700 includes goal summary graphical element 604, which is part of the goal portion of graphical representation 700. Because the graphical elements of the goal portion are more suited to being displayed one at a time, in response to a scroll input from the bottom of the display to the top of the display, the display of goal summary graphical element 604 is replaced with goal graphical element 614, as depicted in FIG. 7D.

In the goal portion, the display transition from summary graphical element 604 to goal graphical element 614 or, more generically, from one graphical element to an adjacent graphical element, may take place through various mechanisms. For example the transition from goal graphical element 614 (FIG. 7D) to goal graphical element 702 (FIG. 7F) may, in response to a scroll input, be in the form of a translation of the graphical elements, in the form of a shrinking/growing animation, or in other forms.

Figure 7F:
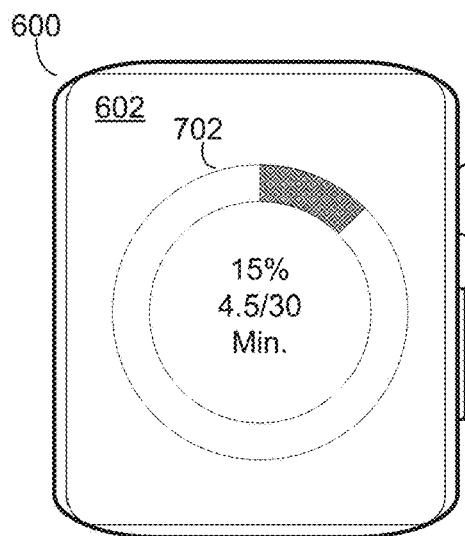
Figure 7D:
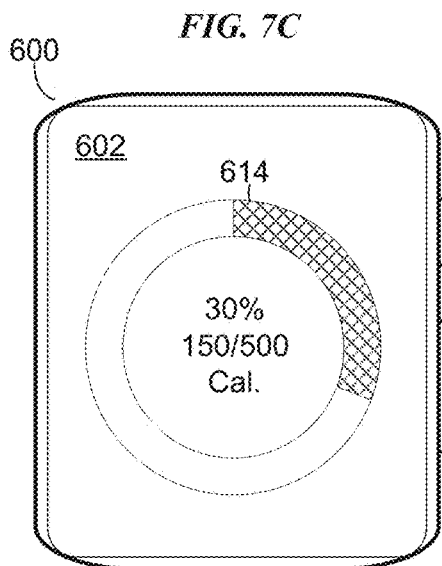
Figure 7G:
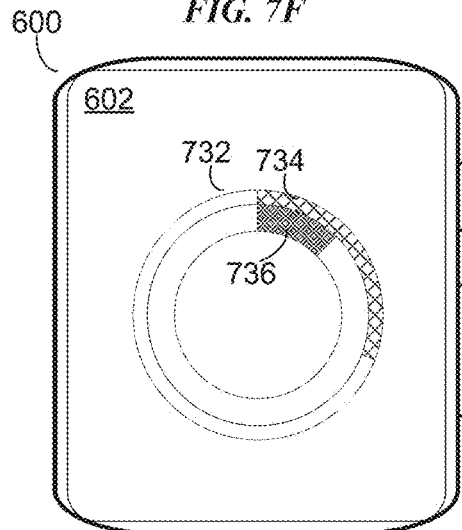
Figure 7E:
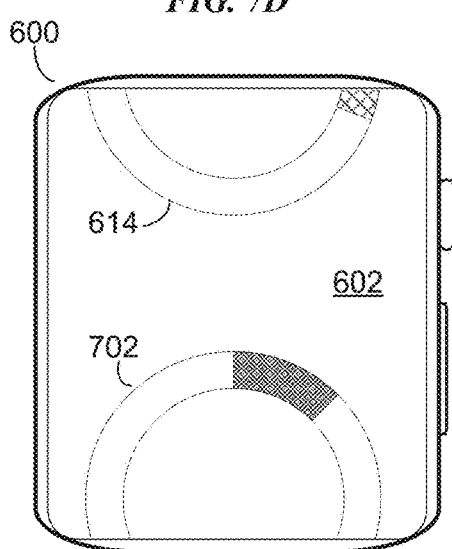
Figure 7H:
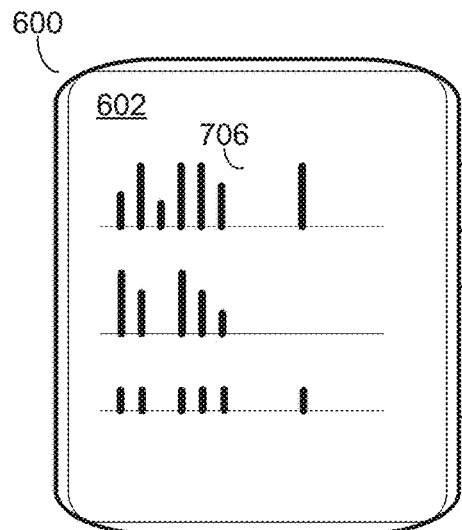
Figure 8:
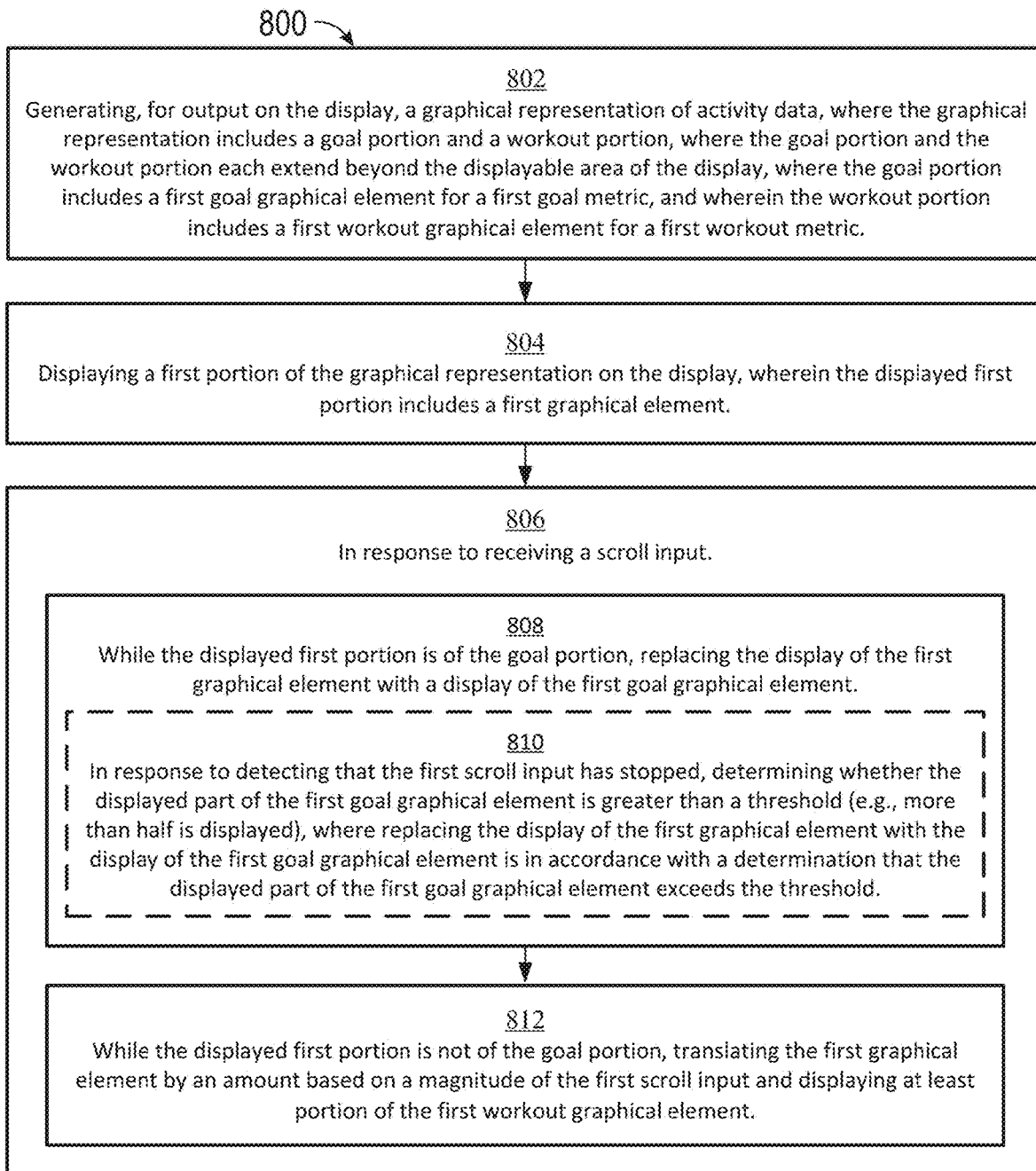
FIG. 8 is a flow diagram illustrating a method for navigating and viewing activity data using a portable electronic device in accordance with some embodiments.

FIG. 7E depicts an instant of a display transition in the form of a translation of the graphical elements. As the scroll input is received, goal graphical element 614 translates up and off of the display while goal graphical element 702 translates up and on to the display. If the scroll input ceases before goal graphical element 702 has fully replaced goal graphical element 614, one of the graphical elements snaps to the display while the other is not displayed. For example, as depicted in FIG. 7E, more than half of goal graphical element 614 has translated off of the display and more than half of goal graphical element 702 has translated on to the display. In this case, because more than half of goal graphical element 702 is now displayed, in response to the scroll input ceasing and without further user input, all of goal graphical element 702 may be displayed without displaying any of goal graphical element 702, as depicted in FIG. 7F. Other thresholds beside a half could also be used (e.g., a third or a quarter). If the threshold is not exceeded, the display will return to displaying only goal graphical element 614, as depicted in FIG. 7D.

FIG. 7G depicts an instant of another display transition from FIG. 7D to FIG. 7F in the form of a shrinking/growing transition. As the scroll input is received, goal graphical element 614 shrinks and goal graphical element 702 grows. For example, transition graphical element 732 in FIG. 7G depicts shrinking portion 734 that corresponds to goal graphical indicator 614 and depicts growing portion 736 that corresponds to goal graphical indicator 702. As with the translation transition described in the previous paragraph, if the scroll input ends and the display transition exceeds a threshold level, then the display will snap to goal graphical element 702, as depicted in FIG. 7F, without any additional user input. If the threshold is not exceeded, the display will automatically return to goal graphical element 614, as depicted in FIG. 7D, in response to the scroll input ceasing.

The transition to the rest of the graphical elements (e.g., goal graphical element 706 of FIG. 7H) of the goal portion of graphical representation 700 (FIG. 7A) are performed in a similar manner. In addition to the translation and shrinking/growing animation transitions described above, other transitions could also be used, such as replacing display of the graphical elements in response to a certain level of scroll input or fading the graphical elements in and out in response to the scroll input.

Figure 7I:
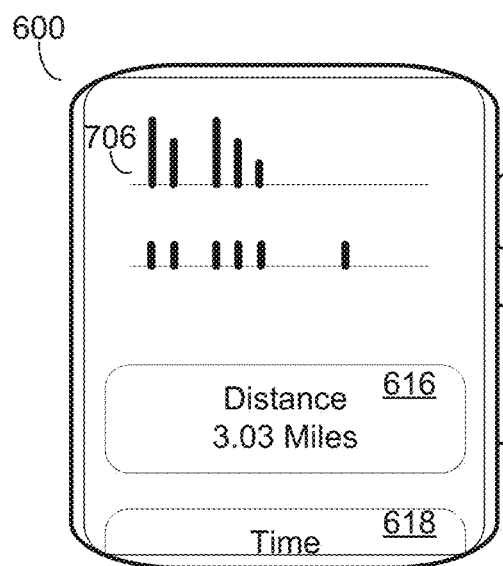

FIG. 7I depicts the transition from displaying graphical elements of the goal portion to graphical elements of the workout portion of graphical representation 700 of activity data. This transition may occur similar to the transitions described above so that when a threshold part of the workout portion or a workout graphical element is displayed in response to a scroll input (e.g., as depicted in FIG. 7I), the display may snap to the first workout graphical element (e.g., workout graphical element 616 in FIG. 7J) automatically without further user input in response to the scroll input ceasing. Alternatively, once a portion of the workout portion is displayed, a scroll input may be more continuous and the display may be maintained in its current state in response to the scroll input ceasing. For example, if the scroll input ceased while the display included part of goal graphical element 706 and graphical element 612, as depicted in FIG. 7I, the display may be maintained.

Figure 7K:
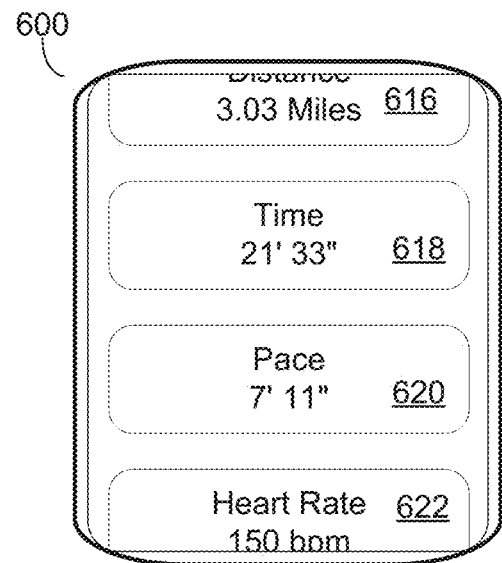
Figure 7J:
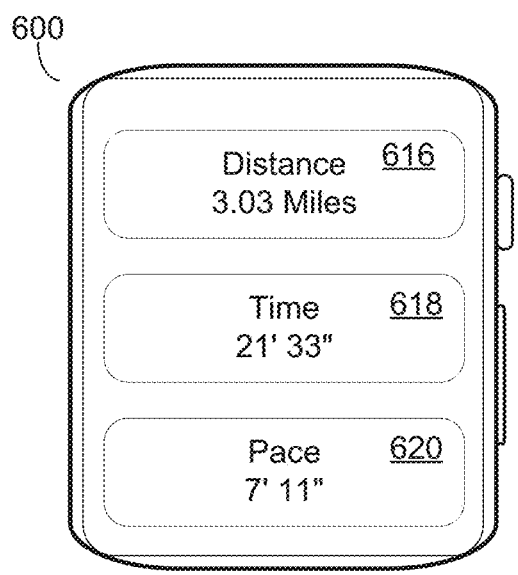

Once workout graphical elements (e.g., workout graphical elements 616, 618, 620, 622, or 714) are being displayed (e.g., as depicted in FIG. 7J), a scroll input may result in a more continuous scroll as opposed to the scroll behavior that snapped to graphical elements discussed above with respect to the goal portion. The displayed workout graphical elements of the work portion may be translated an amount proportional to the scroll input and not automatically translated further in response to the scroll input ceasing. For example, with respect to FIG. 7K, in response to a scroll input ceasing while only parts of workout graphical elements 612 and 618 are displayed, the display may be maintained absent further user input. Alternatively, the display may automatically translate the workout graphical elements so that the closest workout graphical element is aligned with the top of the display.

FIG. 8 is a flow diagram illustrating a method for navigating and viewing activity data using a portable electronic device in accordance with some embodiments. Method 800 is performed at a device (e.g., 100, 300, 500, 600) with a display and, in some cases, a touch sensitive screen. Some operations in method 800 are, optionally, combined, the order of some operations is, optionally, changed, and some operations are, optionally, omitted.

As described below, method 800 provides an intuitive way for navigating and viewing activity data. The method reduces the cognitive burden on a user for navigating menus and view different types of activity metrics, thereby creating a more efficient human-machine interface. For battery-operated computing devices, enabling a user to navigate and comprehend data faster and more efficiently conserves power and increases the time between battery charges.

In block 802, a graphical representation of activity data is generated for output on to a display of the portable electronic device. For example, one or more processors of the portable electronic device may generate the graphical representation. The graphical representation may be, for example, graphical representations 700 or 701 of FIGS. 7A and 7B, respectively. The activity data may be generated on the portable electronic device, for example, by taking measurements with one or more sensors of the portable electronic device. The activity data may also be received from external sources, such as a companion device. Other methods for obtaining the activity data may also be used.

The graphical representation generated in block 802 includes a goal portion and a workout portion. The goal portion includes a goal graphical element for a goal metric. The workout portion includes a workout graphical element for a workout metric. The graphical representation is larger than the displayable area of the display of the portable electronic device. Some embodiments of method 800, allow for easy navigation of the graphical representation and thus make it easy to recognize and comprehend the data represented in the graphical representation. More description and examples of graphical representations for activity may be found in FIGS. 7A and 7B and associated descriptions.

In block 804, a portion of the graphical representation is displayed on the display of the portable electronic device. The displayed first portion includes a first graphical element, which may be a goal graphical element (e.g., goal graphical element 614 of graphical representation 700 of FIG. 7A) of the goal portion, a workout graphical element (e.g., workout graphical element 614 of graphical representation 700 of FIG. 7A) of the workout portion, or another graphical element.

In block 806, a scroll in input is received at the portable electronic device. For example, a scroll input may be any input that is interpreted as a scroll, such as a swipe gesture or drag gesture on the touch screen or a rotation of a rotatable input. Other types of scroll inputs could also be used.

In block 808, while the displayed portion is of the goal portion, the display of the first graphical element is replaced with display of the first goal graphical element. For example, if the first graphical element of block 804 is another goal graphical element (e.g., goal graphical element 604 of FIG. 7A) the displayed portion is of the goal portion. In this example, in response to receiving the scroll input of block 806, goal graphic element 604 is replaced with the first goal graphical element (e.g., goal graphical element 614 of FIG. 7A). This result is depicted in the transition from FIG. 7C to FIG. 7D. This block may be performed by one or processors, including graphics processors, of the portable electronic device.

In some variations of method 800, the transition from display of the first graphical element to the display of the first goal graphical element includes an animation. For example, the shrinking/growing animation described with respect to FIG. 7G could be used. This animation may be generated via one or processors, including graphics processors, of the portable electronic device.

Optionally in block 810 as part of block 808, in response to detecting that the scroll input has stopped, an amount that the first goal graphical element is being displayed is determined, for example, by one or more processors of the portable electronic device. If the displayed amount is greater than a threshold amount, display of the first goal graphical element may automatically and completely replace the display of the first graphical element. If the displayed amount is less than the threshold amount, the display of the first graphical element may be automatically restored and the first goal graphical element will be not displayed at all. This block is also described with respect to the transitions from FIG. 7D to FIG. 7F via FIG. 7E or 7G.

There are many possible values for the threshold. For example, the threshold may be 50%. Determining the displayed amount of the first goal graphical element may be carried out with various methods, include directly determining the amount of the first goal graphical element that is displayed, determining the amount of the first graphical element that is displayed, or determining the magnitude of the scroll input that was received.

In some variations of method 800, after displaying the first goal graphical element (e.g., goal graphical element 614 of FIG. 7A) as described in block 808, another scroll input is received (e.g., in a similar manner as the scroll input of block 806 was received. In response to the scroll input, a part of a second goal graphical element (e.g., goal graphical element 702 of FIG. 7E) is displayed with a part of first goal graphical element (e.g., goal graphical element 614 of FIG. 7E). In accordance with the displayed part of the second goal graphical element exceeding a threshold, the second goal graphical element is displayed without displaying the first goal graphical element. For example, as described above with respect to the description of the transition from FIG. 7D to FIG. 7F via FIG. 7E, either first goal graphical element 614 or second goal graphical element 702 will be displayed (but not both) in response to detecting the scroll input has ceased. If the scroll amount (e.g., the displayed part of the second goal graphical) has exceeded a threshold, the second goal graphical element will be displayed without the first goal graphical element. Otherwise, the display of the first goal graphical element is restored without display of the second goal graphical element.

In block 812, while the displayed portion is not of the goal portion, the display of the first graphical element is translated an amount based on a magnitude of the scroll input. Additionally, at least part of the first workout graphical element is also displayed. For example, if the first graphical element of block 804 is another workout graphical element (e.g., workout graphical element 616 of FIG. 7J) the displayed portion is of the workout portion (i.e., not of the goal portion). In this example, in response to receiving the scroll input of block 806, workout graphic element 616 is translated up the display so that only part of the element is displayed. At the same time, part of a first workout graphical element (e.g., workout graphical element 622 of FIG. 7A) is also displayed. This result is depicted in the transition from FIG. 7J to FIG. 7K. This block may be performed by one or processors, including graphics processors, of the portable electronic device. In response to detecting that the scroll input has ceased, the partial displays of workout graphical elements 616 and 622 is maintained, as depicted in FIG. 7K.

In some variations of process 800, after displaying the first workout graphical element (e.g., workout graphical element 616 of FIG. 7A) as described in block 808, another scroll input is received (e.g., in a similar manner as the scroll input of block 806 was received). In response to the scroll input, a part of a second workout graphical element (e.g., workout graphical element 622 of FIG. 7K) is displayed with a part of first workout graphical element (e.g., workout graphical element 616 of FIG. 7K). This display is maintained even when the scroll input ceases. For example, as described above with respect to the description of the transition from FIG. 7J to FIG. 7K, both first workout graphical element 616 or second workout graphical element 622 will be displayed in response to detecting the scroll input has ceased.

Note that details of the processes described above with respect to method 800 (e.g., FIG. 8) are also applicable in an analogous manner to the methods described below. For example, method 1100 (FIG. 11), method 1400 (FIG. 14), method 1700 (FIG. 17), method 2000 (FIG. 20) and method 2300 (FIG. 23) optionally includes one or more of the characteristics of the various methods described above with reference to method 800. For example, method 800's scrolling style may be applicable to view data in these other methods. For brevity, these details are not repeated below.

Figure 9:
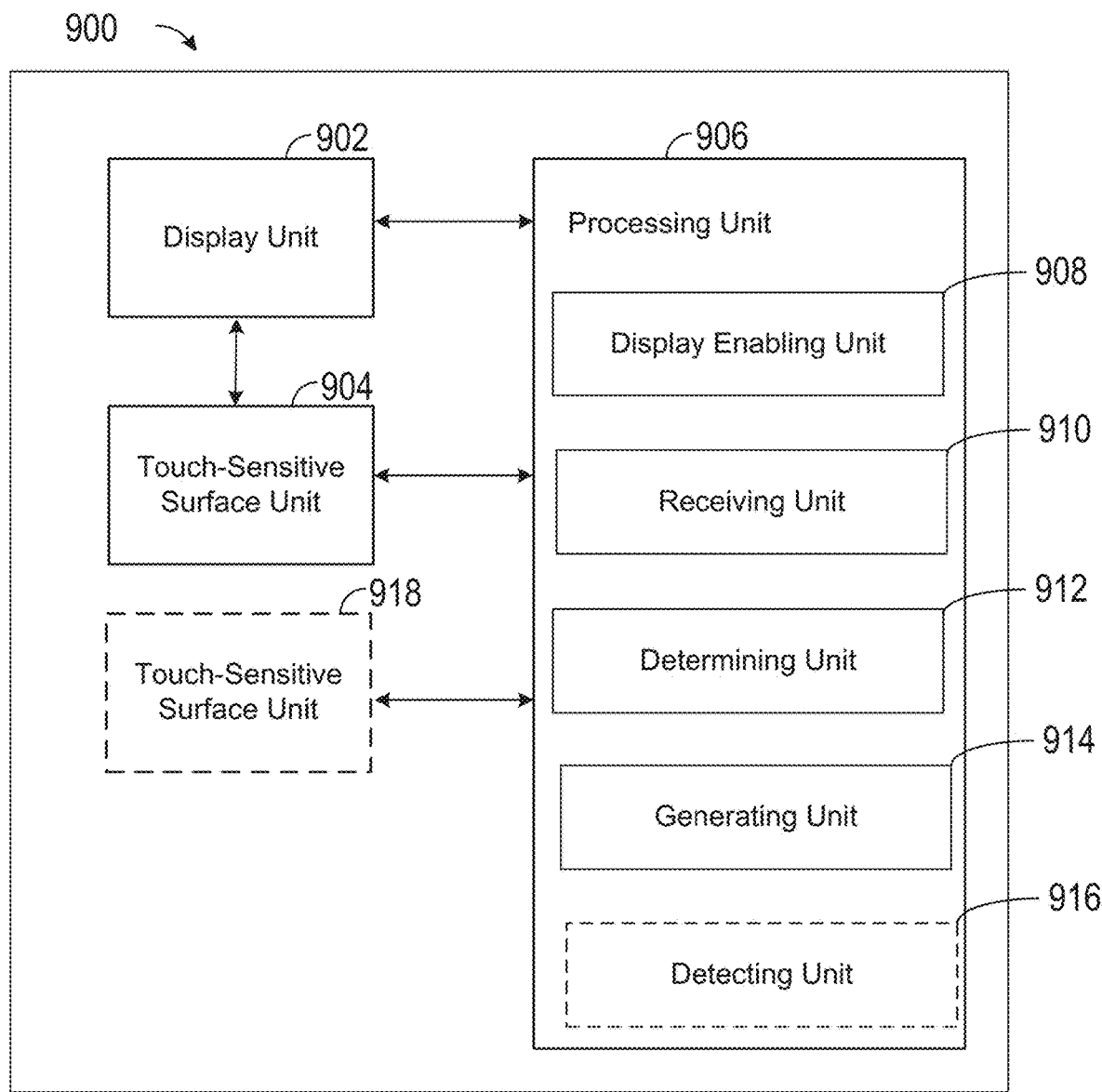
FIG. 9 shows an exemplary functional block diagram of an electronic device in accordance with the principles of the various described embodiments.

In accordance with some embodiments, FIG. 9 shows an exemplary functional block diagram of an electronic device 900 configured in accordance with the principles of the various described embodiments. In accordance with some embodiments, the functional blocks of electronic device 900 are configured to perform the techniques described above. The functional blocks of the device 900 are, optionally, implemented by hardware, software, or a combination of hardware and software to carry out the principles of the various described examples. It is understood by persons of skill in the art that the functional blocks described in FIG. 9 are, optionally, combined or separated into sub-blocks to implement the principles of the various described examples. Therefore, the description herein optionally supports any possible combination or separation or further definition of the functional blocks described herein.

As shown in FIG. 9, an electronic device 900 includes a display unit 902 configured to display a graphic user interface, a touch-sensitive surface unit 904 configured to receive contacts (i.e., touches), optionally a pressure-sensitive surface unit 918, and a processing unit 906 coupled to the display unit 902 and the touch-sensitive surface unit 904. In some embodiments, the processing unit 906 includes a display enabling unit 908, receiving unit 910, a determining unit 912, a generating unit 914, and, optionally, a detecting unit 916.

The processing unit 906 is configured to: generate (e.g., with generating unit 914), for output on the display, a graphical representation of activity data, wherein the graphical representation includes a goal portion and a workout portion, where: the goal portion and the workout portion each extend beyond the displayable area of the display, the goal portion includes a first goal graphical element for a first goal metric, and the workout portion includes a first workout graphical element for a first workout metric. The processing unit 906 is further configured to enable display (e.g., with display enabling unit 908) of a first portion of the graphical representation on the display unit 902, where the displayed first portion includes a first graphical element. The processing unit 906 is further configured to in response to receiving a first scroll input (e.g., with touch-sensitive surface unit 904): while the displayed first portion is of the goal portion, enable replacing (e.g., with displaying enabling unit 908) of the display of the first graphical element with a display of the first goal graphical element; and while the displayed first portion is not of the goal portion, enable translating (e.g., with displaying enabling unit 908) the first graphical element by an amount based on a magnitude of the first scroll input and displaying at least portion of the first workout graphical element.

In some embodiments replacing the display of the first graphical element with a display of the first goal graphical element includes transitioning the first graphical element to the first goal graphical element via an animation.

In some embodiments, the processing unit 906 is further configured to, in response to receiving (e.g., with receiving unit 910) the first scroll input, enabling display (e.g., with display enabling unit 908) of a part of the first graphical element while displaying a part of the first goal graphical element. The processing unit 906 is further configured to, while the displayed first portion is of the goal portion and in response to detecting (e.g., with detecting unit 916) that the first scroll input has stopped, determining (e.g., with determining unit 912) whether the displayed part of the first goal graphical element is greater than a threshold, wherein replacing the display of the first graphical element with the display of the first goal graphical element is in accordance with a determination that the displayed part of the first goal graphical element exceeds the threshold.

In some embodiments, the goal portion includes a second goal graphical element for a second goal metric and the processing unit 902 is further configured to, while displaying the first goal graphical element, receiving (e.g., with receiving unit 910) a second scroll input. The processing unit 902 is further configured to, in response to receiving the second scroll input, enable display (e.g., with display enabling unit 909) display of a part of the first goal graphical element while displaying a part of the second goal graphical element. The processing unit 902 is further configured to, in response to detecting that the first scroll input has stopped, determining (e.g., with determining unit 912) whether the displayed part of the second goal graphical element is greater than a threshold. The processing unit 906 is further configured to, in accordance with a determination that the displayed part of the second goal graphical element is greater than the threshold intensity, enabling replacement (e.g., with the display enabling unit 908) of the display of the first goal graphical element with display of the second goal graphical element.

In some embodiments, the graphical representation includes a goal summary portion having a summary graphical element representing chronological data for the first goal metric.

In some embodiments, a color of the summary graphical element corresponds to a color of the first goal metric.

In some embodiments, the workout portion includes a second workout graphical element for a second workout metric and the processing unit 906 is further configured to, while displaying the first workout graphical element, receiving (e.g., with the receiving unit 910) a third scroll input. The processing unit 906 is further configured to, in response to receiving the third scroll input, enabling translation (e.g., with display enabling unit 908) of the display of the first workout graphical element an amount based on the third scroll input while displaying a part of the second workout graphical element. The processing unit 906 is further configured to, after the second scroll input has ceased, enabling the maintaining (e.g. with displaying enabling unit 908) of display of a part of the first workout graphical element and display of the part of the second workout graphical element.

In some embodiments, the portable electronic device includes a pressure sensitive touch screen unit 918 and the processing unit 906 is further configured to receive (e.g., with receiving unit 910) user input on the pressure sensitive touch screen unit (918) while displaying part of the goal portion of the graphical representation of activity data, where the user input has a characteristic intensity. The processing unit 906 is further configured to determine whether the characteristic intensity exceeds an intensity threshold in accordance with a determination that the user input exceeds the intensity threshold: enable display (e.g., with display enabling unit 908) of an affordance for entering a goal setting interface and in response to receiving user input selecting the affordance, enabling display (e.g., with display enabling unit 908) of the goal setting interface. The processing unit 906 is further configured to receive (e.g., with the receiving unit 912) via the goal setting interface user input indicating a new value for the first goal via a displayed user interface element.

FIGS. 10A-10G illustrate user interfaces of a portable electronic device navigating and viewing activity data in accordance with some embodiments. The user interfaces in these figures are used to illustrate the processes described below, including the processes in FIG. 11.

FIG. 10A (which is the same as FIG. 6B) depicts user interface 660 on portable electronic device 600. User interface 660 includes contact information graphical element 662, 664, and 668 (only partially visible) for the contacts corresponding to names Adam, Jeff, and Nancy (name not visible). User interface 600 also includes information graphical element 666 (labeled "Me") for the user of portable electronic device 600. Each contact information graphical element includes contact information, which in this case is the name of each contact represented by the contact information graphical element. Each contact information graphical element and the other information graphical element also includes a goal graphical element for a goal metric (in this case, the progress towards the calories goal for the day). Other graphical elements for other goal metrics, workout metrics, and other contact information could also be included.

The contact information accessible through user interface 660 provides access to contacts that share activity data, including goal or workout data, with the user of portable electronic device 600. User interface 660 provides an easy interface for the user of portable electronic device 600 to rank herself or himself against friends, co-workers, and/or other acquaintances represented by the contact information. In FIG. 10A, the contact information is sorted alphabetically according to the name of each corresponding contact. A sort interface, such as sort interface 1000 of FIG. 10B, may be provided to allow the user to select how to sort the contact information displayed in user interface 660.

For example, sort interface 1000 of FIG. 10B may be displayed in response to receiving corresponding user input on user interface 660 as displayed in FIG. 10A. If portable electronic device 600 has a pressure sensitive touch screen, then sort interface 1000 may be displayed in response to a touch on the pressure sensitive touch screen that has a characteristic intensity that is greater than a threshold intensity. Sort interface 1000 includes affordances 1002, 1004, and 1006 that allow a user to select a parameter that will be used to sort the contact information. Affordance 1002 selects the contact names for sorting, which is displayed in FIG. 10A. Affordance 1004 selects the progress towards the calories goal for sorting the contact information, the result of which is depicted in FIG. 10C. Affordance 1006 selects the number of completed workouts that day as the parameter for sorting the contact information. Other parameters are also possible, such as other goal metrics, types of workouts completed, and other workout metrics.

Referring to FIG. 10C, in response to receiving user input selecting contact information graphical element 664, graphical representation 1008 (FIG. 10D) of activity data for Jeff may be generate for display on the display of portable electronic device 600, as depicted in FIGS. 10E-10G. Alternatively, graphical representation 1008 could be generated prior to selecting of a contact information graphical element or could be generated on the fly as portions of graphical representation 1008 are displayed. The activity data may be received from an external electronic device, such as an electronic device that is associated with Jeff. The activity data could be received from the electronic device associated with Jeff via a server that stores and distributes such data. The activity data may be, for example, received on a periodic basis, when user interface 660 is first displayed, when a contact information graphical element is selected, or at other times.

Referring to FIG. 10D, graphical representation 1008 of activity data for Jeff may be similar to the graphical representations of activity data described with respect to FIGS. 7A and 7B. Graphical representation 1008 of activity data for Jeff may include goal graphical elements 1010, 1012, 1014, 1016, 1018, and 1022. These graphical elements may provide information about the progress that Jeff has made towards various activity goals. Graphical representation 1008 of activity data for Jeff may also include workout graphical elements 1024, 1026, and 1028 that may provide data for a workout that Jeff has completed today or someone other time period. Multiple sets of workout elements could also be included for additional workouts that Jeff has completed. While one example graphical representation of activity data has been provided in FIG. 10D, may other representations that contain other combinations and/or types of data could also be displayed.

Referring to FIGS. 10E and 10F, portions of graphical representation 1008 (FIG. 10D) of activity data for Jeff are displayed. Graphical representation 1008 can be navigated using a scroll input (e.g., a swipe or drag on the touch sensitive screen or rotation of a rotatable input mechanism). In addition to graphical representation 1008 of activity data for Jeff, affordances 1030 and 1032 may also be displayed after the end of graphical presentation 1008, as depicted in FIG. 10G, so that communication may be initiated with the contact (Jeff in the case of FIG. 10G). Selection of affordance 1030 or 1032 may open a communication application (e.g., email, messaging, or social networking) with Jeff's contact information for the communication application. A message may then be entered or a pre-defined message may be selected for sending to Jeff. Pre-defined message can include any type of messages, such as messages of encouragement, competition, or praise.

FIG. 11 is a flow diagram illustrating a method for navigating and viewing contact's activity data using a portable electronic device in accordance with some embodiments. Method 1100 is performed at a device (e.g., 100, 300, 500, 600) with a display and, in some cases, a touch sensitive screen or a touch sensitive screen that is also pressure sensitive. Some operations in method 1100 are, optionally, combined, the order of some operations are, optionally, changed, and some operations are, optionally, omitted.

As described below, method 1100 provides an intuitive way for navigating and viewing contact's activity data. The method reduces the cognitive burden on a user for navigating menus and view different types of activity metrics, thereby creating a more efficient human-machine interface. For battery-operated computing devices, enabling a user to navigate and comprehend data faster and more efficiently conserves power and increases the time between battery charges.

In block 1102, contact information for a plurality of contacts is displayed on a display of a device. The contact information includes information for a first contact. FIGS. 10A and 10C depict examples displays resulting from the performance of block 1102. The contact information for a first contact is, for example, contact information graphical element 664 of FIGS. 10A and 10C. In some variations of method 1100, the contact information graphical elements may include workout data or goal data as well, as depicted in contact graphical elements 662, 664, and 668 of FIGS. 10A and 10C.

In some variations of method 1100, an information graphical element is also displayed for the user of the device. For example, as depicted in FIG. 10A, user interface 660 includes information graphical element 666 that includes goal data for the owner (labeled as "Me") of portable electronic device 600.

In some variation of method 1100, a parameter for sorting the contact information is received via a sort interface. The sort interface may be accessed from or through a user interface displaying the contact information by, for example, touching a touch sensitive screen of the device that is also pressure sensitive. If the touch has a characteristic intensity that exceeds an intensity threshold, then the sort interface is entered. The sort interface (e.g., sort interface 1000 of FIG. 10B) allows a user to select a parameter for sorting the contact information. The parameter may be selected via touches on displayed affordances associated with the various parameters. After the parameter is selected (e.g., selecting affordance 1004 of FIG. 10B for the calories progress parameter), the contact information is updated based on the sorting parameters (e.g., the display of FIG. 10A is updated with the display of FIG. 10C).

In block 1104, activity summary data is received from one or more external devices. Block 1104 may occur before or after block 1102 and before, after, or in response to block 1106. The activity summary data may include at least a first goal metric, such as the progress towards a calories burned goal, an activity measurement goal (e.g., standing up every hour), an exercise time goal, or other types of goals. In variations of method 1100, activity summary data may also include data for one or workout metrics, such as performance data for a recent workout or other workout related data (e.g., a pace, a distance, a time, a calorie value, and a heart rate). The activity summary data may be received from one or more external devices, such as an electronic device associated with the contact (e.g., with respect the example of Jeff as the first contact, a smartphone and/or an activity monitor belonging to Jeff). The activity summary data may also be received via one or more servers.

In block 1106, first user input selecting the first contact is received. For example, with respect to FIGS. 10A and 10C, contact information graphical elements 662, 664, and 668 may be affordances that are selectable via a touch sensitive screen. Alternatively, a first contact may be selected via hardware inputs, such as buttons, keyboards, rotatable inputs, or other types of interface devices inputs.

In block 1108, in response to receiving the first user input selecting the first contact in block 1106, a portion of a graphical representation of the activity summary data is displayed on the display, such as the portions depicted in and described with respect to FIGS. 10E-10G. The graphical representation includes at least a first goal graphical element, such as a graphical indicator or text, for the first goal metric. The graphical representation may be, for example, graphical representation 1008 of FIG. 10D. The graphical representation may include any number of different activity graphical elements, including goal graphical elements and workout graphical elements.

In addition to displaying a portion of the graphical representation, affordances for communicating with the selected contact may be displayed. For example, with respect to FIG. 10G, affordances 1030 and 1032 may allow a user of the device to send a message Jeff, as described above. Alternatively, the affordances may be a part of the graphical representation.

Figure 12:
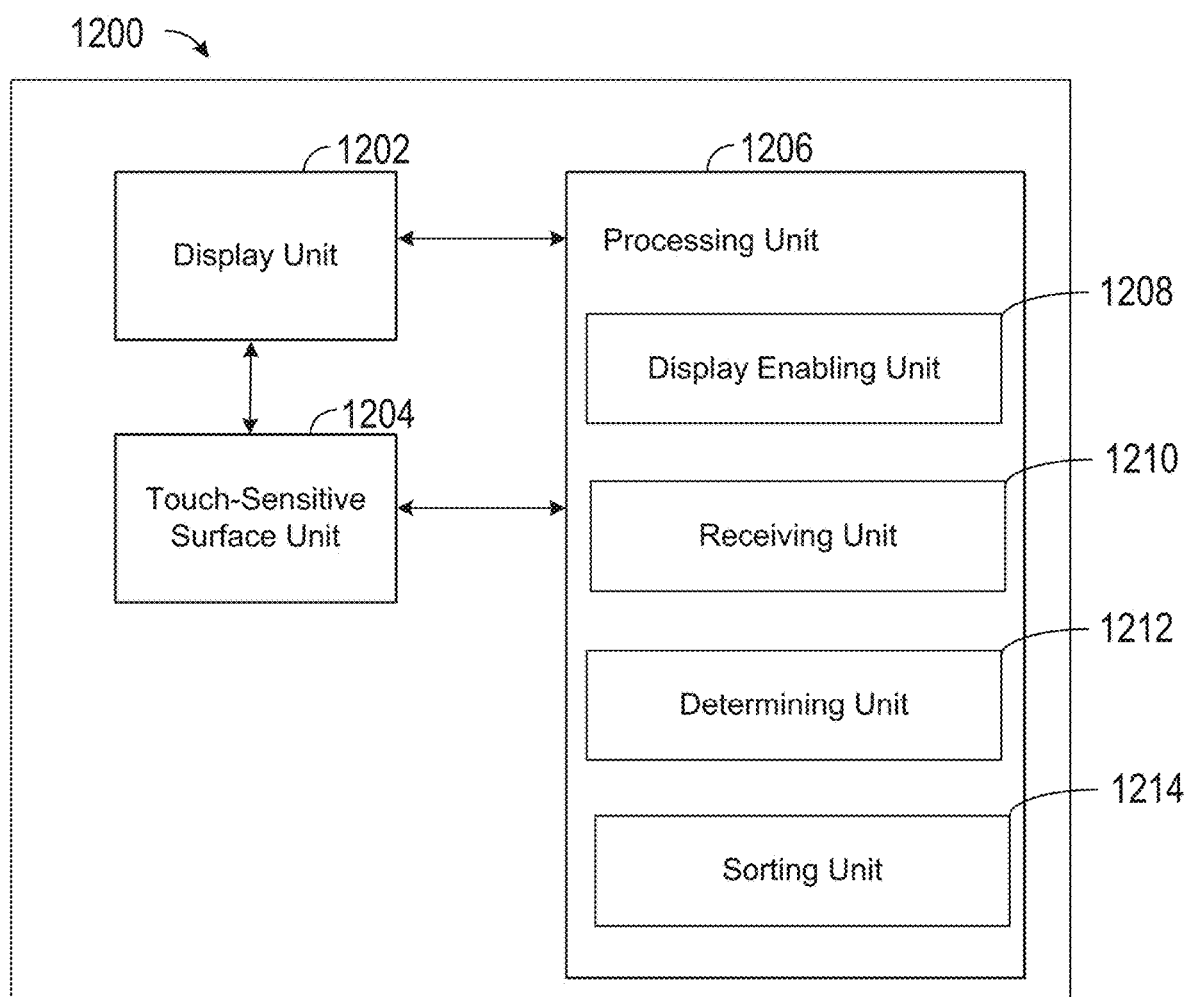
FIG. 12 shows an exemplary functional block diagram of an electronic device in accordance with the principles of the various described embodiments.

In accordance with some embodiments, FIG. 12 shows an exemplary functional block diagram of an electronic device 1200 configured in accordance with the principles of the various described embodiments. In accordance with some embodiments, the functional blocks of electronic device 1200 are configured to perform the techniques described above. The functional blocks of the device 1200 are, optionally, implemented by hardware, software, or a combination of hardware and software to carry out the principles of the various described examples. It is understood by persons of skill in the art that the functional blocks described in FIG. 12 are, optionally, combined or separated into sub-blocks to implement the principles of the various described examples. Therefore, the description herein optionally supports any possible combination or separation or further definition of the functional blocks described herein.

As shown in FIG. 12, an electronic device 1200 includes a display unit 1202 configured to display a graphic user interface, a touch-sensitive surface unit 1204 configured to receive contacts (i.e., touches), optionally a pressure-sensitive surface unit 1216, and a processing unit 1206 coupled to the display unit 1202 and the touch-sensitive surface unit 1204. In some embodiments, the processing unit 1206 includes a display enabling unit 1208 and receiving unit 1210 and optionally a determining unit 1212, a sorting unit 1214.

The processing unit 1206 is configured to enable display of (e.g., with display enabling unit 1208) of contact information for a plurality of contacts, including a first contact. The processing unit 1206 is further configured to receive (e.g., with receiving unit 1210), from one or more external electronic devices, activity summary data for the first contact, where the activity summary data for the first contact includes a first goal metric and to receive (e.g., with receiving unit 1210) first user input selecting the first contact. The processing unit 1206 is further configured to, in response to receiving the first user input selecting the first contact, enable display of (e.g., with display enabling unit 1208) a portion of a graphical representation of the activity summary on the display, where the graphical representation includes a first goal graphical element for the first goal metric.

In some embodiments, the displayed contact information includes workout data or goal data for each of the plurality of contacts.

In some embodiments, the portable electronic device includes a pressure sensitive touch screen and the processing unit 1206 is further configured to, while displaying the contact information, receive (e.g., with receiving unit 1210) second user input on the pressure sensitive touch screen, where the second user input has a characteristic intensity. The processing unit 1206 is further configured to, in response to receiving the second user input, determine (e.g., with determining unit 1212) whether the characteristic intensity exceeds a threshold intensity. The processing unit 1206 is further configured to, in accordance with a determination that the second user input exceeds the threshold intensity, enable display of (e.g., with display enabling unit 1208) a sort interface for selecting a parameter by which to sort the first plurality of contacts. The processing unit 1206 is further configured to, while displaying the sort interface, receive (e.g., with receiving unit 1210) a third user input identifying a parameter for sorting the plurality of contacts. The processing unit 1206 is further configured to, in response to receiving the second user input, sort (e.g., with sort interface 1214) the first plurality of contacts to generate a sorted first plurality of contacts based on the parameter. The processing unit 1206 is further configured to enable update of the display of (e.g., with display enabling unit 1208) the contact information based on the sorted first plurality of contacts.

In some embodiments, the graphical representation of the activity summary includes an affordance for contacting the first contact and the processing unit 1206 is further configured to receive (e.g., with receiving unit 1210) third user input indicating selection of the affordance. The processing unit 1206 is further configured to, in response to receiving the third user input, enable display of (e.g., with display enabling unit 1208) a messaging user interface configured to receive message input for the first contact on the portable electronic device.

In some embodiments, the first goal metric is at least one of a number of calories burned or a measurement of an activity.

In some embodiments, the activity summary includes a first workout metric and the graphical representation includes a first workout graphical element for the first workout metric.

In some embodiments, the first workout metric is selected from the group consisting of a pace, a distance, a time, a calorie value, and a heart rate.

In some embodiments, the processing unit 1206 is further configured to, while displaying the contact information, enable display of (e.g., with display enabling unit 1208) a graphical element corresponding to a user of the portable electronic device, where the graphical element includes an activity graphical element for the user.

FIGS. 13A-13F illustrate exemplary user interfaces for activity and workout monitoring and sharing, in accordance with some embodiments. The user interfaces in these figures are used to illustrate the processes described below, including the processes in FIG. 14.

Figure 13A:
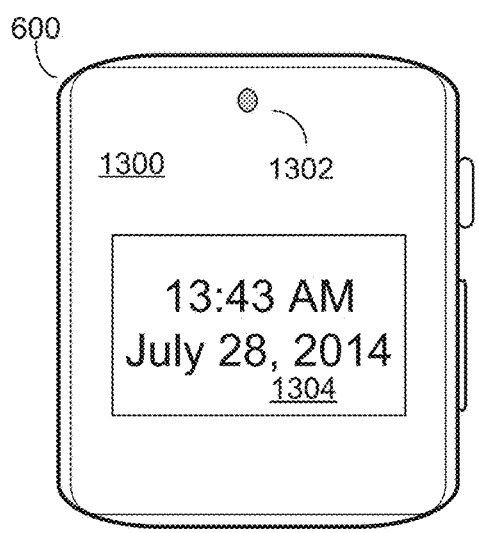
FIGS. 13A-13F illustrate exemplary user interfaces for activity and workout monitoring and sharing, in accordance with some embodiments.
Figure 14:
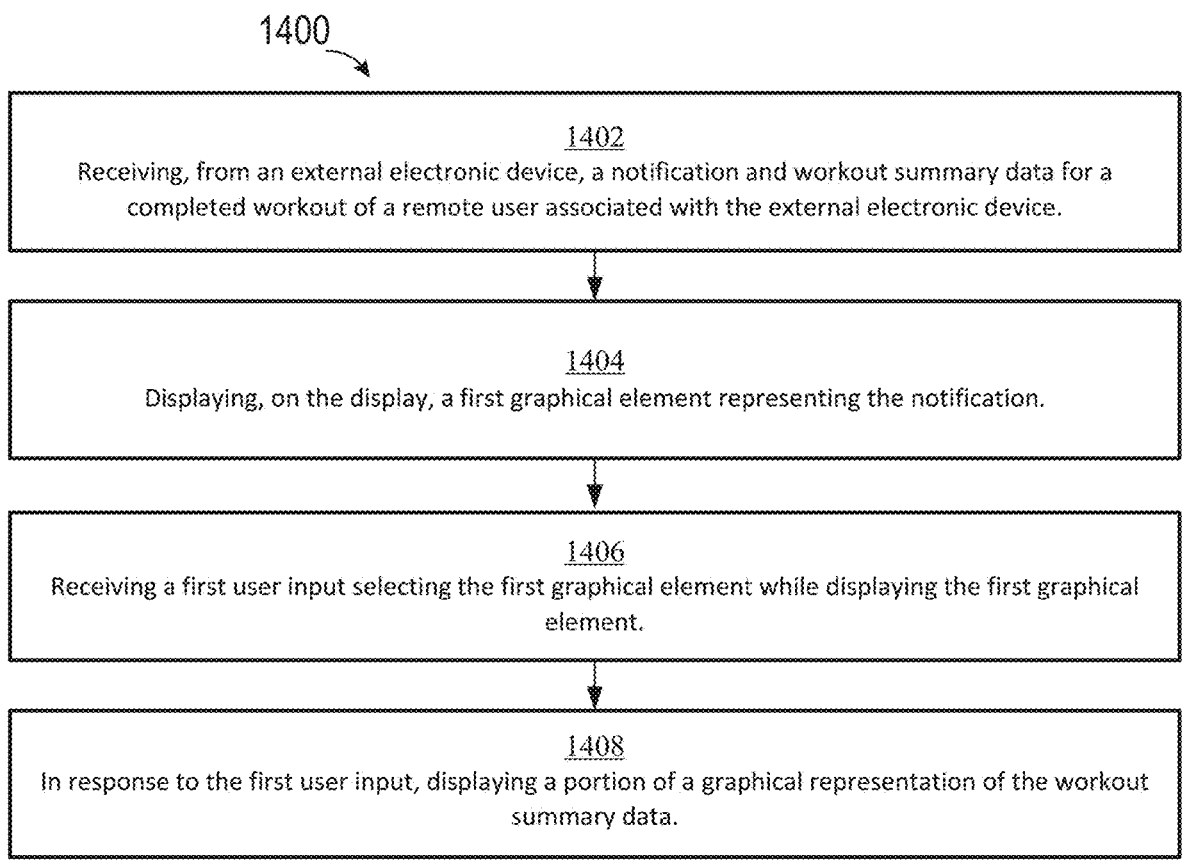
FIG. 14 is a flow diagram illustrating a method for activity and workout monitoring and sharing using a portable electronic device in accordance with some embodiments.

FIG. 13A depicts user interface 1300 on portable electronic device 600. User interface 1300 includes a graphical element in the form of notification indicator 1302 and graphical element 1304, which is displaying the current date and time. In addition to notification indicator 1302 indicating that a notification has been received, portable electronic device 600 may also alert a user in other ways that a notification has been received, such as haptic feedback, an audio indicator, other visual indications, or other ways of notifying the user. Indicator 1302 may indicate that any number of notifications have been received, including a notification of a completed workout of a remote user.

The notification may be received from one or more external devices. For example, the notification may be received from a device associated with the remote user of an electronic device. The notification may be received via one or more servers. The notification may also be received via an electronic device that is associated with the user. For example, the portable electronic device may be a watch and the notification may be received at the watch via communication with a paired smartphone, which may receive the notification via one or more servers that received the notification from the external electronic device associated with the remote user.

In addition to receiving the notification, workout summary data may also be received in a similar manner. The workout summary data can be received via the same or different paths described previously. Additionally, the workout summary data and notification could be received at the same time or at different times. The workout summary data and notification also could be the same data (i.e., the notification is the workout summary data).

Figure 13D:
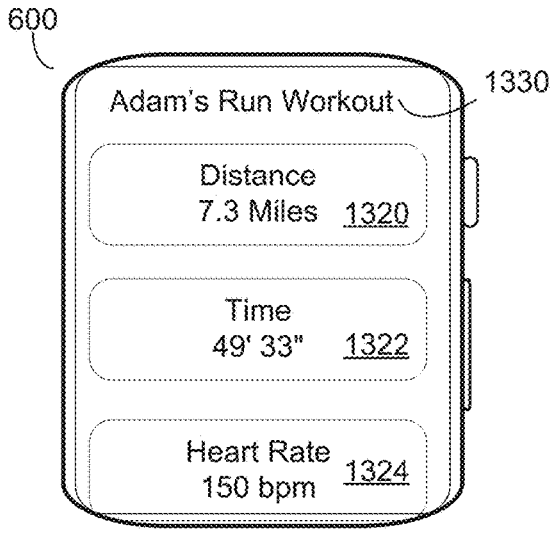
Figure 13B:
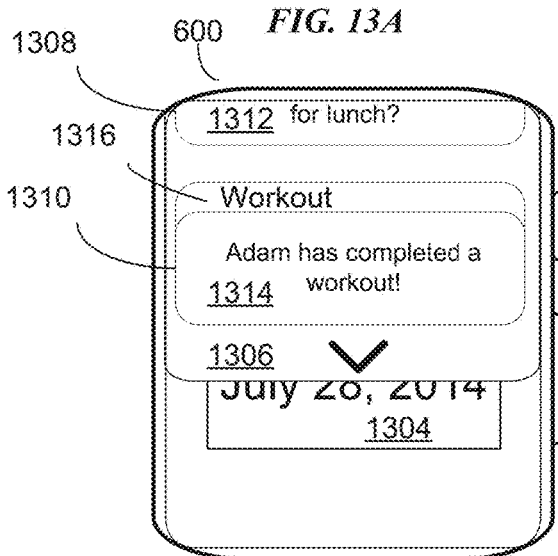

Referring to FIG. 13B, user input may be received that initiates access to a notification center that includes information for the received notification. For example, a user may touch indicator 1302 on the touch sensitive screen and drag down the touch to pull down the notification center from the top of the display. FIG. 13B depicts notification center 1306 about half-way through being pulled down. Notification alert graphical element 1310 is displayed with notification information 1314 and indication 1316, which indicates an application that is associated with the notification. Notification alert graphical element 1308 along with notification information 1312 are partially visible.

Figure 13E:
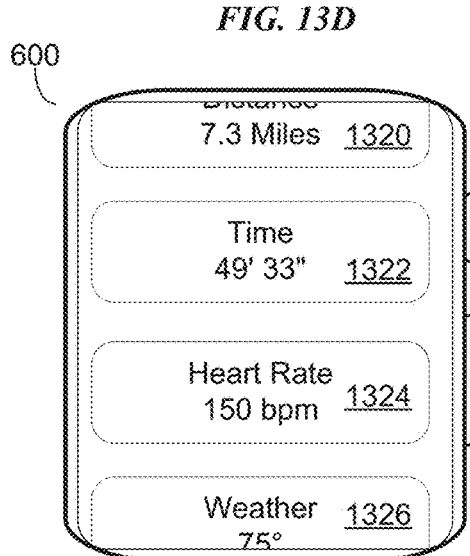
Figure 13C:
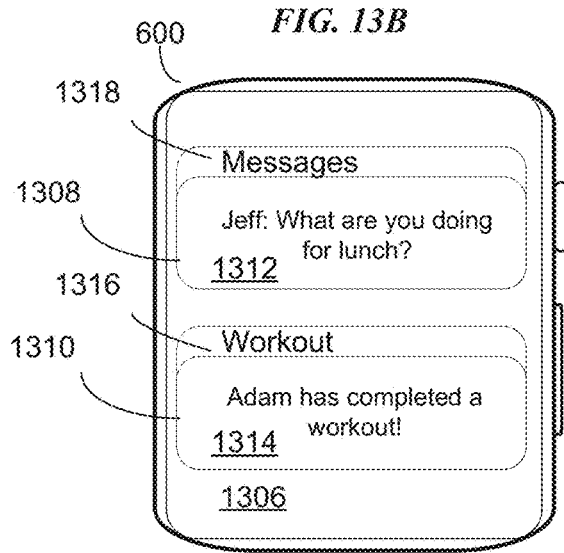

Referring to FIG. 13C the interface for notification center 1306 is fully visible. Two notification alert graphical elements (1308 and 1310) are present. If additional notifications were available, the associated notification alert graphical elements could be displayed via a scrolling input (e.g., via a swipe or drag gesture). Notification alert graphical alert 1308 includes indication 1318, which indicates an application that is associated with the notification.

Notification alert graphical elements 1308 and 1310 may be affordances for selecting the associated notification or associated application. For example, a user may select one of the affordances via a touch sensitive screen. Other input methods could also be used to select a notification alert.

Figure 13F:
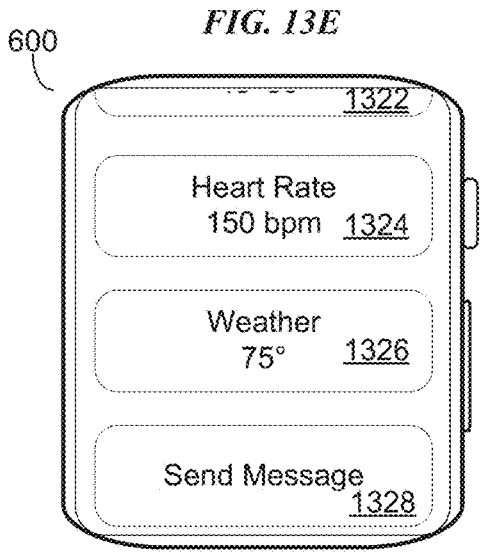

In response to a selection of a notification alert graphical element for the Workout application (graphical element 1310), a graphical representation of the received workout summary data that corresponds to the notification is at least partially displayed in the Workout application, as depicted in FIGS. 13D-13F. If the graphical representation extends beyond the size of the displayable area of the display, the other portions may be accessed by scrolling the display via a user input (e.g., touch sensitive screen or other hardware user inputs), as depicted in FIGS. 13D-13F (FIG. 13E depicts the result of a first scroll input and FIG. 13F depicts the result of a second scroll input). In this example, the graphical representation includes workout graphical elements 1320, 1322, 1324, 1326, and 1330 that all relate to different aspects of the workout. For example, workout graphical element 1330 in FIG. 13D includes a graphical element indicating the type of workout completed; workout graphical elements 1326 includes a graphical element indicating the weather associated with the completed workout; and workout graphical elements 1320, 1322, and 1324 include graphical elements for workout metric data (e.g., pace, distance, time, calories burned, or a heart rate) for the completed workout. The graphical representation could also include graphical elements for other types of data, such as goal metrics (e.g., for calories burned, number of steps, a count of hours when time was spent standing, or other measurements of an activity).

As part of or in addition to the graphical representation, one or more affordances may be displayed, such as affordance 1328 of FIG. 13F. The one or more affordances may provide various actions that the user may perform by selecting an affordance. For example with respect to affordance 1328 of FIG. 13F, selecting affordance 1328 will open a messaging user interface that a user can use to enter a message for the contact associated with the graphical representation. In the case of FIGS. 13D-13F, selecting affordance 1328 would result in a messaging interface for sending Adam a message. The messaging interface can also include the ability to select and send pre-defined messages. Pre-defined message can include any type of messages, such as messages of encouragement, competition, or praise.

FIG. 14 is a flow diagram illustrating a method for activity and workout monitoring and sharing using a portable electronic device in accordance with some embodiments. Method 1400 is performed at a device (e.g., 100, 300, 500, 600) with a display. Some operations in method 1400 are, optionally, combined, the order of some operations is, optionally, changed, and some operations are, optionally, omitted.

As described below, method 1400 provides an intuitive way for navigating and viewing completed activity notifications and associated workout data. The method reduces the cognitive burden on a user for navigating menus and view different types of activity metrics, thereby creating a more efficient human-machine interface. For battery-operated computing devices, enabling a user to navigate and comprehend data faster and more efficiently conserves power and increases the time between battery charges.

In block 1402, a notification and workout summary data are received from an external electronic device. The workout summary data may be for a completed workout of a remote user associated with the external electronic device. The notification may be, for example, a Push Notification or other type of notification that is generated in response to an indication from the external electronic device that the remote user completed a workout. The workout summary data may include data for one or more workout metrics, such as those described above with respect to FIGS. 13D-13F.

In block 1404, a first graphical element representing the notification is displayed on the display, such as described above with respect to FIG. 13C. The display of the first graphical element may occur after receipt of the workout summary data or, if the notification and workout summary data are different data, the display of the first graphical element could occur before the receipt of the workout summary data.

In block 1406, while displaying the first graphical element, a first user input selecting the first graphical element is received. The first user input may be, for example, a touch on the touch sensitive screen while displaying the first graphical element. In other words, the first graphical element may be an affordance, as described above with respect to FIG. 13C.

In block 1408, in response to the first user input, a portion of a graphical representation of the workout summary data is displayed. For example, the graphical representation may be similar to the graphical representations described previously with respect to FIGS. 7A, 7B, and 10D except the graphical representation in block 1408 is for the workout summary data. Portions of an example graphical representation of workout summary data are depicted in FIGS. 13D-13F.

Figure 15:
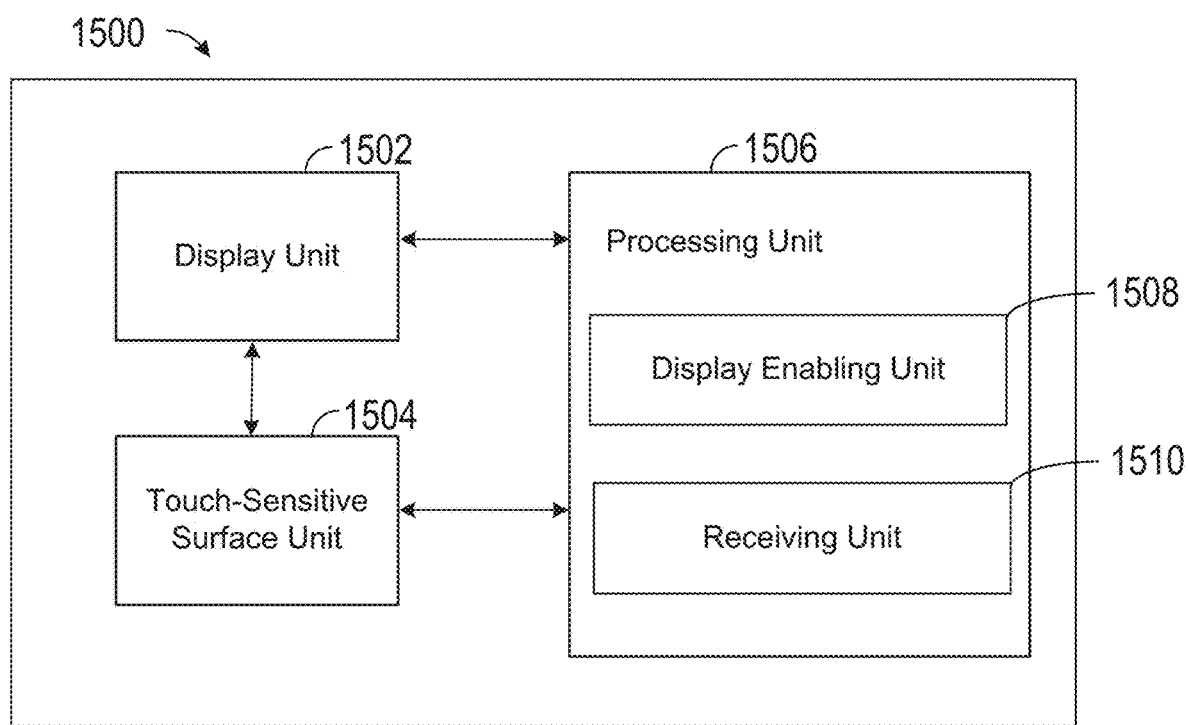
FIG. 15 shows an exemplary functional block diagram of an electronic device in accordance with the principles of the various described embodiments.

In accordance with some embodiments, FIG. 15 shows an exemplary functional block diagram of an electronic device 1500 configured in accordance with the principles of the various described embodiments. In accordance with some embodiments, the functional blocks of electronic device 1500 are configured to perform the techniques described above. The functional blocks of the device 1500 are, optionally, implemented by hardware, software, or a combination of hardware and software to carry out the principles of the various described examples. It is understood by persons of skill in the art that the functional blocks described in FIG. 15 are, optionally, combined or separated into sub-blocks to implement the principles of the various described examples. Therefore, the description herein optionally supports any possible combination or separation or further definition of the functional blocks described herein.

As shown in FIG. 15, an electronic device 1500 includes a display unit 1502 configured to display a graphic user interface, a touch-sensitive surface unit 1504 configured to receive contacts (i.e., touches), and a processing unit 1506 coupled to the display unit 1502 and the touch-sensitive surface unit 1504. In some embodiments, the processing unit 1506 includes a display enabling unit 1508 and receiving unit 1510.

The processing unit 1506 is configured to: receive (e.g., with receiving unit 1510), from an external electronic device, a notification and workout summary data for a completed workout of a remote user associated with the external electronic device; enable display (e.g., with display enabling unit 1508) of, on the display (e.g., display unit 1502), a first graphical element representing the notification; receive (e.g., with receiving unit 1510) a first user input selecting the first graphical element while displaying the first graphical element; and in response to the first user input, enable display (e.g., with display enabling unit 1508) of a portion of a graphical representation of the workout summary data.

In some embodiments, the graphical representation includes a graphical element indicating a type of the workout.

In some embodiments, the graphical representation includes a graphical element indicating weather data associated with the workout.

In some embodiments, the graphical representation includes a graphical element of a first goal metric and wherein the first goal metric is a number of calories burned or a measurement of activity.

In some embodiments, the graphical representation includes a graphical element for a first workout metric for the completed workout and the first workout metric is selected from the group consisting of a pace, a distance, a time, a number of calories burned, and a heart rate.

In some embodiments, the graphical representation includes a graphical element of a second workout metric for the workout different than the first workout metric and the second workout metric is selected from the group consisting of a pace, a distance, a time, a calorie value, and a heart rate.

In some embodiments, receiving the workout summary occurs after receiving the first user input selecting the notification.

In some embodiments, the graphical representation of the activity summary includes an affordance for contacting the first contact and the processing unit 1506 is further configured to receive (e.g., with receiving unit 1510) a second user input indicating selection of the affordance. The processing unit 1506 is further configured to, in response to receiving the second user input, enabling display (e.g., with display enabling unit 1508) of a messaging user interface configured to receive message input for the first contact on the portable electronic device.

In some embodiments, the messaging user interface includes a plurality of pre-defined messages, and wherein at least one of the pre-defined messages is based on type of the current workout.

In some embodiments, the messaging user interface includes a plurality of pre-defined messages and at least one of the pre-defined messages is based on the workout summary data.

FIGS. 16A-16J illustrate exemplary user interfaces navigating and sharing activity data, in accordance with some embodiments. The user interfaces in these figures are used to illustrate the processes described below, including the processes in FIG. 17.

FIG. 16A illustrates portable electronic device 1600, such as the multifunction electronic device described above with respect to FIGS. 1A-1B, 2-3, 4A-4B, and 5A-5H. Portable electronic device includes user interface 1602 for a workout or activity application, which may help track data relating to the physical activity, health, and/or biological state of a user of portable electronic device 1600. Portable electronic device 1600 may be carried with or worn on a user. For example, portable electronic device 600 may be a smartphone. Portable electronic device 1600 may also be other types of devices and connect to other devices, such as portable electronic device 600 of FIG. 6A, to measure and collect workout and activity data.

User interface 1602 includes goal summary graphical element 1604 that represents the progress towards various activity goals for the day. Goal summary graphical element 1604 may be the same or similar as goal summary graphical element 604 described above with respect to FIG. 6A. Goal summary graphical elements 1606 may be smaller versions of goal graphical element 1604 with each one being associated with a day of the week. Goal graphical element 1606 associated with Saturday (labeled "S") is the same as and updated with goal graphical element 1604 as the day's activities are measured and recorded.

User interface 1602 can include other graphical elements. For example, goal summary graphical element 1608 is a chronological representation of one of the goal metrics associated with goal summary graphical element 1604. Additional information and graphical elements may be accessible by scrolling user interface 1602.

User interface 1602 also includes affordances 1610, 1612, 1614, and 1616 for selecting various modes of user interface 1602 or the application. Affordance 1610 corresponds to a goral history interface for accessing data about past activity goals, including past daily goal metrics. Affordance 1612 corresponds to a workout history interface for accessing data about past workouts, including workout metrics. Affordance 1614 corresponds to a sharing interface where activity and workout data can be shared with friends.

FIG. 16B depicts user interface 1617, which is displayed in response to receiving user input selecting affordance 1616 of FIG. 16A (e.g., via a touch on the touch sensitive screen). In FIG. 16B, user interface 1602 includes affordance 1618 for initializing the sharing of data and graphical element 1619. In response to user input selecting affordance 1618, graphical element 1619 transforms into S-shaped graphical element 1620 of FIG. 16C via an animation to indicate that workout and activity sharing is initializing.

After the animation of graphical element 1619 of FIG. 16B transforming into graphical element 1620 of FIG. 16C, a list of potential friends is loaded. For example, the list of friends depicted in FIG. 16D may be the list of contacts 1622, 1624, 1626, 1628, 1630, 1632, 1634, and 1636 from other applications, such as an email application, a contacts application, or a phone application. The list of contacts could also be loaded from a remote server or other device.

After retrieving the list of contacts, a determination is made of which contacts support the sharing of activity data, such as goal metrics or workout metrics. For example, a determination can be made as to whether each contact is associated with an electronic device that measures and/or records activity data. This association may be stored on a central server. With respect to FIG. 16D, the presence of selection indicators 1638, 1640, 1642, 1644, 1646, and 1648 indicate that the associated contact supports the sharing of activity data. The absence of a selection indicator for contacts 1630 and 1634 indicate that those contacts do not support the sharing of activity data.

FIG. 16E depicts the selection of several of the selection indicators via, for example, touches on the screen where the selection indicators are displayed. In this example, the selection indicators are affordances for indicating that the user wants to share activity data with the associated contact. The selection is depicted as a check mark over the selection indicators. The entire contact regions could alternatively be the affordances for selecting the various contacts. Once the selection of contacts is completed, affordance 1650 can be selected via user input to complete the initialization procedure. In response to the selection of affordance 1650, invitation messages may be sent to the selected contacts indicating that the user would like to be an activity friend with the contact. If the contact accepts the invitation, the user and the contact can share activity data as described below.

FIG. 16F depicts user interface 1602 in the sharing mode after initialization. After initialization has been completed once, this sharing mode may be entered in response to selection of affordance 1616 instead of entering the initialization mode. The sharing mode includes affordance 1662 for entering a sort interface for selecting a parameter for ordering the activity friends. Affordance 1660 allows a user to enter a messaging interface to message the activity friends. Affordance 1650 corresponds to the user and provides for the user to view the user's own activity data as will be seen by the activity friends. Affordances 1652, 1654, 1658, and 1660 correspond to activity friends (i.e., contacts that either accepted the user's invitation to share activity data or contacts that sent an invitation that the user accepted) and provide for the user to view an activity friend's activity data.

For example, in response to user input selecting affordance 1652 of FIG. 16F, a determination is made as to whether activity data for Adam is available (e.g., locally or on a server). The presence of the actual activity data may be checked or other configuration or variables may be checked. If activity data is available, which indicates that Adam is not hiding activity data, a portion of a graphical representation of Adam's activity data is displayed, as depicted in FIG. 16G. Selection of affordance 1664 in FIG. 16G returns to the activity friend listing in FIG. 16F. The graphical representation includes goal summary graphical elements 1666 and 1668 of FIG. 16G and achievement graphical elements 1670 of FIG. 16H. FIG. 16H also depicts affordances 1672, 1674, and 1676 that allow the user to control activity sharing with the contact. For example, affordance 1672 may prevent further notifications regarding Adam's activities (e.g., notifications described with respect to FIGS. 13A-13F and 14) from being provided to the user. Affordance 1674 may prevent the user's activity data from being provided to Adam. This may be important, for example, if the relationship between the user and Adam is one that it is not appropriate for the user to share activity data with Adam but the user should be able to see Adam's activity data. One such example case is if the user is a trainer or healthcare provider that is monitoring Adam's activities but the user does not want to share their activities and make Adam feel as though he must compete with the user's activities. Affordance 1676 allows for the user to remove Adam as an activity friend.

Graphical element 1678 may be another affordance for performing other actions with respect to Adam, may be a graphical element depicting additional activity information, may be a graphical element providing information regarding the history or status of Adam as an activity friend (e.g., when the friendship began, how long data has been hidden), or may be another type of graphical element.

Similar graphical representations of activity data may be displayed in response to selecting other affordances for activity friends depicted in FIG. 16F (and for affordance 1650 for the daily summary of the user's activity data) when activity data is available for the contact associated with the corresponding affordance. If, however, activity data is not available, either because activity data has not been received or because an activity friend has decided to hide their data from the user, an indication that activity data is not available in response to selection of the affordance.

Figure 16I:
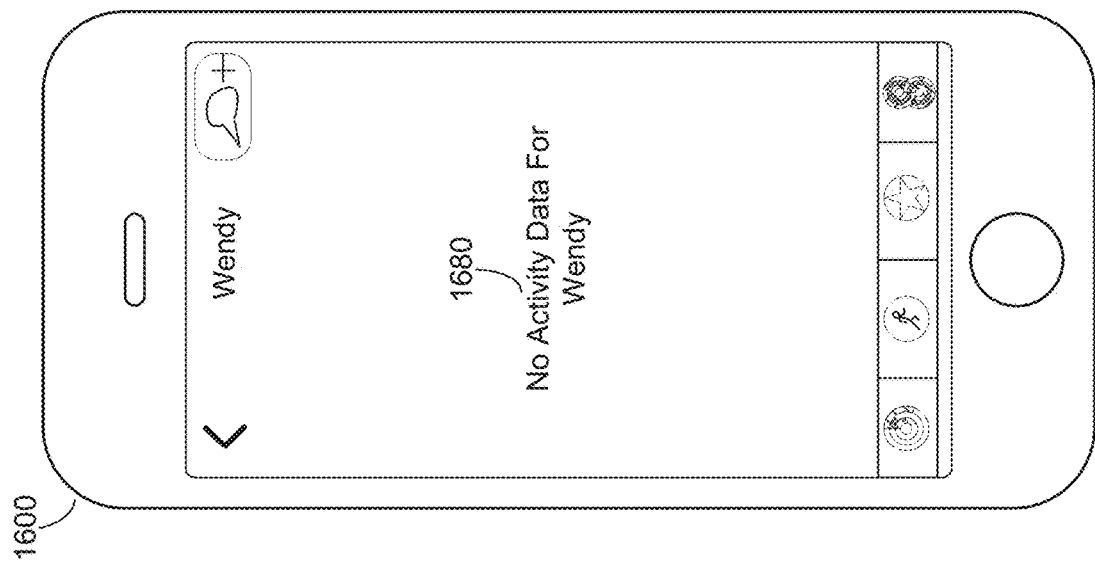
Figure 17:
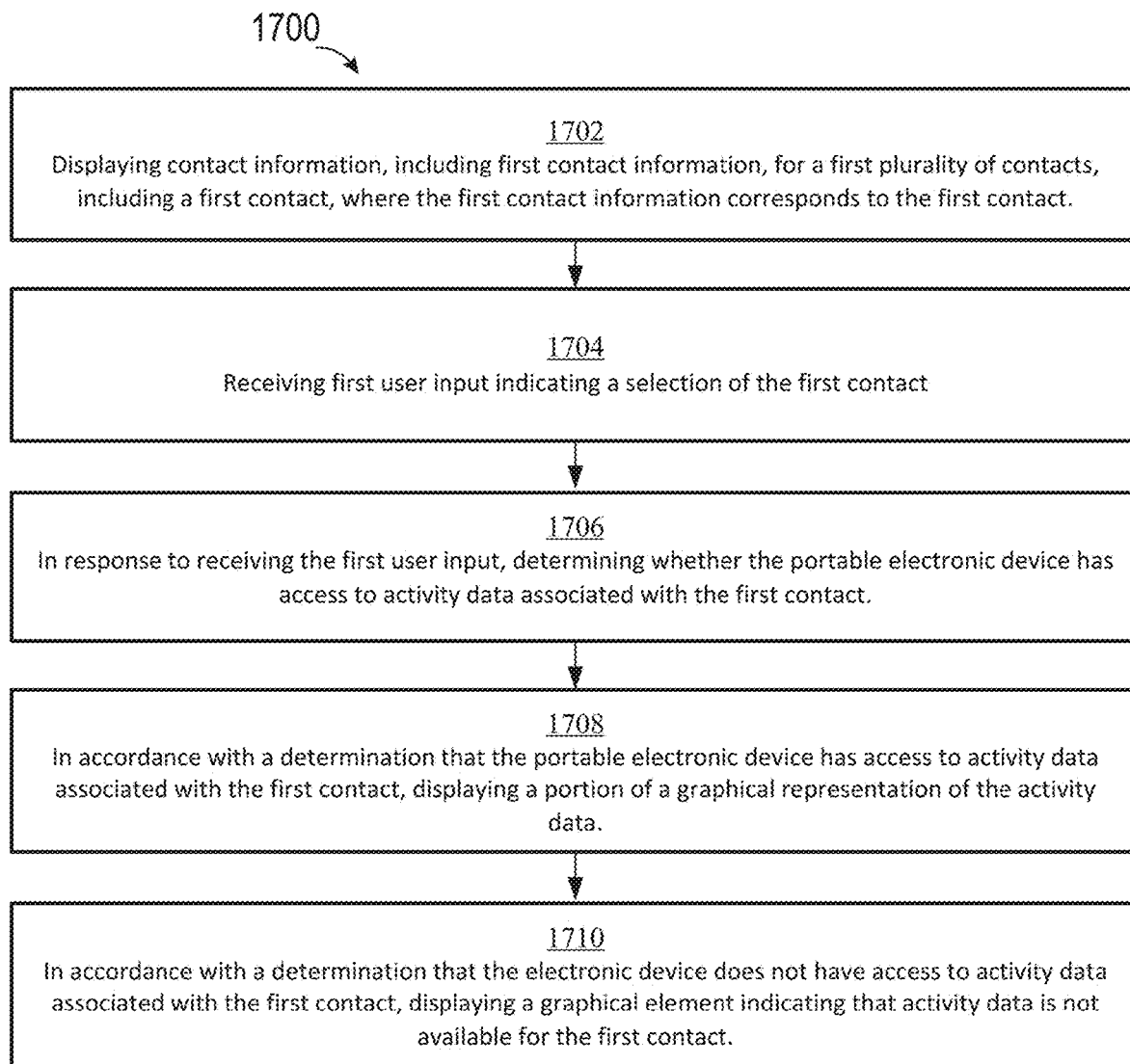
FIG. 17 is a flow diagram illustrating a method for navigating and sharing activity data using a portable electronic device in accordance with some embodiments.

For example, if affordance 1660 of FIG. 16F is selected but activity data for Wendy is not available, then graphical element 1680 may be displayed indicating that the activity data is not available, as depicted in FIG. 16I. Alternative, the graphical element could also state that Wendy is hiding her activity data.

An activity friend interface, such as that of FIG. 16J, may be used to view and manage activity friends. For example, with reference to FIG. 16J, each potential activity friend and current activity friend may be listed. Graphical element 1682 is associated with a potential activity friend that has sent the user an invitation to share activity data. Affordances 1684 and 1686 can be used to accept or decline the invitation, respectively. Graphical elements 1688 and 1690 indicate activity friends with mutual sharing of activity data. Graphical element 1692 indicates an activity friend that the user is hiding activity data from. Graphical element 1694 indicates an activity friend that is hiding activity data from the user. Graphical elements 1682, 1688, 1690, 1692, and 1694 may also be affordances that, when selected, provide additional information about activity friend (e.g., summary of activity data or other contact information).

FIG. 17 is a flow diagram illustrating a method for navigating and sharing activity data using a portable electronic device in accordance with some embodiments. Method 1700 is performed at a device (e.g., 100, 300, 500, 600, 1600) with a display and, in some cases, a touch sensitive screen. Some operations in method 1700 are, optionally, combined, the order of some operations is, optionally, changed, and some operations are, optionally, omitted.

In block 1702, contact information is displayed, including first contact information, for a first plurality of contacts, including a first contact, where the first contact information corresponds to the first contact. The contact information may be, for example, the name or a contact. The contract information could also include activity data, such as a goal metric. Graphical element 1652 of FIG. 16F is an example of displaying contact information (e.g., the contact's name) for a first contact (the contact named "Adam").

Variations of method 1700 may include, prior to the display of the contact information in block 1702, generating the first plurality of contacts. This process may start by displaying an affordance for generating the first plurality of contact, such as affordance 1618 of FIG. 16B. In response to receiving user input selecting the affordance, a second plurality of contacts are retrieved. For example, the second plurality of contacts may be contacts from an email application, a phone application, a contact application, a database, or other source. The second plurality of contacts can be retrieved from a source locally or remotely. The second plurality of contacts includes the first contact and a second contact.

Next a determination is made whether an electronic device associated with the second contact supports sharing of activity data. This determination may be made in several manners. For example, a determination can be made as to whether an electronic device associated with the second contact can measure and/or record activity data. Local or remote databases may be queried to make this determination. In accordance with a determination that the second contact is not associated with an electronic device that supports sharing of activity data, the second contact is excluded from the first plurality of contacts. For example, the second contact may be excluded by preventing the second contact from being selected to be included in the first plurality of contacts. This is illustrated with respect to FIG. 16D and described above. For example, if "Tina" is the second contact in FIG. 16D, Tina cannot be added to the first plurality of contacts displayed in FIG. 16F because it has been determined that Tina is not associated with a device that can share activity data and a selection indicator has not been provided for Tina. In contrast, if the first contact is "Adam," it has been determined that Adam is associated with an electronic device that supports sharing of activity data. Accordingly, selection indicator 1638 (FIG. 16D) is provided for Adam so that a user may add Adam to the first plurality of contacts.

Variations of method 1700 may include sorting the first plurality of contacts for display. An affordance for a sort interface may be displayed and selected via a user input (e.g., affordance 1662 of FIG. 16F). The sort interface may provide for receipt of user input that indicates a parameter for sorting the first plurality of contacts. For example, contact information (e.g., name) or activity data (e.g., goal metrics or workout metrics) may also be selected as the sort parameter. In response to a selection of a parameter, the first plurality of contacts are sorted based on the selected parameter to generate a sorted first plurality of contacts and the display of the contact information is based on the sort first plurality of contacts.

In block 1704, first user input indicating a selection of the first contact is received. For example, the first user input may be received via a touch sensitive screen or other form of input. With reference to FIG. 16F, graphical element 1652 may also be an affordance that is selectable via the touch sensitive screen of portable electronic device 1600. In this example, the first contact is selected via a user touch on the touch screen where graphical element 1652 is displayed.

In block 1706, in response to receiving the first user input, a determination is made whether the portable electronic device has access to activity data associated with the first contact. This determination may be carried out in various manners. For example, one or more processors of the portable electronic device may check local memory for activity data associated with the first contact. A database of contact information that includes a flag or other configuration data may also indicate whether activity data is available for the first contact. As another example, a remote server or an electronic device associated with the contact can be checked. The determination may also check for whether there is an indication available that the first contact is hiding their activity data.

In block 1708, in accordance with a determination that the portable electronic device has access to activity data associated with the first contact, displaying a portion of a graphical representation of the activity data. The graphical representation of the activity data may be similar to the graphical representations of activity, goal, and workout data previously described. For example, an example graphical representation for the first contact "Adam" of FIG. 16F is depicted in FIGS. 16G and 16H.

In addition to displaying the graphical representation for activity data of the first contact, other data and/or affordances may be displayed. For example, an affordance for hiding activity data from the first contact may be included (e.g., affordance 1674 of FIG. 16H). In response to receiving user input selecting this affordance, an indication may be stored that prevents sending of the user's activity data to the contact.

As another example, an affordance for muting future notifications regarding activities from the first contact may be displayed (e.g., affordance 1672 of FIG. 16H). In response to receiving user input selecting this affordance, future notifications regarding the first contact's activities or activity data will not be presented to the user.

As another example, an affordance for removing the first contact from the first plurality of contacts may be displayed (e.g., affordance 1676 of FIG. 16H). In response to receiving user input selecting this affordance, the first contact is removed from the first plurality of contacts. Removing the first contact from the first plurality of contacts does not necessarily affect the first contact's presence in the second plurality of contacts.

In block 1710, in accordance with a determination that the electronic device does not have access to activity data associated with the first contact, displaying a graphical element indicating that activity data is not available for the first contact. An example of this display is depicted in FIG. 16I. As another example, the graphical element indicating that activity data is not available may also indicate that the first contact is hiding activity data.

In some variations of method 1700, in response to receiving user input selecting an affordance for a friend control interface, display of the contact information is replaced with display of a graphical representation of summary status data, such as depicted FIG. 16J. The graphical representation of the summary data includes a hiding portion, an invitation portion, and a sharing portion. The hiding portion includes contact information for a set of contacts that are hiding activity data. The invitation portion includes contact information for a set of contacts from which a notification has been received indicating an offer to share activity data. The sharing portion includes contact information for a set of contacts that are sharing activity data.

Figure 18:
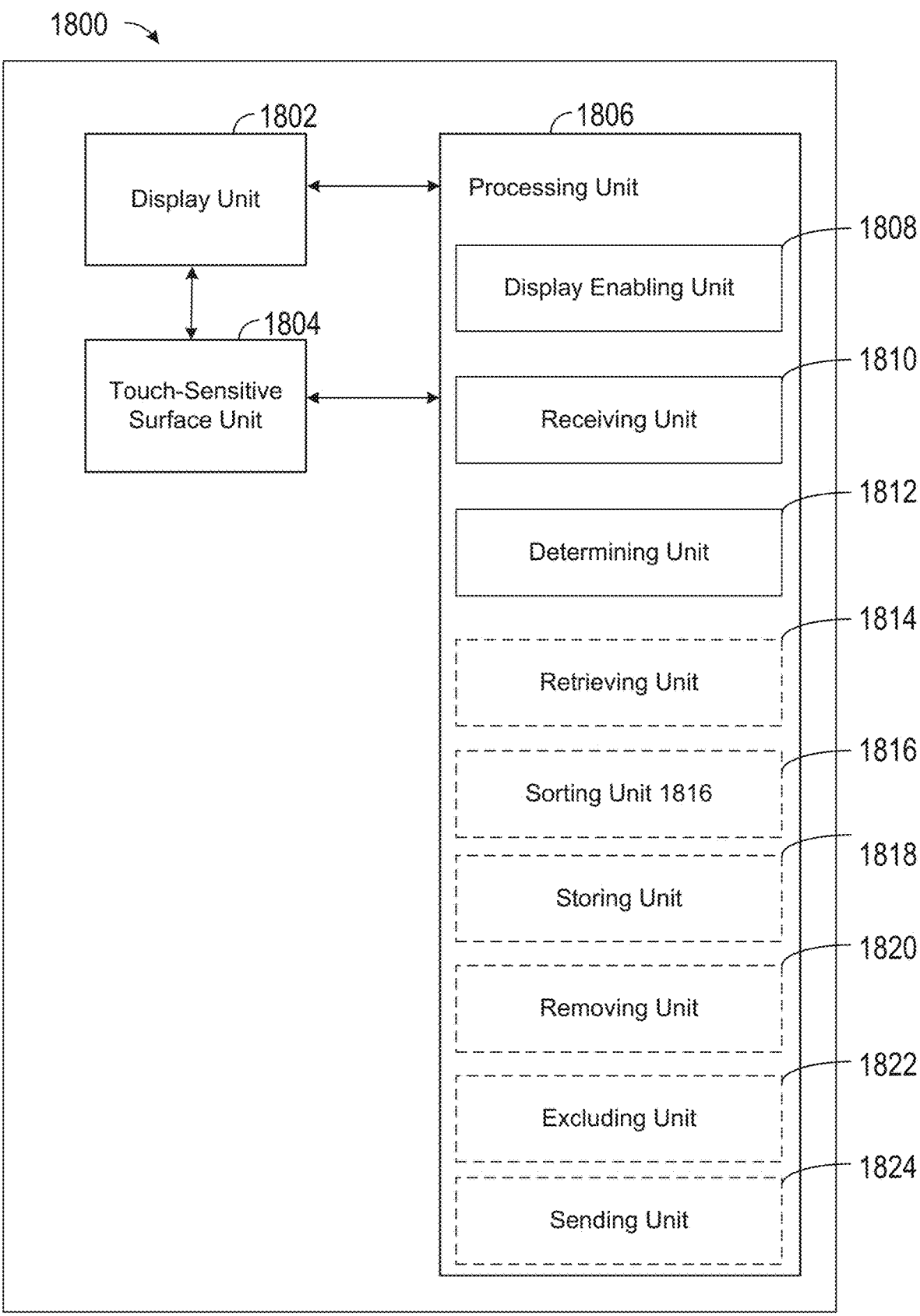
FIG. 18 shows an exemplary functional block diagram of an electronic device in accordance with the principles of the various described embodiments.

In accordance with some embodiments, FIG. 18 shows an exemplary functional block diagram of an electronic device 1800 configured in accordance with the principles of the various described embodiments. In accordance with some embodiments, the functional blocks of electronic device 1800 are configured to perform the techniques described above. The functional blocks of the device 1800 are, optionally, implemented by hardware, software, or a combination of hardware and software to carry out the principles of the various described examples. It is understood by persons of skill in the art that the functional blocks described in FIG. 18 are, optionally, combined or separated into sub-blocks to implement the principles of the various described examples. Therefore, the description herein optionally supports any possible combination or separation or further definition of the functional blocks described herein.

As shown in FIG. 18, an electronic device 1800 includes a display unit 1802 configured to display a graphic user interface, a touch-sensitive surface unit 1804 configured to receive contacts (i.e., touches) and a processing unit 1806 coupled to the display unit 1802 and the touch-sensitive surface unit 1804. In some embodiments, the processing unit 1806 includes a display enabling unit 1808, receiving unit 1810, and a determining unit 1812 and, optionally, a retrieving unit 1814, a sorting unit 1816, a storing unit 1818, a removing unit 1820, an excluding unit 1822, and a sending unit 1824.

The processing unit 1806 is configured to enable display (e.g., with display enabling unit 1808) of contact information, including first contact information, for a first plurality of contacts, including a first contact, where the first contact information corresponds to the first contact. The processing unit 1806 is further configured to receive (e.g., with receiving unit 1812) first user input indicating a selection of the first contact. The processing unit 1806 is further configured to, in response to receiving the first user input, determine (e.g., with determining unit 1812) whether the portable electronic device has access to activity data associated with the first contact.

The processing unit 1806 is configured to, in accordance with a determination that the portable electronic device has access to activity data associated with the first contact, enable display (e.g., with display enabling unit 1808) of a portion of a graphical representation of the activity data.

The processing unit 1806 is configured to, in accordance with a determination that the electronic device does not have access to activity data associated with the first contact, enable display (e.g., with display enabling unit 1808) of a graphical element indicating that activity data is not available for the first contact.

In some embodiments, before displaying the contact information, the processing unit 1806 is configured to enable display (e.g., with display enabling unit 1808) of a first affordance for generating the first plurality of contacts and receive (e.g., with receiving unit 1812) second user input indicating selection of the first affordance. The processing unit 1806 is further configured to, in response to receiving the second user input, retrieve (e.g., with retrieving unit 1814) a second plurality of contacts, where the second plurality of contacts includes the first contact and a second contact. The processing unit 1806 is further configured to determine (e.g., with determining unit 1812) whether an electronic device associated with the second contact of a second plurality of contacts supports sharing of activity data. The processing unit 1806 is further configured to, in accordance with a determination that the second contact is not associated with an electronic device that supports sharing of activity data, excluding the second contact from the first plurality of contacts. The processing unit 1806 is further configured to determine (e.g., with determining unit 1812) whether an electronic device associated with the first contact supports sharing of activity data. The processing unit 1806 is further configured to, in accordance with a determination that the electronic device associated with the first contact supports sharing of activity data, add (e.g., with adding unit 1818) the first contact to the first plurality of contacts.

In some embodiments, the processing unit 1806 is further configured to determine (e.g., with determining unit 1812) whether the electronic device associated with the first contact supports sharing of activity data includes determining whether the electronic device is capable of measuring activity data.

In some embodiments, the processing unit 1806 is configured to receive (e.g., with receiving unit 1812) user input selecting an affordance for a sort interface and, in response to receiving the user input selecting the affordance for the sort interface, enable display (e.g., with display enabling unit 1808) of the sort interface. The processing unit 1806 is configured to, while displaying the sort user interface, receive (e.g., with receiving unit 1812) a third user input corresponding to a parameter by which to sort the first plurality of contacts and, in response to receiving the third user input, sort (e.g., with sorting unit 1818) the first plurality of contacts to generate a sorted first plurality of contacts based on the parameter, where display of the contact information is based on the sorted first plurality of contacts.

In some embodiments, the graphical representation includes a second affordance indicating that activity data should not be shared with the first contact and the processing unit 1806 is further configured to, while displaying the second affordance, receive (e.g., with receiving unit 1812) a fourth user input indicating selection of the first affordance. The processing unit 1806 is further configured to, in response to receiving the fourth user input, store (e.g., with storing unit 1818) data indicating that activity data should not be sent to the first contact.

In some embodiments, the graphical representation includes a third affordance indicating completed workouts of the first contact should not generate a message on the portable electronic device and the processing unit 1806 is further configured to, while displaying the third affordance, receive (e.g., with receiving unit 1812) a fifth user input indicating selection of the third affordance and, in response to receiving the fifth user input, store (e.g. with storing unit 1818) data indicating that a notification processed in response to the first contact completing a workout.

In some embodiments, the processing unit 1806 is configured to, in accordance with a determination that the portable electronic device does not have access to activity data associated with the first contact, enable display (e.g., with display enabling unit 1808) an indication that the first contact is hiding activity data.

In some embodiments, the graphical representation includes a fourth affordance indicating the first contact should be removed from the first plurality of contacts and the processing unit 1806 is further configured to, while displaying the fourth affordance, receive (e.g., with receiving unit 1812) a sixth user input indicating selection of the fourth affordance. The processing unit 1806 is further configured to, in response to receiving the sixth user input, remove (e.g., with removing unit 1820) the first contact from the first plurality of contacts while maintaining the first contact in the second plurality of contacts.

In some embodiments, the processing unit 1806 is further configured to enable display (e.g., with display enabling unit 1808) of a fifth affordance for displaying summary status data for the first plurality of contacts and to receive (e.g., with receiving unit 1812) a seventh user input selecting the fifth affordance. The processing unit 1806 is further configured to, in response to receiving the seventh user input, enable the replacing of display (e.g., with display enabling unit 1808) of the contact information with display of a graphical representation of the summary status data, where the graphical representation of the summary data includes a hiding portion, an invitation portion, and a sharing portion, where the hiding portion includes contact information for a set of contacts that are hiding activity data, where the invitation portion includes contact information for a set of contacts from which a notification has been received indicating an offer to share activity data, and where the sharing portion includes contact information for a set of contact that are sharing activity data.

In some embodiments, the processing unit 1806 is further configured to receive (e.g., with receiving unit 1812) from an external electronic device paired with the portable electronic device, an indication that a user workout is completed and receive (e.g., with receiving unit 1812), from the external electronic device, data for the user workout; and send (e.g., with sending unit 1824) the data to at least one of the first plurality of contacts.

FIGS. 19A-19D illustrate exemplary user interfaces for viewing and navigating workout data in accordance with some embodiments. The user interfaces in these figures are used to illustrate the processes described below, including the processes in FIG. 20.

Figure 19A:
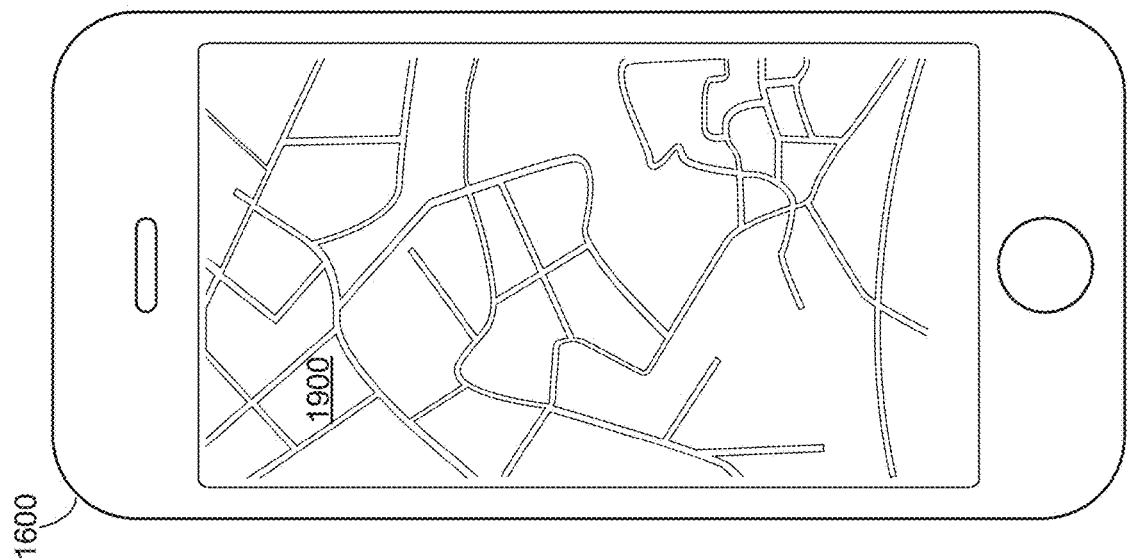
Figure 20:
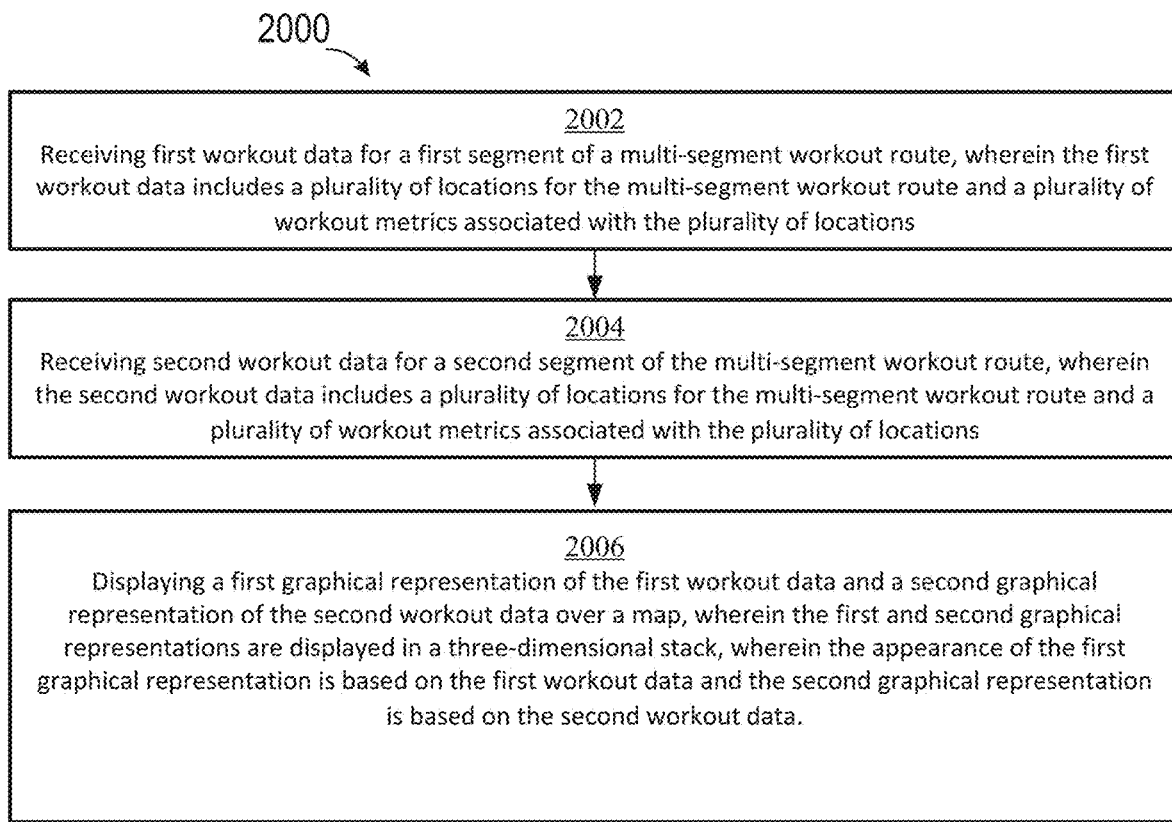
FIG. 20 is a flow diagram illustrating a method 2000 for viewing and navigating workout data using a portable electronic device in accordance with some embodiments.

FIG. 19A depicts street map 1900 on portable electronic device 1600. While map 1900 is depicted as a two-dimensional map, three-dimensional maps could also be used.

The portable electronic device receives workout data that includes position-dependent workout metrics for a workout. The locations of the workout data coincide with the locations in map 1900. The workout data may include data for multiple segments of the workout, such as multiple laps of a run or bike loop or multiple swimming laps. The workout data may be received from an external electronic device, such as a workout monitor, or may be measured from sensors included within the portable electronic device.

FIG. 19B depicts workout segments 1902, 1904, and 1906 stacked in a three-dimensional stack on map 1900. Workout segments 1902, 1904, and 1906 are pattern-coded based on the position-dependent data in the workout data. For example, the pattern coding may correspond to a corresponding workout pace at the location on the map. Other coding, such as color, may be used instead of pattern coding.

Affordance 1901 allows a user to share displayed workout information with a contact. In response to user input selecting affordance 1901, a messaging interface may be displayed that allows the user to include additional text and to select a recipient. The data and information necessary to generate the display then may be transmitted to the recipient. Alternatively, an image capture of the display may be transmitted.

FIG. 19C depicts graph 1908 representing data associated with workout segments 1902, 1904, and 1906. Graph 1908 includes curve 1910 that represents data associated with the workout segments. For example, the x-axis may be distance and the y-axis is elevation. Other values could also be used for the axes, such as time, pace, stroke (in the case of a swim workout), heart rate, and other parameters. Additionally, curve 1910 may be color-coded or have other coding to indicate additional information, such as pace. The coloring or other coding may coordinate with or be different than the coloring or other coding of the workout segments.

FIG. 19D depicts selection indicator 1912 that selects a point or portion of curve 1910. In response to receiving the user input specifying the position for selection indicator 1912, selection marker 1914 and graphical element 1916 are displayed on map 1900 based on the location in one of the workout segments that correspond to selection market 1914. Graphical element 1916 may include workout metrics associated with the workout for the selected location.

FIG. 20 is a flow diagram illustrating a method 2000 for viewing and navigating workout data using a portable electronic device in accordance with some embodiments. Method 2000 is performed at a device (e.g., 100, 300, 500, 600, 1600) with a display. Some operations in method 2000 are, optionally, combined, the order of some operations is, optionally, changed, and some operations are, optionally, omitted.

As described below, method 2000 provides an intuitive way for reviewing workout data. The method reduces the cognitive burden on a user for reviewing workout data, thereby creating a more efficient human-machine interface. For battery-operated computing devices, enabling a user to review workout data faster and more efficiently conserves power and increases the time between battery charges.

In block 2002, first workout data for a first segment of a multi-segment workout route is received. The workout data may be received from sensors of the device, from sensors on an external device, such as an exercise monitor, or from a remote source.

The multi-segment workout route can be any number of different types of workouts. For example, in the case of a running or cycling workout, each segment of the multi-segment workout may be one loop of a route (e.g., each of workout segments 1902, 1904, and 1906 of FIG. 19B). As another example, in a swimming workout, each segment may be one lap of a pool or a lap of a route in a body of water.

The first workout data includes a plurality of locations for the multi-segment workout route and a plurality of workout metrics associated with the plurality of locations. For example, each segment of the multi-segment workout route may have one or more workout metrics, such as speed, pace, or heart rate, associated with each of a plurality of locations along the route (e.g., every 1 m, 3 m, 10 m, etc. or the locations could be recorded based on a time period, such as recording a location every 1 s, 5 s, 10 s, etc.). In other words, the workout data includes position-dependent workout metric data for the segment.

In block 2004, second workout data for a second segment of the multi-segment workout route is received. The second workout data is similar to the first workout data received in block 2002, except it is for a different segment.

In block 2006, a first graphical representation of the first workout data and a second graphical representation of the second workout data are displayed on a map. The map may be a two-dimensional or three-dimensional map. The first and second graphical representations are displayed in a three-dimensional stack, wherein the appearance of the first graphical representation is based on the plurality of workout metric of the first workout data and the second graphical representation is based on the plurality of workout metrics of the second workout data. For example, the appearance of the first graphical representation and the second graphical representation may be color-coded or otherwise coded based on the workout metrics at each point along the segment. An example of this is depicted in FIG. 19B. The appearance of the segments may be coded according to any of the workout metrics, such as pace or heart rate.

In variations of method 2000, a two-dimensional graph of the first workout data and the second workout data is displayed with the first and second graphical representations. This is depicted in FIG. 19C that includes graph 1908 with curve 1910 showing the elevation of the workout segments. In some variations, the two-dimensional graph includes an indicator of a location on one of the workout segments. The corresponding location of the corresponding segment may be marked in the three-dimensional stack of the graphical representations of the workout segments and additional workout metrics may be displayed for the location. This is illustrated in FIG. 19D where indicator 1912 on graph 1908 corresponds to the location on segment 1904 indicated by indicator 1914. Graphical element 1916 provides additional workout metrics for the work at the location indicated by indicators 1912 and 1914.

In variations of method 2000, an affordance to sharing the displayed workout data is provided. In response to user input selecting the affordance, a messaging interface may be displayed that allows the user to select a recipient and add additional text. Then, the data and information necessary to generate the display or an image capture of the display is transmitted to the recipient along with any text that the user entered.

Figure 21:
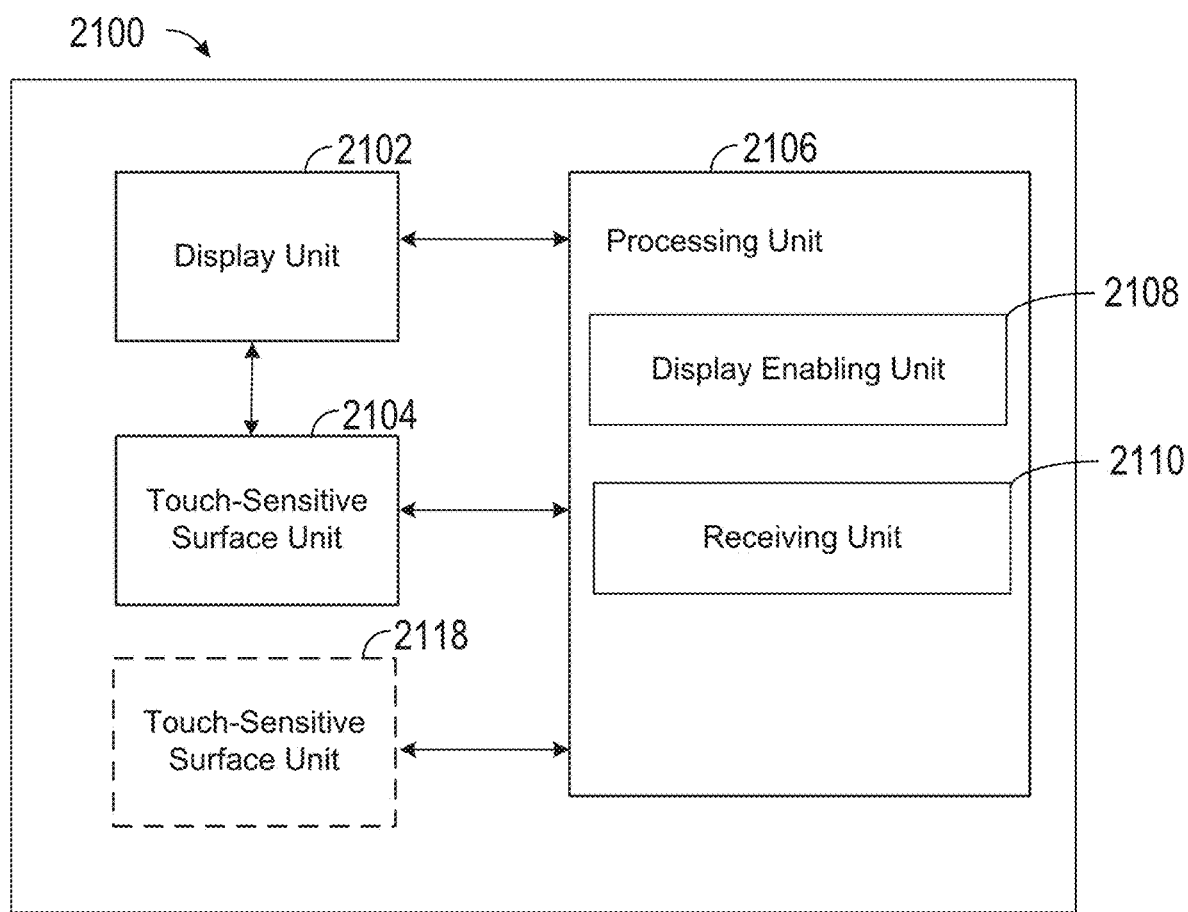
FIG. 21 shows an exemplary functional block diagram of an electronic device in accordance with the principles of the various described embodiments.

In accordance with some embodiments, FIG. 21 shows an exemplary functional block diagram of an electronic device 2100 configured in accordance with the principles of the various described embodiments. In accordance with some embodiments, the functional blocks of electronic device 2100 are configured to perform the techniques described above. The functional blocks of the device 2100 are, optionally, implemented by hardware, software, or a combination of hardware and software to carry out the principles of the various described examples. It is understood by persons of skill in the art that the functional blocks described in FIG. 21 are, optionally, combined or separated into sub-blocks to implement the principles of the various described examples. Therefore, the description herein optionally supports any possible combination or separation or further definition of the functional blocks described herein.

As shown in FIG. 21, an electronic device 2100 includes a display unit 2102 configured to display a graphic user interface, a touch-sensitive surface unit 2104 configured to receive contacts (i.e., touches), optionally a pressure-sensitive surface unit 2118, and a processing unit 2106 coupled to the display unit 2102 and the touch-sensitive surface unit 2104. In some embodiments, the processing unit 2106 includes a display enabling unit 2108 and receiving unit 2110.

The processing unit 2106 is configured to: receive (e.g., with receiving unit 2108) first workout data for a first segment of a multi-segment workout route, where the first workout data includes a plurality of locations for the multi-segment workout route and a plurality of workout metrics associated with the plurality of locations; receive (e.g., with receiving unit 2108) second workout data for a second segment of the multi-segment workout route, where the second workout data includes a plurality of locations for the multi-segment workout route and a plurality of workout metrics associated with the plurality of locations; and enable display (e.g., with display enabling unit 2108) of a first graphical representation of the first workout data and a second graphical representation of the second workout data over a map, where the first and second graphical representations are displayed in a three-dimensional stack, where the appearance of the first graphical representation is based on the plurality of workout metrics of the first workout data and the second graphical representation is based on the plurality of workout metrics of the second workout data.

In some embodiments, the processing unit 2106 is further configured to enable display (e.g., with display enabling unit 2108) of a two-dimensional graph of the first workout data and the second workout data with the display of the first graphical representation and the second graphical representation.

In some embodiments, the processing unit 2106 is further configured to enable display (e.g., with display enabling unit 2108) of a first indicator on the two-dimensional graph for a portion of the first workout data or a portion of the second workout data enable display (e.g., with display enabling unit 2108) of a second indicator on the display of the first workout data or the second workout data, where the first indicator and second indicator correspond to the same portion of the first workout data or the second workout data.

In some embodiments, the two-dimensional graph includes an indication of an elevation for the first workout data and the second workout data.

In some embodiments, the first graphical representation has a position-dependent color based on a position-dependent workout metric from the first workout data and the second graphical representation has a position-dependent color based on the position-dependent workout metric from the second workout data.

In some embodiments, the position-dependent workout metric is a workout pace or a swim stroke.

In some embodiments, the processing unit 2106 is further configured to enable display (e.g., with display enabling unit 2108) of concurrently with the first graphical representation and the second graphical representation on the map an affordance for sharing an image of the display of the first graphical representation and the second graphical representation on the map.

FIGS. 22A-22F illustrate exemplary user interfaces for pausing a workout and preventing inadvertent activation of other functions on the portable electronic device in accordance with some embodiments. The user interfaces in these figures are used to illustrate the processes described below, including the processes in FIG. 23.

A workout may be started on the portable electronic device by a user selecting from a plurality of workout types and providing any additional information need to a specific workout type. For example, if a swimming workout type is selected, the user may also need to specify whether the swim workout is in a pool or open water. Alternatively, these may be separated out as different types of workouts. In the case of a pool swim workout, the user may need to specify the length of the pool. Other example workout types include running, cycling, wheelchair, rowing, and elliptical.

Once a workout is selected and running, the portable electronic device may turn off its display to conserve battery power. However, the device may still process touch inputs on the touch screen even with the display turned off. Specifically, the touch screen may not only detect touch inputs, but it may also detect characteristic intensity of the touches, as described above. The device is then configured to respond differently depending whether the received touch has a characteristic intensity that exceeds a threshold. This may be useful, for example, when the touch interface has the potential to receive inadvertent inputs that could be interpreted as a touch. In the case of a swimming workout, water running over the touch screen may be interpreted at a touch on the touch screen. This can cause inadvertent actions to occur on the portable electronic device, including ending the workout, sending messages, or dismissing notifications. By requiring a touch to have a characteristic intensity that exceeds a threshold intensity before further interaction may occur, the possibility of inadvertent actions taking place based on inadvertent touches is greatly reduced.

Figure 22A:
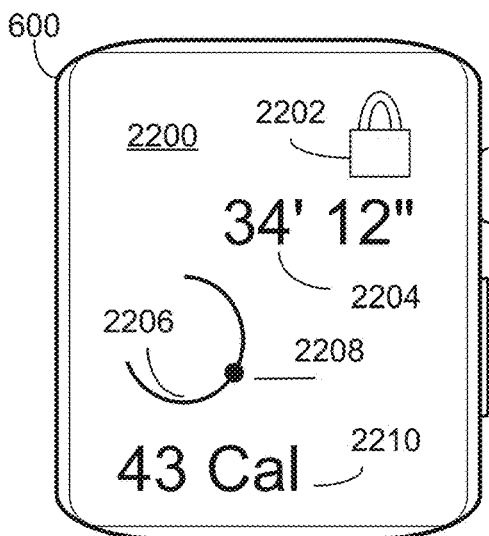
FIGS. 22A-22F illustrate exemplary user interfaces for pausing a workout and preventing inadvertent activation of other functions on the portable electronic device in accordance with some embodiments.
Figure 23:
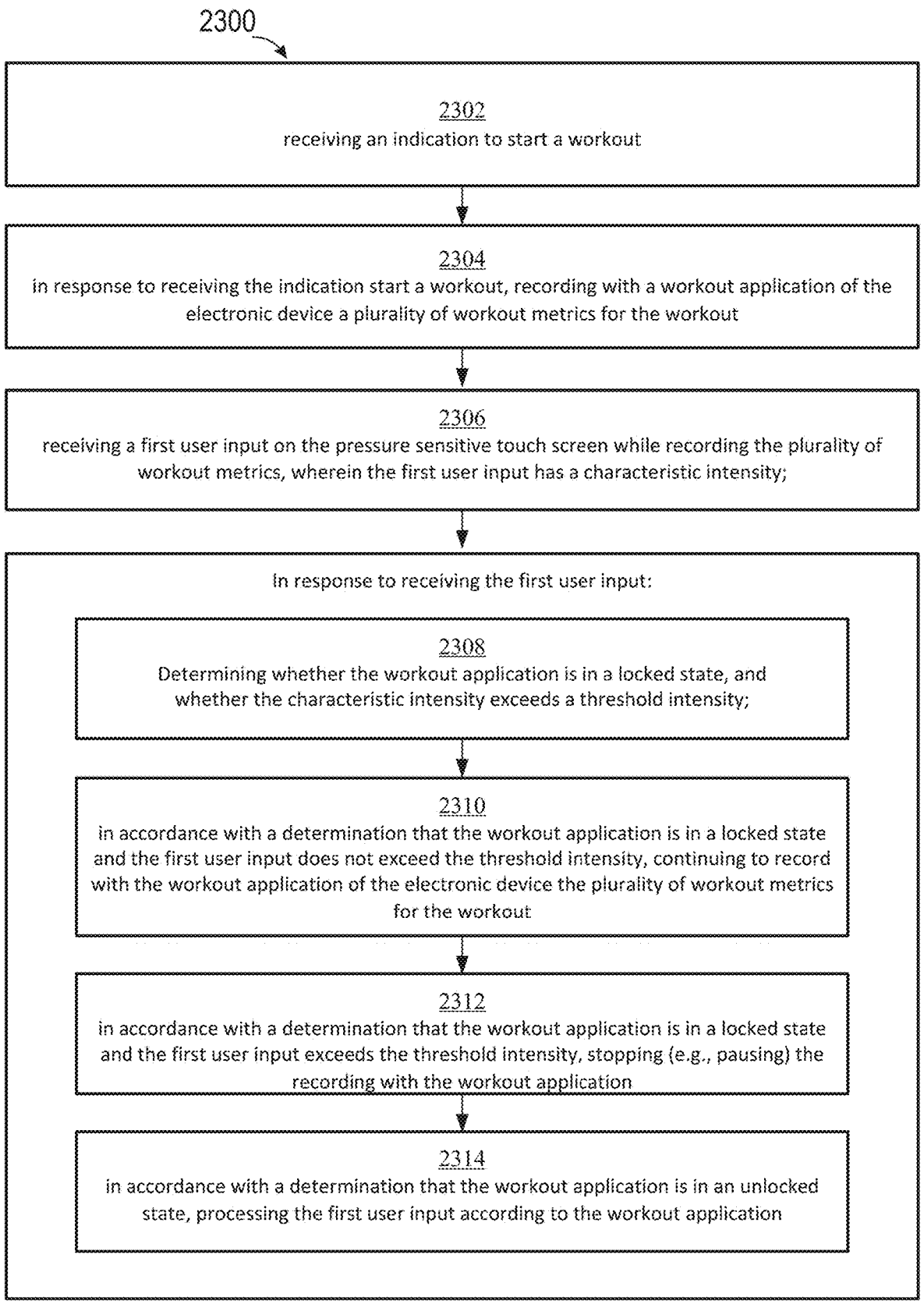
FIG. 23 is a flow diagram illustrating a method 2300 for pausing a workout and preventing inadvertent activation of the other functions on a portable electronic device during a workout in accordance with some embodiments.

FIG. 22A depicts user interface 2200 that includes lock indication 2002 indicating that the current workout is in the locked state. User interface 2200 also includes: workout metric graphical element 2004, which is displaying the time elapsed for the workout; goal metric graphical elements 2006 and 2008, where goal metric graphical element 2008 indicates progress towards a goal represented by goal metric graphical element 2008; and workout metric graphical element 2010, which represents the total calories burned so far for the workout. FIG. 22A may occur in response to a touch on the touch sensitive screen that has a characteristic intensity that does not exceed a threshold while the ongoing workout is in a locked state.

A workout is in a locked state if it will not respond normally to touches on the touch screen that do not have characteristic intensities that exceed an intensity threshold. For example, user interface 2200 of FIG. 22A would normally allow a user to further interface with the display through other gestures on the touch screen. When the workout is in a locked state, however, further touches on user interface 2200 may have limited effect, as described below.

Figure 22D:
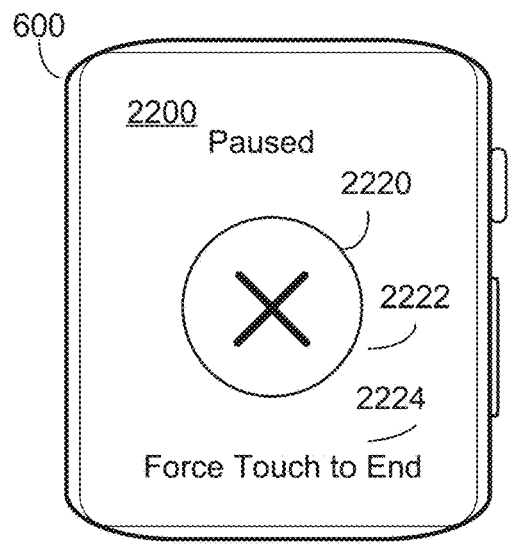
Figure 22B:
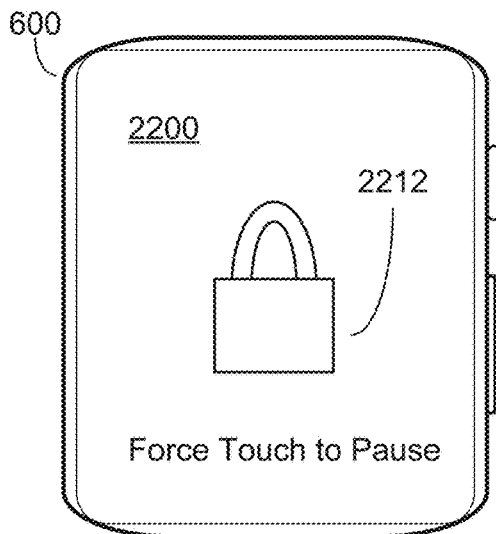

FIG. 22B depicts use interface 2200 that includes indication 2212 indicating that the workout is in a locked state and a force touch (e.g., a touch with a characteristic intensity greater than a threshold) should be used to pause the workout. FIG. 22B may appear after another touch is detected on user interface 2200 of FIG. 22A that has a characteristic intensity that does not exceed an intensity threshold. In some cases, when a workout is in a locked state, the displays in FIGS. 22A and 22B are the only displays that are accessible to a user without first performing a touch with a characteristic intensity greater than a threshold intensity.

Figure 22E:
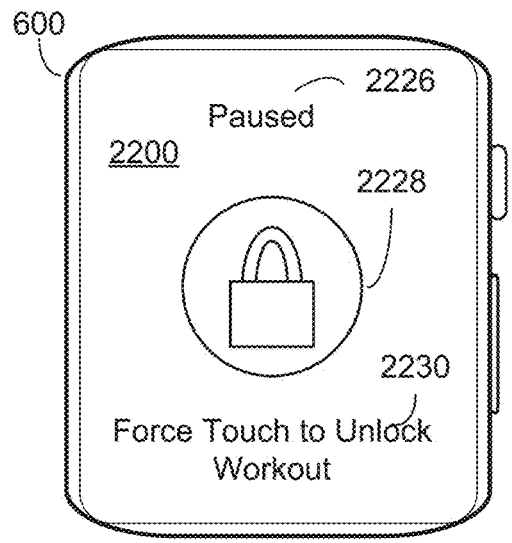
Figure 22C:
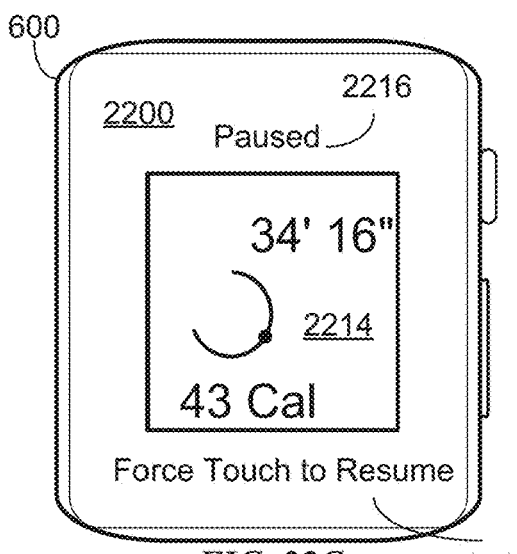

FIG. 22C depicts user interface 2200 in response to portable electronic device 600 receiving a touch input with a characteristic intensity that exceeds a threshold intensity. In FIG. 22C, user interface 2200 includes a pause indicator 2216, workout summary graphical element 2214, and indicator 2218 indicating how to resume the workout. Workout summary graphical element 2214 may be further interacted with to reveal additional workout data. In response to user interface 2200 receiving a touch with a characteristic intensity that exceed a threshold intensity, the workout may resume in the locked state and the user interface 2200 may return to a state of limited response to low intensity touches, as described with respect to FIGS. 22A and 22B.

In response to portable electronic device 600 in FIG. 22C receiving user input, such as a scroll or swipe input, FIG. 22D depicts user interface 2200 with graphical elements 2220, 2222, 2224 providing, respectively, the workout state, a graphical representation of a potential action, and instructions for executing the potential action. In response to user interface 2200 receiving a touch with a characteristic intensity that exceed a threshold intensity, the workout may end.

Figure 22F:
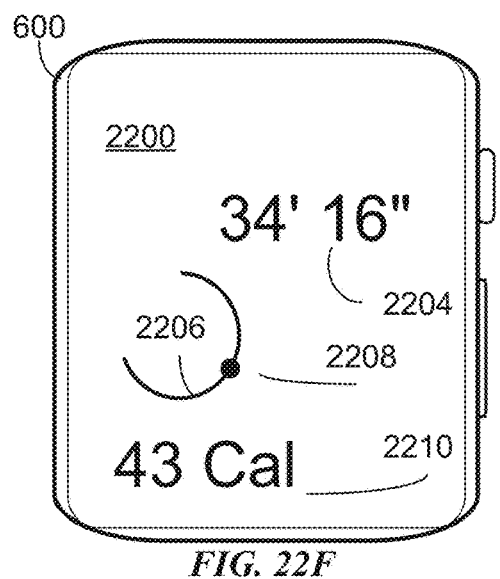

In response to portable electronic device 600 in FIG. 22D receiving further user input, such as a scroll or swipe input, FIG. 22E depicts user interface 2200 with graphical elements 2226, 2228, 2230 providing, respectively, the workout state, a graphical representation of a potential action, and instructions for executing the potential action. In response to user interface 2200 receiving a touch with a characteristic intensity that exceed a threshold intensity, the workout may be resumed in the unlocked state. FIG. 22F depicts user interface 2200 as described in FIG. 22A, except that the workout is ongoing in the unlocked state, such as would be the result from user input with a sufficient characteristic intensity being received in FIG. 22E. A touch input with a characteristic intensity that exceeds a threshold on user interface 2200 may display an interface that allows the workout to be locked again.

FIG. 23 is a flow diagram illustrating a method 2300 for pausing a workout and preventing inadvertent activation of the other functions on a portable electronic device during a workout in accordance with some embodiments. Method 2300 is performed at a device (e.g., 100, 300, 500, 600, 1600) with a display and a touch sensitive screen that is also pressure sensitive. Some operations in method 2300 are, optionally, combined, the order of some operations are, optionally, changed, and some operations are, optionally, omitted.

As described below, method 2300 provides an intuitive way for pausing a workout application and preventing inadvertent activations or deactivations of functions on the portable electronic device during a workout. The method reduces the cognitive burden on a user for pausing a workout application and preventing inadvertent activations or deactivations of functions on the portable electronic device during a workout, thereby creating a more efficient human-machine interface. For battery-operated computing devices, enabling a user to pause a workout application and prevent inadvertent activations or deactivations of functions on the portable electronic device during a workout faster and more efficiently conserves power and increases the time between battery charges.

In block 2302, an indication to start a workout is received. A workout may be started on the portable electronic device by a user selecting from a plurality of workout types and providing any additional information need to a specific workout type. For example, if a swimming workout type is selected, the user may also need to specify whether the swim workout is in a pool or open water. Alternatively, these may be separated out as different types of workouts. In the case of a pool swim workout, the user may need to specify the length of the pool. Other example workout types include running, cycling, wheelchair, rowing, and elliptical.

In block 2304, in response to receiving the indication start a workout, a workout application of the portable electronic device starts recording a plurality of workout metrics for the workout. For example, workout metrics may include speed, pace, swim stroke, heart rate, distance, and time.

In block 2306, a first user input is received on the pressure sensitive touch screen while recording the plurality of workout metrics. The first user input has a characteristic intensity. Blocks 2308-2314 are in response to receiving the first user input. The first user input may be received while the display is powered off or while a user interface (e.g., user interface 2200 of FIG. 22A) is displayed on the display.

In block 2308, a determination is made as to (1) whether the workout application is in a locked state and (2) whether the characteristic intensity exceeds a threshold intensity. The determination of whether the workout application is in the locked stated may be made based on status bits associated with the workout application or by some other means.

In block 2310, in accordance with a determination that the workout application is in a locked state and the first user input does not exceed the threshold intensity, the workout application continues to record the plurality of workout metrics for the workout. In other words, the touch first input does not affect the workout application's operation. Subsequent touches of this type while the workout application is in the same state would produce the same result. In some variations, in accordance with these determinations, the workout application may display a limited user interface, as depicted in FIGS. 22A and 22B.

In block 2312, in accordance with a determination that the workout application is in a locked state and the first user input exceeds the threshold intensity, the recording with the workout application is stopped (e.g., paused). In addition to pausing the recording of the plurality of workout metrics, a pause screen may also be displayed, as depicted in FIG. 22C. User input received while displaying the pause screen may present additional workout metrics or information for the workout.

In some variations of method 2300, after stopping the recording with the workout application, a third user input is received on the pressure sensitive. In response to receiving the third user input, a determination is made as to whether the third user input has a characteristic intensity exceeds a threshold intensity. In accordance with a determination that the third user input does not exceed the threshold intensity and in response to the second user input, a workout metric for the workout is displayed. In accordance with a determination that the third user input exceeds the threshold intensity, recording the workout metrics with the workout application is resumed.

In some variations of method 2300, after stopping the recording with the workout application and while displaying a resume user interface, a fourth user input to resume the recording with the workout application and changing the workout application to an unlocked state is received, as described with respect to FIG. 22E above. In response to receiving the fourth user input, the recording with the workout application is resumed. Data is also stored indicating the workout application is in an unlocked state.

In block 2314, in accordance with a determination that the workout application is in an unlocked state, processing the first user input according to the workout application. This is normal operation of the workout application.

In some variations of method 2300, after completion of the workout, data is stored associating a type of the completed workout with an indication of a locked or unlocked state based on whether the state of the workout application when the workout ended.

In some variations of method 2300, a fifth user input is received and processed via a hardware input of the portable electronic device while recording the plurality of workout metrics and while the workout application is in the locked state. In other words, hardware inputs are still processed normally even when the workout is in the locked state.

FIGS. 22A-22F and 23 and the associated description, describe an embodiment of an input-intensity-to-unlock system. With this type of system having an input-intensity-sensitive and touch-sensitive screen, a device can have two states and moving from one state to the other state may occur in response to a touch on the screen having a characteristic intensity that is greater than an intensity threshold. For example, a first state of the device may be a limited or a locked state while the second state may allow for full functionality. While the device is in the first state, in response to receiving a touch having a characteristic intensity that does not exceed the intensity threshold, no action is taken or an action of a limited set of available actions is taken (e.g., an action that does not require that the characteristic intensity meet an intensity threshold). The limited set of available actions is less than the full functionality of the device available in the second state and may include, for example, displaying instruction for switching the device into the other state, displaying an indication of the state the device is in, displaying summary information, or other limited functions. While the device is in the first state, in response to receiving a touch that exceeds the threshold intensity, the device is switched to the second state that provides full or near full functionality (e.g., when the device is a locked device, the device is switched to an unlocked state). In some embodiments, changing state (e.g., unlocking) requires, in addition to requiring an input intensity greater than the intensity threshold, that one or more additional criterion be met (e.g., that the input includes a required component of motion or that the input includes two or more contacts). Stated another way, the device may receive an input having a characteristic intensity; determine whether the input meets state change criteria, where the state change criteria includes a criterion that is met when the characteristic intensity of the input exceeds an intensity threshold; in response to a determination that the state change criteria are met, changing an access state of the device; and in response to a determination that the state change criteria are not met, processing the input as a non-state changing function (e.g., as a touch input that does not result in state change) or forgoing any further action in response to the input.

Figure 24:
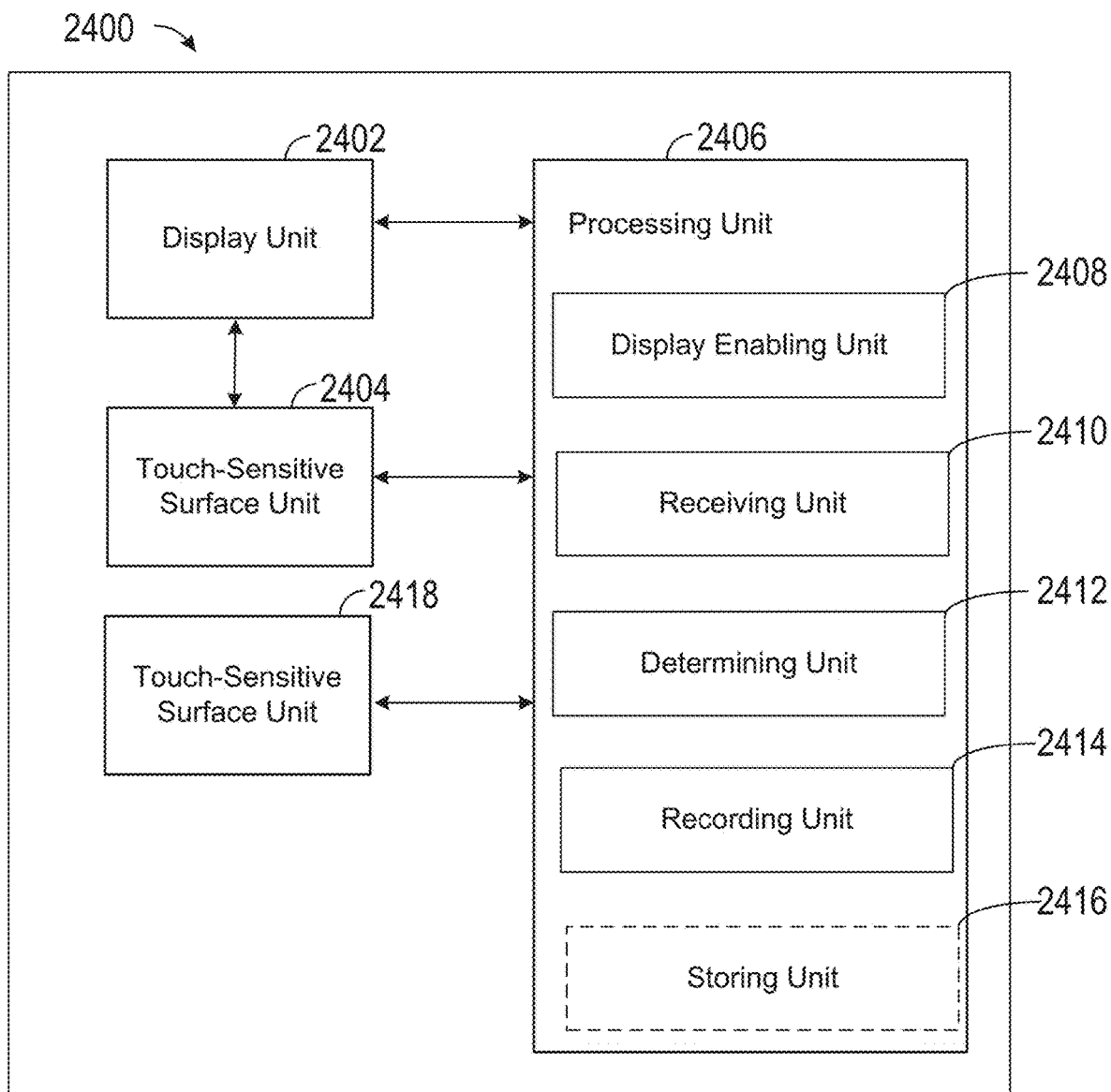
FIG. 24 shows an exemplary functional block diagram of an electronic device in accordance with the principles of the various described embodiments.

In accordance with some embodiments, FIG. 24 shows an exemplary functional block diagram of an electronic device 2400 configured in accordance with the principles of the various described embodiments. In accordance with some embodiments, the functional blocks of electronic device 2400 are configured to perform the techniques described above. The functional blocks of the device 2400 are, optionally, implemented by hardware, software, or a combination of hardware and software to carry out the principles of the various described examples. It is understood by persons of skill in the art that the functional blocks described in FIG. 24 are, optionally, combined or separated into sub-blocks to implement the principles of the various described examples. Therefore, the description herein optionally supports any possible combination or separation or further definition of the functional blocks described herein.

As shown in FIG. 24, an electronic device 2400 includes a display unit 2402 configured to display a graphic user interface, a touch-sensitive surface unit 2404 configured to receive contacts (i.e., touches), a pressure-sensitive surface unit 2418, and a processing unit 2406 coupled to the display unit 2402 and the touch-sensitive surface unit 2404. In some embodiments, the processing unit 2406 includes a display enabling unit 2408, receiving unit 2410, a determining unit 2412, a recording unit 2414, and, optionally, a storing unit 2416.

The processing unit 2406 is configured to: receive (e.g., with receiving unit 2410) an indication to start a workout; in response to receiving the indication start a workout, record (e.g., with recording unit 2414) a plurality of workout metrics for the workout; receive (e.g., with receiving unit 2410) a first user input on the pressure sensitive touch screen while recording the plurality of workout metrics, wherein the first user input has a characteristic intensity; and in response to receiving the first user input, determine (e.g., with determining unit 2412) whether the workout application is in a locked state and whether the characteristic intensity exceeds a threshold intensity.

The processing unit 2406 is configured to, in accordance with a determination that the workout application is in a locked state and the first user input does not exceed the threshold intensity, continue to record (e.g., with recording unit 2414) the plurality of workout metrics for the workout; in accordance with a determination that the workout application is in a locked state and the first user input exceeds the threshold intensity, stop the recording (e.g., with recording unit 2414); and in accordance with a determination that the workout application is in an unlocked state, process (e.g., with input processing unit 2422) the first user input according to the workout application.

In some embodiments, processing unit 2402 is further configured to, in accordance with a determination that the workout application is in a locked state and the first user input exceeds the threshold intensity, enable display (e.g., with display enabling unit 2408) of a pause screen for the workout.

In some embodiments, processing unit 2402 is further configured to, in response to receiving a second user input while the recording is stopped, enabling the scrolling (e.g., with display enabling unit 2408) of a display of a workout metric for the workout.

In some embodiments, processing unit 2402 is further configured to, after stopping the recording with the workout application, receive (e.g., with receiving unit 2410) a third user input on the pressure sensitive touch screen, wherein the third user input has a characteristic intensity. The processing unit 2406 is further configured to, in response to receiving the third user input: determine (e.g., with determining unit 2412) whether the characteristic intensity exceeds a threshold intensity and in accordance with a determination that the third user input does not exceed the threshold intensity and in response to the second user input, enabling display (e.g., with display of display enabling unit 2408) of a workout metric for the workout. The processing unit 2406 is further configured to, in accordance with a determination that the third user input exceeds the threshold intensity, resume (e.g., with recording unit 2414) the recording.

In some embodiments, processing unit 2402 is further configured to, after stopping the recording with the workout application and while displaying a resume user interface, receive (e.g., with receiving unit 2410) a fourth user input to resume the recording with the workout application and changing the workout application to an unlocked state and, in response to receiving the fourth user input, resume (e.g., with recording unit 2414) recording and store (e.g., with storing unit 2416) data indicating the workout application is in an unlocked state.

In some embodiments the workout is a swim workout.

In some embodiments, processing unit 2402 is further configured to, after completion of the workout, store (e.g., with storing unit 2416) data associating a type of the workout with an indication of a locked or unlocked state.

In some embodiments, determining whether the first user input exceeds a threshold pressure occurs while the display is off.

In some embodiments, processing unit 2402 is further configured to receive (e.g., with receiving unit 2410) a fifth user input via a hardware input of the portable electronic device while recording the plurality of workout metrics and while the workout application is in the locked state and process (e.g., with input processing unit 2422) the fourth user input.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, home addresses, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

What is claimed is:

1. An electronic device, comprising:
a display device;
one or more processors;
memory; and
one or more programs, where in the one or more programs are stored in the memory and configured to be executed by the one or more processors, the one or more programs including instructions for:
displaying a first user interface that includes a representation of a current time;
subsequent to displaying the first user interface, receiving a notification corresponding to a completed workout of a remote user associated with an external electronic device, wherein the completed workout is a workout selected by the remote user from a plurality of workout types;
displaying, via the display device, a first graphical element representing the notification, wherein the first graphical element at least partially overlaps the representation of the current time;
receiving a first user input corresponding to selection of the first graphical element while displaying the first graphical element; and
in response to the first user input:
ceasing to display the first graphical element representing the notification; and
displaying, via the display device, a workout summary interface for the completed workout of the remote user associated with the external electronic device.

2. The electronic device of claim 1, wherein the workout summary interface includes a graphical element indicating a type of the workout.

3. The electronic device of claim 1, wherein the workout summary interface includes a graphical element indicating weather data associated with the workout.

4. The electronic device of claim 1, wherein the workout summary interface includes a graphical element of a first goal metric, and wherein the first goal metric is a number of calories burned or a measurement of activity.

5. The electronic device of claim 1, wherein the workout summary interface includes a graphical element for a first workout metric for the completed workout, and wherein the first workout metric is selected from a group consisting of a pace, a distance, a time, a number of calories burned, and a heart rate.

6. The electronic device of claim 5, wherein the workout summary interface includes a graphical element of a second workout metric for the workout different than the first workout metric, and wherein the second workout metric is selected from a group consisting of a pace, a distance, a time, a calorie value, and a heart rate.

7. The electronic device of claim 1, wherein displaying the workout summary interface occurs after receiving the first user input selecting the notification.

8. The electronic device of claim 1, wherein the workout summary interface includes an affordance for contacting a first contact, the one or more programs further including instructions for:
receiving a second user input indicating selection of the affordance; and
in response to receiving the second user input, displaying a messaging user interface configured to receive message input for the first contact on the electronic device.

9. The electronic device of claim 8, wherein the messaging user interface includes a plurality of pre-defined messages, and wherein at least one of the pre-defined messages is based on type of a current workout.

10. The electronic device of claim 8, wherein the messaging user interface includes a plurality of pre-defined messages, and wherein at least one of the pre-defined messages is based on the workout summary interface.

11. A method, comprising:
at an electronic device with a display device:
displaying a first user interface that includes a representation of a current time;
subsequent to displaying the first user interface, receiving a notification corresponding to a completed workout of a remote user associated with an external electronic device, wherein the completed workout is a workout selected by the remote user from a plurality of workout types;
displaying, via the display device, a first graphical element representing the notification, wherein the first graphical element at least partially overlaps the representation of the current time;
receiving a first user input corresponding to selection of the first graphical element while displaying the first graphical element; and
in response to the first user input:
ceasing to display the first graphical element representing the notification; and
displaying, via the display device, a workout summary interface for the completed workout of the remote user associated with the external electronic device.

12. The method of claim 11, wherein the workout summary interface includes a graphical element indicating a type of the workout.

13. The method of claim 11, wherein the workout summary interface includes a graphical element indicating weather data associated with the workout.

14. The method of claim 11, wherein the workout summary interface includes a graphical element of a first goal metric, and wherein the first goal metric is a number of calories burned or a measurement of activity.

15. The method of claim 11, wherein the workout summary interface includes a graphical element for a first workout metric for the completed workout, and wherein the first workout metric is selected from a group consisting of a pace, a distance, a time, a number of calories burned, and a heart rate.

16. The method of claim 15, wherein the workout summary interface includes a graphical element of a second workout metric for the workout different than the first workout metric, and wherein the second workout metric is selected from a group consisting of a pace, a distance, a time, a calorie value, and a heart rate.

17. The method of claim 11, wherein displaying the workout summary interface occurs after receiving the first user input selecting the notification.

18. The method of claim 11, wherein the workout summary interface includes an affordance for contacting a first contact, further comprising:
- receiving a second user input indicating selection of the affordance; and
- in response to receiving the second user input, displaying a messaging user interface configured to receive message input for the first contact on the electronic device.

19. The method of claim 18, wherein a messaging user interface includes a plurality of pre-defined messages, and wherein at least one of the pre-defined messages is based on type of a current workout.

20. The method of claim 18, wherein the messaging user interface includes a plurality of pre-defined messages, and wherein at least one of the pre-defined messages is based on the workout summary interface.

21. A non-transitory computer-readable storage medium comprising one or more programs for execution by one or more processors of an electronic device with a display device, the one or more programs including instructions for:
- displaying a first user interface that includes a representation of a current time;
- subsequent to displaying the first user interface, receiving a notification corresponding to a completed workout of a remote user associated with an external electronic device, wherein the completed workout is a workout selected by the remote user from a plurality of workout types;
- displaying, via the display device, a first graphical element representing the notification, wherein the first graphical element at least partially overlaps the representation of the current time;
- receiving a first user input corresponding to selection of the first graphical element while displaying the first graphical element; and
- in response to the first user input:
  - ceasing to display the first graphical element representing the notification; and
  - displaying, via the display device, a workout summary interface for the completed workout of the remote user associated with the external electronic device.

22. The non-transitory computer-readable storage medium of claim 21, wherein the workout summary interface includes a graphical element indicating a type of the workout.

23. The non-transitory computer-readable storage medium of claim 21, wherein the workout summary interface includes a graphical element indicating weather data associated with the workout.

24. The non-transitory computer-readable storage medium of claim 21, wherein the workout summary interface includes a graphical element of a first goal metric, and wherein the first goal metric is a number of calories burned or a measurement of activity.

25. The non-transitory computer-readable storage medium of claim 21, wherein the workout summary interface includes a graphical element for a first workout metric for the completed workout, and wherein the first workout metric is selected from a group consisting of a pace, a distance, a time, a number of calories burned, and a heart rate.

26. The non-transitory computer-readable storage medium of claim 25, wherein the workout summary interface includes a graphical element of a second workout metric for the workout different than the first workout metric, and wherein the second workout metric is selected from a group consisting of a pace, a distance, a time, a calorie value, and a heart rate.

27. The non-transitory computer-readable storage medium of claim 21, wherein displaying the workout summary interface occurs after receiving the first user input selecting the notification.

28. The non-transitory computer-readable storage medium of claim 21, wherein the workout summary interface includes an affordance for contacting a first contact, the one or more programs further including instructions:
- receiving a second user input indicating selection of the affordance; and
- in response to receiving the second user input, displaying a messaging user interface configured to receive message input for the first contact on the electronic device.

29. The non-transitory computer-readable storage medium of claim 28, wherein a messaging user interface includes a plurality of pre-defined messages, and wherein at least one of the pre-defined messages is based on type of a current workout.

30. The non-transitory computer-readable storage medium of claim 28, wherein the messaging user interface includes a plurality of pre-defined messages, and wherein at least one of the pre-defined messages is based on the workout summary interface.

* * * * *